(12) United States Patent
Van Ingelgem et al.

(10) Patent No.: US 11,806,220 B2
(45) Date of Patent: *Nov. 7, 2023

(54) APPARATUS FOR MANUFACTURING AN ABSORBENT ARTICLE WITH CHANNELS

(71) Applicant: Drylock Technologies NV, Zele (BE)

(72) Inventors: Werner Van Ingelgem, Zele (BE); Steven Smet, Zele (BE); Tom Derycke, Zele (BE); Dries Verduyn, Zele (BE)

(73) Assignee: Drylock Technologies NV, Zele (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/658,989

(22) Filed: Apr. 12, 2022

(65) Prior Publication Data

US 2022/0233364 A1   Jul. 28, 2022

Related U.S. Application Data

(63) Continuation of application No. 16/613,555, filed as application No. PCT/EP2018/062386 on May 14, 2018, now Pat. No. 11,331,228.

(30) Foreign Application Priority Data

May 15, 2017 (EP) .................................... 17171110
Jul. 27, 2017 (EP) .................................... 17183453
(Continued)

(51) Int. Cl.
*A61F 13/15* (2006.01)
*A61F 13/475* (2006.01)
(Continued)

(52) U.S. Cl.
CPC .... *A61F 13/4756* (2013.01); *A61F 13/15658* (2013.01); *A61F 13/15699* (2013.01);
(Continued)

(58) Field of Classification Search
None
See application file for complete search history.

(56) References Cited

U.S. PATENT DOCUMENTS 4,674,966 A   6/1987   Johnson et al.
5,300,053 A   4/1994   Genaro
(Continued)

FOREIGN PATENT DOCUMENTS

CN   104939978 A   9/2015
CN   105616073 A   6/2016
(Continued)

OTHER PUBLICATIONS

"U.S. Appl. No. 16/613,555, Non Final Office Action dated Jun. 1, 2021", 11 pgs.
(Continued)

*Primary Examiner* — Barbara J Musser
(74) *Attorney, Agent, or Firm* — Schwegman Lundberg & Woessner, P.A.

(57) ABSTRACT

A method for manufacturing an absorbent article, said method comprising guiding a first sheet material along a rotating member, wherein a surface of said rotating member is provided with a pattern with at least one suction zone and at least one non-suction zone; applying an absorbent material on said first sheet material on the rotating member; locally removing the absorbent material applied on at least one attachment portion of the first sheet material located above the at least one non-suction zone, such that at least one remaining portion of the first sheet material located above the at least one suction zone is covered with absorbent material and substantially no absorbent material is present on the at least one attachment portion; applying a second sheet material on top of the absorbent material on the first sheet material.

20 Claims, 92 Drawing Sheets

(30) Foreign Application Priority Data

| | | |
|---|---|---|
| Sep. 11, 2017 | (EP) | 17190395 |
| Oct. 13, 2017 | (EP) | 17196434 |
| Oct. 25, 2017 | (EP) | 17198349 |
| Oct. 25, 2017 | (EP) | 17198368 |
| Oct. 26, 2017 | (EP) | 17198652 |
| Nov. 9, 2017 | (EP) | 17200847 |
| Nov. 16, 2017 | (EP) | 17202006 |

(51) Int. Cl.
*A61F 13/49* (2006.01)
*A61F 13/511* (2006.01)
*A61F 13/533* (2006.01)
*A61F 13/534* (2006.01)
*A61F 13/535* (2006.01)
*A61F 13/538* (2006.01)
*A61F 13/539* (2006.01)
*B29C 65/78* (2006.01)
*B29C 65/00* (2006.01)
*A61F 13/53* (2006.01)
*A61F 13/531* (2006.01)
*B29L 31/48* (2006.01)

(52) U.S. Cl.
CPC .. *A61F 13/15707* (2013.01); *A61F 13/15764* (2013.01); *A61F 13/15804* (2013.01); *A61F 13/49001* (2013.01); *A61F 13/51108* (2013.01); *A61F 13/533* (2013.01); *A61F 13/535* (2013.01); *A61F 13/538* (2013.01); *A61F 13/539* (2013.01); *A61F 13/53436* (2013.01); *B29C 65/7847* (2013.01); *B29C 66/45* (2013.01); *A61F 2013/530007* (2013.01); *A61F 2013/5315* (2013.01); *A61F 2013/5349* (2013.01); *A61F 2013/530065* (2013.01); *A61F 2013/530481* (2013.01); *A61F 2013/53908* (2013.01); *A61F 2013/53925* (2013.01); *B29L 2031/4878* (2013.01)

(56) References Cited

U.S. PATENT DOCUMENTS

| | | |
|---|---|---|
| 5,447,677 A | 9/1995 | Griffoul et al. |
| 5,494,622 A | 2/1996 | Heath et al. |
| 5,807,365 A | 9/1998 | Luceri |
| 6,627,130 B2 | 9/2003 | Kugler et al. |
| 9,216,116 B2 | 12/2015 | Roe et al. |
| 11,331,228 B2 | 5/2022 | Van Ingelgem et al. |
| 2002/0065498 A1 | 5/2002 | Ohashi et al. |
| 2002/0153634 A1 | 10/2002 | Kugler et al. |
| 2003/0093047 A1 | 5/2003 | Nguyen et al. |
| 2003/0132556 A1 | 7/2003 | Venturino et al. |
| 2005/0148973 A1 | 7/2005 | Tamura et al. |
| 2007/0246147 A1 | 10/2007 | Venturino et al. |
| 2007/0250026 A1 | 10/2007 | Venturino et al. |
| 2009/0270825 A1 | 10/2009 | Wciorka et al. |
| 2011/0130737 A1 | 6/2011 | Sagisaka et al. |
| 2011/0319851 A1 | 12/2011 | Kudo et al. |
| 2014/0027066 A1 | 1/2014 | Jackels et al. |
| 2014/0039437 A1 | 2/2014 | Van De Maele |
| 2014/0163500 A1 | 6/2014 | Roe et al. |
| 2014/0163503 A1 | 6/2014 | Arizti et al. |
| 2014/0163511 A1 | 6/2014 | Roe et al. |
| 2014/0371701 A1 | 12/2014 | Bianchi et al. |
| 2015/0065973 A1 | 3/2015 | Roe et al. |
| 2015/0080837 A1 | 3/2015 | Rosati et al. |
| 2016/0143790 A1 | 5/2016 | Umemoto |
| 2016/0206482 A1 | 7/2016 | Nishikawa et al. |
| 2016/0354260 A1 | 12/2016 | Roe et al. |
| 2020/0078229 A1 | 3/2020 | Van Ingelgem et al. |
| 2020/0078232 A1 | 3/2020 | Smet et al. |
| 2020/0085640 A1 | 3/2020 | Smet et al. |
| 2020/0138640 A1 | 5/2020 | Smet et al. |
| 2020/0197238 A1 | 6/2020 | Smet et al. |
| 2021/0161727 A1 | 6/2021 | Van Ingelgem et al. |
| 2021/0290449 A1 | 9/2021 | Smet et al. |

FOREIGN PATENT DOCUMENTS

| | | |
|---|---|---|
| DE | 69927464 T2 | 2/2006 |
| DE | 602004006262 T2 | 6/2007 |
| EP | 0067916 A1 | 12/1982 |
| EP | 1862155 A1 | 12/2007 |
| EP | 2532328 A1 | 12/2012 |
| EP | 2532329 A1 | 12/2012 |
| EP | 2679209 | 1/2014 |
| EP | 2740449 A1 | 6/2014 |
| EP | 2870951 A1 | 5/2015 |
| EP | 2886093 A1 | 6/2015 |
| EP | 2905001 A1 | 8/2015 |
| EP | 2949301 A1 | 12/2015 |
| EP | 2949302 A1 | 12/2015 |
| EP | 3342386 A1 | 7/2018 |
| JP | 01141707 U | 9/1989 |
| RU | 69399 U1 | 12/2007 |
| RU | 2519992 | 6/2014 |
| RU | 2523978 C2 | 7/2014 |
| RU | 2540596 | 2/2015 |
| WO | WO-8901325 A1 | 2/1989 |
| WO | WO-2012170798 A1 | 12/2012 |
| WO | WO-2014093128 A1 | 6/2014 |
| WO | WO-2015031225 A1 | 3/2015 |
| WO | WO-2016154400 A1 | 9/2016 |
| WO | WO-2018172860 A1 | 9/2018 |

OTHER PUBLICATIONS

"U.S. Appl. No. 16/613,555, Notice of Allowance dated Jan. 14, 2022", 7 pgs.
"U.S. Appl. No. 16/613,555, Response filed Dec. 1, 2021 to Non Final Office Action dated Jun. 1, 2021", 16 pgs.
"U.S. Appl. No. 16/613,588, Non Final Office Action dated Sep. 16, 2021", 23 pgs.
"U.S. Appl. No. 16/613,588, Response filed Mar. 15, 2022 to Non Final Office Action dated Sep. 16, 2021", 14 pgs.
"International Application No. PCT/EP2018/062383, International Search Report dated Jun. 14, 2018", (dated Jun. 14, 2018), 3 pgs.
"International Application No. PCT/EP2018/062383, Written Opinion dated Jun. 14, 2018", (dated Jun. 14, 2018), 6 pgs.
"International Application No. PCT/EP2018/062385, International Search Report dated Jun. 25, 2018", (dated Jun. 25, 2018), 3 pgs.
"International Application No. PCT/EP2018/062385, Written Opinion dated Jun. 25, 2018", (dated Jun. 25, 2018), 5 pgs.
"International Application No. PCT/EP2018/062386, International Search Report dated Jun. 25, 2018", (dated Jun. 25, 2018), 3 pgs.
"International Application No. PCT/EP2018/062386, Written Opinion dated Jun. 25, 2018", (dated Jun. 25, 2018), 6 pgs.
"International Application No. PCT/EP2018/062388, International Search Report dated Jul. 2, 2018", (dated Jul. 2, 2018), 3 pgs.
"International Application No. PCT/EP2018/062388, Written Opinion dated Jul. 2, 2018", (dated Jul. 2, 2018), 5 pgs.
"International Application No. PCT/EP2018/062391, International Search Report dated Mar. 16, 2017", (dated Jun. 22, 2018), 3 pgs.
"International Application No. PCT/EP2018/062391, Written Opinion dated Mar. 16, 2017", (dated Jun. 22, 2018), 5 pgs.
"International Application No. PCT/EP2018/062392, International Search Report dated Jun. 25, 2018", (dated Jun. 25, 2018), 3 pgs.
"International Application No. PCT/EP2018/062392, Written Opinion dated Jun. 25, 2018", (dated Jun. 25, 2018), 5 pgs.
"International Application No. PCT/EP2018/062395, International Search Report dated Jul. 4, 2018", (dated Jul. 4, 2018), 3 pgs.
"International Application No. PCT/EP2018/062395, Written Opinion dated Jul. 4, 2018", (dated Jul. 4, 2018), 5 pgs.
"Universal Signature (TM) Spray Nozzles", [Online]. Retrieved from the Internet: <URL: https://www.nordson.com/en/divisions/

(56) References Cited

OTHER PUBLICATIONS adhesive-dispensing-systems/products/nozzles/universal-signature-spray-nozzles>, (Jan. 20, 2021), 1 pg.
"Affidavit Signed by Serge Bax D12", (Feb. 21, 2020), 1 pg.
"Fippi internal sotware D12b", (Nov. 26, 2019), 1 pg.
"Technical Drawing D12a", (Feb. 24, 2017), 1 pg.
"Invoice Fippi D12c", (Mar. 3, 2017), 1 pg.
"Diaper Shipment Document D12d", (Feb. 3, 2017), 32 pgs.
"Affadavit with Translation Pillo CEO Defabiani D14a and b", (May 10, 2021), 2 pgs.
"Email Guarnerio D15", (1 16 202017), 1 pg.
"Image glue on tissue D16", (Feb. 24, 2017), 1 pg.
"U.S. Appl. No. 16/613,588, Non Final Office Action dated Aug. 4, 2022", 11 pgs.
"Brazilian Application No. 112019023927-8, Non-Final Office Action dated Sep. 12, 2022", w English Translation, 6 pgs.
"Brazilian Application No. 112019023933-2, Non-Final Office Action dated Sep. 12, 2022", w English Translation, 6 pgs.
"Brazilian Application No. 112019023931-6, Non-Final Office Action dated Sep. 12, 2022", w English Translation, 6 pgs.
"U.S. Appl. No. 16/613,588, Response filed Feb. 3, 2023 to Non Final Office Action dated Aug. 4, 2022", 12 pgs.
"U.S. Appl. No. 16/613,588, Final Office Action dated Feb. 15, 2023", 12 pgs.
"Russian Application Serial No. 2019143740, Office Action dated Dec. 30, 2022", w English Translation, (Dec. 30, 2022), 7 pgs.
"U.S. Appl. No. 16/613,588, Response filed May 15, 2023 to Final Office Action dated Feb. 15, 2023", 12 pgs.
"European Application No. 18722592.5 Communication pursuant to Rule 114(2) dated Mar. 5, 2022", 6 pgs.
"Polish Application Serial No. 425519.1, Office Action dated Nov. 25, 2022", w/ English Translation, (dated Nov. 25, 2022), 5 pgs.
U.S. Appl. No. 16/613,508, filed Nov. 14, 2019, Absorbent Article With Channels and Method for Manufacturing Thereof.
U.S. Appl. No. 16/613,544, filed Nov. 14, 2019, Absorbent Article With Channels and Method for Manufacturing Thereof.
U.S. Appl. No. 16/613,555 U.S. Pat. No. 11,331,228, filed Nov. 14, 2019, Absorbent Article With Channels and Method for Manufacturing Thereof.
U.S. Appl. No. 16/613,562, filed Nov. 14, 2019, Absorbent Article With Channels and Method for Manufacturing Thereof.
U.S. Appl. No. 16/613,588, filed Nov. 14, 2019, Absorbent Article With Channels and Method for Manufacturing Thereof.
U.S. Appl. No. 16/613,574, filed Nov. 14, 2019, Absorbent Article With Channels and Method for Manufacturing Thereof.
U.S. Appl. No. 16/613,602, filed Nov. 14, 2019, Absorbent Article With Channels and Method for Manufacturing Thereof.
"Advice of delivery", (Jan. 10, 2022), 176 pgs.
"Advice of delivery", (Mar. 26, 2021), 16 pgs.
"Amended claims filed after receipt of European search report", (dated Jul. 16, 2018), 3 pgs.
"Amended claims with annotations", (Jul. 16, 2018), 3 pgs.
"Amended claims with annotations II", (Apr. 24, 2023), 3 pgs.
"Amended claims with annotations VII", (Apr. 24, 2023), 3 pgs.
"Amended claims with annotations VIII", (Apr. 24, 2023), 3 pgs.
"Amended claims with annotations I", (Apr. 24, 2023), 3 pgs.
"Amended claims with annotations III", (Apr. 24, 2023), 3 pgs.
"Amended claims with annotations IV", (Apr. 24, 2023), 3 pgs.
"Amended claims with annotations IX", (Apr. 24, 2023), 3 pgs.
"Amended claims with annotations V", (Apr. 24, 2023), 3 pgs.
"Amended claims with annotations VI", (Apr. 24, 2023), 3 pgs.
"Amended claims with annotations X", (Apr. 24, 2023), 3 pgs.
"Amended claims with annotations XI", (Apr. 24, 2023), 3 pgs.
"Amended description filed after receipt of (European) search report", (dated Jul. 16, 2018), 77 pgs.
"Amended description with annotations", (Jul. 16, 2018), 86 pgs.
"Amended drawings filed after receipt of (European) search report", (Jul. 16, 2018), 1 pg.
"Amendments received before examination", (dated Jul. 16, 2018), 3 pgs.
"Annex to the communication—opposition", (Jan. 10, 2022), 7 pgs.
"Annex to the communication—opposition", (Mar. 25, 2021), 11 pgs.
"Any annexes (other than citation) to an opposition letter", (Sep. 14, 2020), 8 pgs.
"U.S. Appl. No. 16/613,588, Non Final Office Action dated Jun. 9, 2023", 12 pgs.
"Auxiliary request during Opposition procedure 02", (Sep. 29, 2021), 3 pgs.
"Auxiliary request during Opposition procedure IX", (Sep. 29, 2021), 3 pgs.
"Auxiliary request during Opposition procedure 01", (Sep. 29, 2021), 3 pgs.
"Auxiliary request during Opposition procedure 01", (Oct. 29, 2020), 3 pgs.
"Auxiliary request during Opposition procedure 02", (Oct. 29, 2020), 3 pgs.
"Auxiliary request during Opposition procedure 03", (Oct. 29, 2020), 3 pgs.
"Auxiliary request during Opposition procedure 03", (Sep. 29, 2021), 3 pgs.
"Auxiliary request during Opposition procedure 04", (Sep. 29, 2021), 3 pgs.
"Auxiliary request during Opposition procedure 04", (Oct. 29, 2020), 3 pgs.
"Auxiliary request during Opposition procedure 05", (Oct. 29, 2020), 3 pgs.
"Auxiliary request during Opposition procedure 05", (Sep. 29, 2023), 3 pgs.
"Auxiliary request during Opposition procedure 06", (Sep. 29, 2021), 3 pgs.
"Auxiliary request during Opposition procedure 07", (Sep. 29, 2021), 3 pgs.
"Auxiliary request during Opposition procedure 08", (Sep. 29, 2021), 3 pgs.
"Auxiliary request during Opposition procedure 09", (Sep. 29, 2021), 3 pgs.
"Auxiliary request during Opposition procedure 10", (Sep. 29, 2021), 3 pgs.
"Auxiliary request during Opposition procedure I", (Sep. 29, 2021), 3 pgs.
"Auxiliary request during Opposition procedure I", (Oct. 29, 2020), 3 pgs.
"Auxiliary request during Opposition procedure II", (Sep. 29, 2021), 3 pgs.
"Auxiliary request during Opposition procedure II", (Oct. 29, 2020), 3 pgs.
"Auxiliary request during Opposition procedure III", (Oct. 29, 2020), 3 pgs.
"Auxiliary request during Opposition procedure III", (Sep. 29, 2021), 3 pgs.
"Auxiliary request during Opposition procedure IV", (Sep. 29, 2021), 3 pgs.
"Auxiliary request during Opposition procedure IV", (Oct. 29, 2020), 3 pgs.
"Auxiliary request during Opposition procedure V", (Sep. 29, 2021), 3 pgs.
"Auxiliary request during Opposition procedure V", (Oct. 29, 2020), 3 pgs.
"Auxiliary request during Opposition procedure VI", (Sep. 29, 2021), 3 pgs.
"Auxiliary request during Opposition procedure VII", (Sep. 29, 2021), 3 pgs.
"Auxiliary request during Opposition procedure VIII", (Sep. 29, 2021), 3 pgs.
"Auxiliary request during Opposition procedure X", (Sep. 29, 2021), 3 pgs.
"Brief communication—Opposition proceedings", EI28016-01EP WE/kl, (Nov. 3, 2020), 69 pgs.
"Brief communication—Opposition proceedings", OPP0129, (Nov. 3, 2020), 69 pgs.
"Brief communication—Opposition proceedings", 2H/2WB22/10-10, (Nov. 12, 2021), 15 pgs.

(56) References Cited

OTHER PUBLICATIONS

"Brief communication—Opposition proceedings", EI28016-01EP WE/kl, (Nov. 12, 2021), 15 pgs.
"Brief communication—Opposition proceedings", EI28016-01EP WE/kl, (Oct. 6, 2021), 75 pgs.
"Brief communication—Opposition proceedings", OPP0129, (Oct. 6, 2021), 75 pgs.
"Brief communication—Opposition proceedings", OPP0129, (Oct. 4, 2021), 13 pgs.
"Brief communication—Opposition proceedings", 2H/2WB22/10-10, (Oct. 4, 2021), 20 pgs.
"Brief communication—Opposition proceedings", EI28016-01EP WE/kl, (Oct. 4, 2021), 8 pgs.
"Brief communication—Opposition proceedings", 2H/2WB22/10-10. (Jan. 20, 2022), 3 pgs.
"Brief communication—Opposition proceedings", EI28016-01EP WE/kl, (Jan. 20, 2022), 3 pgs.
"Brief communication—Opposition proceedings", 2H/2WB22/10-10, (Jan. 13, 2022), 2 pgs.
"Brief communication—Opposition proceedings", EI28016-01EP WE/kl, (Jan. 13, 2022), 2 pgs.
"Brief communication—Opposition proceedings", 2H/2WB22/10-10, (Nov. 30, 2021), 20 pgs.
"Brief communication—Opposition proceedings", OPP0129, (Nov. 30, 2021), 20 pgs.
"Brief communication—Opposition proceedings", 2H/2WB22/10-10, (Sep. 21, 2020), 3 pgs.
"Brief communication—Opposition proceedings", EI2016-01EPWE/kl, (Sep. 21, 2020), 3 pgs.
"Claims I", (Apr. 24, 2023), 3 pgs.
"Claims II", (Apr. 24, 2023), 3 pgs.
"Claims III", (Apr. 24, 2023), 3 pgs.
"Claims IV", (Apr. 24, 2023), 3 pgs.
"Claims IX", (Apr. 24, 2023), 3 pgs.
"Claims V", (Apr. 24, 2023), 3 pgs.
"Claims VI", (Apr. 24, 2023), 3 pgs.
"Claims VII", (Apr. 24, 2023), 3 pgs.
"Claims VIII", (Apr. 24, 2023), 3 pgs.
"Claims X", (Apr. 24, 2023), 3 pgs.
"Claims XI", (Apr. 24, 2023), 3 pgs.
"Communication about intention to grant a European patent", (dated Apr. 10, 2019), 5 pgs.
"Communication of a notice of opposition—first information to patent proprietor", (Jun. 2, 2020), 49 pgs.
"Communication of a notice of opposition—first information to patent proprietor", (Feb. 18, 2020), 18 pgs.
"Communication of a notice of opposition and request to file observations", (Jun. 19, 2020), 1 pg.
"Communication of amended entries", (Sep. 18, 2020), 2 pgs.
"Communication of amended entries", the appointment of a representative, (Jan. 20, 2022), 3 pgs.
"Communication of amended entries", the withdrawal from the representation, (Jan. 20, 2022), 1 pg.
"Communication regarding the transmission of the European search report", (dated Mar. 12, 2018), 1 pg.
"Consolidated list of cited opposition documents", (May 14, 2020), 1 pg.
"Decision of the Opposition Division and instruction", (Jan. 10, 2022), 160 pgs.
"Decision of the Opposition Division and instruction", (Jan. 10, 2022), 2 pgs.
"Decision to grant a European Patent", (dated Jul. 18, 2019) 3 pgs.
"Declaration of SMEs", (Mar. 10, 2022), 1 pg.
"Druckexemplar in opposition procedure", (Jan. 10, 2022), 123 pgs.
"Electric Receipt", (Apr. 24, 2023), 1 pgs.
"Electric Receipt", (Apr. 21, 2023), 1 pg.
"Electric Receipt", (May 20, 2022), 1 pg.
"Electric Receipt", (Nov. 9, 2021), 1 pg.
"Electric Receipt", (Sep. 29, 2021), 2 pgs.
"Electric Receipt", (Oct. 29, 2020), 2 pgs.
"Electric Receipt", (Mar. 26, 2021), 1 pg.
"Electric Receipt", (Sep. 28, 2021), 1 pg.
"Electric Receipt", (Sep. 14, 2020), 1 pg.
"Electric Receipt", (May 14, 2020), 2 pgs.
"Electronic Receipt", (Jul. 16, 2018), 2 pgs.
"Electronic receipt", (Feb. 4, 2020), 1 pg.
"Electronic receipt", (Jan. 10, 2022), 1 pg.
"Electronic receipt", (May 10, 2022), 1 pg.
"Electronic receipt", ONT-0036-OP, (Mar. 18, 2022), 1 pg.
"Electronic receipt", 2H/OP169422EP00, (Mar. 18, 2022), 1 pg.
"European search opinion", (dated Mar. 12, 2018), 3 pgs.
"European Search Report", (dated Mar. 12, 2018), 2 pgs.
"F3345 Forwarding of Submissions to parties", EI28016-01EP WE/kl, (May 3, 2023), 18 pgs.
"F3345 Forwarding of Submissions to parties", OPP0129, (May 3, 2023), 18 pgs.
"F3345 Forwarding of Submissions to parties", 2H/2WB22/10-10, (May 2, 2023), 10 pgs.
"F3345 Forwarding of Submissions to parties", EI28016-01EP WE/ki, (May 2, 2023), 10 pgs.
"Grounds for the decision (Annex)—opposition", (Jan. 10, 2022), 31 pgs.
"Information about the result of oral proceedings", (Nov. 29, 2021), 7 pgs.
"Information concerning oral proceedings", (Mar. 25, 2021), 3 pgs.
"Information on Search Strategy", (Mar. 12, 2018), 1 pg.
"Intention to grant (signatures)", (dated Apr. 10, 2019), 1 pg.
"Interlocutory decision in opposition proceedings", 2H/2WB22/10-10, (Jan. 10, 2022), 2 pgs.
"Interlocutory decision in opposition proceedings", OPP0129, (Jan. 10, 2022), 2 pgs.
"Interlocutory decision in opposition proceedings", EI28016-01EP WE/kl, (Jan. 10, 2022), 2 pgs.
"Letter accompanying subsequently filed items", (Jan. 10, 2022), 1 pg.
"Letter accompanying subsequently filed items", application No. 17202006.7, (Mar. 18, 2022), 2 pgs.
"Letter accompanying subsequently filed items", application No. EP17202006.7-EP3403632, (Mar. 10, 2022), 2 pgs.
"Letter accompanying subsequently filed items", (Apr. 24, 2023), 1 pgs.
"Letter accompanying subsequently filed items", (Apr. 21, 2023), 1 pg.
"Letter accompanying subsequently filed items", (Apr. 21, 2023), 2 pgs.
"Letter accompanying subsequently filed items", (Mar. 26, 2021), 1 pg.
"Letter accompanying subsequently filed items", (Sep. 28, 2021), 1 pg.
"Letter accompanying subsequently filed items", (Sep. 29, 2021), 2 pgs.
"Letter accompanying subsequently filed items", (May 10, 2022), 1 pg.
"Letter accompanying subsequently filed items", (Nov. 9, 2021), 1 pg.
"Letter accompanying subsequently filed items", (Feb. 4, 2020), 2 pgs.
"Letter accompanying subsequently filed items", (Jul. 16, 2018), 2 pgs.
"Letter accompanying subsequently filed items", (Sep. 14, 2020), 1 pg.
"Letter accompanying subsequently filed items", (Oct. 29, 2020), 2 pgs.
"Letter regarding the opposition procedure (no time limit)", (Nov. 29, 2021), 19 pgs.
"Letter relating to Appeal Procedure", (Mar. 14, 2022), 2 pgs.
"Means of redress", (Oct. 1, 2022), 2 pgs.
"Minutes of the oral proceedings (Opposition Division)—conclusion of the proceedings", (Jan. 10, 2022), 2 pgs.
"Minutes of the oral proceedings (Opposition Division)—introduction of the parties", (Jan. 10, 2022), 1 pg.
"Notice of Appeal", Arnold&Siedsma, (Mar. 18, 2022), 1 pgs.
"Notice of Appeal", Oxon, (Mar. 18, 2022), 1 pg.

(56) References Cited

OTHER PUBLICATIONS

"Notice of appeal", (Mar. 9, 2022), 2 pgs.
"Notice of further oppositions to opponent(s)", OPP0129, (Jun. 19, 2020), 50 pgs.
"Notice of further oppositions to opponent(s)", EI2018-01EP WE/kl, (Jun. 19, 2020), 19 pgs.
"Notice of Opposition A", (May 14, 2020), 40 pgs.
"Notice of Opposition A", (Feb. 4, 2020), 4 pgs.
"Notice of Opposition B", (Feb. 4, 2020), 13 pgs.
"Notice of Opposition B", (May 14, 2020), 7 pgs.
"Observations by third parties", (Apr. 13, 2023), 4 pgs.
"Priority Search Results copy provided by EPO A", (Mar. 7, 2018), 7 pgs.
"Priority Search Results copy provided by EPO A", (Jul. 20, 2018), 5 pgs.
"Priority Search Results copy provided by EPO B", (Jul. 20, 2018), 5 pgs.
"Priority Search Results copy provided by EPO B", (Mar. 7, 2018), 6 pgs.
"Priority Search Results copy provided by EPO C", (Mar. 7, 2018), 13 pgs.
"Priority Search Results copy provided by EPO C", (Jul. 20, 2018), 5 pgs.
"Priority Search Results copy provided by EPO D", (Jul. 20, 2018), 5 pgs.
"Priority Search Results copy provided by EPO E", (Jul. 20, 2018), 5 pgs.
"Provision of the minutes—opposition procedure", 2H/2WB22/10-10, (Jan. 10, 2022), 19 pgs.
"Provision of the minutes—opposition procedure", EI28016-01EP WE/kl, (Jan. 10, 2022), 1 pg.
"Provision of the minutes—opposition procedure", OPP0129, (Jan. 10, 2022), 1 pg.
"Reply of the patent proprietor to the notice(s) of opposition", (Oct. 29, 2020), 38 pgs.
"Reply to appeal", (Apr. 17, 2023), 11 pgs.
"Reply to appeal", (Apr. 21, 2023), 7 pgs.
"Reply to appeal", (Apr. 24, 2023), 15 pgs.
"Request concerning representative opponent", (Oct. 25, 2021), 1 pg.
"Scanned annex to a communication—opposition procedure", EP3403632B1 marked up copy, (Jan. 10, 2022), 3 pgs.
"Scanned annex to a communication—opposition procedure", Auxiliary Request III, (Jan. 10, 2022), 3 pgs.
"Statement of ground of appeal", (May 20, 2022), 18 pgs.
"Statement of grounds of appeal", (May 19, 2022), 34 pgs.
"Statement of grounds of appeal", (May 25, 2022), 34 pgs.
"Statement of grounds of appeal", (May 10, 2022), 15 pgs.
"Summons to attend oral proceedings", OPP0129, (Mar. 25, 2021), 1 pg.
"Summons to attend oral proceedings", EI28016-01EP WE, (Mar. 25, 2021), 1 pg.
"Summons to attend oral proceedings", 2H/WB22/10-10, (Mar. 25, 2021), 1 pg.
"Text intended for grant (clean copy)", (dated Apr. 10, 2019), 162 pgs.
"Transmission of the certificate for a European patent pursuant to Rule 74 EPC", (Aug. 26, 2019), 1 pg.
"Transmittal of decision—summons—opposition", (Mar. 25, 2021), 16 pgs.
"Transmittal of decision—summons—opposition", EI2016-01EP WE/II, (Mar. 25, 2021), 16 pgs.
"Transmittal of decision—summons—opposition", OPP0129, (Mar. 25, 2021), 16 pgs.
"Transmittal of decision—summons—opposition", OPP0129, (Jan. 10, 2022), 176 pgs.
"Transmittal of decision—summons—opposition", 2H/2WB22/10-10, (Jan. 10, 2022), 176 pgs.
"Transmittal of decision—summons—opposition", EI2016-01EP WE/kl, (Jan. 10, 2022), 176 pgs.
"Written submission in preparation to-during oral proceedings", (Sep. 29, 2021), 14 pgs.
"Written submission in preparation to-during oral proceedings", (Sep. 28, 2021), 7 pgs.
"Written submission in preparation to-during oral proceedings", (Sep. 28, 2021), 12 pgs.
"Written submission in preparation to-during oral proceedings", (Nov. 24, 2021), 19 pgs.
"Written submission in preparation to-during oral proceedings", (Nov. 9, 2021), 14 pgs.
"Written submission in preparation to-during oral proceedings", (Sep. 3, 2021), 12 pgs.

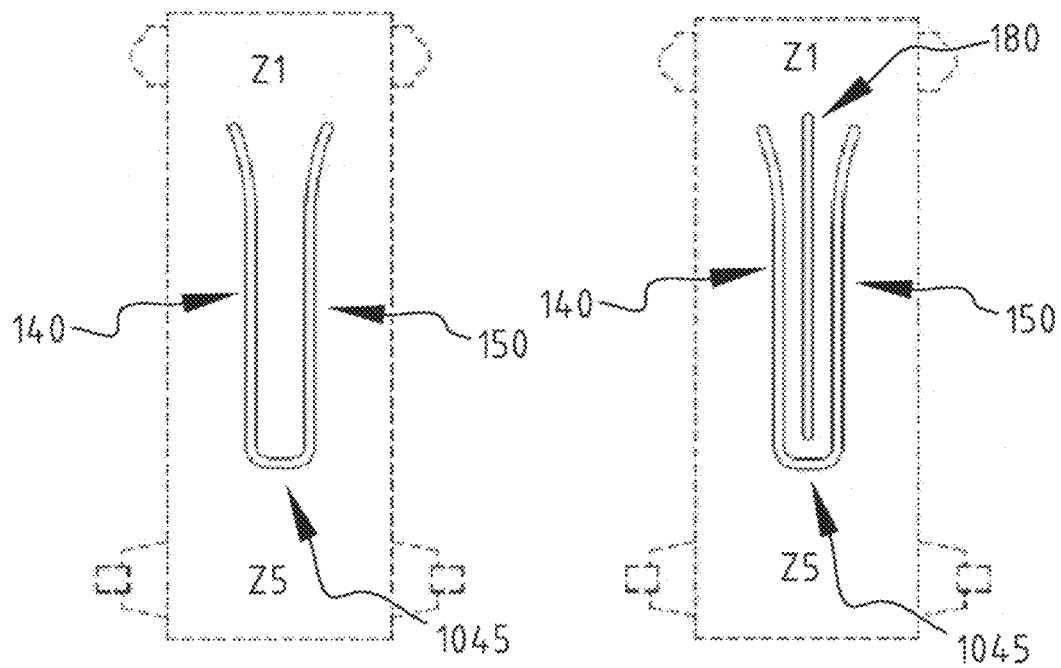
FIG. 20I
FIG. 20J
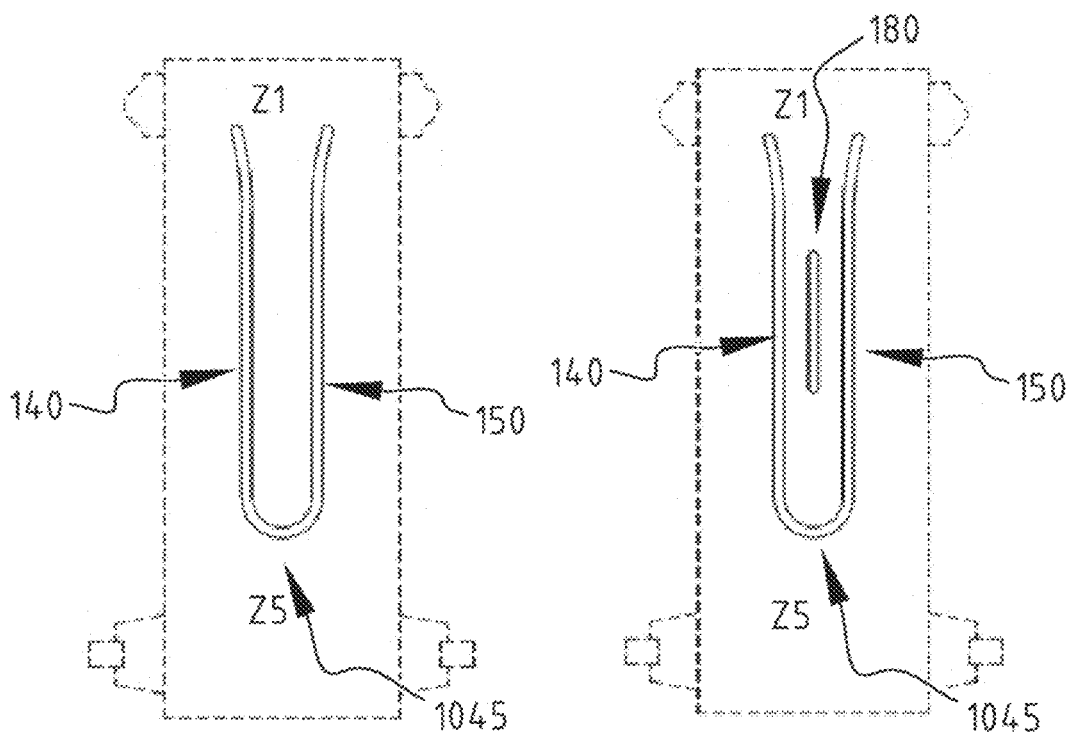
FIG. 20K
FIG. 20L

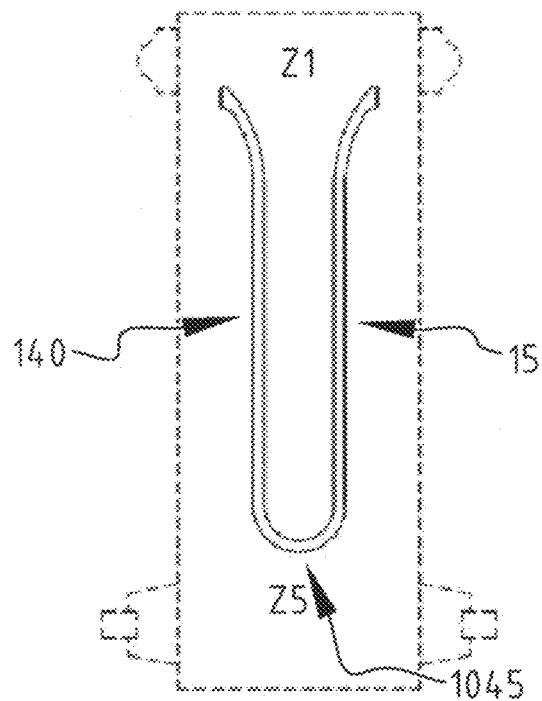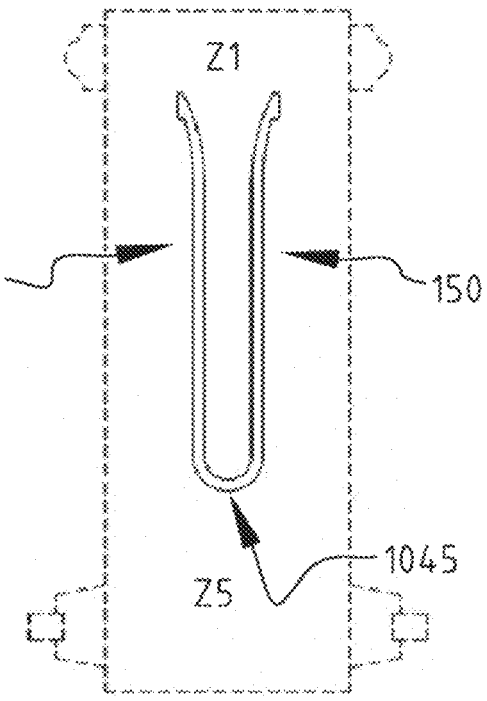
FIG. 20M  FIG. 20N
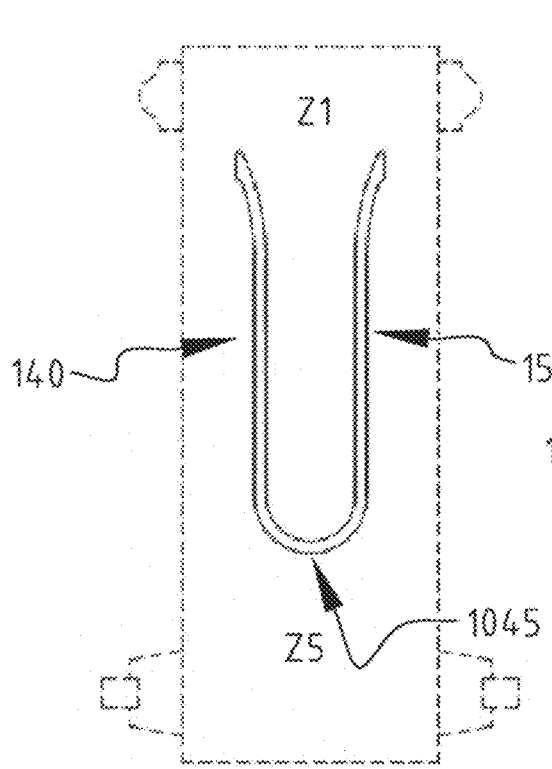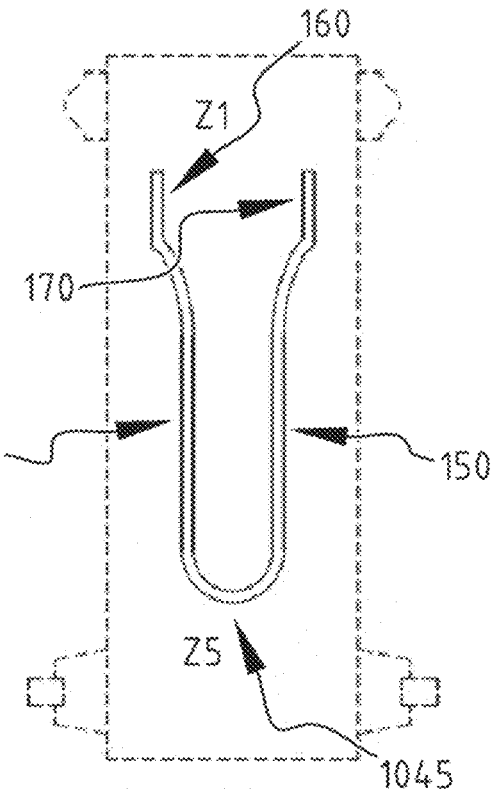
FIG. 20O  FIG. 20P

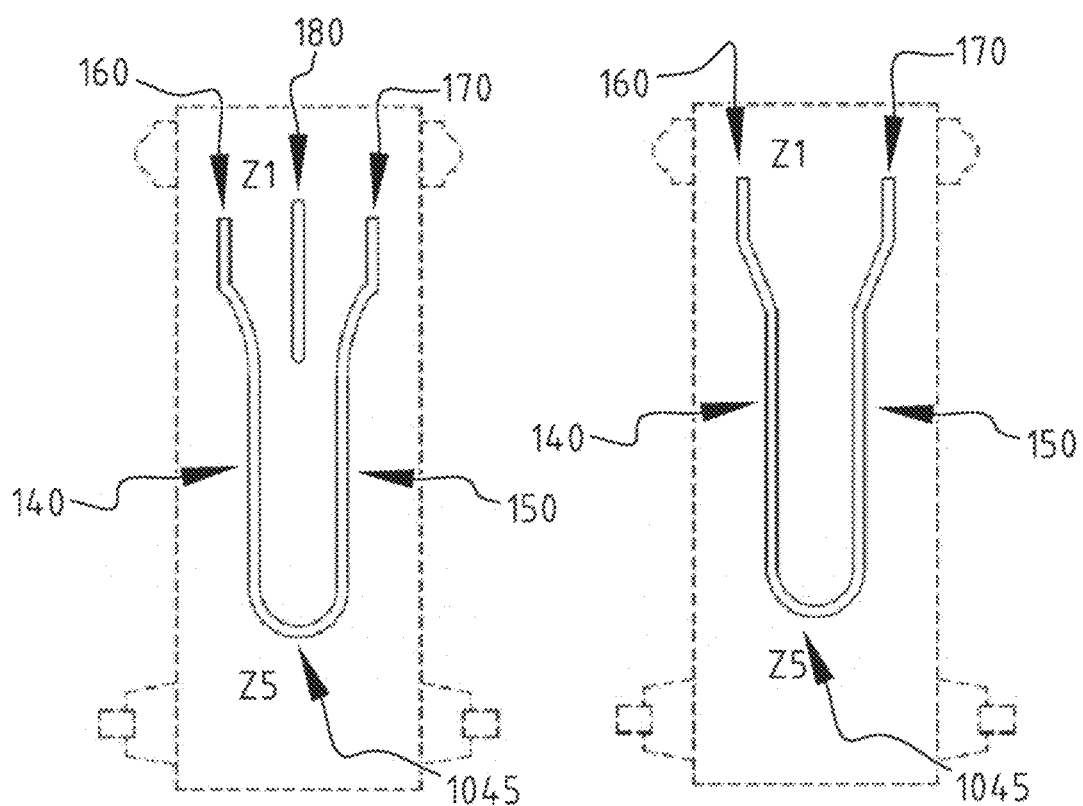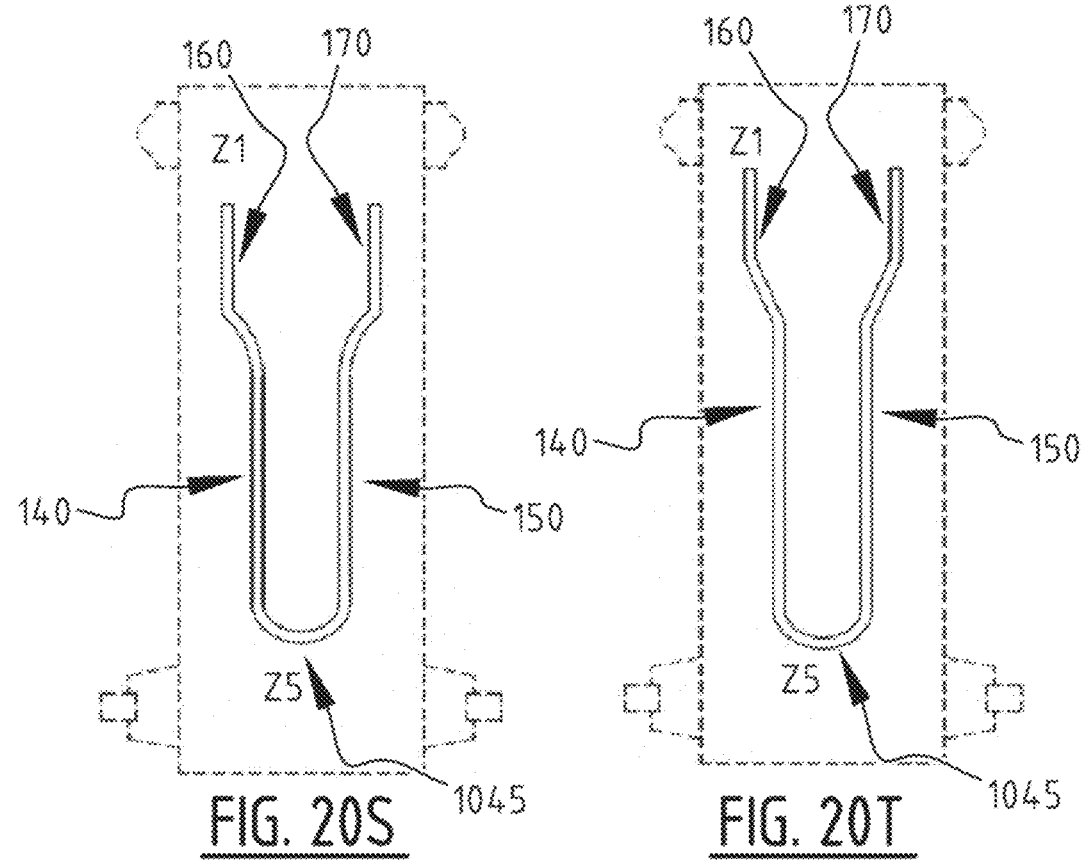

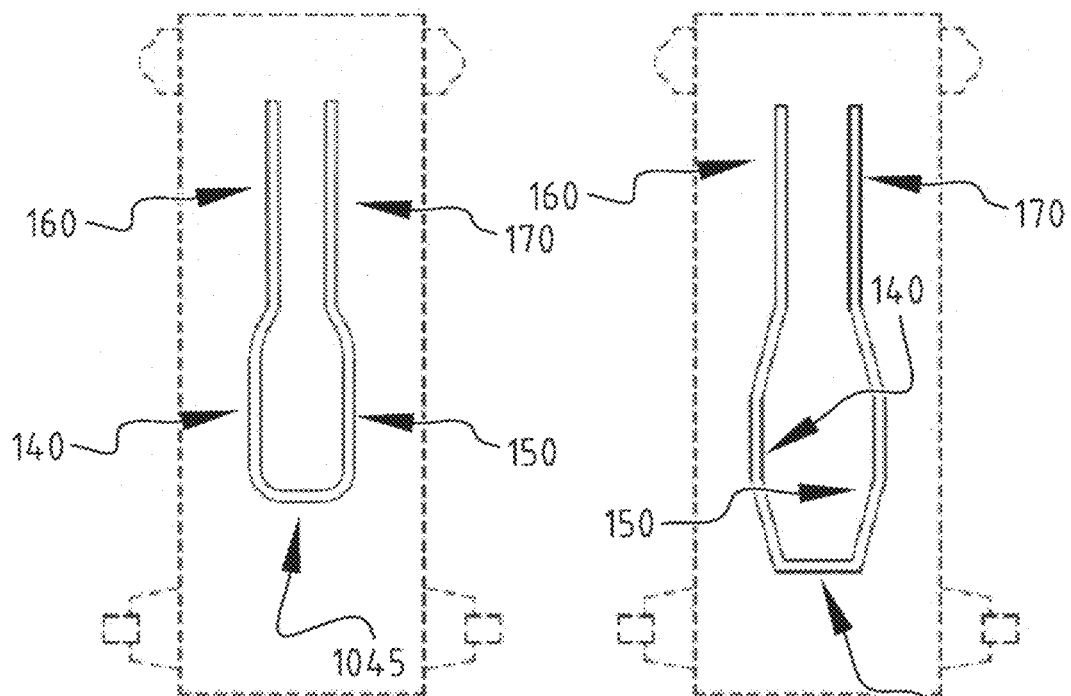
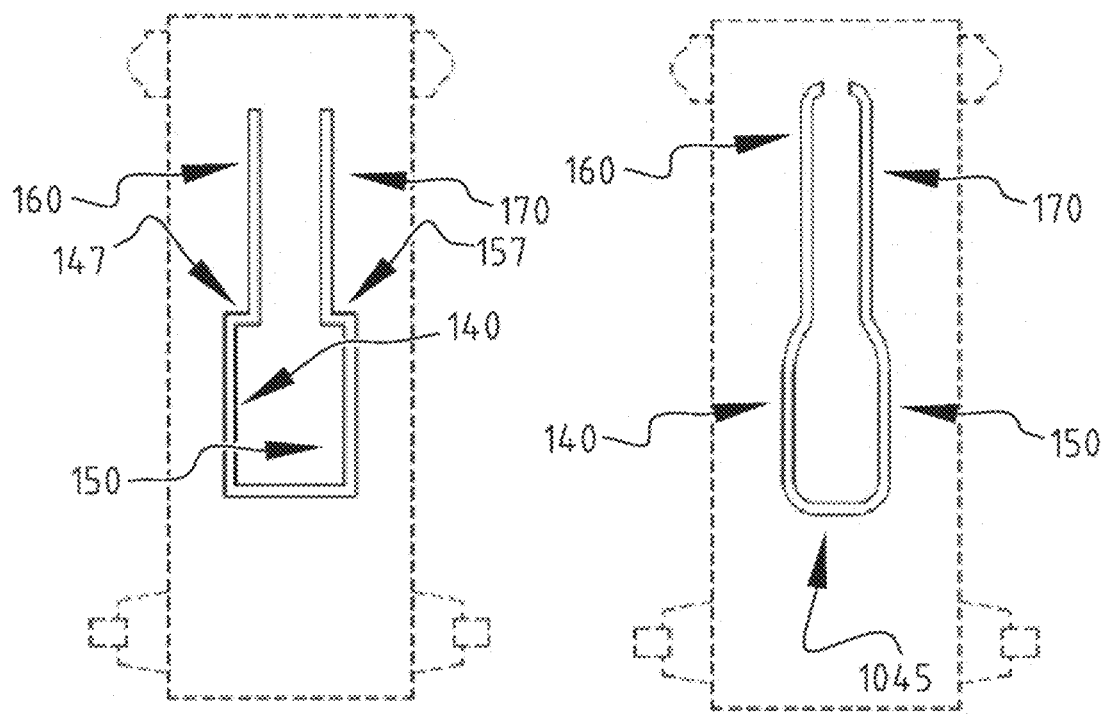

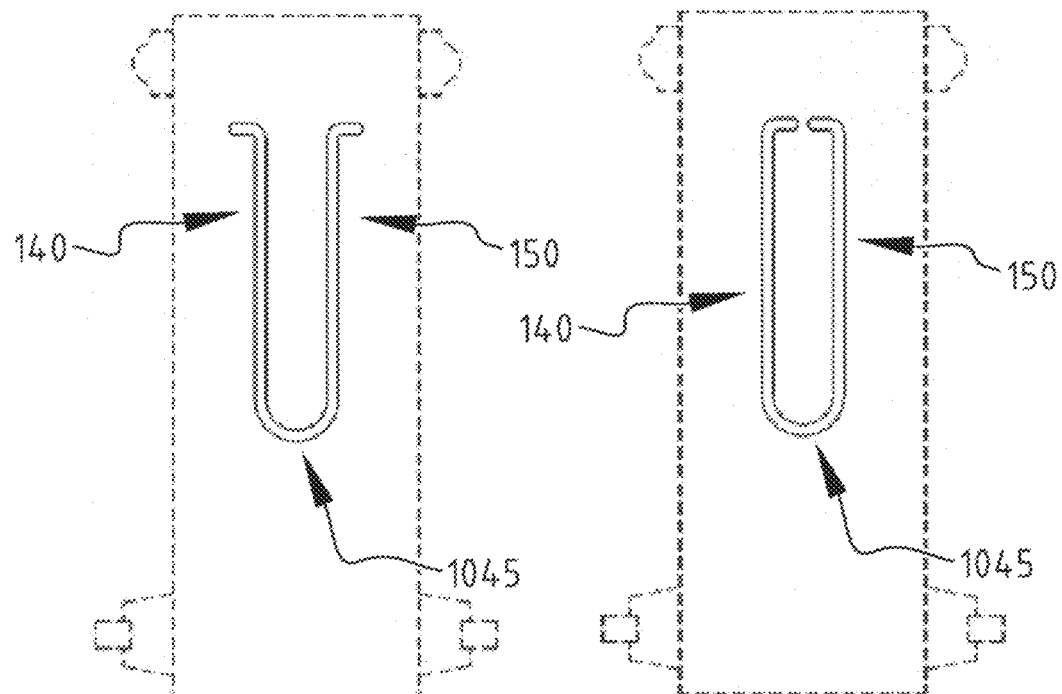
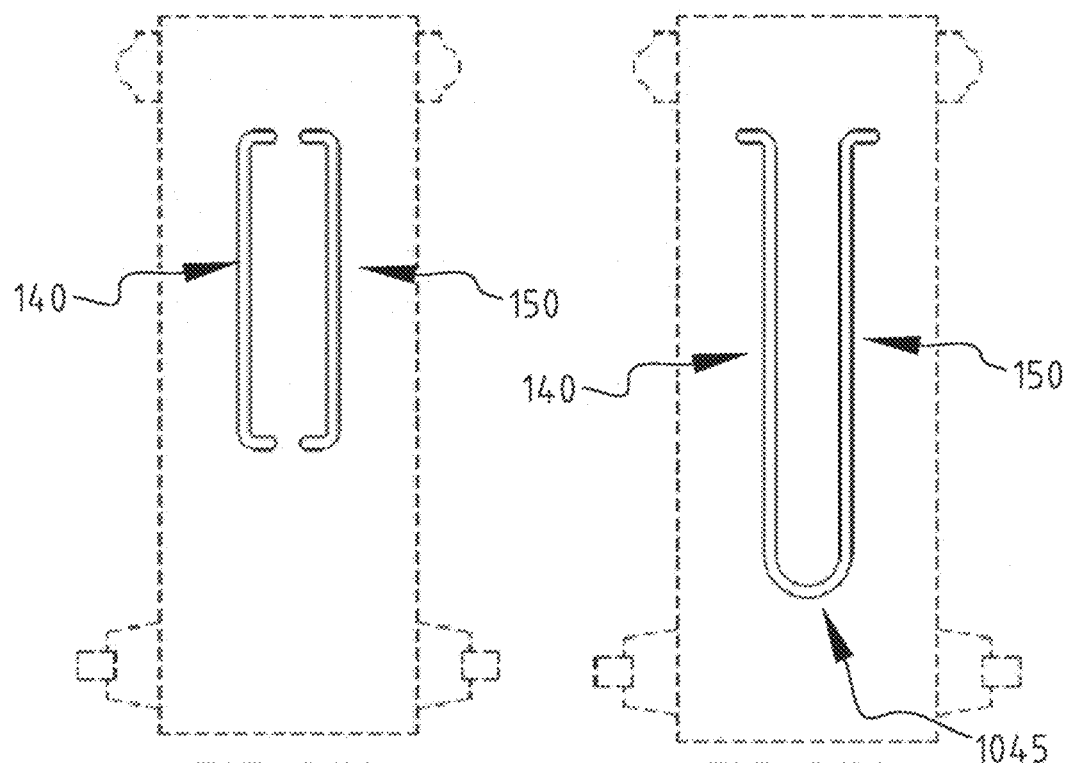

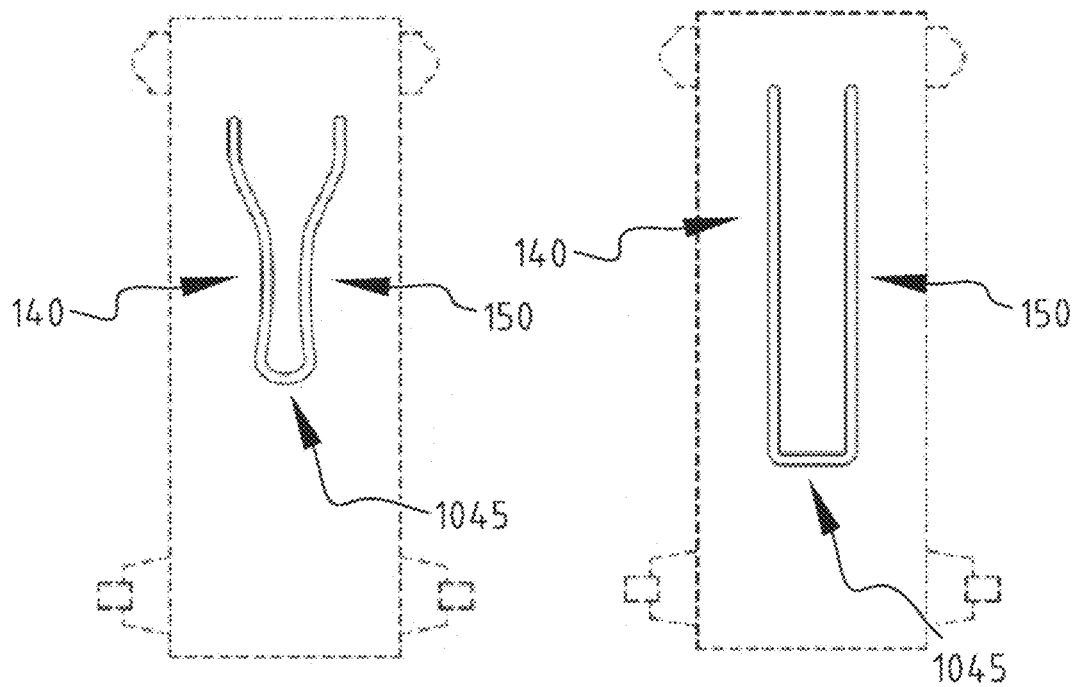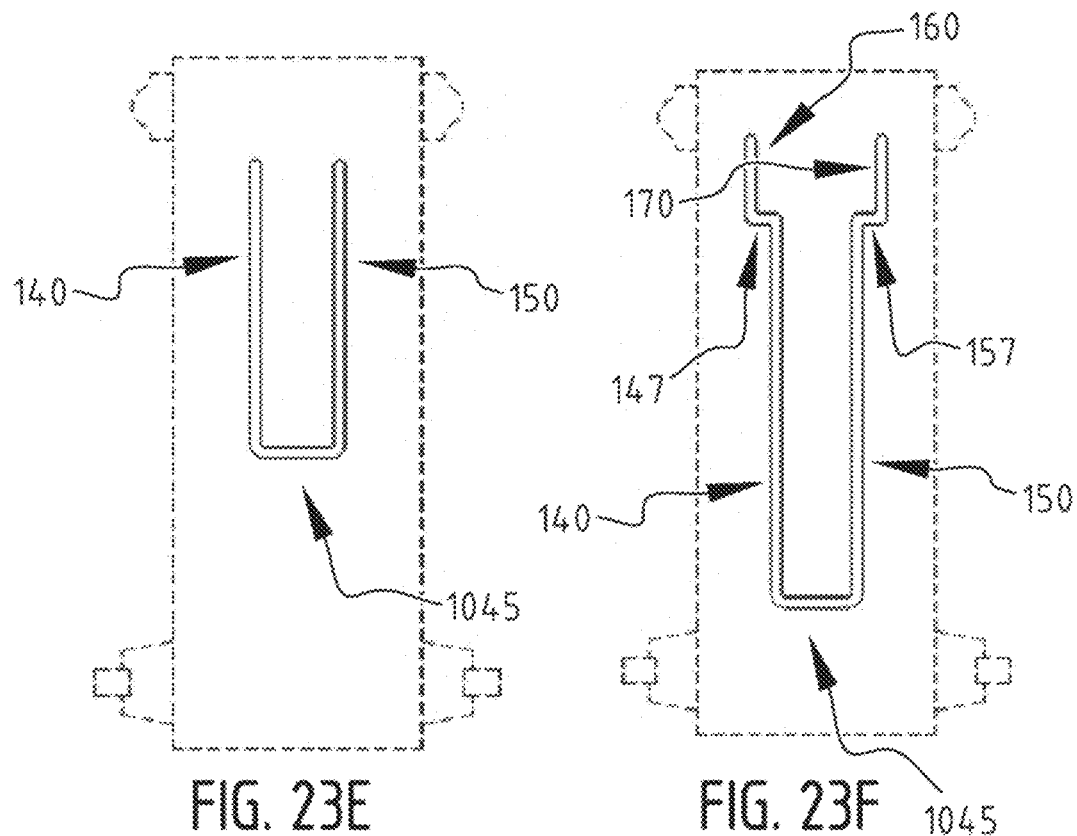

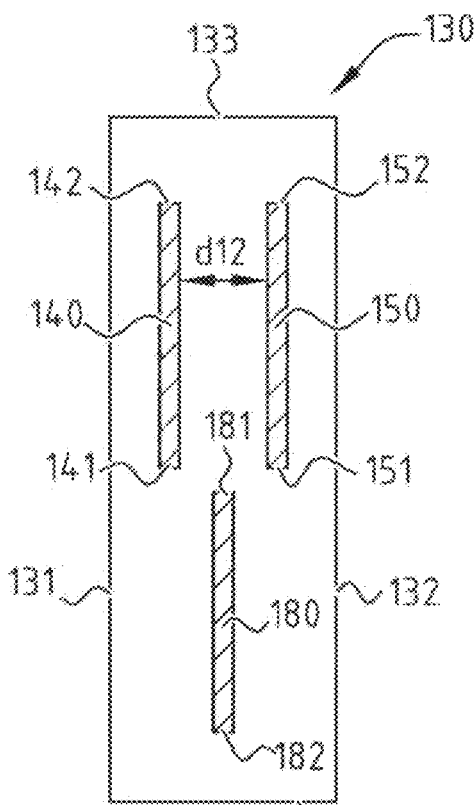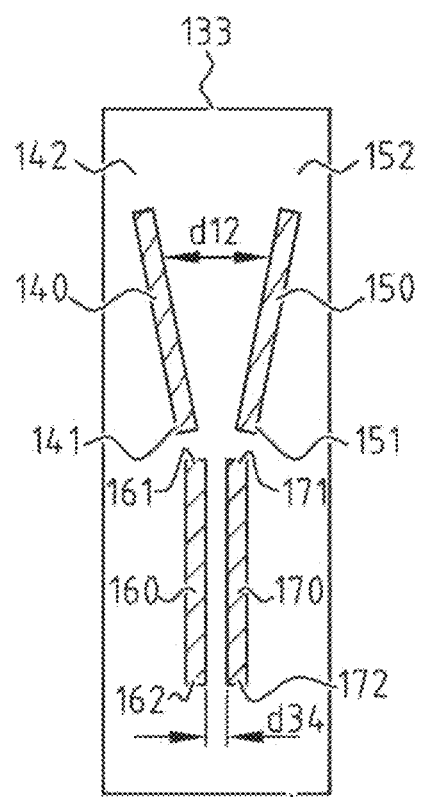
FIG. 28  FIG. 29
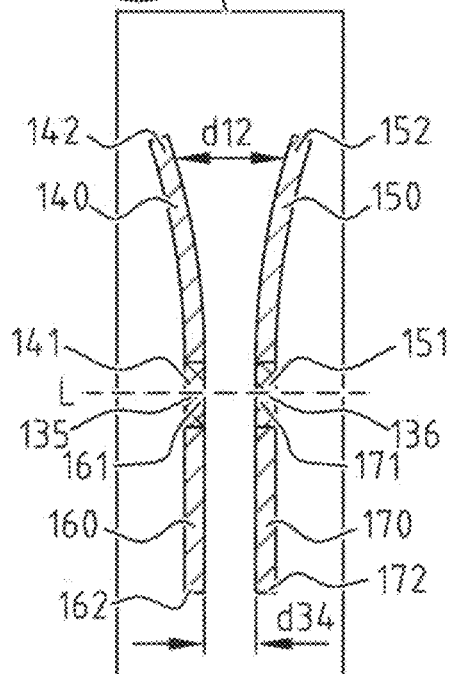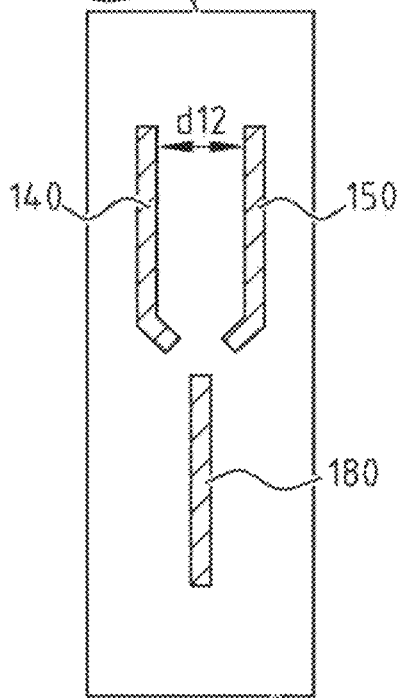
FIG. 30  FIG. 31

APPARATUS FOR MANUFACTURING AN ABSORBENT ARTICLE WITH CHANNELS

CLAIM FOR PRIORITY

This application is a continuation of and claims the benefit of priority of U.S. application Ser. No. 16/613,555, filed Nov. 14, 2019 now U.S. Pat. No. 11,331,228, which is a U.S. National Stage Filing under 35 U.S.C. 371 from International Application No. PCT/EP2018/062386, filed on May 14, 2018, and published as WO2018/210753 on Nov. 22, 2018, which claims the benefit of priority to European Application No. 17202006.7, filed on Nov. 16, 2017 and to European Application No. 17200847.6, filed on Nov. 9, 2017 and to European Application No. 17198652.4, filed on Oct. 26, 2017 and to European Application No. 17198368.7, filed on Oct. 25, 2017 and to European Application No. 17198349.7, filed on Oct. 25, 2017 and to European Application No. 17196434.9, filed on Oct. 13, 2017 and to European Application No. 17190395.8, filed on Sep. 11, 2017 and to European Application No. 17183453.4, filed on Jul. 27, 2017 and to European Application No. 17171110.4, filed on May 15, 2017; the benefit of priority of each of which is hereby claimed herein, and which applications and publication are hereby incorporated herein by reference in their entirety.

TECHNICAL FIELD

The present invention pertains to the technical field of absorbent articles, more preferably disposable personal care articles such as diapers, baby pants, adult incontinent garments, and the like, and to absorbent structures for use in such absorbent articles. More specifically the present invention relates to an absorbent structure comprising an absorbent core between a topsheet and a backsheet. The present invention also relates to a method and apparatus for manufacturing such an absorbent article.

BACKGROUND

Absorbent articles such as diapers, baby pants, adult incontinent garments and the like, typically comprise an absorbent core, positioned in between a liquid permeable or pervious, hydrophilic or semi hydrophilic topsheet and a liquid impermeable or impervious backsheet. The absorbent core comprises absorbent material that is able to absorb fluid and liquid bodily excretions of the user of the absorbent article.

The absorbent material of the absorbent core may be an absorbent particulate polymer material which is dispersed in a matrix of cellulose fibers or fluff pulp in order to prevent the particulate material from aggregating, as well as to prevent gel blocking. Gel blocking can occur when the absorbent particulate polymer material absorbs liquid, as they tend to typically swell and form a gel structure. This gel structure often blocks the further transfer of liquid into the remaining absorbent core. As a result, the liquid may be unable to reach the remaining absorbent particulate polymer material and the efficiency of the overall absorbent article decreases significantly. Existing fluff pulp materials are not suited to cope with rapid, subsequent insults of fluid since they possess limited distribution capacities. Moreover existing fluff pulp materials exhibit a limited capacity of overall liquid intake. Furthermore, existing absorbent cores containing fluff pulp have a limited wet integrity, which leads to the shape and fit of the absorbent article being deformed when e.g. an absorbent article is being worn by a baby which moves around.

In recent years, there has been a strong demand for more flexible, thinner, light-weight, absorbent articles to resolve various problems associated with manufacturing, marketing, design, fit, wearing comfort, distribution, garbage disposal, material and energy consumption, transport and storage costs and the like. This lead to the search for and the development and production of absorbent articles of which the absorbent cores contains little to no cellulose fibers or fluff pulp, as the latter tend to be quite bulky, thus rendering generally more thick absorbent cores which reduces the overall wearing comfort of the user of the absorbent article.

Hence, various absorbent cores containing little to no cellulose fibers or fluff pulp were developed in the past few years to try and overcome the above drawbacks, whereby the relative high amounts of absorbent polymer materials necessary to replace the absorption, distribution and retention capacity of the excluded cellulose fibers and/or fluff pulp were loaded, distributed and immobilized within these new absorbent cores according to several techniques. However given the ability and capacity of the absorbent core to absorb, transport and retain fluid and liquids is heavily dependent upon the form, position and/or manner wherein these absorbent polymer materials are incorporated within the absorbent core several drawback remained unsolved. In general the substantially heterogeneously distributed absorbent cores having non-continuous compartments and/or clusters of absorbent polymer material have in general proven to be better in coping with the above mentioned problems, nevertheless they also proved to remain unsatisfactory within most of the available absorbent articles. Especially problematic however, were the substantially homogenously distributed absorbent structures having continuous layers of absorbent polymer particulate material given they exhibit a substantially homogenous swollen absorbent polymer material area for second, third and next liquid insults wherein the dry and/or wetted absorbent polymer material layer may actually act as a liquid barrier. These problems and complications are especially prevalent within very flexible, thin, lightweight absorbent structures wherein high amounts of absorbent polymer material are distributed within the absorbent core of the absorbent article. Adding even more, thicker and larger overlying acquisition and dispersing layers did not at all resolve the above cited absorption, distribution and retention problems and moreover made the absorbent articles commercially unviable, environmentally unsustainable and more difficult to manufacture, store and transport.

Furthermore an existing problem which has been associated with such absorbent cores containing no or little cellulose fibers or fluff pulp is related to the migration, loss and leakage of the absorbent particulate polymer material from the absorbent article during dry and/or wet state, which leads to irritation, skin problems and overall discomfort for the user. This again is also especially true in the more homogenously distributed absorbent structures given their immobilization and liquid distribution properties remain unsatisfactory to date. This lack of effective and efficient immobilization and liquid distribution lead to dysfunctional absorbent articles due to lowered uptake capacity, gel blocking, enhanced rewet values, leakages and the creation of ruptures and/or pinholes through the liquid pervious topsheet and/or liquid impervious backsheet of such absorbent articles.

Absorbent cores generally have a high absorbent capacity and the absorbent core may expand several times its weight and volume. These increases may cause the absorbent article to deform and/or to sag in the crotch region as they become saturated with liquid. This may cause leaks to occur via a longitudinal and/or transversal edge of the absorbent article.

A further existing problem of absorbent articles is that an absorbent capacity of an absorbent core of the absorbent article is often not fully used when liquid insults are received by the absorbent core at regions which are close to an edge of the absorbent article and/or absorbent core. This might occur especially when a wearer of the absorbent article is lying down (sideways) and/or is moving frequently and/or intensively. This makes the absorbent articles prone to leakage.

SUMMARY

The object of embodiments of the invention is to provide an absorbent article of the type stated in the preamble, with improved liquid distribution and absorption capacities.

Aspects—Channel Width

According to an aspect of the invention there is provided an absorbent article comprising a liquid pervious topsheet, a liquid impervious backsheet, and an absorbent core comprising an absorbent material between a top core wrap sheet and a back core wrap sheet, said absorbent core being positioned in between said topsheet and said backsheet. The absorbent core has a first and second longitudinal edge and a first and second transverse edge. The absorbent core is provided with a plurality of attachment Zones comprising at least a first and a second attachment zone, said first and second attachment zone extending next to each other from a crotch region in the direction of the first and/or second transverse edge. In the first and second attachment zone any one of the following conditions is fulfilled: the top core wrap sheet is attached to said back core wrap sheet along an attachment which extends, seen in a transverse direction of the absorbent core, over a transverse distance which is at least 1 mm, preferably at least 2 mm, more preferably at least 3 mm, and most preferably at least 4 mm; the top core wrap sheet is attached to said back core wrap sheet along a discontinuous attachment at a plurality of locations at a distance of each other, seen in the transverse direction of the absorbent core, preferably over a transverse distance which is at least 1 mm, preferably at least 2 mm, more preferably at least 3 mm, and most preferably at least 4 mm. Upon wetting of the absorbent material of the absorbent article, any one of the above described conditions leads to the creation of a first and second channel at the first and second attachment zone, respectively.

Embodiments are based inter alia on the inventive insight that, by providing a plurality of attachment zones in the absorbent core, a corresponding plurality of channels is created in the absorbent core upon wetting such that liquid can be distributed and absorbed in an improved manner. Indeed, liquid can flow in the plurality of attachment zones and can be absorbed by the absorbent core through the side walls delimiting the plurality of attachment zones, in addition to liquid being absorbed through the top surface of the absorbent core. Because the first and second attachment zones extend in the direction of the first and/or second transverse edge as do the created first and second channel, liquid can be distributed adequately. Both the plurality of attachments zones, before swelling of the absorbent material, and the plurality of created channels, during and after swelling of the absorbent material, allow for a more rapid distribution of liquid, especially towards the transverse edges of the absorbent core. In addition to a fast and adequate distribution of liquid in the longitudinal direction, the presence of the plurality of attachment zones and/or the creation of the corresponding plurality of channels leads to a more rapid and efficient distribution of liquid in both the transverse direction of the absorbent core and in the depth direction of the absorbent core. Furthermore, overall liquid intake by the absorbent core is faster as a result. By giving the attachment zones a sufficient width, depth and/or length a quantity of liquid can be held temporarily whilst the absorption takes place. Because the liquid is distributed quickly, this effect is established not only during a first liquid insult, but also during an eventual second liquid insult, a third liquid insult and a fourth liquid insult. Further, the first and second attachment zones allow the absorbent core to swell in the shape of a tub while the first and second channels are formed. Indeed, a portion of the absorbent core between the first longitudinal edge and the first attachment zone will be allowed to rotate inward and upward and a portion of the absorbent core between the second longitudinal edge and the second attachment zone will be allowed to rotate inward and upward, which is made possible thanks to the sufficiently wide first and second attachment zone.

In a preferred embodiment, the first attachment zone and the attachment zone are substantially parallel and extend in a longitudinal direction of the absorbent core. In an alternative embodiment an angle between the first attachment zone and a longitudinal direction of the absorbent core and an angle between the second attachment zone and the longitudinal direction of the absorbent core is smaller than 5. In that manner appropriate first and second channels and an appropriate tub-shape of the absorbent product can be obtained upon wetting of the absorbent material.

In an exemplary embodiment, the attachment between the top core wrap sheet and the back core wrap sheet in the first and the second attachment zone is a permanent attachment, and the absorbent core is configured such that, in a wetted state of the absorbent material, the absorbent material extends over the first and second attachment zone. In that matter, the absorbent material bulges over the first and second attachment zone, thereby causing a tension in the absorbent core which causes the absorbent core, which is in a substantially flat state when dry, to curl up to form a tub shaped and/or cup shaped absorbent core including the first and second channel.

According to an aspect of the invention, there is provided an absorbent article comprising a liquid pervious topsheet, a liquid impervious backsheet, and an absorbent core comprising an absorbent material between a top core wrap sheet and a back core wrap sheet, said absorbent core being positioned in between said topsheet and said backsheet. The absorbent core has a first and second longitudinal edge and a first and second transverse edge. The absorbent core is provided with a plurality of attachment zones comprising at least a first and a second attachment zone, said first and second attachment zone each extending from a crotch region in the direction of the first and/or second transverse edge. Preferably, the first channel is arranged adjacent to the second channel, seen in a transverse direction of the absorbent core. In the first and second attachment zone the top core wrap sheet is attached to the back core wrap sheet through a semi-permanent attachment configured to release after having been in contact with liquid.

Embodiments are based inter alia on the inventive insight that, by providing a plurality of attachment zones in the absorbent core, in combination with semi-permanent attachments, the absorbent core can swell in an improved manner, resulting in an improved liquid absorption. Indeed, when liquid flows in the attachments zones, the attachments are released and the absorbent core can "fill" or "overlap" the attachment zones and/or channels, wherein a portion of the absorbent core between the first longitudinal edge and the first channel will be allowed to rotate inward and upward and a portion of the absorbent core between the second longitudinal edge and the second channel will be allowed to rotate inward and upward, which is made possible thanks to the first and second channel and the swelling underneath the released top core wrap sheet.

In an exemplary embodiment of the second aspect, the top core wrap sheet is attached to the back core wrap sheet along a continuous or discontinuous attachment which extends, seen in a transverse direction of the absorbent core, over a transverse distance which is at least 1 mm, preferably at least 2 mm, more preferably at least 3 mm, and most preferably at least 4 mm.

In an exemplary embodiment of the second aspect, the semi-permanent attachment is configured to release after having been in contact with urine for a period of time, e.g. a period of time is smaller than 30 s.

According to an aspect of the invention, there is provided an absorbent article comprising a liquid pervious topsheet, a liquid impervious backsheet, and an absorbent core comprising an absorbent material between a top core wrap sheet and a back core wrap sheet, the absorbent core being positioned in between said topsheet and said backsheet. The absorbent core has a first and second longitudinal edge and a first and second transverse edge. The absorbent core is provided with at least a first attachment zone. In the first attachment zone any one of the following conditions is fulfilled: the top core wrap sheet is attached to the back core wrap sheet along an attachment which extends, seen in a transverse and/or longitudinal direction of the absorbent core, over a transverse and/or longitudinal distance which is at least 1 mm, preferably at least 2 mm, more preferably at least 3 mm, most preferably at least 4 mm; the top core wrap sheet is attached to the back core wrap sheet along a discontinuous attachment at a plurality of locations at a distance of each other, seen in the transverse and/or longitudinal direction of the absorbent core. Upon wetting of the absorbent material, a first channel is created at said first attachment zone.

According to an exemplary embodiment, the first attachment zone extends from a crotch region in the direction of the first and/or second transverse edge.

According to an alternative embodiment, the first attachment zone extends in the transversal direction of the absorbent core in between the first and second longitudinal edge.

According to a preferred embodiment of the fourth aspect, the absorbent core is provided with at least a second attachment zone. The at least one second attachment zone extends in the transversal direction of the absorbent core in between the first and second longitudinal edge.

According to a preferred embodiment the plurality of attachment zones further comprises a third and a fourth attachment zone located at a distance of each other, the third and fourth attachment zone each extending in the direction of the first and/or second transverse edge.

Preferably, the distance between the first and the second attachment zone is different from the distance between the third and the fourth attachment zone.

According to an exemplary embodiment, the absorbent core has a front portion extending at one side of a transverse crotch line and a rear portion extending at the other side of the transverse crotch line. The first and second attachment zone extend at least in the front portion of the absorbent core; and the third and fourth attachment zone extend at least in the rear portion of the absorbent core.

The distance between the first and the second attachment zone may be smaller or bigger than the distance between the third and the fourth attachment zone.

In a preferred embodiment, the first attachment zone is connected to the third attachment zone through a first transverse attachment zone, and the second attachment zone is connected to the fourth attachment zone through a second transverse attachment zone.

In a possible embodiment, the first and the second attachment zone extend in a longitudinal direction of the absorbent core over a length which is longer than the length of the third and fourth attachment zone, and the first and the second attachment zone are located between the third and fourth attachment zone.

In an exemplary embodiment, the third attachment zone and the fourth attachment zone are arranged symmetrically with respect to a longitudinal center line of the absorbent core extending between the first and second transverse edge.

In a preferred embodiment the distance between the first and the second attachment zone is between 10 mm and 50 mm, preferably between 15 mm and 30 mm.

According to an exemplary embodiment, the length of the first and the second attachment zone is larger than 60 mm, preferably larger than 70 mm.

According to an exemplary embodiment, the absorbent article further comprises at least one transversal attachment zone extending from an end portion of the first attachment zone to a corresponding end portion of the second attachment zone, wherein upon wetting of the absorbent material, a third channel is created at said transversal attachment zone, thus connecting the first and second channels.

The skilled person will understand that the hereinabove described technical considerations and advantages for absorbent article embodiments also apply to the below described method embodiments, mutatis mutandis.

According to a fifth aspect, there is provided a method for manufacturing an absorbent article, said method comprising the steps of:

guiding a first sheet material along a rotating member, wherein a surface of said rotating member is provided with a pattern with suction zones and non-suction zones; wherein said non-suction zones comprise at least a first and a second elongate zone extending in a circumferential direction of the rotating member;

applying an absorbent material on said first sheet material on the rotating member such that the suction zones are covered with absorbent material and substantially no absorbent material is present on the non-suction zones;

applying a second sheet material on top of the absorbent material on the first sheet material; wherein one of said first and second sheet material is a top core wrap sheet material, and the other one is a back core wrap sheet material;

attaching said first sheet material to said second sheet material at least in the areas where substantially no absorbent material is present, and such that at least a first and a second attachment zone are formed.

In a preferred embodiment, the attaching is done by applying pressure and heat on the top core wrap sheet material and/or the back core wrap sheet material in the areas where substantially no absorbent material is present.

According to a further embodiment, the attaching is done by a rotating member which is provided with at least a first and a second seal rib dimensioned for applying pressure and heat on the top core wrap sheet material and/or the back core wrap sheet material in the areas where substantially no absorbent material is present in order to create the first and second attachment zone, respectively.

In a preferred embodiment, a binder is applied to at least one portion of the first sheet material at a distance from the intended position of the first and second attachment zones, before the absorbent material is applied on said first sheet material and a binder is applied to at least one portion of the second sheet material before it is applied on top of the absorbent material on the first sheet material. Preferably, the at least one portion of the first sheet material and the at least one portion of the second sheet material are chosen such that in the application and attachment of the first sheet material to the second sheet material the plurality of portions are complementary, wherein preferably substantially the entire surface of the absorbent article is provided with binder on either the first sheet material or the second sheet material.

According to a further aspect there is provided a method for manufacturing an absorbent article, said method comprising:
  a. guiding a first sheet material along a conveying or rotating member, wherein a surface of said conveying member is provided with a pattern with at least one suction zone and non-suction zone; wherein said at least one non-suction zone comprises at least a first zone extending in a conveying direction of the conveying member;
  b. applying an absorbent material on said first sheet material on the rotating member such that the at least one suction zone is covered with absorbent material and substantially no absorbent material is present on the at least one non-suction zone;
  c. applying a second sheet material on top of the absorbent material on the first sheet material; wherein one of said first and second sheet material is a top core wrap sheet material, and the other one is a back core wrap sheet material;
  d. attaching said first sheet material to said second sheet material at least in the areas where substantially no absorbent material is present, and such that at least at least a first attachment zone is formed.

The attaching may be done by applying pressure and heat on the top core wrap sheet material and/or the back core wrap sheet material in the areas where substantially no absorbent material is present.

The attaching may be done by a rotating member which is provided with at least a first seal rib dimensioned for applying pressure and heat on the top core wrap sheet material and/or the back core wrap sheet material in the areas where substantially no absorbent material is present in order to create the first attachment zone.

A first binder may be applied to at least one portion of the first sheet material at a distance from the intended position of the first attachment zone, prior to step b, and a second binder may be applied to at least one portion of the second sheet material prior to step c. Preferably, the at least one portion of the first sheet material and the at least one portion of the second sheet material are chosen such that in the application and attachment of the first sheet material to the second sheet material the plurality of portions are complementary, wherein preferably substantially the entire surface of the absorbent article is provided with binder on either the first sheet material or the second sheet material.

The first binder applied on at least one portion of the first sheet material may be different from, preferably less strong than, the second binder applied on the at least one portion of the second sheet material.

The binder may be applied on at least one portion of the first sheet material as a first layer having a first thickness, and on the at least one portion of the second sheet material as a second layer having a second thickness which is different from, preferably higher than, the first thickness.

The binder may be applied on the first sheet material as a plurality of parallel first longitudinal stripes and on the second sheet material as a plurality of parallel second longitudinal stripes, wherein preferably a second longitudinal stripe thereof is located in between two first longitudinal stripes of the plurality of first longitudinal stripes.

Aspect—Color

According to an aspect of the invention, there is provided an absorbent article comprising a liquid pervious topsheet, a liquid impervious backsheet, and an absorbent core comprising an absorbent material between a top core wrap sheet and a back core wrap sheet, said absorbent core being positioned in between said topsheet and said backsheet. The absorbent core has a first and second longitudinal edge and a first and second transverse edge. The absorbent core is provided with a plurality of attachment zones comprising at least a first and a second attachment zone located a distance of each other, said first and second attachment zone each extending from a crotch region in the direction of the first and/or second transverse edge. A position and/or shape of one or more attachment zones of the plurality of attachment zone is indicated by means of a distinguishable color and/or colored pattern.

Such embodiments have the advantage that, on the one hand the attachment zones result in an improved liquid distribution and absorption of the liquid, and on the other hand, the color and/or pattern allows a user to easily distinguish a front and a rear portion of the absorbent article. Indeed, by giving e.g. the first attachment zone a color and/or pattern which is different from the color and/or pattern of the second attachment zone, a user can remember easily e.g. which color has to be on the left or right side. The person skilled in the art understands that many color and/or pattern variants are possible which will allow a user to easily recognize a front and a rear portion. In addition to or alternative to allow a user to easily recognize the correct orientation of the absorbent article, the color and/or pattern which indicate the position and/or shape of the attachment zones may be utilized to provide more information to a user about the absorbent article by linking a particular color and/or pattern of the visual indication to a certain characteristic of the absorbent article such as size, type (e.g. diaper versus pants), etc.

In a preferred embodiment, the position of one or more of the plurality of attachment zones is indicated by means of a printed ink layer.

In exemplary embodiments the distinguishable color and/or colored pattern is provided on at least one of the topsheet, the top core wrap sheet, the backsheet and the back core wrap sheet. The color and/or colored pattern may be provided on either side of the topsheet, the top core wrap sheet, the backsheet and/or the back core wrap sheet. In addition or alternatively, the color and/or colored pattern is provided on an acquisition and/or a distribution layer of the absorbent article.

Features of the "channel width" aspects may be combined with the features of the "color" aspect.

Aspects—Local Removing

According to an aspect of the invention there is provided a method for manufacturing an absorbent article, said method comprising:
a. guiding a first sheet material along a rotating member, wherein a surface of said rotating member is provided with a pattern with at least one suction zone and at least one non-suction zone;
b. applying an absorbent material on said first sheet material on the rotating member;
c. locally removing the absorbent material applied on at least one attachment portion of the first sheet material located above the at least one non-suction zone, such that at least one remaining portion of the first sheet material located above the at least one suction zone is covered with absorbent material and substantially no absorbent material is present on the at least one attachment portion;
d. applying a second sheet material on top of the absorbent material on the first sheet material; wherein one of said first and second sheet material is a top core wrap sheet material, and the other one is a back core wrap sheet material;
e. attaching said first sheet material to said second sheet material at least in the at least one attachment portion, and such that at least one attachment zone is formed.

By locally removing the absorbent material on the at least one attachment portion it is ensured that the at least one attachment portion is substantially free of absorbent material which will result in a better attachment of the second sheet material to the first sheet material in the at least one attachment zone.

The at least one non-suction zone may comprise at least one elongate zone extending in a circumferential direction of the rotating member. In that manner an elongate attachment zone is created allowing realizing elongate channels in the absorbent article.

The at least one non-suction zone may be formed by at least one element protruding outwardly from the surface of the rotating member. In other words the at least one suction zone may be delimited by an outwardly protruding non-suction element. In that manner the areas containing absorbent material and the areas containing substantially no absorbent material may be neatly delimited. For example, the at least one outwardly protruding element may be at least one elongated element, more preferably a curved elongate element fixed to the outer surface of the rotating member. Preferably the at least one element is removable. In that manner, depending on the amount and/or the type of absorbent material and/or sheet material that is used, a suitably dimensioned element may be chosen.

The locally removing of the absorbent material may be done by mechanical means. In that manner a robust and simple means may be used to obtain an accurate cleaning of the at least one attachment portion. The mechanical means may be a rotatable mechanical means or a non-rotatable mechanical means.

The locally removing of the absorbent material may be done by a first brush, e.g. a first roller brush. In other embodiments a scraper of a wiper may be used with a scraping blade or a wiper blade, optionally in combination with a removal means. e.g. a suction means to remove the locally removed absorbent material.

In addition or alternatively the locally removing of the absorbent material may be done by causing an air flow above the at least one attachment portion, e.g. using an air jet system.

The method may further comprise scraping the absorbent material applied on the at least one remaining portion by a second roller brush, such that surface of the absorbent material is substantially even. This second roller brush will be different from the first roller brush. Preferably the bristles of the second roller brush will be less flexible than the bristles of the first roller brush.

For example, the bristles of the second roller brush may be made of metal, whilst the bristles of the first roller brush may be made of a flexible plastic such as nylon.

The method further may comprise discarding and/or collecting and/or recycling of the absorbent material removed from the at least one attachment portion.

A binder may be applied to at least one portion of the first sheet material at a distance from the intended position of the first attachment zone, prior to step b, and/or wherein a binder may be applied to at least one portion of the second sheet material including the intended position of the at least one attachment zone prior to step d. In that manner the fixation of the absorbent material to the first sheet material in the at least one suction zone may be further improved.

The at least one portion of the first sheet material and the at least one portion of the second sheet material may be chosen such that in the application and attachment of the first sheet material to the second sheet material the plurality of portions are complementary, wherein preferably substantially the entire surface of the absorbent article is provided with binder on either the first sheet material or the second sheet material.

The binder applied on at least one portion of the first sheet material may be different from, preferably less strong than, the binder applied on the at least one portion of the second sheet material.

The binder may be applied on at least one portion of the first sheet material as a first layer having a first thickness, and on the at least one portion of the second sheet material as a second layer having a second thickness which is different from, preferably higher than, the first thickness.

The binder may be applied on the first sheet material as a plurality of parallel first longitudinal stripes and on the second sheet material as at least one second longitudinal stripe located in between two first longitudinal stripes of the plurality of first longitudinal stripes.

The attaching may be done by applying pressure and/or heat on the top core wrap sheet material and/or the back core wrap sheet material in the at least one attachment portion.

The attaching may be done by a rotating member which is provided with at least one seal rib dimensioned for applying pressure and heat on the top core wrap sheet material and/or the back core wrap sheet material in the at least one attachment portion in order to create the at least one attachment zone. This may be a seal rib having a substantially continuous sealing surface or a seal rib provided with a pattern of sealing element. In that manner the realized attachment zone may comprise a continuous attachment zone or may comprise a series of adjacent attachment areas.

According to a further aspect there is provided an apparatus for manufacturing an absorbent article, said apparatus comprising:
a. a rotating member (10) for guiding a first sheet material along a surface thereof, wherein the surface of said rotating member is provided with at least one suction zone and at least one non-suction zone;
b. an application unit configured for applying an absorbent material on said first sheet material on the rotating member;

c. a removing unit configured for locally removing the absorbent material applied on at least one attachment portion of the first sheet material located above the at least one non-suction zone, such that at least one remaining portion of the first sheet material located above the at least one suction zone is covered with absorbent material and substantially no absorbent material is present on the at least one attachment portion;

d. a sheet feed unit configured for applying a second sheet material on top of the absorbent material on the first sheet material; wherein one of said first and second sheet material is a top core wrap sheet material, and the other one is a back core wrap sheet material;

e. an attachment unit configured for attaching said first sheet material to said second sheet material at least in the at least one attachment portion.

The technical features and advantages explained above for the method apply mutatis mutandis for the apparatus.

Preferably, the at least one non-suction zone may be provided with at least one removable insert (forming the above stated protruding element). Even more preferably the at least one insert has a substantially trapezoidal cross section having a bottom edge, a top edge and two side edges leading from the bottom edge to a top edge, wherein the top edge and the bottom edge are perpendicular on the transport direction of the first sheet material in the apparatus, the bottom edge is fixed to the rotating member, and the side edges delimit the suction zones. Preferably the side edges converge towards each other in the direction from the bottom edge to the top edge.

The removing unit may comprise a mechanical removal means configured for removing the absorbent material applied on the at least one non-suction zone of said first sheet material. In that manner a robust and simple means may be used to obtain an accurate cleaning of the at least one attachment portion. The mechanical means may be a rotatable mechanical means or a non-rotatable mechanical means.

The mechanical means may comprise a first brush, e.g. a first roller brush. The first roller brush may have bristles comprising a flexible plastic material, such as nylon. An axis of the first roller brush may be parallel to an axis of the rotating member.

The removing unit may comprise a first adjusting means configured for adjusting a distance between the mechanical removal means (e.g. the first roller brush) and rotating member. The removing unit may comprise a first variable-speed motor configured for driving the mechanical removal means, such as the first roller brush.

The removing unit may comprise an air jet system configured for removing the absorbent material applied on the first sheet material above the at least one non-suction zone.

The apparatus may further comprises a second roller brush configured for scraping the absorbent material applied on the at least one suction zone such that surface of the absorbent material is substantially even. The bristles of the second roller brush may be less flexible than the bristles of the first roller brush. The bristles of the second roller brush may comprise metal material. An axis of the second roller brush may be parallel to the axis of the rotating member.

The apparatus may further comprise a discharge means configured for discarding and/or collecting and/or recycling of the removed absorbent material. The discharge means may comprise a vacuum source.

The attaching unit may be a rotating member which is provided with at least one seal rib dimensioned for applying pressure and/or heat on the top core wrap sheet material and/or the back core wrap sheet material in the at least one attachment portion in order to create the at least one attachment zone.

The apparatus may further comprise first means to apply binder to at least one portion of the first sheet material at a distance from the first zone before the application unit applies absorbent material, and further comprise second means to apply binder to at least one portion of the second sheet material including the intended position of the at least one attachment zone before the sheet feed unit applies this second sheet material on top of the absorbent material on the first sheet material.

The first means may be configured to apply a first binder on the first sheet material as a plurality of parallel first longitudinal stripes and the second means may be configured to apply a second binder on the second sheet material as at least one second longitudinal stripe located in between two first longitudinal stripes of the plurality of first longitudinal stripes.

The first means may be configured to apply a first binder and the second means may be configured to apply a second binder which is different from the first binder.

Aspect—Binder

According to another aspect of the invention there is provided an absorbent article comprising a liquid pervious topsheet, a liquid impervious backsheet, and an absorbent core comprising an absorbent material between a top core wrap sheet and a back core wrap sheet, said absorbent core being positioned in between said topsheet and said backsheet. The absorbent core has a first and second longitudinal edge and a first and second transverse edge. The absorbent core is provided with a plurality of attachment zones comprising at least a first and a second attachment zone, said first and second attachment zone extending next to each other from a crotch region in the direction of the first and/or second transverse edge. A first binder is arranged in a first area between the top core wrap sheet and the back core wrap sheet at a distance from the first and second attachment zone, and a second binder is arranged in a second area between the top core wrap sheet and the back core wrap sheet. Preferably, the first area is substantially complementary to the second area. Preferably, the second area includes the first and second attachment zone.

According to yet another aspect of the invention there is provided an absorbent article comprising a liquid pervious topsheet, a liquid impervious backsheet, and an absorbent core comprising an absorbent material between a top core wrap sheet and a back core wrap sheet, said absorbent core being positioned in between said topsheet and said backsheet. The absorbent core has a first and second longitudinal edge and a first and second transverse edge. The absorbent core is provided with at least a first attachment zone extending from a crotch region in the direction of the first and/or second transverse edge. A first binder is arranged in a first area between the top core wrap sheet and the back core wrap sheet at a distance from the first attachment zone, and a second binder is arranged in a second area between the top core wrap sheet and the back core wrap sheet. Preferably, the first area is substantially complementary to the second area. Preferably, the second area includes the first and second attachment zone.

According to an exemplary embodiment the first binder is different from the second binder.

According to another exemplary embodiment the first binder is the same as the second binder, and a transition zone is distinguishable between the first area and the second area.

According to an exemplary embodiment the first binder is arranged as a layer having a first thickness and the second binder is arranged as a layer having a second thickness which is different from the first thickness, preferably higher than the first thickness.

According to an exemplary embodiment the first area comprises a plurality of longitudinal stripes, and/or the second area comprises a plurality of longitudinal stripes.

According to an embodiment, a first binder is applied to at least one portion of the back core wrap sheet at a distance from the intended position of the first and/or second attachment zones before the absorbent material is applied, and a second binder is applied to at least one portion of the top core wrap sheet before it is applied on top of the absorbent material on the back core wrap sheet.

According to an alternative embodiment, a first binder is applied to at least one portion of the top core wrap sheet at a distance from the intended position of the first and/or second attachment zones before the absorbent material is applied, and a second binder is applied to at least one portion of the back core wrap sheet before it is applied on top of the absorbent material on the back core wrap sheet. Preferably, the at least one portion of the top core wrap sheet and the at least one portion of the back core wrap sheet are chosen such that in the application and attachment of the top core wrap sheet to the back core wrap sheet the plurality of portions are complementary, wherein preferably substantially the entire surface of the absorbent article is provided with binder on either the top core wrap sheet or the back core wrap sheet. According to an embodiment the first and second binder are the same binder. In alternative embodiments, the first and second binder are mutually different binders, such as different glues. It is clear to the skilled person that the first and second binder may be applied in either layers with the same thickness, or layers with a different thickness.

The skilled person understands that an absorbent article as described above, more in particular in view of the application of binder, can be distinguished from absorbent articles which are manufactured otherwise. More in particular, the above described application of binder, such as glue, is distinguishable in an absorbent article by examining the present bonds within the particular absorbent article by means of any one of the following: color analysis, UV analysis, chemical analysis, and the like. In other words, by examining the absorbent article, the skilled person can determine which type of binder has been used, where the particular binder has been applied, how many layers of binder have been applied, etc.

Aspects—Bridging Zone

According to an aspect of the invention there is provided an absorbent article comprising a liquid pervious topsheet, a liquid impervious backsheet, and an absorbent core comprising an absorbent material between a top core wrap sheet and a back core wrap sheet, said absorbent core being positioned in between said topsheet and said backsheet. The absorbent core has a first and second longitudinal edge and a first and second transverse edge, wherein the absorbent core is provided with a plurality of attachment zones comprising at least one front attachment zone and at least one rear attachment zone and with at least one bridging zone extending at least partially between said front and rear attachment zone. The at least one front attachment zone and at least one rear attachment zone, when projected on a longitudinal direction of the absorbent core, do not overlap or overlap only partially and the bridging zone extends from a first longitudinal portion of the absorbent core to a second longitudinal portion of the absorbent core, wherein the first longitudinal portion is defined between the first longitudinal edge and a longitudinal center axis of the absorbent core and the second longitudinal portion is defined between the second longitudinal edge and the longitudinal center axis of the absorbent core, such that upon wetting of the absorbent material, a front and rear channel are created at said front and rear attachment zone, respectively, wherein the bridging zone allows a liquid flow between the first longitudinal portion and the second longitudinal portion.

Embodiments are based inter alia on the inventive insight that, by providing a plurality of attachment zones in the absorbent core, a corresponding plurality of channels is created in the absorbent core upon wetting such that liquid can be distributed and absorbed in an improved manner. Indeed, liquid can flow in the plurality of attachment zones and can be absorbed by the absorbent core through the side walls of the plurality of attachment zones, in addition to liquid being absorbed through the top surface of the absorbent core. Both the at least one front and at least one rear attachments zones, before swelling of the absorbent material, and the plurality of created channels, during and after swelling of the absorbent material, allow for a more rapid distribution of liquid, especially towards the transverse edges of the absorbent core. In addition to a fast and adequate distribution of liquid in the longitudinal direction by providing at least one front and one rear attachment zone, the presence of the plurality of attachment zones and/or the creation of the corresponding plurality of channels leads to a more rapid and efficient distribution of liquid in the depth direction of the absorbent core. Further in addition, by providing at least one bridging zone which extends at least partially between the front and rear attachment zone, liquid distribution in the transverse direction is enabled and/or improved such that liquid is able to "cross" the attachments zones and/or resulting channels to flow from the first longitudinal portion and the second longitudinal portion. This may be particularly useful in situations wherein liquid insults are received at a longitudinal portion, e.g. near one of the longitudinal edges. In such situations, provided attachments zones may block liquid from flowing transversally through the absorbent core, which leads to only a longitudinal portion of the absorbent core being used to absorb the liquid, which may cause leakage since the amount of absorbent material within said one longitudinal portion is limited. However, by providing a bridging zone between a front an rear attachment zone, interconnecting two longitudinal portions of the absorbent core, liquid is enabled to flow from one longitudinal portion through the bridging zone, to a neighboring longitudinal portion. In this manner, liquid can reach the absorbent material within the neighboring longitudinal portion and may be absorbed there. In other words, by providing at least one bridging zone an available liquid absorbing capacity is increased, especially in the transverse direction of the absorbent core. Furthermore, overall liquid intake by the absorbent core is faster as a result. Also, the use of at least one bridging zone can improve the structure and integrity of the absorbent article. For example, the use of at least one bridging zone may improve the formation of a tub-shape upon wetting of the absorbent article.

According to an embodiment the bridging zone allows a liquid flow between the first longitudinal portion and the second longitudinal portion by capillary action. In this manner, liquid can flow through the absorbent material of the bridging zone without being obstructed and move between and/or beyond and/or throughout the front and/or rear attachment zone(s). By providing at least one front attachment zone and at least one rear attachment as defined above channels are created when the absorbent core is wetted. By providing a bridging zone, e.g. a capillary bridging zone, between the front and rear attachment zone, liquid taken up in absorbent material near a first side edge may migrate by capillary action in the direction of a second side edge. In other words, the liquid is on the one hand distributed by the channels and on the other hand allowed to migrate through the absorbent material from one side edge to the other side edge. This is advantageous, especially when a person wearing the absorbent article is lying down sideways. Indeed, when lying down the liquid may e.g. flow towards one side edge by gravity. This will cause a swelling of the absorbent material near that side edge, and the capillary bridge will allow the liquid to migrate towards the other side edge, in a transverse direction of the absorbent core, independently of the orientation of the absorbent article. The bridging zone enables liquid flow opposite to the forces of gravity, when a wearer of the absorbent article is lying down sideways. The presence of the bridging zone will prevent that liquid flow from one longitudinal portion to another longitudinal portion is blocked by attachments zones and/or channels positioned between and/or in the longitudinal portions. On the other hand the channels will be able to provide for a fast liquid distribution in a longitudinal direction of the absorbent core.

Preferably, the capillary bridging zone extends between the first front attachment zone and the first rear attachment zone, such that upon wetting of the absorbent material, a front and rear channel are created at said first front and rear attachment zone, respectively, wherein the capillary bridging zone extends between said front and rear channel. In that manner, after channel formation upon wetting, liquid can still flow, e.g. by capillary action, between the first rear and front attachment zone. It is noted that the capillary bridging zone may comprise temporary or semi-permanent attachment zones which loosen upon wetting, whilst the first front attachment zone and the first rear attachment zone remain attached upon wetting. Preferably, a minimum distance between the first front attachment zone and the first rear attachment zone is preferably larger than 3 mm, more preferably larger than 5 mm, even more preferably larger than 8 mm. In that way a sufficient flow can be guaranteed. This minimum distance (which is related to the capillary flow) may be varied depending on the size of the absorbent article.

According to an embodiment the bridging zone allows a liquid flow between the first longitudinal portion and the second longitudinal portion by mass flow. In this manner, liquid can benefit from channels formed by permanent and/or semi-permanent attachment zones to flow through the bridging zone and to move between and/or beyond and/or throughout the front and/or rear attachment zone(s).

According to a further embodiment, absorption capacity of the absorbent core may benefit from both capillary action and mass flow of liquid in order to enable liquid to be distributed quickly and adequately, for example when the bridging zone comprises one or more semi-permanent attachments. In reaction to a first liquid insult the liquid will be distributed by mass flow by means of the channel(s) formed at the semi-permanent attachment(s). However, in reaction to further liquid insults, the semi-permanent attachment(s) will release, loosen and/or dissolve which will lead to the bridging zone allowing the liquid to pass through by capillary action. In other words, the bridging zone may comprise a (semi-)permanent attachment in a first stage of wetting, and may comprise substantially no attachments in a further stage of wetting.

According to an embodiment, the at least one bridging zone is substantially free of attachments. In this manner, the bridging zone is formed in both a dry and a wet state of the absorbent core. No obstructions are present within the bridging zone such that liquid can flow or travel via the bridging zone from one longitudinal portion to a neighboring longitudinal portion.

According to an embodiment the at least one bridging zone comprises at least one semi-permanent attachment. In this manner, the bridging zone comprises one or more attachments in a dry state of the absorbent core. This may allow liquid to be distributed via corresponding channels formed at the one or more attachments, during a first liquid insult. In other words, liquid may flow through the bridging zone by mass flow. However, the bridging zone is transformed in a wet state of the absorbent core when the semi-permanent attachments are loosened because of the swelling of nearby absorbent material. When liquid is absorbed by the absorbent core in proximity of the semi-permanent attachments, the semi-permanent attachments will be released, such that no obstructions are present within the bridging zone such that liquid can flow or travel via the bridging zone from one longitudinal portion to a neighboring longitudinal portion via capillary action.

According to an embodiment the at least one bridging zone comprises fluff fibers. In this manner, the bridging zone is provided in both a dry and a wet state of the absorbent core such that liquid can flow or travel via the fluff fibers from one longitudinal portion to a neighboring longitudinal portion.

According to an embodiment the at least one bridging zone comprises at least one strip of airlaid material. In this manner, the bridging zone is provided in both a dry and a wet state of the absorbent core. No obstructions are present within airlaid material such that liquid can flow or travel via the airlaid material from one longitudinal portion to a neighboring longitudinal portion. According to an embodiment a minimal width of the bridging zone is at least 5 mm, preferably at least 10 mm and more preferably at least 15 mm. In this manner, a sufficient width is available to allow liquid to flow and/or travel through the bridging zone. The minimal width of the bridging zone is the smallest distance between the front attachment zone and the rear attachment zone between which liquid is allowed to flow.

According to an embodiment the front attachment zone and the rear attachment zone are continuous attachment zones and have a length, seen in the longitudinal direction, of at least 30 mm, preferably at least 40 mm and more preferably at least 50 mm. In this manner, by providing continuous attachment zones with a suitable length, a fast and adequate distribution of liquid in the longitudinal direction of the absorbent core is achieved, while enabling a fast and adequate distribution of liquid in the transverse direction of the absorbent core via the bridging zone(s) between the front attachment zone and the rear attachment zone.

According to an embodiment the front attachment zone and rear attachment zone extend in the longitudinal direction of the absorbent core; and/or wherein an angle between the front attachment zone and the longitudinal direction of the absorbent core and an angle between the rear attachment zone and the longitudinal direction of the absorbent core is smaller than 10°, preferably smaller than 5°. In this manner, by providing front an rear attachment zones which extend in a substantially longitudinal direction of the absorbent core, a fast and adequate distribution of liquid in the longitudinal direction of the absorbent core is achieved, while enabling a fast and adequate distribution of liquid in the transverse direction of the absorbent core via the bridging zone(s) between the front attachment zone(s) and the rear attachment zone(s).

According to an embodiment the plurality of attachment zones further comprises a second front attachment zone and/or a second rear attachment zone, wherein the at least one bridging zone extends between, on the one hand the first and/or second front attachment zones and, on the other hand the first and/or second rear attachment zones.

According to an embodiment said first and second front attachment zone extend next to each other from a crotch region in the direction of the first transverse edge. In this manner, by providing front attachment zones which extend in a substantially longitudinal direction of the absorbent core, a fast and adequate distribution of liquid in the longitudinal direction of the absorbent core is achieved, while enabling a fast and adequate distribution of liquid in the transverse direction of the absorbent core via the bridging zone(s) between the front attachment zone(s) and the rear attachment zone(s). According to an embodiment said first and second rear attachment zone extend next to each other from a crotch region in the direction of the second transverse edge. In this manner, by providing rear attachment zones which extend in a substantially longitudinal direction of the absorbent core, a fast and adequate distribution of liquid in the longitudinal direction of the absorbent core is achieved, while enabling a fast and adequate distribution of liquid in the transverse direction of the absorbent core via the bridging zone(s) between the front attachment zone(s) and the rear attachment zone(s).

According to an embodiment a distance between said first and second front attachment zone is larger than a distance between said first and second rear attachment zone. In this manner, a surface of absorbent material extending between the first and second front attachment zone is increased. By having a broader region of absorbent material located near the front part of the absorbent core, the absorbent core is especially suited for incorporation in absorbent articles for male users, since male users typically produce liquid insults closer to a front portion of the absorbent core as compared to liquid insults produced by female users.

According to an embodiment a distance between said first and second rear attachment zone is larger than a distance between said first and second front attachment zone. In this manner, a surface of absorbent material extending between the first and second rear attachment zone is increased. By having a broader region of absorbent material located near the central/rear part of the absorbent core, the absorbent core is especially suited for incorporation in absorbent articles for female users, since female users typically produce liquid insults closer to a central/rear portion of the absorbent core as compared to liquid insults produced by male users.

The skilled person will understand that the hereinabove described technical considerations and advantages for absorbent article embodiments also apply to the described absorbent core embodiment described below, mutatis mutandis.

According to a further aspect there is provided an absorbent core comprising an absorbent material between a top core wrap sheet and a back core wrap sheet, said absorbent core having a first and second longitudinal edge and a first and second transverse edge. The absorbent core is provided with a plurality of attachment zones comprising at least one front attachment zone and at least one rear attachment zone and with at least one bridging zone extending at least partially between said front and rear attachment zone, wherein the at least one front attachment zone and at least one rear attachment zone, when projected on a longitudinal direction of the absorbent core, do not overlap or overlap only partially; and the bridging zone extends from a first longitudinal portion of the absorbent core to a second longitudinal portion of the absorbent core. The first longitudinal portion is defined between the first longitudinal edge and a longitudinal center axis of the absorbent core and the second longitudinal portion is defined between the second longitudinal edge and the longitudinal center axis of the absorbent core, such that upon wetting of the absorbent material, a front and rear channel are created at said front and rear attachment zone, respectively, wherein the bridging zone allows a liquid flow between the first longitudinal portion and the second longitudinal portion.

Aspects—4 or 3 Attachment Zones

According to an aspect of the invention there is provided an absorbent article comprising a liquid pervious topsheet, a liquid impervious backsheet, and an absorbent core comprising an absorbent material between a top core wrap sheet and a back core wrap sheet. The absorbent core is positioned in between the topsheet and the backsheet. The absorbent core has a first and second longitudinal edge and a first and second transverse edge. The absorbent core has a first portion and a second portion on either side of a transverse crotch line. The absorbent core is provided with a plurality of attachment zones where the top core wrap sheet is attached to the back core wrap sheet, said plurality of attachment zones comprising at least a first and a second elongate attachment zone extending next each other, at least in the first portion of the absorbent core in the direction of the first transverse edge, and a third and a fourth elongate attachment zone extending next to each other, at least in the second portion of the absorbent core, in the direction of the second transverse edge.

Measured in a transverse direction, a first maximum distance between the first and the second attachment zone is bigger than a second maximum distance between the third and the fourth attachment zone.

It is noted that the first transverse edge may be a front edge or a rear edge depending on the desired use of the absorbent article. Similarly, the first portion may be a front portion or a rear portion depending on the desired use of the absorbent article. By having a different distance between the attachment zones in the front portion and in the rear portion, it is possible to tailor the absorbent article to the wearer. For example, for a male person the maximum distance may be larger in the front portion than in the rear portion, whilst for a female person the maximum distance may be larger in the rear portion than in the front portion. Further it is possible to optimize the difference between the front and the rear portion for obtaining an unisex absorbent article.

Also, by having a different distance between the attachment zones in the front portion and in the rear portion, the absorbent article can be better tailored to the needs of the wearer, wherein any one or more of the following may be taken into account: age, weight, type of bodily exudates (urine, stool, etc.), pelvis size, etc. Not only for baby diapers but also for adult incontinence absorbent articles, the liquid absorption and management properties can be significantly improved in that manner.

According to another aspect of the invention there is provided an absorbent article comprising a liquid pervious topsheet, a liquid impervious backsheet, and an absorbent core comprising an absorbent material between a top core wrap sheet and a back core wrap sheet. The absorbent core is positioned in between said topsheet and said backsheet.

The absorbent core has a first and second longitudinal edge and a first and second transverse edge. The absorbent core is provided with a plurality of attachment zones where the top core wrap sheet is attached to the back core wrap sheet, said plurality of attachment zones comprising at least
- a first and a second attachment zone extending next to each other from a crotch region in the direction of the first transverse edge, and
- a third attachment zone extending from the crotch region in the direction of the second transverse edge, wherein seen in a projection on a transverse direction the third attachment zone is located between the first and the second attachment zone.

It is noted that the first transverse edge may be a front edge or a rear edge depending on the desired use of the absorbent article. By having a first and a second attachment zone in the front or rear portion and a third attachment zone in the rear or front portion, respectively, said third attachment zone being such that it is between the first and the second attachment zone, seen in a projection as defined above, it is possible to tailor the absorbent article to the wearer. For example, for a male person the first and second attachment zone may be in the front portion and the third attachment zone may be in the rear portion, whilst for a female person the first and second attachment zone may be in the rear portion and the third attachment zone in the front portion. Further it is possible to optimize the difference between the front and the rear portion for obtaining an unisex absorbent article.

For an embodiment with a third and fourth attachment zone, the first distance between the first and the second attachment zone may be at least 5%, preferably at least 10% bigger, even more preferably at least 20% bigger than a second distance between the third and the fourth attachment zone. This difference may be optimized in function of the desired used. For example, for male persons the difference may be bigger.

In an embodiment which is preferred for a male person, the first and the second elongate attachment zone may each have a front end adjacent to absorbent material and a rear end adjacent to absorbent material or on the transverse crotch line. And the third and the fourth elongate attachment zone may each have a rear end adjacent to absorbent material and a front end adjacent to absorbent material or on the transverse crotch line (L). It is noted that the first attachment zone may be connected to the third attachment zone: in that case the rear end of the first attachment zone and the front end of the third attachment zone will be on the transverse crotch line. Similarly, the second attachment zone may be connected to the fourth attachment zone: in that case the rear end of the second attachment zone and the front end of the fourth attachment zone will be on the transverse crotch line.

In an embodiment which is preferred for a female person, the first and the second elongate attachment zone may each have a rear end adjacent to absorbent material and a front end adjacent to absorbent material or on the transverse crotch line. And the third and the fourth elongate attachment zone may each have a front end adjacent to absorbent material and a rear end adjacent to absorbent material or on the transverse crotch line (L). It is noted that the first attachment zone may be connected to the third attachment zone: in that case the front end of the first attachment zone and the rear end of the third attachment zone will be on the transverse crotch line. Similarly, the second attachment zone may be connected to the fourth attachment zone: in that case the front end of the second attachment zone and the rear end of the fourth attachment zone will be on the transverse crotch line.

For an embodiment with a third central attachment zone which is preferred for a male person, the first and the second elongate attachment zone may each have a front end adjacent to absorbent material and a rear end adjacent to absorbent material or on the transverse crotch line. And the third elongate attachment zone may have a rear end adjacent to absorbent material and a front end adjacent to absorbent material or on the transverse crotch line (L). It is noted that the first attachment zone may be connected to the third attachment zone: in that case the rear end of the first attachment zone and the front end of the third attachment zone will be on the transverse crotch line. Similarly, the second attachment zone may be connected to the third attachment zone: in that case the rear end of the second attachment zone and the front end of the third attachment zone will be on the transverse crotch line.

For an embodiment with a central third attachment zone, which is preferred for a female person, the first and the second elongate attachment zone may each have a rear end adjacent to absorbent material and a front end adjacent to absorbent material or on the transverse crotch line. And the third elongate attachment zone may have a front end adjacent to absorbent material and a rear end adjacent to absorbent material or on the transverse crotch line (L). It is noted that the first attachment zone may be connected to the third attachment zone: in that case the front end of the first attachment zone and the rear end of the third attachment zone will be on the transverse crotch line. Similarly, the second attachment zone may be connected to the third attachment zone: in that case the front end of the second attachment zone and the rear end of the third attachment zone will be on the transverse crotch line.

For an embodiment with a third and fourth attachment zone, seen in a projection on the longitudinal direction of the absorbent core, the first and the second attachment zone may extend over a length which is less than the length of the third and fourth attachment zone. To fit better to the body the third and fourth attachment zones which are closer to each other may be longer to extend over a longer part of the crotch region, for example the third and fourth attachment zones may extend both in the first and the second portion of the absorbent core. Preferably, the first and the second attachment zone extend over a length which is at least 5% less, more preferably at least 10% less than the length of the third and fourth attachment zone. Preferably the first and the second attachment zone extend over a length which is at least 25%, more preferably at least 35%, even more preferably at least 45% of the length of the third and fourth attachment zone.

For an embodiment with a central third attachment zone, seen in a projection on the longitudinal direction of the absorbent core, the first and the second attachment zone may extend over a length which is less than the length of the third attachment zone. To fit better to the body the third attachment zone may be longer to extend over a longer part of the crotch region, for example the third attachment zone may extend both in the first and the second portion of the absorbent core.

Preferably, the first and the second attachment zone extend over a length which is at least 5% less, more preferably at least 10% less than the length of the third attachment zone. Preferably the first and the second attachment zone extend over a length which is at least 25%, more preferably at least 35%, even more preferably at least 45% of the length of the third attachment zone.

In preferred embodiments, especially suitable for male persons, the first transverse edge may be a front edge intended to be positioned at a front side of a person, and the second transverse edge may be a rear edge intended to be positioned at a rear side of a person; wherein the first portion of the absorbent core is a front portion and the second portion is a rear portion.

In preferred embodiments, especially suitable for female persons, the first transverse edge may be a rear edge intended to be positioned at a rear side of a person, and the second transverse edge may be a front edge intended to be positioned at a front side of a person; wherein the first portion of the absorbent core is a rear portion and the second portion is a front portion.

The first attachment zone and the second attachment zone may be arranged symmetrically with respect to a longitudinal center axis of the absorbent core extending between the first and second transverse edge. Since the body is more or less symmetrical this is usually preferred.

The distance between the first and the second attachment zone may be between 15 and 70% of the width of the absorbent core, more preferably between 20 and 50%. For example, the distance between the first and the second attachment zone may be between 10 mm and 100 mm, more preferably between 20 mm and 80 mm, preferably between 30 mm and 70 mm.

The distance between the third and the fourth attachment zone may be between 5 and 60% of the width of the absorbent core, more preferably between 10 and 40%. For example, the distance between the third and the fourth attachment zone may be between 5 mm and 60 mm, more preferably between 10 mm and 50 mm, even more preferably between 15 mm and 40 mm. The length of the first and the second attachment zone may be larger than 5% of the length of the absorbent core; preferably larger than 10%, more preferably larger than 15%. e.g. larger than 20%. Similarly, the length of the third and the fourth attachment zone may be larger than 5% of the length of the absorbent core; preferably larger than 10%, more preferably larger than 15%. e.g. larger than 20%. Also, for an embodiment with a third central attachment zone, the length of the third attachment zone may be larger than 5% of the length of the absorbent core; preferably larger than 10%, more preferably larger than 15%, e.g. larger than 20%.

The length of the third and the fourth attachment zone may be larger than the length of the first and the second attachment zone, preferably at least 10% larger, more preferably at least 20% larger. In a possible embodiment, seen in a projection on a longitudinal direction of the absorbent article, a projection of the first and second attachment zone does not overlap with a projection of the third and fourth attachment zone. However, in other embodiments there may be a partial or even a full overlap. For example, the third and fourth attachment zone may extend in between the first and second attachment zone.

In a possible embodiment with a central third attachment zone, seen in a projection on a longitudinal direction of the absorbent article, a projection of the first and second attachment zone does not overlap with a projection of the third attachment zone. However, in other embodiments there may be a partial or even a full overlap. For example, the third attachment zone may extend in between the first and second attachment zone.

In a possible embodiment the first attachment zone may be separated from the third attachment zone by absorbent material, and the second attachment zone may be separated from the fourth attachment zone by absorbent material. In that manner a capillary bridge is created between the first and second attachment zones on the one hand and the third and fourth attachment zones on the other hand. In an exemplary embodiment a minimum distance between an end on the first attachment zone and an end of the third attachment zone is at least 1% of the length of the absorbent core, preferably at least 2%. Preferably this distance is smaller than 50% of the length of the absorbent core, more preferably smaller than 20%. The same may apply for a minimum distance between the second and fourth attachment zone.

In another possible embodiment the first attachment zone may be connected to the third attachment zone through a first semi-permanent attachment zone and the second attachment zone may be connected to the fourth attachment zone through a second semi-permanent attachment zone. Such semi-permanent attachment zones are configured to be detached upon wetting, so that liquid can flow in a transverse direction through the absorbent material of the absorbent core.

In a possible embodiment one or more permanent or semi-permanent transverse attachment zones may be provided to further improve the liquid distribution in the transverse direction.

Preferably, the first, second, third and fourth attachment zones are permanent attachment zones which remain attached upon wetting. Also, in an embodiment with a central third attachment zone, preferably the first, second, and third attachment zones are permanent attachment zones which remain attached upon wetting.

The length of the first and the second attachment zone may be larger than 30 mm, preferably larger than 40 mm, more preferably larger than 50 mm. The length of the third and the fourth attachment zone may be larger than 30 mm, preferably larger than 40 mm, more preferably larger than 50 mm. The first and second attachment extend, seen in the transverse direction of the absorbent core, over the transverse distance which may be at least 1 mm, preferably at least 3 mm, more preferably at least 4 mm, even more preferably at least 5 mm, most preferably at least 6 mm.

The first attachment zone and the second attachment zone may be substantially parallel and extend in a longitudinal direction of the absorbent core; or wherein an angle between the first attachment zone and a longitudinal direction of the absorbent core and an angle between the second attachment zone and the longitudinal direction of the absorbent core may be smaller than 5°.

The third attachment zone and the fourth attachment zone may be substantially parallel and extend in a longitudinal direction of the absorbent core; or an angle between the third attachment zone and a longitudinal direction of the absorbent core and an angle between the fourth attachment zone and the longitudinal direction of the absorbent core may be smaller than 5°. Also, in the embodiment with a central third attachment zone, the third attachment zone may extend in a longitudinal direction of the absorbent core; or an angle between the third attachment zone and a longitudinal direction of the absorbent core may be smaller than 5°.

Seen in a projection on a longitudinal direction of the absorbent core, the plurality of attachment zones together may cover at least 30%, preferably at least 40% of a length of the absorbent core. In yet other embodiments which are suitable for both male and female persons (unisex), the difference between the first distance and the second distance may be less than 20% of the width of the absorbent article, preferably less than 15%, e.g. between 10 and 15%. In an exemplary embodiment the first distance may be less than 10%, e.g. between 0 and 8% or between 1 and 5%, wherein the width is measured in the transverse direction of the absorbent core.

Aspects—5 Zones

According to an aspect of the invention there is provided an absorbent article comprising a liquid pervious topsheet, a liquid impervious backsheet, and an absorbent core comprising an absorbent material between a top core wrap sheet and a back core wrap sheet, said absorbent core being positioned in between said topsheet and said backsheet. It is noted that the top core wrap sheet and the bottom core wrap sheet may be formed as one integral sheet or may comprise separate portions around the absorbent material. The absorbent core has a first and second side edge, a front edge and a rear edge. The absorbent core is provided with a plurality of attachment zones where the top core wrap sheet is attached to the back core wrap sheet, and where substantially no absorbent material is present. Seen in a longitudinal direction of the absorbent article, looking from the front edge to the rear edge, the absorbent core comprises subsequently a first, second, third, fourth and fifth zone. The absorbent core comprises a front portion extending between the front edge and a transverse crotch line of the absorbent core, and a rear portion extending between the rear edge and the transverse crotch line of the absorbent core. The first, second and third zone extend in the front portion of the absorbent core and the fourth and fifth zone extend in the rear portion.

Preferably, in the first and fifth zone substantially no permanent attachment zones with a liquid guidance or distribution function are present. In other words, the first and fifth zones may comprise small local attachment points provided for other reasons that liquid distribution management.

The second zone comprises at least a first elongate front attachment zone of the plurality of attachment zones, said first front attachment zone extending from an edge of the first zone in the direction of the third zone.

At least the fourth zone comprises at least a first rear elongate attachment zone of the plurality of attachment zones, said first rear attachment zone extending from an edge of the fifth zone in the direction of the third zone.

Preferably at least one of said second, third and fourth zone comprises a bridging zone (B) allowing a liquid flow between the first and the second side edge by capillary action through the absorbent material and/or by mass flow. It is noted that the liquid path through the bridging zone may be any path going from an area near the first side edge to an area near the second edge. Preferably the distance between the transverse crotch line and the transverse center line passing through the middle of the core is less than 10% of the length of the core.

It is noted that the first rear attachment zone may extend in the third zone, i.e. in the front portion of the absorbent core.

It is noted that the first front attachment zone may extend in the third and/or the fourth zone, i.e. in the rear portion of the absorbent core.

By providing at least one elongate front attachment zone and at least one elongate rear attachment as defined above channels are created when the absorbent core is wetted. By providing a bridging zone in at least one of the second, third and fourth zone, notwithstanding the creation of a channel, liquid taken up in absorbent material near the first side edge may migrate by capillary action and/or mass flow in the direction of the second side edge. In other words, the liquid is on the one hand distributed by the channels formed by the at least one front attachment zone and at least one rear attachment zone, and on the other hand allowed to be transported from one side edge to the other side edge by capillary action and/or by mass flow via the bridging zone. This is advantageous, especially when a person wearing the absorbent article is lying down on its side. Indeed, when lying down the liquid may flow towards one side edge by gravity. This will cause a swelling of the absorbent material near that side edge, and the bridging zone will allow the liquid to flow towards the other side edge against the gravity force by capillary action. On the other hand the channels will be able to provide for a fast liquid distribution through the second, third and fourth zone.

Preferably, the bridging zone extends between the first front attachment zone and the first rear attachment zone, such that upon wetting of the absorbent material, a front and rear channel are created at said first front and rear attachment zone, respectively, wherein the bridging zone extends between said front and rear channel. In that manner, after channel formation upon wetting, liquid can still flow by capillary action and/or mass flow between the first rear and front attachment zone. It is noted that the bridging zone may comprise secondary temporary attachment zones which loosen upon wetting, whilst the first front attachment zone and the first rear attachment zone remain attached upon wetting. Also the bridging zone may comprise attachment zones extending between the first side edge and the second side edge to promote a mass flow action between an area near the first side edge to an area near the second side edge, wherein said areas are located at opposite sides of the first front/rear attachment zone. It is noted that the liquid path through the bridging zone may be any path going from an area near the first side edge to an area near the second edge. It may be a straight transverse zone, but it may also be a curved zone, or a partially straight and partially curved zone. Preferably, a minimum distance between the first front attachment zone and the first rear attachment zone is larger than 3 mm, more preferably larger than 5 mm, even more preferably larger than 8 mm. In that way a sufficient flow can be guaranteed. This minimum distance (which is related to the capillary flow and/or mass flow) may be varied depending on the size of the absorbent article. In a preferred embodiment the bridging zone is configured to cause a capillary flow so that a flow against the gravity force is possible.

In an advantageous embodiment the first rear elongate attachment zone extends into the third zone. In that manner a continuous channel is formed between the front and the rear portion of the absorbent core.

Preferably, the first zone extends over a length corresponding with at least 5%, more preferably at least 10% of the length of the absorbent core seen in the longitudinal direction.

Preferably, the fifth zone extends over a length corresponding with at least 10% of the length of the absorbent core seen in the longitudinal direction, preferably at least 20%, more preferably at least 25%. In that manner the absorbent material in the first zone and the fifth zone will swell upon wetting and created bands at both sides of the crotch region. Such bands will create a barrier such that it is more difficult for any liquid in the crotch region to flow out of the absorbent core.

Preferably, the second, the third and/or the fourth zone each extends over a length corresponding with at least 10% of the length of the absorbent core, seen in the longitudinal direction, preferably at least 15%. More preferably the front and rear attachment zone, when projected on the longitudinal direction extend over at least 70%, more preferably at least 80% of the total length of the second, the third and/or the fourth zone. In that manner a good channel creation with sufficient liquid distribution through the absorbent core is achieved.

Preferably the first front attachment zone extends in a longitudinal direction of the absorbent core; or an angle between the first front attachment zone and a longitudinal direction of the absorbent core may be smaller than 5°.

Preferably the first rear attachment zone extends in a longitudinal direction of the absorbent core; or an angle between the first rear attachment zone and a longitudinal direction of the absorbent core may be smaller than 5°.

Preferably, the length of the first front attachment zone is larger than 5% of the length of the absorbent core; preferably larger than 10%, more preferably larger than 15%; and/or wherein the length of the first rear attachment zone is larger than 5% of the length of the absorbent core, preferably larger than 10%, more preferably larger than 15%. Preferably the length of the first front attachment zone is at least 10%, more preferably at least 25%, even more preferably at least 35%, or even at least 50 or 75% of the length of the first rear attachment zone. Alternatively, the length of the first rear attachment zone is at least 10%, more preferably at least 25%, even more preferably at least 35%, or even at least 50 or 75% of the length of the first front attachment zone.

In an exemplary embodiment the second zone comprises a second front attachment zone extending next to the first front attachment zone, seen in the longitudinal direction. Preferably the first front attachment zone and the second front attachment zone are arranged symmetrically with respect to a longitudinal center line of the absorbent core. Preferably the distance between the first and the second front attachment zone is between 20 mm and 70 mm, more preferably between 30 mm and 60 mm, even more preferably between 40 mm and 55 mm. Preferably the distance between the first and the second front attachment zone is between 15 and 70% of the width of the absorbent core, more preferably between 20 and 50%. Especially for male persons, this distance is preferably sufficiently large such that urine is captured mainly in the area between the first front attachment zone and the second front attachment zone.

The first front attachment zone and the second front attachment zone may be substantially parallel and may extend in a longitudinal direction of the absorbent core; or an angle between the first front attachment zone and a longitudinal direction of the absorbent core and an angle between the second front attachment zone and the longitudinal direction of the absorbent core may be smaller than 5°. For example the first and second front attachment zones may diverge in the direction of the first zone.

In an exemplary embodiment the fourth zone comprises a second rear attachment zone extending next to the first rear attachment zone, seen in the longitudinal direction, said second rear attachment zone extending preferably into the third zone. Preferably the first rear attachment zone and the second rear attachment zone are arranged symmetrically with respect to a longitudinal center line of the absorbent core. Preferably the distance between the first and the second rear attachment zone is between 10 mm and 50 mm, preferably between 15 mm and 40 mm, more preferably between 20 mm and 30 mm. Preferably the distance between the first and the second rear attachment zone is between 5 and 60% of the width of the absorbent core, more preferably between 10 and 40%. Preferably the first rear attachment zone and the second rear attachment zone are substantially parallel and extend in a longitudinal direction of the absorbent core; or an angle between the first rear attachment zone and a longitudinal direction of the absorbent core and an angle between the second rear attachment zone and the longitudinal direction of the absorbent core is smaller than 5°. For example the first and second rear attachment zones may diverge in the direction of the fifth zone.

Preferably a first smallest distance (d12) between the first and the second front attachment zone is bigger than a second smallest distance (d34) between the first and the second rear attachment zone, more preferably at least 10% bigger, even more preferably at least 15% bigger. In that manner the channels formed by the first and the second rear attachment zone will be closer to each other in the center of the crotch region making the absorbent article more agreeable to wear, also when wetted, and will give the absorbent article a tub-shape when wetted, see further. On the other hand the channels created by the first and the second front attachment zone will be further away from each other to obtain a good liquid distribution, especially for male persons.

Preferably, the first and the second front attachment zone extend in a longitudinal direction of the absorbent core over a length which is less than the length of the first and second rear attachment zone, more preferably at least 10% less, even more preferably at least 15% less. In that manner the first and the second front attachment zone can extend from the fourth zone into the third zone such that the absorbent article fits better to the body of the wearer.

Preferably, the bridging zone extends from a first portion of the absorbent core, preferably in the second or third zone, to a second portion of the absorbent core, preferably in the second or third zone, wherein the first portion is defined between the first side edge and a longitudinal center axis (CL) of the absorbent core and the second portion is defined between the second side edge and the longitudinal center axis (CL) of the absorbent core.

Preferably, the length of the first front attachment zone is larger than 30 mm, more preferably larger than 40 mm, even more preferably larger than 50 mm.

Preferably, the length of the first rear attachment zone is larger than 30 mm, more preferably larger than 40 mm, even more preferably larger than 50 mm.

Preferably, said plurality of attachment zones are permanent attachment zones which remain attached when wetted.

Preferably, said plurality of attachment zones extend, seen in the transverse direction of the absorbent core, over the transverse distance which is at least 1 mm, preferably at least 3 mm, more preferably at least 4 mm, even more preferably at least 5 mm, most preferably at least 6 mm. In that manner the channels created upon wetting will be sufficiently wide to cause a good liquid distribution.

In an exemplary embodiment, the bridging zone comprises one or more temporary attachments which are configured to detach when wetted. In that manner, upon wetting the one or more temporary attachments may first function to guide a mass flow of the liquid, whereupon, after loosening a capillary flow through the absorbent material is made possible. In a possible embodiment, the bridging zone comprises at least one permanent attachment zone in a direction from the first to the second side edge, e.g. in a transverse direction.

Aspects—Connecting Attachment Zone (e.g. U-Shape, O-Shape)

According to an aspect of the invention there is provided an absorbent article comprising a liquid pervious topsheet, a liquid impervious backsheet, and an absorbent core comprising an absorbent material between a top core wrap sheet and a back core wrap sheet. The absorbent core is positioned in between said topsheet and said backsheet. The absorbent core has a first and second longitudinal edge and a front and rear transverse edge. The absorbent core is provided with a plurality of attachment zones where the top core wrap sheet is attached to the back core wrap sheet. The plurality of attachment zones comprises:

at least a first and a second elongate attachment zone, said first and second elongate attachment zone extending next to each other from a crotch region in the direction of the front and/or rear transverse edge;

at least one connecting attachment zone connecting said first attachment zone with said second attachment zone.

By providing a first and a second elongate attachment zone which are interconnected by at least one connecting attachment zone, upon wetting of the absorbent core two elongate channels are created which are interconnected by at least one interconnecting channel which is in liquid communication with the first and second elongate channel. In that manner, immediately after wetting, liquid can flow from the first elongate channel to the second elongate channel and vice versa, improving the liquid distribution, whereupon the liquid can be absorbed by the absorbent material.

According to an exemplary embodiment the at least one connecting attachment zone comprises at least one of:

a front connecting attachment zone which connects a front end portion of the first attachment zone to a corresponding front end portion of the second attachment zone;

a rear connecting attachment zone which connects a rear end portion of the first attachment zone to a corresponding rear end portion of the second attachment zone.

In that manner a good distribution is obtained in the front portion and/or in the back portion. Especially for a male person, it may be desirable to have a front connecting attachment zone.

The absorbent core has a transverse crotch line dividing the absorbent core in a front portion and a rear portion on either side of the transverse crotch line. Preferably, the front connecting attachment zone is located in the front portion and/or the rear connecting attachment zone is located in the rear portion.

In an exemplary embodiment a connecting attachment zone extends substantially in a transverse direction of the absorbent core. This may be advantageous when the first and second elongate channel extend substantially parallel. In that manner an absorbent core is obtained which may be substantially symmetrical with respect to a longitudinal center axis. In other symmetrical embodiments the connecting attachment zone may be substantially V-shaped or U-shaped, wherein the V-shape or U-shape is arranged such that it is symmetrical with respect to the longitudinal center axis of the absorbent core.

In an exemplary embodiment, upon wetting of the absorbent material, a first and second channel are created at said first and second elongate attachment zone, respectively, and the first and second channel are directly connected to each other through the at least one connecting attachment zone; wherein a first, second, and at least one connecting channel are created at said first, second, and at least one connecting attachment zone, respectively.

In a preferred embodiment the at least one connecting attachment zone corresponds with at least one permanent attachment zone which remains attached upon wetting, or at least one semi-permanent attachment zone configured to release after having been in contact with liquid for a predetermined period of time, wherein said predetermined period of time is preferably smaller than 30 s.

In an exemplary embodiment the at least one connecting attachment zone comprises one or more straight portions, and/or one or more curved portions.

In an exemplary embodiment the first attachment zone, the second attachment zone, and the at least one connecting attachment zone collectively form a substantially "U" shaped zone, or a substantially "V" shaped zone. A U-shape or V-shape provides for a good guidance of the liquid. Moreover, with a U-shaped attachment zone sharp angles may be avoided further improving a good liquid transport from a first elongate attachment zone (one leg) of the U-shaped attachment zone to the second elongate attachment zone (the other leg) of the U-shaped attachment zone. Further, with a V-shape, liquid may be guided from e.g. a left and right front portion to a center portion in the crotch region.

In an exemplary embodiment, the first attachment zone, the second attachment zone, and the at least one connecting attachment zone collectively delimit a substantially enclosed region. For example, the substantially enclosed region may be a substantially "O" shaped region, or a substantially polygon shaped region, such as a substantially rectangular shaped region, a substantially triangular shaped region, a diamond shaped region, a substantially hexagonal shaped region. In that manner liquid can be distributed around the boundary of the enclosed region, such that it can be absorbed from the entire boundary by the absorbent material in the enclosed region and by the absorbent material in a region surrounding the enclosed region.

In an exemplary embodiment, the first attachment zone and the second attachment zone are substantially parallel and extend in a longitudinal direction of the absorbent core. In another exemplary embodiment, an angle between the first attachment zone and a longitudinal direction of the absorbent core and an angle between the second attachment zone and the longitudinal direction of the absorbent core is smaller than 5°.

In an exemplary embodiment, the plurality of attachment zones is arranged symmetrically with respect to a longitudinal center axis of the absorbent core extending between the front and rear transverse edge.

In an exemplary embodiment, the largest distance between the first and the second attachment zone in the transverse direction is between 15 and 70% of the width of the absorbent core, more preferably between 20 and 50%; wherein preferably the largest distance between the first and the second attachment zone in the transverse direction is between 10 mm and 100 mm, more preferably between 20 mm and 80 mm, even more preferably between 30 mm and 70 mm.

In an exemplary embodiment, the first and second attachment zones are permanent attachment zones which remain attached upon wetting, or semi-permanent attachment zones configured to release after having been in contact with liquid for a predetermined period of time, wherein said predetermined period of time is preferably smaller than 30 s.

The absorbent core has a first and second transverse edge, wherein the first edge may be the front edge or the rear edge, and the second edge may be the rear edge or the front edge, respectively. The absorbent core has a first portion and a second portion on either side of the transverse crotch line. The first and the second elongate attachment zone extend next to each other, at least in the first portion of the absorbent core in the direction of the first transverse edge.

In a first possible embodiment, the plurality of attachment zones may further comprise a third and a fourth elongate attachment zone extending next to each other, at least in the second portion of the absorbent core, in the direction of the second transverse edge. Optionally the third and fourth elongate attachment zone may be connected by a connecting attachment zone.

Measured in a transverse direction, a first maximum distance between the first and the second attachment zone is preferably bigger than a second maximum distance between the third and the fourth attachment zone.

It is noted that the first transverse edge may be a front edge or a rear edge depending on the desired use of the absorbent article. Similarly, the first portion may be a front portion or a rear portion depending on the desired use of the absorbent article. By having a different distance between the attachment zones in the front portion and in the rear portion, it is possible to tailor the absorbent article to the wearer. For example, for a male person the maximum distance may be larger in the front portion than in the rear portion, whilst for a female person the maximum distance may be larger in the rear portion than in the front portion. Further it is possible to optimize the difference between the front and the rear portion for obtaining a unisex absorbent article.

In a second possible embodiment, the plurality of attachment zones may further comprise a third attachment zone extending from the crotch region in the direction of the second transverse edge, wherein seen in a projection on a transverse direction the third attachment zone is located between the first and the second attachment zone. By having a first and a second attachment zone in the front or rear portion and a third attachment zone in the rear or front portion, respectively, said third attachment zone being such that it is between the first and the second attachment zone, seen in a projection as defined above, it is possible to tailor the absorbent article to the wearer. For example, for a male person the first and second attachment zone may be in the front portion and the third attachment zone may be in the rear portion, whilst for a female person the first and second attachment zone may be in the rear portion and the third attachment zone in the front portion. Further it is possible to optimize the difference between the front and the rear portion for obtaining a unisex absorbent article.

For an embodiment with a third and fourth attachment zone, the first distance between the first and the second attachment zone may be at least 5%, preferably at least 10% bigger, even more preferably at least 20% bigger than a second distance between the third and the fourth attachment zone. This difference may be optimized in function of the desired used. For example, for male persons the difference may be bigger.

In an embodiment which is preferred for a male person, the first and the second elongate attachment zone may each have a front end adjacent to absorbent material and a rear end adjacent to absorbent material or on the transverse crotch line. And the third and the fourth elongate attachment zone may each have a rear end adjacent to absorbent material and a front end adjacent to absorbent material or on the transverse crotch line (L). It is noted that the first attachment zone may be connected to the third attachment zone: in that case the rear end of the first attachment zone and the front end of the third attachment zone will be on the transverse crotch line. Similarly, the second attachment zone may be connected to the fourth attachment zone: in that case the rear end of the second attachment zone and the front end of the fourth attachment zone will be on the transverse crotch line.

In an embodiment which is preferred for a female person, the first and the second elongate attachment zone may each have a rear end adjacent to absorbent material and a front end adjacent to absorbent material or on the transverse crotch line. And the third and the fourth elongate attachment zone may each have a front end adjacent to absorbent material and a rear end adjacent to absorbent material or on the transverse crotch line (L). It is noted that the first attachment zone may be connected to the third attachment zone: in that case the front end of the first attachment zone and the rear end of the third attachment zone will be on the transverse crotch line. Similarly, the second attachment zone may be connected to the fourth attachment zone: in that case the front end of the second attachment zone and the rear end of the fourth attachment zone will be on the transverse crotch line.

For an embodiment with a central third attachment zone (instead of a third and fourth attachment zone) which is preferred for a male person, the first and the second elongate attachment zone may each have a front end adjacent to absorbent material and a rear end adjacent to absorbent material or on the transverse crotch line. And the third elongate attachment zone may have a rear end adjacent to absorbent material and a front end adjacent to absorbent material or on the transverse crotch line (L). It is noted that the first attachment zone may be connected to the third attachment zone: in that case the rear end of the first attachment zone and the front end of the third attachment zone will be on the transverse crotch line. Similarly, the second attachment zone may be connected to the third attachment zone: in that case the rear end of the second attachment zone and the front end of the third attachment zone will be on the transverse crotch line.

For an embodiment with a central third attachment zone which is preferred for a female person, the first and the second elongate attachment zone may each have a rear end adjacent to absorbent material and a front end adjacent to absorbent material or on the transverse crotch line. And the third elongate attachment zone may have a front end adjacent to absorbent material and a rear end adjacent to absorbent material or on the transverse crotch line (L). It is noted that the first attachment zone may be connected to the third attachment zone: in that case the front end of the first attachment zone and the rear end of the third attachment zone will be on the transverse crotch line. Similarly, the second attachment zone may be connected to the third attachment zone: in that case the front end of the second attachment zone and the rear end of the third attachment zone will be on the transverse crotch line.

For an embodiment with a third and fourth attachment zone, seen in a projection on the longitudinal direction of the absorbent core, the first and the second attachment zone may extend over a length which is less than the length of the third and fourth attachment zone. To fit better to the body the third and fourth attachment zones which are closer to each other may be longer to extend over a longer pan of the crotch region, for example the third and fourth attachment zones may extend both in the first and the second portion of the absorbent core. Preferably, the first and the second attachment zone extend over a length which is at least 5% less, more preferably at least 10% less than the length of the third and fourth attachment zone. Preferably the first and the second attachment zone extend over a length which is at least 25%, more preferably at least 35%, even more preferably at least 45% of the length of the third and fourth attachment zone.

For an embodiment with a third attachment zone, seen in a projection on the longitudinal direction of the absorbent core, the first and the second attachment zone may extend over a length which is less than the length of the third attachment zone. To fit better to the body the third attachment zone may be longer to extend over a longer part of the crotch region, for example the third attachment zone may extend both in the first and the second portion of the absorbent core. Preferably, the first and the second attachment zone extend over a length which is at least 5% less, more preferably at least 10% less than the length of the third attachment zone. Preferably the first and the second attachment zone extend over a length which is at least 25%, more preferably at least 35%, even more preferably at least 45% of the length of the third attachment zone.

In preferred embodiments, especially suitable for male persons, the first transverse edge may be a front edge intended to be positioned at a front side of a person, and the second transverse edge may be a rear edge intended to be positioned at a rear side of a person; wherein the first portion of the absorbent core is a front portion and the second portion is a rear portion.

In preferred embodiments, especially suitable for female persons, the first transverse edge may be a rear edge intended to be positioned at a rear side of a person, and the second transverse edge may be a front edge intended to be positioned at a front side of a person; wherein the first portion of the absorbent core is a rear portion and the second portion is a front portion.

The distance between the first and the second attachment zone may be between 15 and 70% of the width of the absorbent core, more preferably between 20 and 50%. For example, the distance between the first and the second attachment zone may be between 10 mm and 100 mm, more preferably between 20 mm and 80 mm, preferably between 30 mm and 70 mm.

The distance between the third and the fourth attachment zone may be between 5 and 60% of the width of the absorbent core, more preferably between 10 and 40%. For example, the distance between the third and the fourth attachment zone may be between 5 mm and 60 mm, more preferably between 10 mm and 50 mm, even more preferably between 15 mm and 40 mm. The length of the first and the second attachment zone may be larger than 5% of the length of the absorbent core; preferably larger than 10%, more preferably larger than 15%, e.g. larger than 20% or even larger than 30% or 40% of the length of the absorbent core. Similarly, the length of the third and the fourth attachment zone may be larger than 5% of the length of the absorbent core; preferably larger than 10%, more preferably larger than 15%. e.g. larger than 20%. Also, for an embodiment with a central third attachment zone, the length of the third attachment zone may be larger than 5% of the length of the absorbent core; preferably larger than 10%, more preferably larger than 15%, e.g. larger than 20%.

The length of the third and the fourth attachment zone may be larger than the length of the first and the second attachment zone, preferably at least 10% larger, more preferably at least 20% larger. In a possible embodiment, seen in a projection on a longitudinal direction of the absorbent article, a projection of the first and second attachment zone does not overlap with a projection of the third and fourth attachment zone. However, in other embodiments there may be a partial or even a full overlap. For example, the third and fourth attachment zone may extend in between the first and second attachment zone.

In a possible embodiment with a central third attachment zone, seen in a projection on a longitudinal direction of the absorbent article, a projection of the first and second attachment zone does not overlap with a projection of the third attachment zone. However, in other embodiments there may be a partial or even a full overlap. For example, the third attachment zone may extend in between the first and second attachment zone.

In a possible embodiment the first attachment zone may be separated from the third attachment zone by absorbent material, and the second attachment zone may be separated from the fourth attachment zone by absorbent material. In that manner a capillary bridge is created between the first and second attachment zones on the one hand and the third and fourth attachment zones on the other hand.

In another possible embodiment the first attachment zone may be connected to the third attachment zone through a first semi-permanent attachment zone and the second attachment zone may be connected to the fourth attachment zone through a second semi-permanent attachment zone. Such semi-permanent attachment zones are configured to be detached upon wetting, so that liquid can flow in a transverse direction through the absorbent material of the absorbent core.

Preferably, the first, second, third and fourth attachment zones are permanent attachment zones which remain attached upon wetting. Also, in an embodiment without the fourth attachment zone, preferably the first, second, and third attachment zones are permanent attachment zones which remain attached upon wetting.

The third attachment zone and the fourth attachment zone may be substantially parallel and extend in a longitudinal direction of the absorbent core; or an angle between the third attachment zone and a longitudinal direction of the absorbent core and an angle between the fourth attachment zone and the longitudinal direction of the absorbent core may be smaller than 5°. Also, in the embodiment with a central third attachment zone, the third attachment zone may extend in a longitudinal direction of the absorbent core; or an angle between the third attachment zone and a longitudinal direction of the absorbent core may be smaller than 5.

In an exemplary embodiment, seen in a longitudinal direction of the absorbent article, looking from the front edge to the rear edge, the absorbent core comprises subsequently a first, second, third, fourth and fifth zone. The absorbent core comprises a front portion extending between the front edge and a transverse crotch line of the absorbent core, and a rear portion extending between the rear edge and the transverse crotch line of the absorbent core. The first, second and third zone extend in the front portion of the absorbent core and the fourth and fifth zone extend in the rear portion.

Preferably, the at least one connecting attachment zone connecting the first and second elongate attachment zone extend in the second, third or fourth zone.

More preferably, the second and/or third zone comprises at least one front connecting attachment zone connecting a first elongate front attachment zone and a second elongate front attachment zone; and/or the fourth zone comprises at least one rear connecting attachment zone connecting a first elongate rear attachment zone and a second elongate rear attachment zone.

Preferably, in the first and fifth zone substantially no permanent attachment zones with a liquid guidance or distribution function are present. In other words, the first and fifth zones may comprise small local attachment points provided for other reasons that liquid distribution management. Preferably, the second zone comprises at least a first elongate front attachment zone of the plurality of attachment zones, said first front attachment zone extending from an edge of the first zone in the direction of the third zone.

Preferably, at least the fourth zone comprises at least a first rear elongate attachment zone of the plurality of attachment zones, said first rear attachment zone extending from an edge of the fifth zone in the direction of the third zone.

Any of the features disclosed above for the "5zone" aspect may also be included in embodiments of the connecting attachment zone aspect.

Aspects—Crossing Point (e.g. V-Shape, X-Shape)

According to an aspect of the invention, there is provided an absorbent article comprising a liquid pervious topsheet, a liquid impervious backsheet, and an absorbent core comprising an absorbent material between a top core wrap sheet and a back core wrap sheet. The absorbent core is positioned in between the topsheet and the backsheet. The absorbent core has a first and second longitudinal edge and a first and second transverse edge. The absorbent core has a longitudinal center line dividing the absorbent core in a first longitudinal portion and a second longitudinal portion on either side of the longitudinal center line, and a transverse crotch line dividing the absorbent core in a front portion and a rear portion on either side of the transverse crotch line. The absorbent core is provided with a plurality of attachment zones where the top core wrap sheet is attached to the back core wrap sheet. The plurality of attachment zones comprises a first and second elongate attachment zone, said first and second elongate attachment zone extending next to each other from a crotch region in the direction of the first and/or second transverse edge. The first elongate attachment zone crosses the longitudinal center line in a first crossing point, from the first longitudinal portion to the second longitudinal portion; and the second elongate attachment zone crosses the longitudinal center line in a second crossing point, from the second longitudinal portion to the first longitudinal portion. The first and second crossing point may be the same point or a different point, and may be located in the front portion or in the rear portion or on the transverse crotch line between connecting the front portion to the rear portion.

By providing a first and a second elongate attachment zone which are crossing the longitudinal center line, upon wetting of the absorbent core two elongate channels are created. The first elongate channel extends from a first left position to a second right side, where the first left position is closer to the first transverse edge than the second right position. Similarly, second elongate channel extends from a second right position to a first left position, where the second right position is closer to the first transverse edge than the first left position. In that manner, immediately after wetting, liquid is guided in the first and/or second elongate channel from left to right and/or from right to left, respectively, whilst flowing towards the crotch region or away from the crotch region, improving the liquid distribution, whereupon the liquid can be absorbed by the absorbent material. Further, by making the first and second attachment zones cross the longitudinal center line, the zones may be longer compared to similar zones extending parallel to the longitudinal center line, resulting in a larger liquid distribution zone.

Preferably, the first and second crossing point correspond with substantially the same point located on the longitudinal center line. In that manner a connection between the first and the second attachment zone is realized further enhancing the liquid distribution.

In another embodiment, the first and second crossing point may be different points, and the first and the second attachment zone may cross each other at a distance of the longitudinal center line. In such an embodiment third and fourth elongate attachment zone arranged symmetrically with respect to the first and second elongate attachment zones may be provided, such that the first and second attachment zone cross each other at one side of the longitudinal center line and the third and fourth attachment zone cross each other at another side of the longitudinal center line.

Preferably, the first and/or second crossing point are located at a distance of the transverse crotch line. For example, the first and/or second crossing point may be located in a front portion. In that way the position of the first and/or second can be optimized e.g. in function of whether the absorbent article is intended for a male or female person. However, in other embodiments, the first and/or second crossing point may be located on the transverse crotch line.

When at a distance of the transverse crotch line, preferably, the distance between the first and/or second crossing point and the transverse crotch line is larger than 1% of the length of the absorbent core, preferably larger than 2%, even more preferably larger than 3%.

In certain embodiments with multiple first crossing points and multiple second crossing points may be provided, wherein these multiple first crossing points may be located a different distances of the transverse crotch line, e.g. two first crossing points, one in the front portion and one in the rear portion, and two second crossing points, one in the front portion (optionally corresponding with the first crossing point in the front portion), and one in the rear portion (optionally corresponding with the first crossing point in the rear portion), see e.g. FIG. 15P.

Preferably, the first elongate attachment zone extends both in the front portion and in the rear portion; and the second elongate attachment zone extends both in the front portion and in the rear portion. In that manner a good liquid distribution from left to right and from front to rear can be obtained.

Preferably, the first elongate attachment zone and the second elongate attachment zone are arranged symmetrically with respect to the longitudinal center line of the absorbent core.

In an exemplary embodiment a maximum distance between the first and the second elongate attachment zone is between 15 and 70% of the width of the absorbent core, more preferably between 20 and 50%.

In an exemplary embodiment a maximum distance between the first and the second attachment zone in the front portion is different from a maximum distance between the first and the second attachment zone in the rear portion. In that manner the liquid distribution zone may be better adapted to the type of person wearing the absorbent article. For example, for a male person, a maximum distance between the distance between the first and the second attachment zone near a front transverse edge may be larger than a maximum distance between the first and the second attachment zone in a rear portion.

Preferably, the length of the first and second attachment zone is larger than 10% of the length of the absorbent core, more preferably larger than 30%, even more preferably larger than 50% In an exemplary embodiment the plurality of attachment zones are permanent attachment zones which remain attached when wetted. In certain embodiments, the first attachment zone may be connected to the second attachment zone through a semi-permanent attachment zone, preferably extending in a substantially transverse direction.

In an exemplary embodiment at least one of said first and second elongate attachment zone comprises a bridging zone (B) allowing a liquid flow between the first and the second longitudinal edge by capillary action through the absorbent material and/or by mass flow, such that upon wetting of the absorbent material, a front and rear channel are created, wherein the bridging zone extends between said front and rear channel; wherein a minimum distance between said front and rear channel is preferably larger than 3 mm more preferably larger than 5 mm.

In an exemplary embodiment, the first and second channel together form a substantially X-shaped zone. Optionally the legs of the "X" may be interrupted to create one or more bridging zones as defined above.

In an exemplary embodiment, the bridging zone extends from the first longitudinal portion of the absorbent core to the second longitudinal portion of the absorbent core; wherein optionally said bridging zone comprises one or more temporary attachments between the top and back core wrap sheet which are configured to detach when wetted; and/or wherein said bridging zone comprises at least one permanent attachment zone in a direction from the first to the second side edge; and/or wherein said bridging zone comprises absorbent material.

According to an exemplary embodiment, the first and second transverse edge correspond with a front and rear transverse edge, and the plurality of attachment zones further comprises at least one connecting attachment zone connecting said first attachment zone with said second attachment zone.

By providing a first and a second elongate attachment zone which are interconnected by at least one connecting attachment zone, upon wetting of the absorbent core two elongate channels are created which are interconnected by at least one interconnecting channel which is in liquid communication with the first and second elongate channel. In that manner, immediately after wetting, liquid can flow from the first elongate channel to the second elongate channel and vice versa, improving the liquid distribution, whereupon the liquid can be absorbed by the absorbent material.

According to an exemplary embodiment the at least one connecting attachment zone comprises at least one of:
 a front connecting attachment zone which connects a front end portion of the first attachment zone to a corresponding front end portion of the second attachment zone;
 a rear connecting attachment zone which connects a rear end portion of the first attachment zone to a corresponding rear end portion of the second attachment zone.

In that manner a good distribution is obtained in the front portion and/or in the back portion. Especially for a male person, it may be desirable to have a front connecting attachment zone. Preferably, the front connecting attachment zone is located in the front portion and/or the rear connecting attachment zone is located in the rear portion.

Other features disclosed above for the "connecting attachment" aspect may be combined with embodiments of the "crossing point" aspect.

Features Applicable to all Aspects

Preferably, a distance between the transverse crotch line (as used/defined above) and a transverse center line extending perpendicular on the longitudinal direction of the absorbent core, through the middle of the absorbent core, is smaller than 10%, more preferably smaller than 5% of the length of the absorbent core.

Preferably, the first and/or second and/or third and/or fourth attachment zone each extends, seen in the transverse direction of the absorbent core, over the transverse distance which is at least 1 mm, preferably at least 3 mm, more preferably at least 4 mm, even more preferably at least 5 mm, most preferably at least 6 mm.

The length of the first and the second attachment zone may be larger than 30 mm, preferably larger than 40 mm, more preferably larger than 50 mm. The length of the third and the fourth attachment zone may be larger than 30 mm, preferably larger than 40 mm, more preferably larger than 50 mm. In possible embodiments one or more permanent or semi-permanent transverse attachment zones may be provided to further improve the liquid distribution in the transverse direction. In the first and second attachment zone said top core wrap sheet may be attached to said back core wrap sheet through permanent and semi-permanent attachment portions, said semi-permanent portions may be configured to release after having been in contact with liquid whilst said permanent portions may be configured not to release after having been in contact with liquid. In an exemplary embodiment, in a front and/or rear attachment zone the top core wrap sheet is attached to the back core wrap sheet through permanent and semi-permanent attachment portions, said semi-permanent portions being configured to release after having been in contact with liquid whilst said permanent portions are configured not to release after having been in contact with liquid. It is noted that different types of semi-permanent attachment portions may be used in the same absorbent article so as to achieve a gradual loosening of the attachments upon wetting. This is described in detail in patent documents WO2012048879A1 and WO2012048878A1, which are included herein by reference.

The absorbent material may comprise cellulosic fluff pulp and/or superabsorbent particles. The absorbent material may be substantially fluffless.

Preferably, substantially no absorbent material is present in the plurality of attachment zones. A position and/or shape of one or more attachment zones may be indicated by means of a distinguishable color and/or colored pattern. E.g., a position and/or shape of one or more attachment zones may be indicated by means of a printed ink layer. The distinguishable color and/or colored pattern may be provided on at least one of the topsheet, the top core wrap sheet, the backsheet and the back core wrap sheet.

Preferably, the plurality of attachment zones cover together at least 20%, preferably at least 30% more preferably at least 40%, more preferably at least 50%, more preferably at least 60%, more preferably at least 70%, more preferably 80% and more preferably at least 90% of a total length of the absorbent core. The covered length may be realized with the first and second attachment zone alone, or with a combination of a first and second attachment zone and one or more additional attachment zones. For example, first and second adjacent longitudinal attachment zones together with third and fourth adjacent longitudinal attachment zones may extend over at least 30%, preferably at least 40%, preferably at least 50%, more preferably at least 6(0%, more preferably at least 70%, more preferably 80% and more preferably at least 90% of a total length of the absorbent core. This will allow a good distribution over the entire absorbent core as well as a good formation of the channels and the tub-shape upon swelling of the absorbent core.

According to a preferred embodiment, outside of the plurality of attachment zones the absorbent core has a maximum thickness; wherein the first and second attachment zone extend through at least 90% of the maximum thickness of the absorbent core, more preferably through 100% of the thickness of the absorbent core such that in the first and second attachment zone substantially no absorbent material is present between the top core wrap sheet and the back core wrap sheet. According to an exemplary embodiment the first attachment zone and the second attachment zone are arranged symmetrically with respect to a longitudinal center line of the absorbent core extending between the first and second transverse edge.

According to a preferred embodiment, the attachment between the top core wrap sheet and the back core wrap sheet is in any one or more of the attachment zones is any one of the following or a combination thereof: pressure bonding, thermal bonding, sonic bonding, chemical bonding, adhesive. The attachment may be a direct or indirect attachment. E.g. an adhesive and/or other intermediate material may be inserted between the top core wrap sheet and the back core wrap sheet. For example, a structure or layer having no or less absorption capacity than the absorbent material may be added in between the top core wrap sheet and the back core wrap in the attachment area.

According to exemplary embodiment, the first and second attachment zone each have a bottom and a top, wherein the top core wrap sheet is attached to the back core wrap sheet at said bottom, at said top, or between said bottom and said top.

In embodiments of the invention the top core wrap sheet and the bottom core wrap sheet may be formed as one integral sheet or may comprise separate portions around the absorbent material.

The absorbent article may further comprise a wetness indicator preferably placed between two attachment zones and/or in one or more attachment zones and/or between an attachment zone and an edge of the absorbent core. The wetness indicator may change appearance when contacted with liquid, e.g. wetness indicator may be configured to generate a color change signal that changes appearance when contacted with liquid. The wetness indicator may comprise a composition that changes appearance when contacted with liquid, in particular a composition comprising a pH indicator and/or a water soluble dye. The composition may comprise a stabilizer, a colorant, and a matrix.

The absorbent article may also comprise an acquisition layer as additional layer, configured to quickly acquire the liquid away from the topsheet so as to provide a good dryness for the wearer. Such an acquisition layer may be placed directly under the topsheet. The absorbent article may also comprise a distribution layer typically placed between the acquisition layer and the absorbent core. The acquisition and distribution layer may also be formed as one integral layer. The acquisition layer may comprise a non-woven material, for example a SMS or SMMS material, comprising a spunbonded, a melt-blown and a further spunbonded layer or alternatively a carded chemical-bonded nonwoven.

In an embodiment, the width of the first and second attachment zone (measured in in a transverse direction of the absorbent core) may be different from the width of the third and fourth attachment zone. Also the width of any one of the attachment zones may vary along a longitudinal direction of the absorbent core.

BRIEF DESCRIPTION OF FIGURES

The accompanying drawings are used to illustrate presently preferred non-limiting exemplary embodiments of devices of the present invention. The above and other advantages of the features and objects of the invention will become more apparent and the invention will be better understood from the following detailed description when read in conjunction with the accompanying drawings, in which:

FIGS. 28-35 illustrate yet other exemplary embodiments of an absorbent core according to the invention;

DESCRIPTION OF EMBODIMENTS

Definitions

Figure 1A:
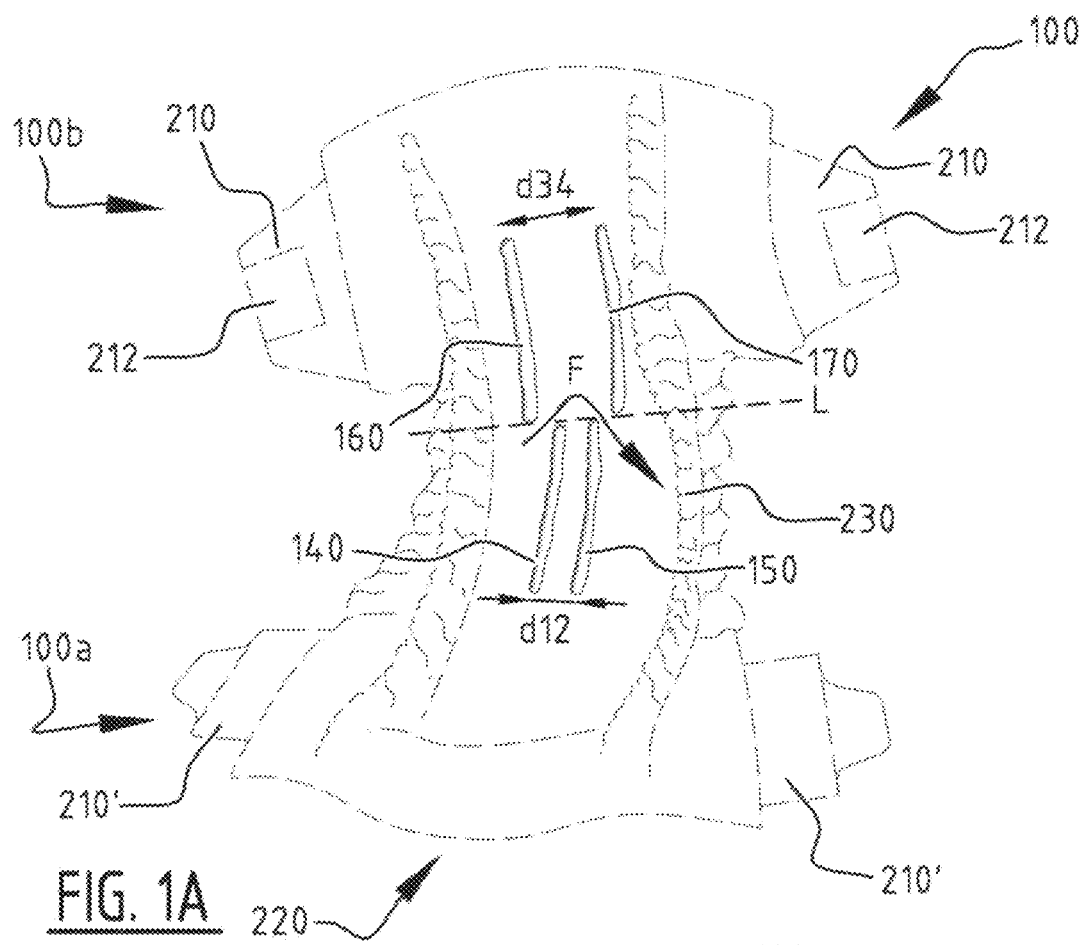
FIG. 1A is a perspective view of an exemplary embodiment of a diaper.

As used herein, the following terms have the following meanings:

"A", "an", and "the" as used herein refers to both singular and plural referents unless the context clearly dictates otherwise. By way of example, "an edge barrier" refers to one or more than one edge barrier.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or variations are appropriate to perform in the disclosed invention. However, it is to be understood that the value to which the modifier "about" refers is itself also specifically disclosed.

"Absorbent article", "absorbent garment", "absorbent product", "absorbing article", "absorbing garment". "absorbing product" and the like as used herein are used interchangeably and refer to devices that absorb and contain bodily exudates, and more specifically, refers to devices that are placed against or in proximity to the body of the wearer to absorb and contain the various liquids discharged from the body. Absorbent articles include but are not limited to feminine hygiene garments, baby diapers and pants, adult incontinence garments, various diaper and pants holders, liners, towels, absorbent inserts and the like.

"Absorbent core" as used herein refers to a three-dimensional part of the absorbent structure, comprising liquid-absorbing material, useful to permanently absorb and/or retain bodily exudates. "Absorbent component" as used herein refers to a structural constituent of an absorbent article. e.g., a piece of an absorbent core, such as one of multiple pieces in a multi-piece absorbent core. "Absorbent element" as used herein refers to a part of a functional constituent of an absorbent structure. e.g., a acquisition layer, a dispersion layer, core layer or a release structure formed of a material or materials having particular liquid handling characteristics suitable for the specific function.

"Absorbent fibrous polymer material" as used herein refers to an absorbent polymer material which is in thread-like from such as fibers, filaments, and the like so as to be less flowable in the dry state than particulates.

"Absorbent insert" as used herein refers to a device adapted for insertion into an "Absorbent layer" as used herein refers to a term referring to a discrete, identifiable sheet-like or web-like element of an absorbent article which may remain detached and relatively movable with respect to another such element or may be attached or joined so as to remain permanently associated with another such element. Each absorbent layer may itself include a laminate or combination of several layers, sheets and/or webs of similar or diverse compositions.

"Absorbent polymer material", "absorbent gelling material", "AGM", "superabsorbent", "superabsorbent material", "super absorbent polymer", "SAP" and the like as used herein are used interchangeably and refer to any suitable particulate (e.g., flaked, particulate, granular, or powdered) or fibrous cross linked polymeric materials that can absorb at least 5 times and preferably at least about 10 times or more its weight of an aqueous 0.9% saline solution as measured using the Centrifuge Retention Capacity test (EDANA 441.2-01).

"Absorbent polymer material area" as used herein refers to the area of the absorbent structure wherein adjacent layers are separated by a multiplicity of absorbent polymer material. Incidental contact areas between these adjacent layers within the absorbent particulate polymer material area may be intentional (e.g bond area's) or unintentional (e.g. manufacturing artifacts).

"Absorbent particulate polymer material" as used herein refers to an absorbent polymer material which is in particulate form such as powders, granules, flakes and the like so as to be flowable in the dry state.

"Absorption" as used herein refers to the process by which a liquid is taken up within a material.

"Absorption rate" as used herein refers to the rate of absorption of liquid, i.e. the amount of liquid which is absorbed per unit of time, typically by an absorbent component, element and/or absorbent layer of the absorbent article, structure and/or core.

"Acquisition layer". "acquisition region". "acquisition surface" or "acquisition material" and the like as used herein refer to the layer overlying the absorbent core having a faster liquid uptake and/or distribution capability.

"Absorbency" is the ability of a material to take up fluids by various means including capillary, osmotic, solvent, chemical and/or other action.

"Adult incontinence garment" as used herein refers to absorbent articles intended to be worn by incontinent adults, for absorbing and containing bodily exudates.

"Adhesion" as used herein refers to the force that holds different materials together at their interface.

"Adhesive" as used herein refers to a material, which may or may not be flowable in solution or when heated, that is used to bond materials together.

"Adsorption" as used herein refers to the process by which a liquid is taken up by the surface of a material.

"Airlaying" as used herein refers to forming a web by dispersing fibers or particles in an air stream and condensing them from the air stream onto a moving screen by means of a pressure and/or vacuum; a web of fibers produced by airlaying is herein referred to an "airlaid"; an airlaid web bonded by one or more techniques to provide fabric integrity is herein referred to an "airlaid nonwoven".

"Apparent density". "density" as used herein refers to the basis weight of the sample divided by the caliper with appropriate unit conversions incorporated therein. Apparent density used herein has the unit g/cm3.

"Attach", "attached" and "attachment" as used herein are synonymous with their counterparts of the terms "fasten", "affix", "secure", "bind", "join" and "link".

"Baby diaper" as used herein refers to absorbent articles intended to be worn by children, for absorbing and containing bodily exudates which the user draws up between the legs and fastens about the waist of the wearer.

"Baby pants" as used herein refers to absorbent articles marketed for use in transitioning children from diapers to underwear intended to cover the lower torso of children, so as to absorb and contain body exudates which article is generally configured like a panty garment and manufactured with a completed waist encircling portion, thereby eliminating the need for the user to fasten the article about the waist of the wearer.

"Back region" as used herein refers to the portion of an absorbent article or part thereof that is intended to be positioned proximate the back of a wearer.

"Backing" as used herein refers to a web or other material that supports and reinforces the back of a product.

"Basis weight" is the weight per unit area of a sample reported in grams per square meter, g/m2 or gsm.

"Bodily exudates", "body exudates", "bodily fluids". "body fluids", "bodily discharges", "body discharges", "fluid(s)", "liquid(s)", "fluid(s) and liquid(s) and the like as used herein are used interchangeably and refer to, but are not limited to urine, blood, vaginal discharges, breast milk, sweats and fecal matter.

"Binder", "adhesive", "glue", "resins", "plastics" and the like as used herein are used interchangeably and refer to substances, generally in a solid form (e.g. powder, film, fiber) or as a foam, or in a liquid form (e.g. emulsion, dispersion, solution) used for example by way of impregnation, spraying, printing, foam application and the like used for attaching or bonding functional and/or structural components, elements and materials, for example including heat and/or pressure sensitive adhesives, hot-melts, heat activated adhesives, thermoplastic materials, chemical activated adhesives/solvents, curable materials and the like.

"Bond strength" as used herein refers to the amount of adhesion between bonded surfaces. It is a measure of the stress required to separate a layer of material from the base to which it is bonded. "Capillary action", "capillarity", or "capillary motion" and the like as used herein are used to refer to the phenomena of the flow of liquid through porous media.

"Chassis" as used herein refers to a foundational constituent of an absorbent article upon which the remainder of the structure of the article is built up or overlaid, e.g., in a diaper, the structural elements that give the diaper the form of briefs or pants when configured for wearing, such as a backsheet, a topsheet, or a combination of a topsheet and a backsheet.

"Cellulose fibers" as used herein refers to naturally occurring fibers based on cellulose, such as, for example cotton, linen, etc; wood pulp fibers are one example of cellulose fibers; man-made fibers derived from cellulose, such as regenerated cellulose (rayon), or partially or fully acetylated cellulose derivatives (e.g. cellulose acetate or triacetate) are also considered as cellulose fibers.

"Cluster" or the like as used herein refers to an agglomeration of particles and/or fibers.

"Chemically stiffened fibers", chemically modified fibers", "chemically cross-linked fibers", "curly fibers" and the like as used herein are used interchangeably and refer to any fibers which have been stiffened by chemical means to increase stiffness of the fibers under both dry and aqueous conditions, for example by way of addition of chemical stiffening agents (e.g. by coating, impregnating, etc), altering the chemical structure of the fibers themselves (e.g. by cross-linking polymer chains, etc) and the like.

"Cohesion" as used herein refers to the resistance of similar materials to be separated from each other.

"Compartment" as used herein refers to chambers, cavities, pockets and the like.

"Comprise," "comprising," and "comprises" and "comprised of" as used herein are synonymous with "include", "including", "includes" or "contain", "containing". "contains" and are inclusive or open-ended terms that specify the presence of what follows e.g. a component and do not exclude or preclude the presence of additional, non-recited components, features, elements, members, steps, known in the art or disclosed therein.

"Coverstock" as used herein refers to a lightweight nonwoven material used to contain and conceal an underlying absorbent core material; examples are the facing layer or materials that cover the absorbent cores of feminine hygiene garment s, baby diapers and pants and adult incontinence garments.

"Crotch region" of an absorbent article as used herein refers to about 50% of the absorbent article's total length (i.e., in the y-dimension), where the crotch point is located in the longitudinal center of the crotch region. That is, the crotch region is determined by first locating the crotch point of the absorbent article, and then measuring forward and backward a distance of 25% of the absorbent article's total length.

"Cross direction (CD)", "lateral" or "transverse" and the like as used herein are used interchangeably and refer to a direction which is orthogonal to the longitudinal direction and includes directions within +45° of the transversal direction.

"Curing" as used herein refers to a process by which resins, binders or plastics are set into or onto fabrics, usually by heating, to cause them to stay in place; the setting may occur by removing solvent or by cross-linking so as to make them in soluble.

"Diaper", "conventional diaper", "diaper-like", "diaper-like garment" and the like as used herein are used interchangeably and refer to disposable absorbent articles, which typically include a front waist portion and a back waist portion which may be releasable connected about the hips of the wearer during use by conventional fasteners such as adhesive tape fasteners or hook and loop type fasteners. In use, the article is positioned between the legs of the wearer and the fasteners are releasable attached to secure the back waist portion to the front waist portion of the diaper, thereby securing the diaper about the waist of the wearer. The front waist portion and a back waist portion are connected by relatively non-stretchable or stretchable members (the term "stretchable" as used herein refers to materials that are extensible when forces are applied to the material, and offer some resistance to extension). Hence, such articles are generally not configured to be pulled up or down over the hips of the wearer when the fasteners are attached.

"Dispersion layer", "dispersion region", "dispersion surface" or "dispersion material" and the like as used herein refer to the layer overlying the absorbent core having a faster liquid uptake and dispersion capability.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Drylaying" as used herein refers to a process for making a nonwoven web from dry fiber; these terms apply to the formation of carded webs, as well as to the air laying formation of random webs; a web of fibers produced by drylaying is herein referred to as a "drylaid"; a drylaid web bonded by one or more techniques to provide fabric integrity is herein referred to a "drylaid nonwoven".

"Dry strength" as used herein refers to the strength of a joint determined in dry state conditions, immediately after drying under specified conditions or after a period of conditioning in the standard laboratory atmosphere.

"Essentially cellulose free". "substantially fluffless" or "little to no cellulose fibers" as used herein refers to an absorbent article, structure, core component and/or element containing less than 20% by weight cellulosic fibers, less than 10% cellulosic fibers, less than 5% cellulosic fibers, no cellulosic fibers, or no more than an immaterial amount of cellulosic fibers which do not materially affect the thinness, flexibility or absorbency thereof.

"Essentially fluffless" or "little to no fluff pulp" as used herein refers to an absorbent article, structure, core, component and/or element containing less than 20% by weight fluff pulp, less than 10% fluff pulp, less than 5% fluff pulp, no fluff pulp, or no more than an immaterial amount of fluff pulp which do not materially affect the thinness, flexibility or absorbency thereof.

"Fabric" as used herein refers to a sheet structure made from fibers, filaments and/or yarns. "Feminine hygiene garments" as used herein refer to absorbent hygiene articles intended to be worn by woman, for absorbing and containing body exudates.

"Fiber" as used herein refers to the basic threadlike structure from which nonwovens, yarns and textiles are made. It differs from a particle by having a length at least 4 times its width; "Natural fibers" are either of animal (wool, silk), vegetable (cotton, flax, jute) or mineral (asbestos) origin, while "Man-made fibers" may be either polymers synthesized from chemical compounds (polyester, polypropylene, nylon, acrylic etc.) or modified natural polymers (rayon, acetate) or mineral (glass). "Fiber" and "filament" are used interchangeably.

"Fluff pulp" or "Pulp fluff" as used herein refers to wood pulp specially prepared to be drylaid. The fibers can be either natural or synthetic or a combination thereof.

"Front region" as used herein refers to the portion of an absorbent article or part thereof that is intended to be positioned proximate the front of a wearer.

"Garment facing layer" as used herein refers to elements of the chassis that form the outer surface of the absorbent article, such as the backsheet, the side panels, the waist fasteners, and the like, when such elements are present.

"Heat activated adhesive" as used herein refers to a dry adhesive that is rendered tacky or fluid by application of heat or heat and pressure to the assembly.

"Heat sealing adhesive" as used herein refers to a thermoplastic adhesive which is melted between the adherent surfaces by heat application to one or both of the adjacent adherent surfaces.

"High loft" as used herein refers to general term of low density, thick or bulky fabrics.

"Hot-melt adhesive" as used herein refers to a solid material that melts quickly upon heating, then sets to a firm bond upon cooling; used for almost instantaneous bonding.

"Hydrophilic" as used herein refers to having an affinity for being wetted by water or for absorbing water.

"Hydrophobic" as used herein refers to lacking the affinity for being wetted by water or for absorbing water.

"Immobilization layer" as used herein refers to a layer able to be applied to the absorbent polymer material or absorbent polymer material area with the intent to gather, bond and/or immobilize absorbent material and/or absorbent layer.

"Join", "joined" and "joining" as used herein refers to encompassing configurations wherein an element is directly secured to another element by affixing the element directly to the other element, as well as configurations wherein the element is indirectly secured to the other element by affixing the element to an intermediate member or members which in turn is or are affixed to the other element.

"Knitting" as used herein refers to the technique for interlocking loops of fibers with needles or similar devices.

"Layer" refers to identifiable components of the absorbent article, and any part referred to as a "layer" may actually comprise a laminate or combination of several sheets or webs of the requisite type of materials. As used herein, the term "layer" includes the terms "layers" and "layered."

"Upper" refers to the layer of the absorbent article which is nearest to and/or faces the wearer facing layer; conversely, the term "lower" refers to the layer of the absorbent article which is nearest to and/or faces the garment facing layer. "Layer" is three dimensional structure with a x dimension width, y dimension length, and z-dimensions thickness or caliper, said x-y dimensions being substantially in the plane of the article, however it should be noted that the various members, layers, and structures of absorbent articles according to the present invention may or may not be generally planar in nature, and may be shaped or profiled in any desired configuration.

"Machine direction (MD)", "longitudinal" and the like as used herein are used interchangeably and refer to a direction running parallel to the maximum linear dimension of the structure and includes directions within ±45' of the longitudinal direction.

"Major surface" as used herein refers to a term used to describe the surfaces of greatest extent of a generally planar or sheet-like structural element and to distinguish these surfaces from the minor surfaces of the end edges and the side edges, i.e., in an element having a length, a width, and a thickness, the thickness being the smallest of the three dimensions, the major surfaces are those defined by the length and the width and thus having the greatest extent.

"Mass flow" as used herein refers to the flow of a liquid from one absorbent element or component to another absorbent element or component by channel flow action.

"Mechanical bonding" as used herein refers to a method of bonding fibers by entangling them. This can be achieved by needling, stitching with fibers or by the use of high-pressure air or water jets and the like.

"Nonwoven" as used herein refers to manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as melt blowing, spun bonding, solvent spinning, electrospinning, and carding. The basis weight of nonwoven fabrics is usually expressed in grams per square meter (gsm).

"Pant", "training pant", "closed diapers", "prefastened diapers", "pull-on diapers" and "diaper-pants" and the like as used herein are used interchangeably and refer to absorbent articles which are typically applied to the wearer by first leading the feet into the respective leg openings and subsequently pulling the pants from the feet to waist area over the hips and buttocks of the wearer and which are capable of being pulled up or down over the hips of the wearer. Typically, such articles may include a front waist portion and a back waist portion which may be connected about the hips of the wearer by integral or releasable members. A pant may be preformed by any suitable technique including, but not limited to, joining together portions of the article using refastenable and/or nonrefastenable bonds (e.g., seam, weld, adhesive, cohesive bond, fastener, etc.). A pant may be preformed anywhere along the circumference of the article (e.g., side fastened, front waist fastened).

"Polymer" as used herein refers to but is not limited to, homopolymers, copolymers, such as for example, block, graft, random and alternating copolymers, terpolymers, etc. and blends and modifications thereof. Unless otherwise specifically limited, the term "polymer" includes all possible spatial configurations of the molecule and include, but are not limited to isotactic, syndiotactic and random symmetries.

"Rear" as used herein refers to the portion of an absorbent article or part thereof that is intended to be positioned proximate the back of the wearer.

"Release structure", "release region", "release surface" or "release material" and the like as used herein are used interchangeably and refer to a structure in fluid communication with the absorbent core having a larger relative liquid absorption capacity and/or rate allowing it to quickly take up, temporarily hold and releasing liquids.

"Resin" as used herein refers to a solid or semisolid polymeric material.

"Thermobonding" as used herein refers to a method of bonding fibers by the use of heat and/or high-pressure.

"Thermoplastic" as used herein refers to polymeric materials that have a melting temperature and can flow or be formed into desired shapes on the application of heat at or below the melting point.

"Ultrasonic" as used herein refers to the use of high frequency sound to generate localized heat through vibration thereby causing thermoplastic fibers to bond to one another.

"Water-absorbing". "liquid-absorbing", "absorbent", "absorbing" and the like as used herein are used interchangeably and refer to compounds, materials, products that absorb at least water, but typically also other aqueous fluids and typically other parts of bodily exudates such as at least urine or blood.

"Wearer facing layer" as used herein refers to elements of the chassis that form the inner surface of the absorbent article, such as the topsheet, the leg cuffs, and the side panels, etc., when such elements are present.

"Weaving" as used herein refers to the process of interlacing two or more sets of yarns at right angles to form a fabric; a web of fibers produced by weaving is herein referred to as a "woven".

"Web material" as used herein refers to an essentially endless material in one direction, i.e. the longitudinal extension or the length, or the x-direction in Cartesian coordinates relative to the web material. Included in this term is an essentially unlimited sequence of pieces cut or otherwise separated from an essentially endless material. Often, though not necessarily, the web materials will have a thickness dimension (i.e. the z-direction) which is significantly smaller than the longitudinal extension (i.e. in x-direction). Typically, the width of web materials (they-direction) will be significantly larger than the thickness, but less than the length. Often, though not necessarily, the thickness and the width of such materials is essentially constant along the length of the web. Without intending any limitation, such web materials may be cellulosic fiber materials, tissues, woven or nonwoven materials and the like. Typically, though not necessarily, web materials are supplied in roll form, or on spools, or in a folded state in boxes. The individual deliveries may then be spliced together to form the essentially endless structure. A web material may be composed of several web materials, such as multilayer non-woven, coated tissues, nonwoven/film laminates. Web materials may comprise other materials, such as added binding material, particles, hydrophilizing agents and the like.

"Wet burst strength" is a measure of a layer's ability to absorb energy, when wet and subjected to deformation normal to the plane of the web.

"Wet strength" as used herein refers to the strength of a joint determined immediately after removal from a liquid in which it has been immersed under specified conditions of time, temperature and pressure. The term is commonly used in the art to designate strength after immersion in water.

"Wetlaying" as used herein refers to the forming a web from an aqueous dispersion of fibers by applying modified paper making techniques; a web of fibers produced by wetlaying is herein referred to as a "wetlaid".

"Wood pulp" as used herein refers to cellulosic fibers used to make viscose rayon, paper and the absorbent cores of products such as feminine hygiene garments, baby diapers and pants and adult incontinence garments.

"X-y dimension" as used herein refers to the plane orthogonal to the thickness of the article, structure or element. The x- and y-dimensions correspond generally to the width and length, respectively, of the article, structure or element.

"Z-dimension" as used herein refers to the dimension orthogonal to the length and width of the article, structure or element. The z-dimension corresponds generally to the thickness of the article, structure or element.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

The same or similar features and components are indicated with the same reference numerals throughout the figures.

As will be illustrated with embodiments of the figures, the absorbent article in accordance with embodiments of the invention can be better tailored to the needs of the wearer, wherein any one or more of the following may be taken into account: sex, age, weight, type of bodily exudates (urine, stool, etc.), pelvis size, etc. Not only for baby diapers but also for adult incontinence absorbent articles, the liquid absorption and management properties can be significantly improved.

FIGS. 1A-1D

Figure 1B:
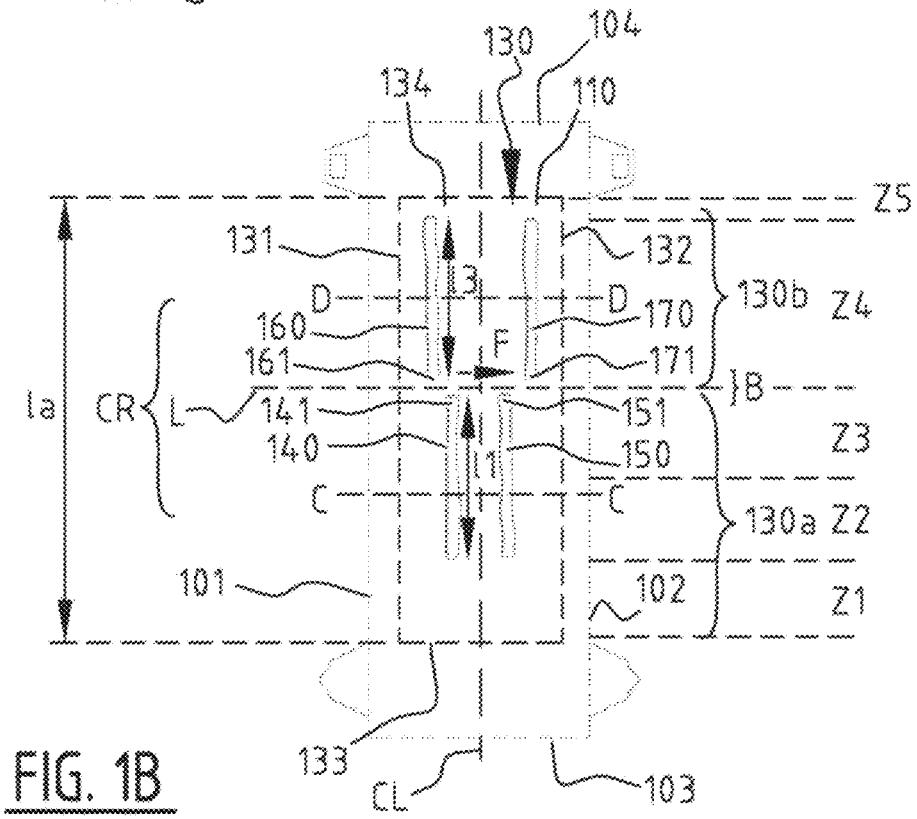
FIG. 1B is a top plan view of the diaper of FIG. 1A.

FIGS. 1A, 1B, 1C and 1D illustrate an exemplary embodiment of an absorbent article, here a diaper. FIG. 1B shows the absorbent article in its flat out, un-contracted state with the wearer side facing the viewer. The skilled person understands that the absorbent article may also be a pant or an adult incontinence garment or the like. The absorbent article 100 comprises a liquid pervious topsheet, a liquid impervious backsheet, and an absorbent core 130 positioned in between the topsheet and the backsheet. The absorbent core 130 comprises absorbent material 105 between a top core wrap sheet 110 and a back core wrap sheet 120. Absorbent core 130 has a first and second longitudinal edge 131, 132 and a first and second transverse edge 133, 134.

The absorbent core 130 is provided with a plurality of attachment zones 145, 155, 165, 175 comprising at least a first attachment zone 145 and a second attachment zone 155. The first and second attachment zones extend next to each other from the crotch region CR in the direction of the first and/or second transverse edge 133, 134. In first and second attachment zone 145, 155 the top core wrap sheet 110 is attached to the back core wrap sheet 120 along an attachment which extends, seen in a transverse direction of the absorbent core, over a transverse distance which is at least 1 mm, preferably at least 2 mm, more preferably at least 3 mm, most preferably at least 4 mm; and/or along a discontinuous attachment at a plurality of locations at a distance of each other, seen in the transverse direction of the absorbent core. In that manner, upon wetting of the absorbent material, a first and second channel 140, 150 are created at said first and second attachment zone 145, 155, respectively.

Absorbent article 100 is provided at said top core wrap sheet with at least a first and a second attachment zone 145, 155 located a distance d12 of each other. In that manner a first and second channel 140, 150 formed upon wetting, each extend from a crotch region CR in the direction of the first transverse edge 133. Preferably the distance d12 is between 10 mm and 50 mm, more preferably between 15 and 30 mm. Preferably, the length of the first and second channel is substantially the same, more preferably the length l1 of the first channel and the length l2 of the second channel is between 60 mm and 140 mm, more preferably between 75 mm and 125 mm. Preferably, the distance between the first attachment zone 145 and the first longitudinal side 131 is between 20 and 30 mm, and the distance between the second attachment zone 155 and the second longitudinal side 132 is between 20 and 30 mm. Preferably, the distance between the first/second attachment zone 145, 155 and the transverse edge 133 is between 50 and 125 mm, more preferably between 75 and 115 mm.

First channel 140 and second channel 150 are substantially parallel and run in the longitudinal direction of absorbent core 130. However, it is also possible for first and second channel 140, 150 to extend under a small angle with respect to the longitudinal direction of absorbent core 130. e.g. an angle between 5 and 10°. For example, first and second attachment zone 145, 155 (and hence first and second channel 140, 150) may be diverging slightly outwardly in the direction of first transverse edge 133. Preferably first channel 140 and second channel 150 are arranged symmetrically with respect to a longitudinal center line CL of absorbent core 130.

Absorbent article 100 is further provided with a third and a fourth channel 160, 170 located at a distance d34 of each other. Third and fourth channel 160, 170 each extend from crotch region CR in the direction of second transverse edge 134. The distance d12 between first and second channel 140, 150 is different from the distance d34 between third and fourth channel 160, 170. Preferably the distance d34 is between 25 mm and 80 mm, more preferably between 35 mm and 55 mm.

Preferably, the length of the third and fourth channel 160, 170 is substantially the same, more preferably the length l3 of the third channel and the length l4 of the fourth channel is between 30 mm and 130 mm, more preferably between 30 mm and 70 mm. Preferably, the distance between the third attachment zone 165/third channel 160 and the first longitudinal side 131 is between 20 and 30 mm, and the distance between the fourth attachment zone 175 and the second longitudinal side 132 is between 20 and 30 mm. Preferably, the distance between the third/fourth attachment zone 165, 175 and the transverse edge 134 is between 30 mm and 100 mm, more preferably between 40 mm and 75 mm.

Third channel 160 and fourth channel 170 are substantially parallel and run in the longitudinal direction of absorbent core 130. However, it is also possible for third and fourth channel 160, 170 to extend under a small angle with respect to the longitudinal direction of absorbent core 130, e.g. an angle between 5 and 10°. For example, third and fourth channel 160, 170 may be diverging slightly outwardly in the direction of second transverse edge 134. Preferably third channel 160 and fourth channel 170 are arranged symmetrically with respect to a longitudinal center line CL of absorbent core 130.

Preferably, the distance between an end point 141 of first channel 140 and an end point 161 of third channel 160 is smaller than 25 mm, more preferably smaller than 20 mm. Similarly, preferably, the distance between an end point 151 of second channel 150 and an end point 171 of fourth channel 170 is smaller than 25 mm, more preferably smaller than 20 mm. More preferably, endpoints 141, 151, 161 and 171 are located on substantially the same transverse line L functioning as a fold line along which the diaper can be folded in two.

Figure 1C:
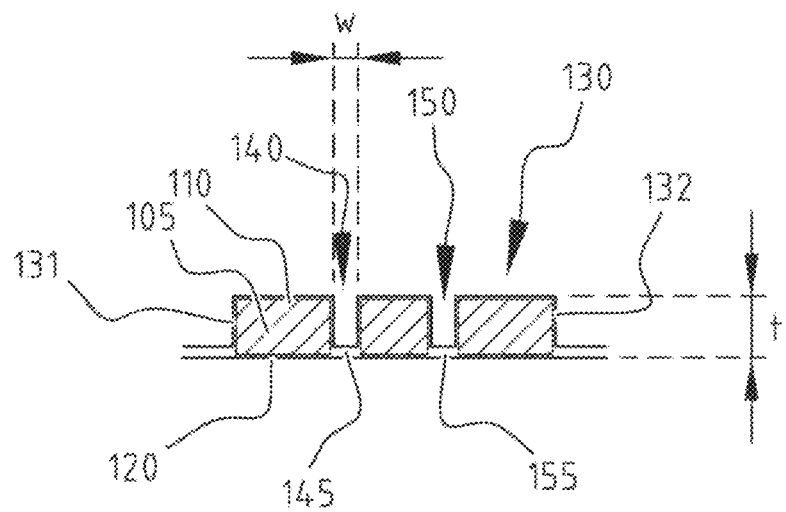
FIG. 1C is a schematic cross-section along line C-C of FIG. 1B.
Figure 1D:
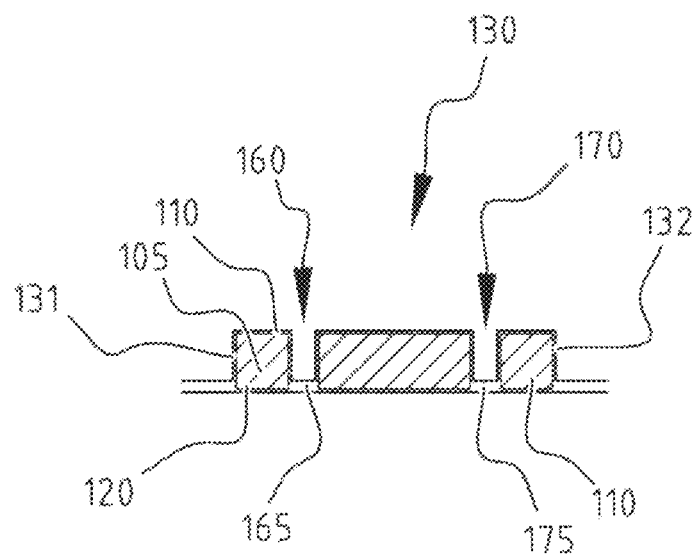
FIG. 1D is a schematic cross-section along line D-D of FIG. 1B.

First, second, third and fourth channel 140, 150, 160, 170 each have a bottom which forms the attachment zone 145, 155, 165, 175, see FIG. 1C and FIG. 1D. At bottom 145, 155, 165, 175 top core wrap sheet 110 is attached to back core wrap sheet 120. The width w of the bottom, seen in a transverse direction of absorbent core 130, is preferably larger than 2 mm, more preferably larger than 3 mm and even more preferable larger than 4 mm. To that end the attachment between top core wrap sheet 110 and the back core wrap sheet 120 may be an attachment extending over a transverse distance which is at least 2 mm, preferably at least 3 mm, more preferably at least 4 mm; and/or the attachment may be a discontinuous attachment in a plurality of locations at a distance of each other, seen in a transverse direction of absorbent core 130.

Preferably the attachment (i.e. the joint) at the bottom between the top core wrap sheet and the back core wrap sheet is realized by any one of the following or a combination thereof: pressure bonding, thermobonding, sonic bonding, chemical bonding, adhesive, mechanical bonding. The attachment/joining may be a direct or indirect attachment/joining. E.g. an adhesive and/or other intermediate material may be inserted between the top core wrap sheet and the back core wrap sheet. For example, a structure or layer having no or less absorption capacity than the absorbent material may be added in between the top core wrap sheet and the back core wrap in the attachment area.

Outside of the plurality of channels 140, 150, 160, 170, absorbent core 130 has a maximum thickness t. Preferably, each channel 140, 150, 160, 170 extends through at least 90% of the maximum thickness of absorbent core 130, more preferably through 100% of the thickness of absorbent core 130, such that, in the channel 140, 150, 160, 170, substantially no absorbent material is present that between top core wrap sheet 110 and back core wrap sheet 120. It is noted that the channel 140, 150, 160, 170 may be located below and/or above the attachment zones 145, 155, 165, 175, as will be explained in more detail below with reference to FIG. 14.

In a possible embodiment the attachment 145, 155, 165, 175 between top core wrap sheet 110 and back core wrap sheet 120, here at a bottom of each channel 140, 150, 160, 170, is a semi-permanent attachment configured to release after having been in contact with urine for a predetermined period of time, wherein said predetermined period of time is preferably smaller than 30 s.

Figure 9A:
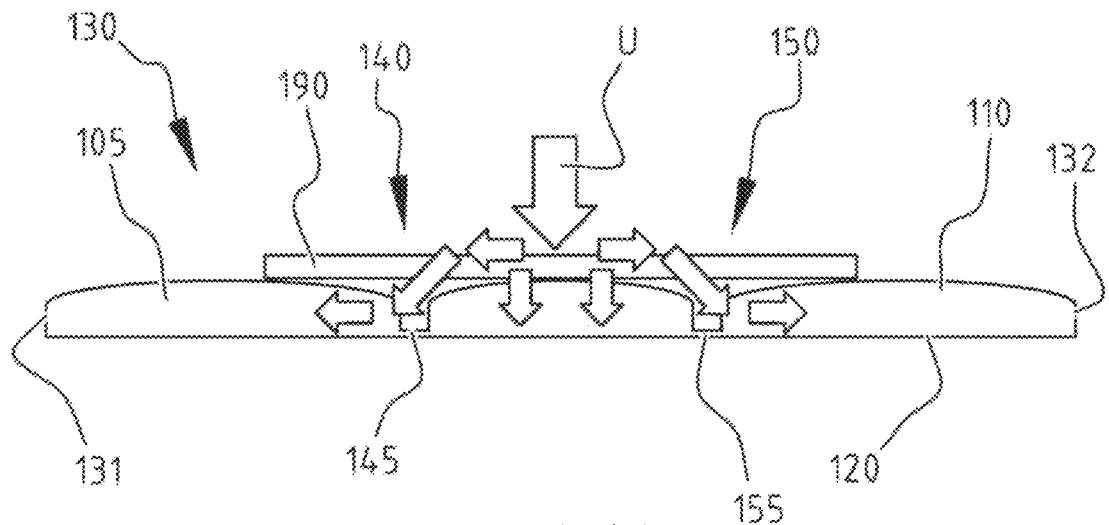
FIGS. 9A and 9B are cross-sectional views illustrating the effect of liquid being absorbed by the absorbent core of an exemplary embodiment of an absorbent article.
Figure 9B:
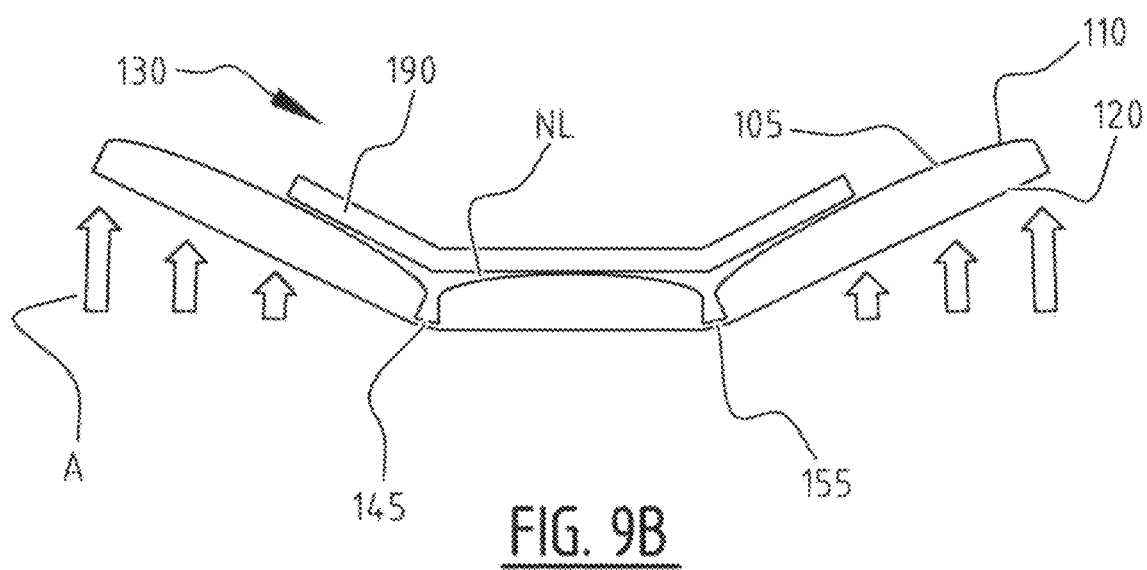

In another possible embodiment the attachment between top core wrap sheet 110 and back core wrap sheet 120, here at the bottom of each channel 140, 150, 160, 170, is a permanent attachment; and absorbent core 130 is configured such that, in a wetted state of absorbent core 130, the absorbent material extends over bottom 145, 155, 165, 175 of channel 140, 150, 160, 170. This is illustrated in FIGS. 9A and 9B for first and second channels 140, 150. Channels 140, 150, 160, 170 guide urine U or any other aqueous liquid through the side walls of channels 140, 150, 160, 170 into absorbent core 130. Those side walls create an additional path along which the liquid can flow into absorbent core 130 and enhance the diffusion of the liquid into absorbent core 130. Also, because of the swelling of the core material of absorbent core 130, the outer bands of absorbent core 130 will rotate around channels 140, 150, 160, 170 as indicated by arrows A in FIG. 9B. In that manner the diaper takes the shape of a tub or cup, such that any liquid NL which would not yet be absorbed by the absorbent material 105 is maintained in the tub shape. This results in a better protection against leakage and a diaper fitting perfectly to the body. Hence the diaper of FIGS. 1A-1D will create more freedom of movement for the wearer of a wetted diaper.

It is clear to the skilled person that the attachment zones may be provided by means of continuous attachments in the transversal direction of the absorbent core and/or continuous attachments in the longitudinal direction of the absorbent core and/or discontinuous attachments in the transversal direction of the absorbent core and/or discontinuous attachments in the longitudinal direction of the absorbent core.

Absorbent core 130 has a front portion 130a extending at one side of a transverse crotch line which corresponds in this embodiment with fold line L, and a rear portion 130b extending at the other side of the transverse crotch line L. First and second channel 140, 150 extend at least in front portion 130a of absorbent core 130, and third and fourth channel 160, 170 extend at least in rear portion 130b of the absorbent core 130. Preferably the distance d12 between first and second channel 140, 150 in front portion 130a is smaller than the distance d34 between third and fourth channel 160, 170 in rear portion 130b.

Absorbent core 130 of FIGS. 1A and 1B is preferred for female persons. Absorbent core 130 has a first and second side edge 131, 132, a front edge 133 and a rear edge 134, wherein the absorbent core 130 is provided with a plurality of attachment zones 140, 150, 160, 170 where the top core wrap sheet is attached to the back core wrap sheet, and where preferably substantially no absorbent material is present. The plurality of attachment zones comprise at least a first and a second elongate attachment zone 140, 150 extending next each other, at least in the front portion of the absorbent core in the direction of the front edge 133, and a third and a fourth elongate attachment zone 160, 170 extending next to each other, at least in the rear portion 130b of the absorbent core 130, in the direction of the rear edge 134. It is noted that the first and second elongate attachment zone 140, 150 correspond with the third and fourth elongate attachment zone of claim 1, and that the third and fourth elongate attachment zone 160, 170 correspond with the first and fourth attachment zone of claim 1.

Measured in a transverse direction, a first largest distance d12 between the first and the second attachment zone 140, 150 is smaller than a second largest distance d34 between the third and the fourth attachment zone 160, 170. Preferably the second distance d34 is at least 5%, more preferably at least 10% bigger, even more preferably at least 20% bigger than a second distance d12. The distance d34 may be between 15 and 70% of the width of the absorbent core, more preferably between 20 and 50%; wherein preferably the distance d34 is between 10 mm and 100 mm, more preferably between 20 mm and 80 mm, even more preferably between 30 mm and 70. The distance d12 is between 5 and 60% of the width of the absorbent core, more preferably between 10 and 40%; wherein preferably the distance d12 is between 5 mm and 60 mm, more preferably between 10 mm and 50 mm, even more preferably between 15 mm and 40 mm. Due to the specific physiological structure of a female at the genital region, such a pattern has the advantage that liquid can be distributed over substantially the entire absorbent core, and that any leakage risks in various positions of the female wearer can be reduced.

The absorbent core 130 comprises a front portion 130a extending between the front edge 133 and a transverse crotch line L of the absorbent core 130, and a rear portion 130b extending between the rear edge 134 and the transverse crotch line L of the absorbent core 130. Preferably a distance between the transverse crotch line L and a transverse center line T extending perpendicular on the longitudinal direction of the absorbent core 130, through the middle of the absorbent core 130, is smaller than 10%, more preferably smaller than 5% of the length of the absorbent core 130. The first and the second elongate attachment zone 140, 150 each have a front end 142, 152 adjacent to absorbent material and a rear end 141, 151 adjacent to absorbent material; and the third and the fourth elongate attachment zone 160, 170 each have a rear end 162, 172 adjacent to absorbent material and a front end 161, 171 adjacent to absorbent material. In other embodiments the first zone 140 may be connected to the third zone 160, and the second zone 150 may be connected to the fourth zone 170.

Seen in a projection on the longitudinal direction of the absorbent core, preferably the first and the second attachment zone 140, 150 extend over a length which is more than the length of the third and fourth attachment zone 160, 170. The length of the first and the second attachment zone 140, 150 may be larger than 30 mm, preferably larger than 40 mm, more preferably larger than 50 mm. The length of the third and the fourth attachment zone may be larger than 30 mm, preferably larger than 40 mm, more preferably larger than 50 mm. The first attachment zone 140 and the second attachment zone 150 may be arranged symmetrically with respect to a longitudinal center axis of the absorbent core 130 extending between the front edge 133 and rear edge 134. Seen in a projection on a longitudinal direction, the first and second attachment zone 140, 150 do not overlap with the third and fourth attachment zone 160, 170. However, in other embodiments there may be some overlap.

The first attachment zone 140 may be separated from the third attachment zone 160 by absorbent material, and the second attachment zone 150 may be separated from the fourth attachment zone 170 by absorbent material. The absorbent material may comprise cellulosic fluff pulp and/or superabsorbent particles. In some embodiments the absorbent material may be substantially fluffless.

In other non-illustrated embodiments, the first attachment zone 140 may also be connected to the third attachment zone 160 through a first semi-permanent attachment zone and the second attachment zone 150 may also be connected to the fourth attachment zone 170 through a second semi-permanent attachment zone. The semi-permanent attachment may be configured to release after having been in contact with urine for a predetermined period of time.

The first attachment zone 140 and the second attachment zone 150 may be substantially parallel and extend in a longitudinal direction of the absorbent core 130; or an angle between the first attachment zone 140 and a longitudinal direction of the absorbent core 130 and an angle between the second attachment zone 150 and the longitudinal direction of the absorbent core 130 may be smaller than 5° (not illustrated). The third attachment zone 160 and the fourth attachment zone 170 may be substantially parallel and extend in a longitudinal direction of the absorbent core 130; or an angle between the third attachment zone 160 and a longitudinal direction of the absorbent core 130 and an angle between the fourth attachment zone 170 and the longitudinal direction of the absorbent core 130 may be smaller than 5° (not illustrated). Seen in a projection on a longitudinal direction of the absorbent core 130, the plurality of attachment zones together may cover at least 30%, preferably at least 40% of a length of the absorbent core 130.

Preferably the plurality of attachment zones comprise substantially no absorbent material, and may be permanent attachment zones which remain attached when wetted. In other embodiments, in the first and second attachment zone 140, 150, the top core wrap sheet may be attached to the back core wrap sheet through permanent and semi-permanent attachment portions, said semi-permanent portions may be being configured to release after having been in contact with liquid whilst said permanent portions may be configured not to release after having been in contact with liquid. In a possible embodiment, the plurality of channels 140, 150, 160, 170 together cover at least 60%, preferably at least 70% of the length la of absorbent core 130; indeed, in the embodiment of FIG. 1A-1D the channels cover a length equal to l1+l3 which is more than 60% of the length la of absorbent core 130.

The plurality of channels 140, 150, 160, 170 may be indicated with a color and/or with a pattern which is different from the color and/or pattern of topsheet. More in particular the area of the channels may comprise a print allowing a user to visually distinguish the channels. This print may be arranged on the topsheet, on the top core wrap sheet, on the back core wrap sheet, on the backsheet, or on any sheet in between the topsheet and the backsheet, as long as it is visible for a user. As the sheets may be partially transparent, the print may be arranged on a sheet in between the topsheet and the backsheet, as long as it is visible through the topsheet and/or the backsheet.

Preferably the print is visible when looking at the topsheet of the diaper. For example, a topsheet area above first and second channels 140, 150 may be printed with an ink of a first color and a topsheet area above third and fourth channels 160, 170 may be printed with the same color or with a different color. In that manner a user will be able to easily recognize the front and rear portion of a diaper, and will recognize more easily how to put on the diaper.

Preferably absorbent core 130 is provided with a plurality of attachment zones 140, 150, 160, 170 where the top core wrap sheet is attached to the back core wrap sheet, and where preferably substantially no absorbent material is present. Seen in a longitudinal direction of the absorbent core 130, looking from the front edge 133 to the rear edge 134, the absorbent core 130 comprises subsequently a first, second, third, fourth and fifth zone Z1, Z2, Z3, Z4, Z5.

The absorbent core 130 comprises a front portion 130a extending between the front edge 133 and a transverse crotch line L of the absorbent core, and a rear portion 130b extending between the rear edge 134 and the transverse crotch line L of the absorbent core 130. The first, second and third zone Z1, Z2, Z3 extend in the front portion 130a of the absorbent core and the fourth and fifth zone Z4, Z5 extend in the rear portion 130b. Preferably, in said first and fifth zone Z1, Z5 substantially no permanent attachment zones are present. However the first and/or fifth zone Z1, Z5 may comprise temporary secondary attachments that loosen upon wetting. The second zone Z2 comprises a first and a second permanent elongate front attachment zone 130, 140, said first and second front attachment zones 130, 140 extending from an edge of the first zone Z1 in the direction of the third zone Z3.

The fourth zone Z4 comprises a first and second rear elongate attachment zone 160, 170, said first and second rear attachment zone extending from an edge of the fifth zone Z5 in the direction of the third zone Z3. At least one of said second, third and fourth zone comprises a capillary bridging zone B allowing a liquid flow F between the first and the second side edge 131, 132 by capillary action through the absorbent material. The capillary bridging zone B extends between the first front attachment zone 140 and the first rear attachment zone 160, such that upon wetting of the absorbent material, a front and rear channel are created at said first front and rear attachment zone 140, 160, respectively, wherein the capillary bridging zone B extends between said front and rear channel. Preferably a minimum distance x between the first front attachment zone 140 and the first rear attachment zone 160 is larger than 3 mm more preferably larger than 5 mm. The capillary bridging zone B further extends between the second front attachment zone 150 and the second rear attachment zone 170, such that upon wetting of the absorbent material, a front and rear channel are created at said second front and rear attachment zone 150, 170, respectively, wherein the capillary bridging zone B further extends between said front and rear channel. Preferably a minimum distance x between the second front attachment zone 150 and the second rear attachment zone 170 is larger than 3 mm more preferably larger than 5 mm.

The use of at least one bridging zone B can improve the structure and integrity of the absorbent article. For example, the use of at least one bridging zone B may improve the formation of a tub-shape upon wetting of the absorbent article, see also FIG. 12 which shows the absorbent article in the wetted state. In the illustrated embodiment the at least one bridge zone B is located in the crotch region, preferably in the third or fourth zone.

The chassis of the diaper 100 in FIGS. 1A-1D comprises a liquid pervious topsheet (not shown in FIGS. 1C and 1D, but the topsheet is a layer above top core wrap sheet 110) and liquid impervious backsheet (not shown in FIGS. 1C and 1D, but the backsheet is a layer below back core wrap sheet 110). The topsheet may be attached to the top core wrap sheet 110. e.g. in the attachment zones 140, 150, 160, 170. Also, the backsheet may be attached to the back core wrap sheet 120, e.g. in the attachment zones 140, 150, 160, 170. Preferably the chassis further includes side panels or ears 210, elasticized leg cuffs 230 and elastic waist elements (not shown). A front end portion of diaper 100 is configured as a front waist region 100*a*. The opposite rear end portion is configured as a back waist region 100*b* of diaper 100. An intermediate portion of diaper 100 is configured as crotch region CR, which extends longitudinally between first and second waist regions 100*a* and 100*b*. Waist regions 100*a* and 100*b* may include elastic waist elements such that they gather about the waist of the wearer to provide improved fit and containment. Crotch region CR is that portion of diaper 100 which, when the diaper 100 is worn, is generally positioned between the wearer's legs. The periphery of diaper 100 is defined by the outer edges of the diaper 100 in which longitudinal edges 101, 102 run generally parallel to a longitudinal axis of diaper 100 and transverse end edges 103, 104 run between the longitudinal edges 101, 102 generally parallel to a transverse axis of diaper 100. The chassis also comprises a fastening system, which may include at least one fastening or securing member 212 and at least one landing zone 220. The various components within diaper 100 may be bound, joined or secured by any method known in the art, for example by adhesives in uniform continuous layers, patterned layers or arrays of separate lines, spirals or spots. Top core wrap sheet, topsheet, back core wrap sheet, backsheet, absorbent material and other components may be assembled in a variety of well-known configurations and are well known in the art.

Backsheet covers absorbent core 130 and preferably extends beyond the absorbent core 130 toward longitudinal edges 101, 102 and end edges 103, 104 of diaper 100 and may be joined with top sheet. Backsheet prevents bodily exudates absorbed by the absorbent core 130 and contained within diaper 100 from soiling other external articles that may contact the wearer, such as bed sheets and undergarments. In preferred embodiments, backsheet is substantially impervious to bodily exudates and comprises a laminate of a nonwoven and a thin plastic film such as a thermoplastic film. Backsheet may comprise breathable materials that permit vapor to escape from diaper 100 while still preventing bodily exudates from passing through backsheet. It may be semi-rigid, non-elastic and can be made fully or partially elasticized and include backing.

The top sheet which is located above the top core wrap sheet 110, is preferably soft, exhibits good strikethroughs and has a reduced tendency to rewet from the liquid absorbent material. Top sheet may be semi-rigid and non-elastic, or may be fully or partially elasticized. Topsheet is intended to be placed in close proximity to the skin of the wearer when diaper 100 is worn. Topsheet permits bodily exudates to rapidly penetrate it so as to flow more quickly toward absorbent core 130 via a top surface thereof and via the plurality of channels 140, 150, 160, 170, preferably not allowing such bodily exudates to flow back through topsheet. Topsheet may be constructed from any one of a wide range of liquid and vapor permeable, preferably hydrophilic, materials. The upper and lower surface of topsheet may be treated differently. Topsheet may include e.g. a surfactant on the upper surface so as to facilitate liquid transfer there through, especially at a central zone or area of topsheet located over absorbent core 130, and/or a hydrophobic agent on the lower surface to minimize the liquid contained within absorbent core 130 from contact wetting topsheet thereby reducing rewet values. Topsheet may be coated with a substance having rash preventing or rash reducing properties. Preferably, topsheet covers substantially the entire wearer facing area of diaper 100, including substantially all of front waist region 100*a*, back waist region 100*b*, and crotch region CR. Optionally, side panels 210, 210' and/or waist feature layers of the inner region may be formed from the same single topsheet material. Alternatively, topsheet may be formed from multiple different materials which vary across of topsheet. Such a multiple piece design allows for creation of preferred properties and different zones of the topsheet.

Absorbent core 130 may comprise any absorbent material that is generally compressible, conformable, non-irritating to the wearers skin, and capable of absorbing and retaining bodily exudates. Absorbent core 130 may comprise a wide variety of liquid absorbent materials commonly used in absorbent articles. Preferably, absorbent core 130 comprises fluff material, typically cellulosic fluff pulp. However, in other embodiments, absorbent core 130 may be substantially fluffless and comprise superabsorbent polymers. Also, absorbent core 130 may comprise a combination of cellulosic fluff pulp and superabsorbent polymers. Absorbent core 130 may be configured to extend substantially the full length and/or width of diaper 100. However, as in the embodiment of FIGS. 1A-1D, preferably absorbent structure 130 is not coextensive with the entire diaper 100 and is limited to certain regions of diaper 100 including crotch region CR. In various embodiments, the absorbent core 130 extends to the edges of diaper 100 but the absorbent material is concentrated in the crotch region CR or another target zone of the diaper 100. In FIGS. 1A-1D, absorbent core 130 is shown as having a substantially rectangular configuration, however, absorbent core 130 may be shaped differently, such as, elliptical, dogbane shaped, T-shaped or I-shaped. More in particular the width of the front portion 130*a* may be smaller than the width of the rear portion 130*b* of the absorbent core.

Examples of commonly occurring absorbent materials used for absorbent core 130 are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times its weight and in an aqueous solution containing 0.9 weight percent of sodium chloride.

Diaper 100) may also utilize a pair of containment walls or cuffs 230. Each cuff 230 is a longitudinally extending wall structure preferably positioned on each side of absorbent core 130 and spaced laterally from the center line CL. Preferably, cuffs 230 are attached, for example, by adhesive or sonic bonding to the lower structure. Preferably, cuffs 230 are equipped with elastic members. When released or otherwise allowed relaxing, the elastic members retract inwardly. When diaper 100 is worn, the elastic members function to contract cuffs 230 about the buttocks and the thighs of the wearer in a manner, which forms a seal between diaper 100, the buttocks and the thighs.

The waist regions 100a and 100b each comprise a central region and a pair of side panels or ears 210, 210' which typically comprise the outer lateral portions of the waist regions. These side panels 210, 210' may be unitary with the chassis or may be attached or joined thereto by any means know in the art. Preferably, the side panels 210 positioned in the back waist region 100b are flexible, extensible and/or elastic in at least the lateral direction. In another embodiment the side panels 210 are non-elastic, semi-rigid, rigid and/or stiff. In order to keep diaper 100 in place about the wearer, preferably at least a portion of the back waist region 100b is attached by fastening or securing members 212 to at least a portion of the front waist region 100a. The fastening or securing members 212 may be e.g. adhesive, mechanical fasteners, hook and loop features, conceivable strings and/or combinations thereof. The fastening or securing members 212 may also be co-adhesive such that they adhere to each other but not other materials. Preferably the materials making up the fastening or securing members 212 are flexible, extensible and/or elastic, allowing them to better conform to the shape and movements of the body and thus, to reduce the likelihood that the fastening system will irritate or injure the wearer's skin. Alternatively, the absorbent article may be pants and the like. In this configuration, the absorbent article may or may not have fastening members.

Diaper 100 may also employ additional layers, such as an acquisition layer and/or dispersion layer situated between topsheet and absorbent core 130, and/or coverstock layers, and/or other layers situated between absorbent core 130 and backsheet. An acquisition layer and/or dispersion layer serves to slow down the flow so that the liquid has adequate time to be absorbed by absorbent core 130. FIGS. 9A and 9B show an acquisition layer 190 above top core wrap layer 110.

Diaper 100 may also include such other features, components and elements as are known in the art including waistbands, waist cap features, elastics and the like to provide better fit, containment and aesthetic characteristics. These features may be assembled in a variety of well-known configurations and are well known in the art.

Figure 2A:
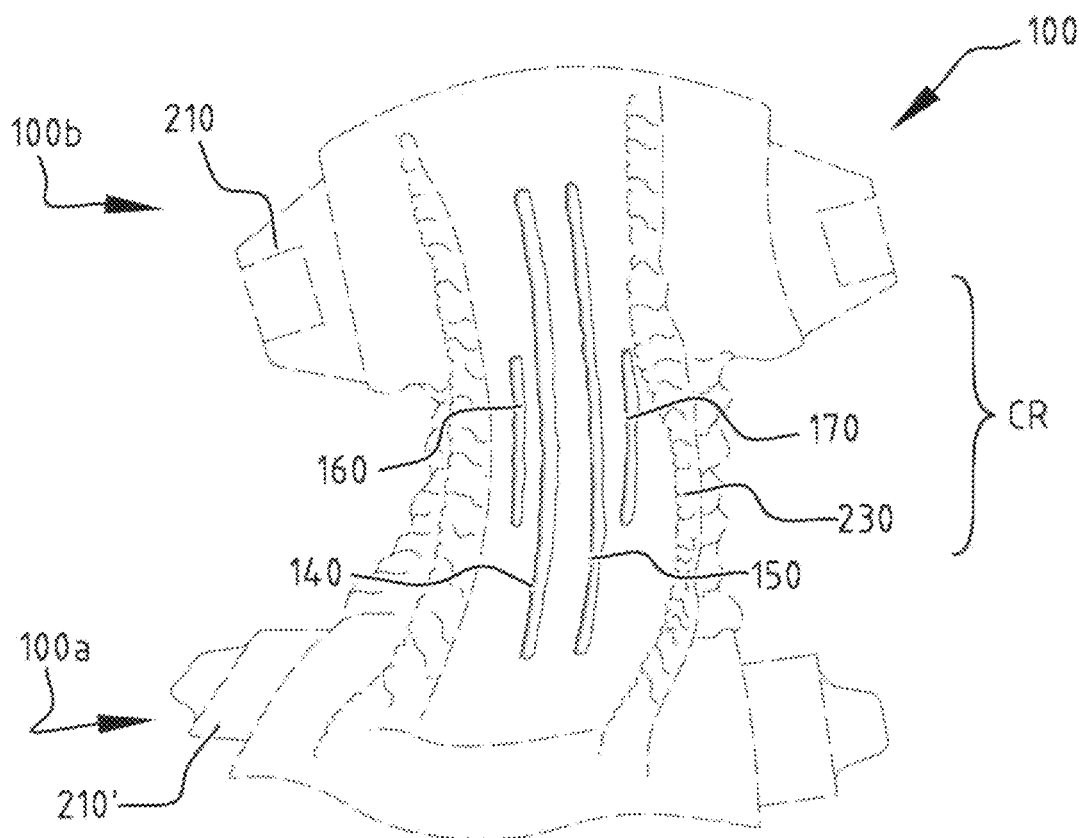
FIG. 2A is a perspective view of an exemplary embodiment of a diaper.
Figure 2B:
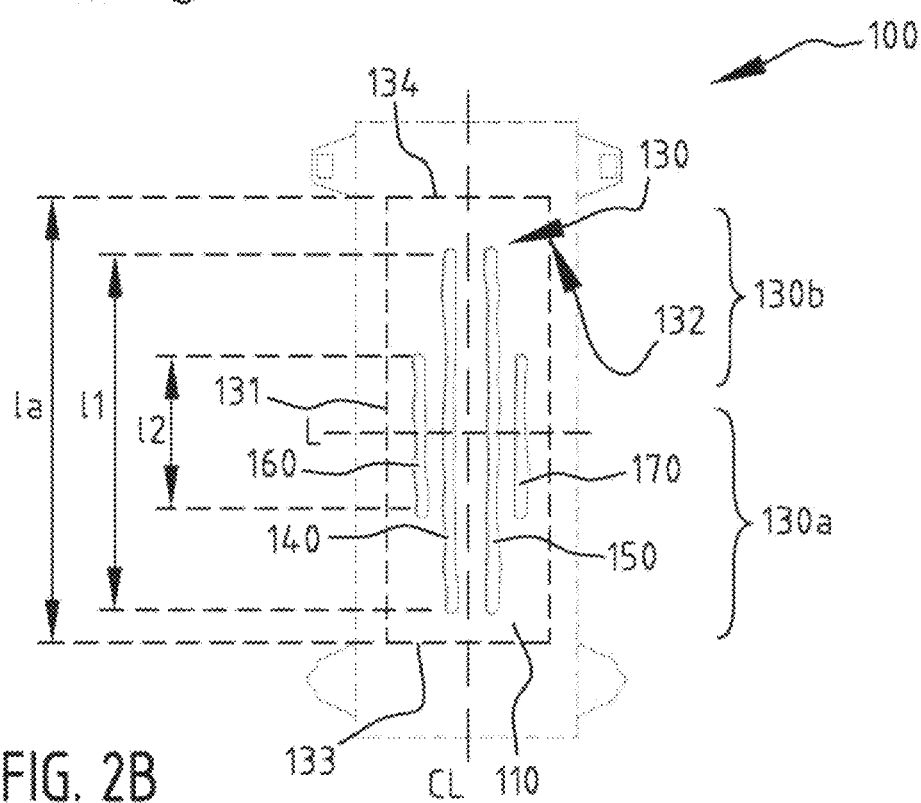
FIG. 2B is a top plan view of the diaper of FIG. 2A.

FIGS. 2A and 2B

FIGS. 2A and 2B illustrate another exemplary embodiment of a diaper 100. Diaper 100 comprises a liquid pervious topsheet, a liquid impervious backsheet, and an absorbent core 130 positioned in between topsheet and backsheet. Absorbent core 130 has a first and second longitudinal edge 131, 132 and a first and second transverse edge 133, 134. Absorbent article 100 is provided at the top core wrap sheet 110 with a first and a second attachment zone 145, 155 for creating a first and second channel 140, 150 located a distance d12 of each other. First and second channel 140, 150 each extend from a crotch region CR in the direction of the first transverse edge 133 and the second transverse edge 134. In this embodiment, preferably, first and second channel extend over more than 80% of the length of absorbent core 130. Preferably the distance d12 is between 10 mm and 50 mm, more preferably between 15 and 30 mm. Preferably, the length of the first and second channel is substantially the same, more preferably the length l1 of the first channel and the length l2 of the second channel is between 100 mm and 300 mm, more preferably between 100 mm and 250 mm. Preferably, the distance between the first/second attachment zone 145, 155 and the transverse edge 133 is between 50 and 125 mm, more preferably between 75 and 115 mm, and the distance between the first/second attachment zone 145, 155 and the transverse edge 134 is between 50 and 125 mm, more preferably between 75 and 115 mm.

First channel 140 and second channel 150 are substantially parallel and run in the longitudinal direction of absorbent core 130. However, it is also possible for first and second channel 140, 150 to extend under a small angle with respect to the longitudinal direction of absorbent core 130, e.g. an angle between 5 and 10°. For example, first and second channel 140, 150 may be diverging slightly outwardly in the direction of first transverse edge 133 and may be diverging slightly outwardly in the direction of second transverse edge 134. Preferably first channel 140 and second channel 150 are arranged symmetrically with respect to a longitudinal center line CL of absorbent core 130.

Absorbent article 100 is further provided with a third and a fourth channel 160, 170 located a distance d34 of each other. Third and fourth channel 160, 170 each extend from crotch region CR in the direction of first and second transverse edge 134. The distance d12 between first and second channel 140, 150 is different from the distance d34 between third and fourth channel 160, 170.

Preferably the distance d34 is between 25 mm and 85 mm, more preferably between 35 mm and 55 mm. Preferably, the length of the third and fourth channel 160, 170 is substantially the same, more preferably the length l3 of the third channel and the length l4 of the fourth channel is between 50 mm and 150 mm, more preferably between 60 mm and 140 mm. Preferably, the distance between the third attachment zone 165 and the first longitudinal side 131 is between 10 and 30 mm, and the distance between the second attachment zone 175 and the second longitudinal side 132 is between 10 and 30 mm.

Third channel 160 and fourth channel 170 are substantially parallel and run in the longitudinal direction of absorbent core 130. However, it is also possible for third and fourth channel 160, 170 to extend under a small angle with respect to the longitudinal direction of absorbent core 130, e.g. an angle between 5 and 10°. For example, third and fourth channel 160, 170 may be diverging slightly outwardly in the direction of first transverse edge 133 and second transverse edge 134.

Preferably third channel 160 and fourth channel 170 are arranged symmetrically with respect to a longitudinal center line CL of absorbent core 130.

In this embodiment, first, second, third and fourth channel 140, 150, 160, 170 each have a bottom 145, 155, 165, 175, similar to the bottom illustrated in FIG. 1C and FIG. 1D for the first embodiment of FIGS. 1A-1D. At bottom 145, 155, 165, 175 top core wrap sheet 110 is attached to back core wrap sheet 120 as described previously. Outside of the plurality of channels 140, 150, 160, 170, absorbent core 130 has a maximum thickness t. Preferably, each channel 140, 150, 160, 170 extends through at least 90% of the maximum thickness of absorbent core 130, more preferably through 100% of the thickness of absorbent core 130, such that, in the channel 140, 150, 160, 170, substantially no absorbent material is present that between top core wrap sheet 110 and back core wrap sheet 120.

Absorbent core 130 has a front portion 130a extending at one side of a transverse crotch line T. and a rear portion 130b extending at the other side of the transverse crotch line T. First, second, third and fourth channel 140, 150, 160, 170 each extend both in front portion 130a and rear portion 130b of absorbent core 130. Preferably the distance d12 between first and second channel 140, 150 is smaller than the distance d34 between third and fourth channel 160, 170, and the length l1 of first and second channel 140, 150 is bigger than the length l3 of third and fourth channel 160, 170. Such a channel pattern has the advantage that liquid can be distributed over substantially the entire absorbent core 130, and that any leakage risks in various positions of the wearer can be reduced.

The plurality of channels 140, 150, 160, 170 together cover at least 60%, preferably at least 70% of the length la of absorbent core 130; indeed, in the embodiment of FIGS. 1A-1D the channels cover a length equal to l1 which is more than 70% of the length la of absorbent core 130. The plurality of channels 140, 150, 160, 170 may be indicated in a color and/or with a pattern which is different from the color and/or pattern of topsheet. More in particular the area of the channels may comprise a print allowing a user to visually distinguish the channels. For example, an area of the topsheet above front portions of channels 140, 150, 160, 170 may be printed with an ink of a first color and an area of the topsheet above rear portions the channels 140, 150, 160, 170 may be printed with a different color. In that manner a user will be able to easily recognize the front and rear portion of a diaper, and will recognize more easily how to put on the diaper. Topsheet, backsheet and absorbent core 130 may have the same features as described above in connection with FIGS. 1A-1D.

FIG. 3

Figure 3:
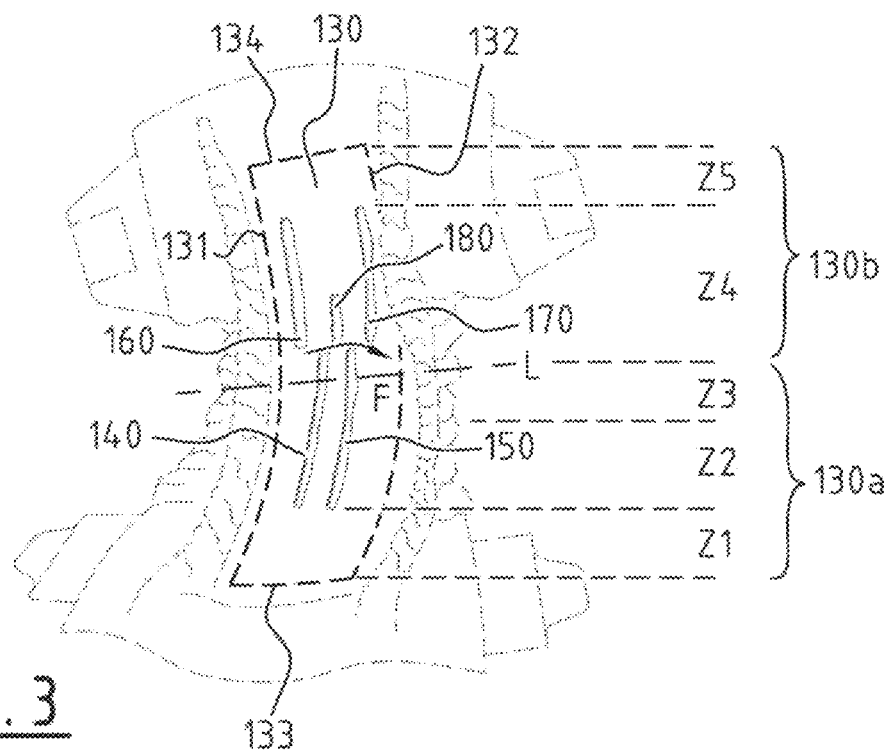
FIGS. 3-8 are perspective view of other exemplary embodiments of a diaper.

FIG. 3 illustrates a variant of diaper 100 of FIGS. 1A-1D. The features and characteristics are similar with this difference that a fifth channel 180 is provided in top core wrap sheet 110, in between third and fourth channel 160, 170 and extending along a longitudinal center line of diaper 100. Further, the first and second channels are slightly longer and extend over transverse fold line L in the direction of second transverse edge 134. The third and fourth channel are slightly shorter compared to the embodiment of FIGS. 1A-1D. By the additional channel 180 the distribution of the liquid can be further improved, especially for larger absorbent articles. Preferably, in the plurality of attachment zones 140, 150, 160, 170, 180 the top core wrap sheet is attached to the back core wrap sheet, and preferably substantially no absorbent material is present. Seen in a longitudinal direction of the absorbent core 130, looking from the front edge 133 to the rear edge 134, the absorbent core 130 comprises subsequently a first, second, third, fourth and fifth zone Z1, Z2, Z3, Z4, Z5.

The absorbent core 130 comprises a front portion 130a extending between the front edge 133 and a transverse crotch line L of the absorbent core, and a rear portion 130b extending between the rear edge 134 and the transverse crotch line L of the absorbent core 130. The first, second and third zone Z1, Z2, Z3 extend in the front portion 130a of the absorbent core and the fourth and fifth zone Z4, Z5 extend in the rear portion 130b. Preferably, in said first and fifth zone Z1, Z5 substantially no permanent attachment zones are present. However the first and/or fifth zone Z1, Z5 may comprise temporary secondary attachments that loosen upon wetting.

The second zone Z2 comprises a first and a second permanent elongate front attachment zone 130, 140, said first and second front attachment zones 130, 140 extending from an edge of the first zone Z1 in the direction of the third zone Z3, and here even into the fourth zone.

The fourth zone Z4 comprises a first, second and third rear elongate attachment zone 160, 170, 180 said first and second rear attachment zone extending from an edge of the fifth zone Z5 in the direction of the third zone Z3.

At least one of said second, third and fourth zone comprises a bridging zone B allowing a liquid flow F between the first and the second side edge 131, 132 by capillary action through the absorbent material. The bridging zone B extends between the first front attachment zone 140 and the first rear attachment zone 160, such that upon wetting of the absorbent material, a front and rear channel are created at said first front and rear attachment zone 140, 160, respectively, wherein the bridging zone B extends between said front and rear channel. Preferably a minimum distance x between the first front attachment zone 140 and the first rear attachment zone 160 is larger than 3 mm more preferably larger than 5 mm. The bridging zone B further extends between the second front attachment zone 150 and the second rear attachment zone 170, such that upon wetting of the absorbent material, a front and rear channel are created at said second front and rear attachment zone 150, 170, respectively, wherein the bridging zone B further extends between said front and rear channel. Preferably a minimum distance x between the second front attachment zone 150 and the second rear attachment zone 170 is larger than 3 mm more preferably larger than 5 mm.

FIGS. 4-6

Figure 4:
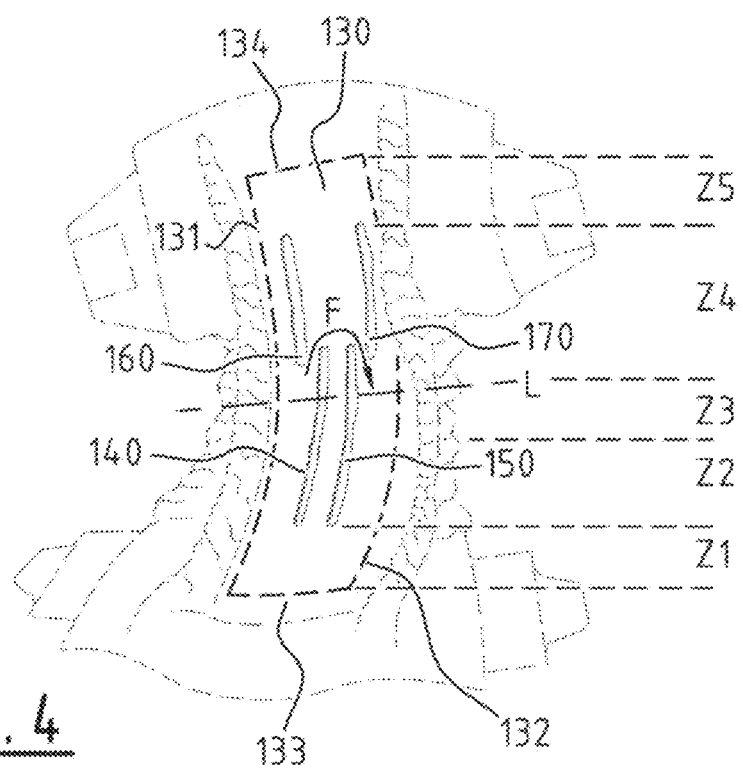

FIG. 4 illustrates a further variant of diaper 100 of FIGS. 1A-1D. The features and characteristics are similar with this difference that the first and second channels are slightly longer and extend over transverse fold line L in the direction of second transverse edge 134, in between third and fourth channel 160, 170. Depending on the shape and size of the absorbent article, the distribution of the liquid and the creation of the cup/tub shape can be further improved by this additional length. Also in FIG. 4 five zones Z1, Z2, Z3, Z4, Z5 can be distinguished with similar properties as those described above for FIG. 3.

Figure 5:
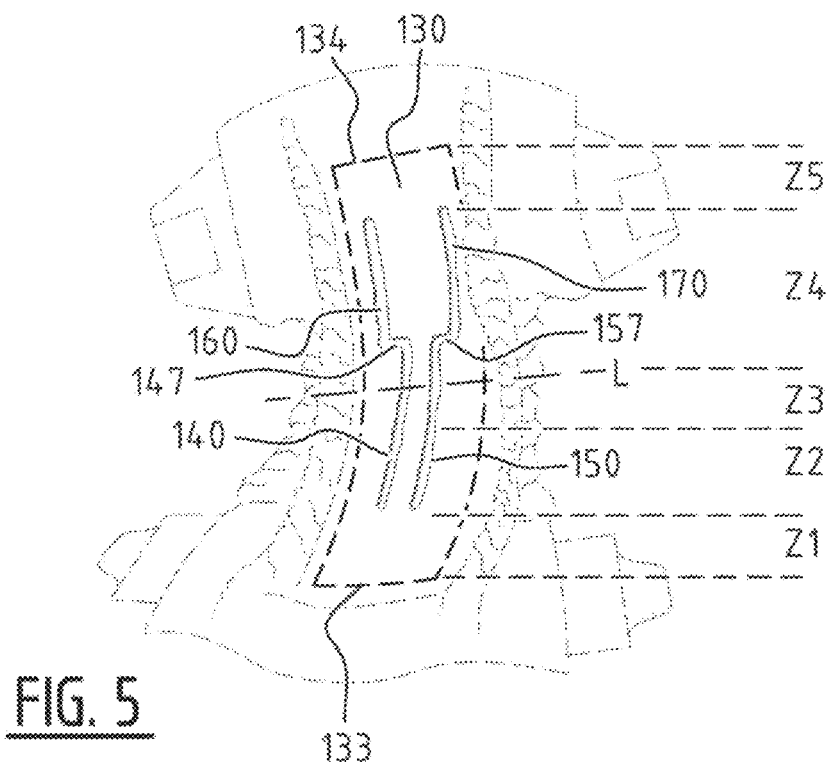

FIG. 5 illustrates a variant of diaper 100 of FIG. 4. The features and characteristics are similar with this difference that first channel 140 is connected to third channel 160 through a first transverse channel portion 147 and that second channel 150 is connected to fourth channel 170 through a second transverse channel portion 157. In that manner any liquid can flow from the first channel 140 to the third channel 160 and vice versa, and liquid can flow from the second channel 150 to the fourth channel 170 and vice versa, resulting in an even better distribution of the liquid.

Also, channel portions 147, 157 may help in creating the tub shape upon wetting of the absorbent core 130. Preferably first and second channel 140, 150 extend in a longitudinal direction of absorbent core 130 over a length which is longer than the length of third and fourth channel 160, 170, wherein third and fourth channel extend between crotch region CR and second transverse edge 134 and first and second channel extend between crotch region CR and first transverse edge 133. Also in FIG. 5 five zones Z1, Z2, Z3, Z4, Z5 can be distinguished with similar properties as those described above for FIG. 3. It is noted that in the embodiment of FIG.

5 e.g. the channel portions 147, 157 could be provided in the form of temporary attachment portions which gradually loosen upon wetting in order to created a bridging zone for a liquid flow from one side edge 131 to the other side edge 132 and vice versa.

Figure 6:
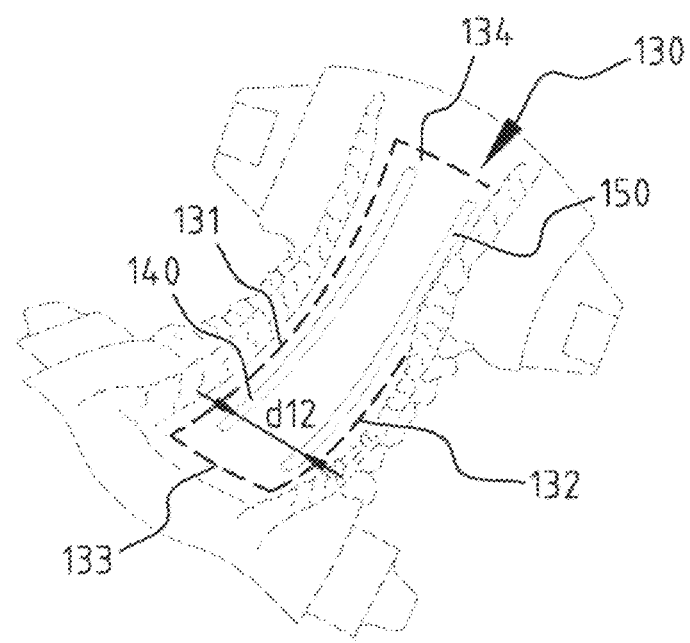

FIG. 6 illustrates another more basic exemplary embodiment of a diaper 100 according to the invention. Diaper 100 comprises a liquid pervious topsheet, a liquid impervious backsheet, and an absorbent core 130 positioned in between topsheet and backsheet. Absorbent core 130 has a first and second longitudinal edge 131, 132 and a first and second transverse edge 133, 134. Absorbent article 100 is provided with a first and a second attachment zone for creating a first and a second channel 140, 150 located a distance d12 of each other, upon wetting of the diaper 100. First and second channel 140, 150 each extend from a crotch region CR in the direction of the first transverse edge 133 and the second transverse edge 134. In this embodiment, preferably, first and second channel extend over more than 80% of the length of absorbent core 130. Preferably the distance d12 is between 10 mm and 90 mm, more preferably between 20 mm and 80 mm, even more preferably between 30 mm and 50 mm. Preferably, the length of the first and second channel is substantially the same, more preferably the length l1 of the first channel and the length l2 of the second channel is between 100 mm and 350 mm, more preferably between 150 mm and 300 mm. Preferably, the distance between the first channel 140 and the first longitudinal side 131 is between 10 mm and 30 mm, and the distance between the second channel 150 and the second longitudinal side 132 is between 10 mm and 30 mm. Preferably, the distance between the first/second channel 140, 150 and the transverse edges 133, 134 is between 20 mm and 100 mm, more preferably between 30 mm and 75 mm.

First channel 140 and second channel 150 are substantially parallel and run in the longitudinal direction of absorbent core 130. However, it is also possible for first and second channel 140, 150 to extend under a small angle with respect to the longitudinal direction of absorbent core 130, e.g. an angle between 5 and 10°. For example, first and second channel 140, 150 may be diverging slightly outwardly in the direction of first transverse edge 133 and may be diverging slightly outwardly in the direction of second transverse edge 134. Preferably first channel 140 and second channel 150 are arranged symmetrically with respect to a longitudinal center line CL of absorbent core 130.

First and second channel 140, 150 may each have a bottom 145, 155, similar to the bottom illustrated in FIG. 1C for the first embodiment of FIGS. 1A-1D. However, it is noted that the channels 140, 150, 160, 170 may be located below and/or above the attachment zones 145, 155, 165, 175, as will be explained in more detail below with reference to FIG. 14.

At the attachment zones 145, 155, 165, 175 top core wrap sheet 110 is attached to back core wrap sheet 120 as described previously. Outside of the plurality of channels 140, 150, 160, 170 absorbent core 130 has a maximum thickness t. Preferably, in the unwetted state, each channel 140, 150, 160, 170 extends through at least 90% of the maximum thickness of absorbent core 130, more preferably through 100% of the thickness of absorbent core 130, such that, in the channel 140, 150, 160, 170, substantially no absorbent material is present between top core wrap sheet 110 and back core wrap sheet 120.

The areas of the channels 140 and/or 150 and/or 160 and/or 170 may be indicated in a color and/or with a pattern which is different from the color and/or pattern of topsheet. More in particular the area of the channels may comprise a print allowing a user to visually distinguish the channels. This print may be arranged on the topsheet, on the top core wrap sheet, on the back core wrap sheet, on the backsheet, or on any sheet in between the topsheet and the backsheet, as long as it is visible for a user. Preferably the print is visible when looking at the topsheet of the diaper.

For example, a front portion of the channel 140 and/or 150 and/or 160 and/or 170 may be indicated with an ink of a first color and a rear portion the channels 140 and/or 150 and/or 160 and/or 170 may be indicated with a different color. In that manner a user will be able to easily recognize the front and rear portion of a diaper. Indeed, the user will know that the first color has to be on the left and the second color on the right. Hence he will recognize more easily how to put on the diaper. Topsheet, backsheet and absorbent core 130 may have the same features as described above in connection with FIGS. 1A-1D.

FIGS. 7-8

Figure 7:
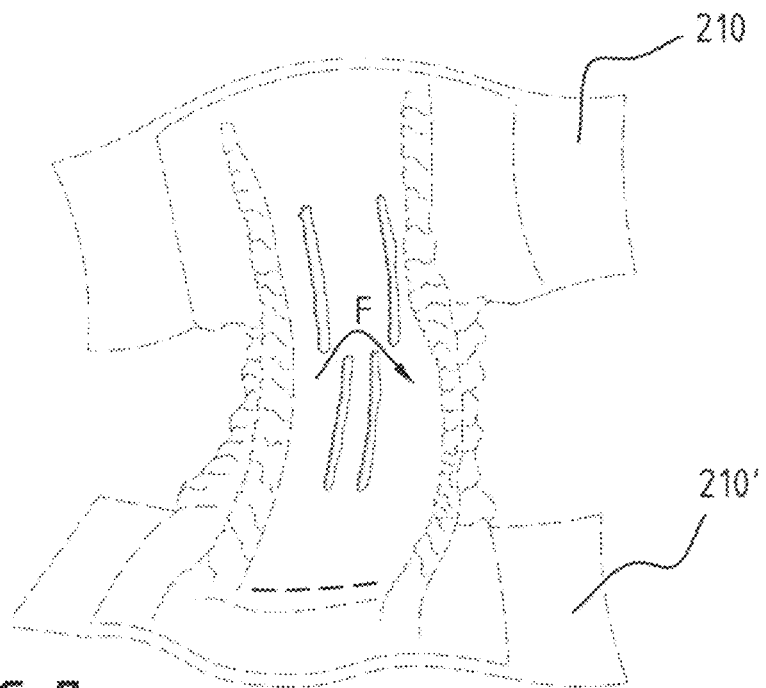
Figure 8:
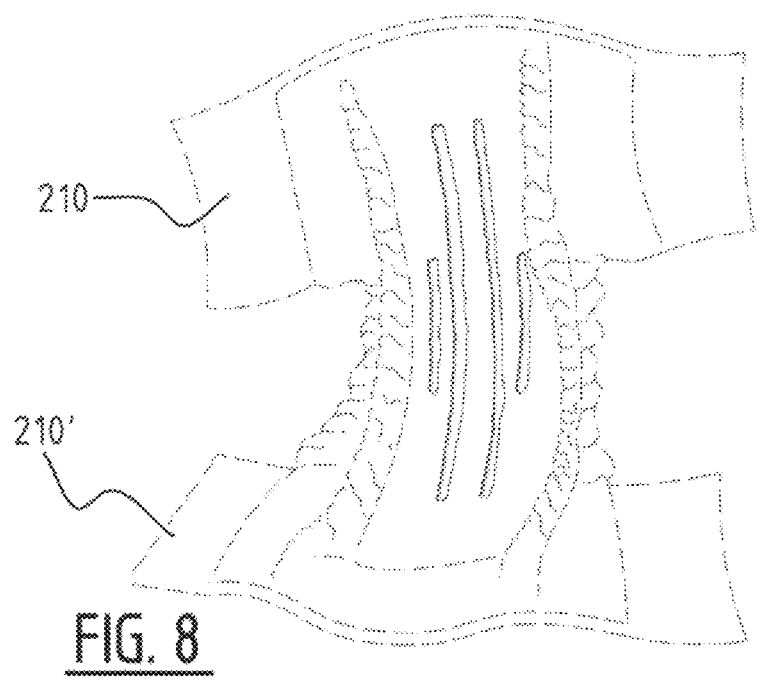

FIGS. 7 and 8 illustrate baby pants variants of the baby diaper embodiments of FIGS. 1A and 2A. In the embodiments of FIGS. 7 and 8 the side panels 210, 210' are larger compared to the embodiments of FIGS. 1A and 2A. It is clear to the skilled person that any embodiment described in view of baby diapers, is applicable in a similar manner to baby pants, mutatis mutandis.

FIGS. 10 and 10A-H

Figure 10:
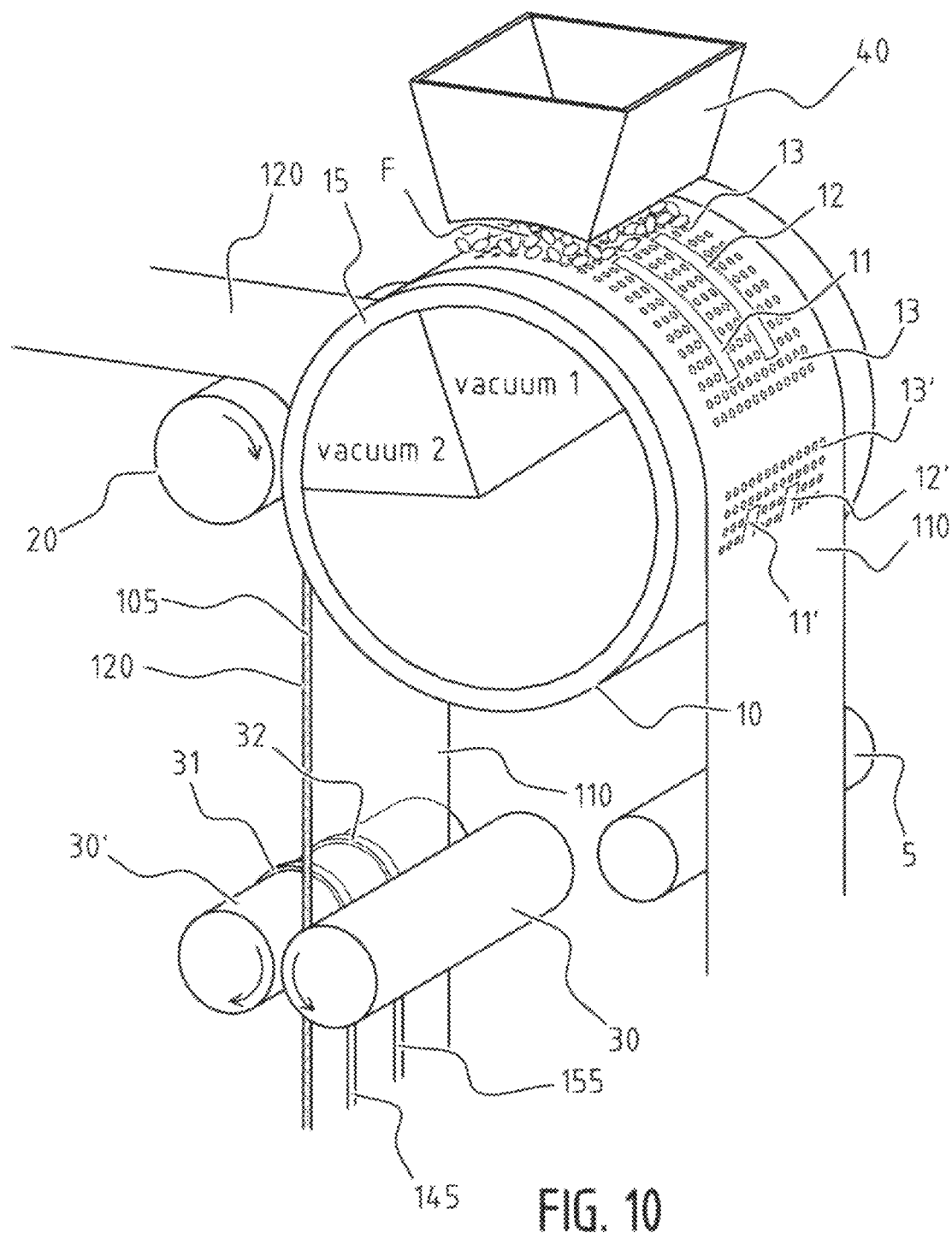
FIG. 10 illustrates schematically an exemplary embodiment of a method and apparatus for manufacturing an absorbent article.
Figure 10A:
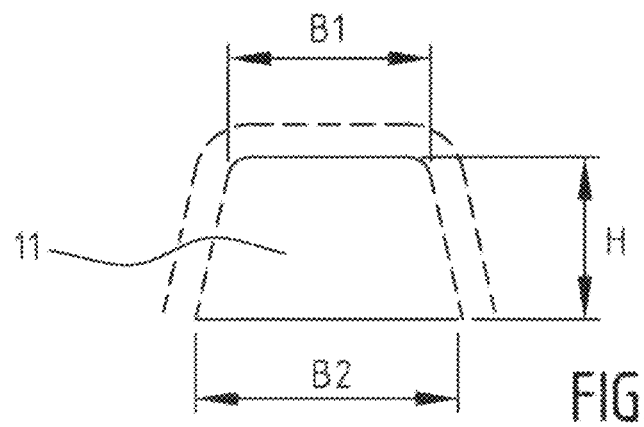
FIG. 10A shows a cross section of an insert placed at a non-suction zone of the exemplary embodiment of FIG. 10.
Figure 10B:
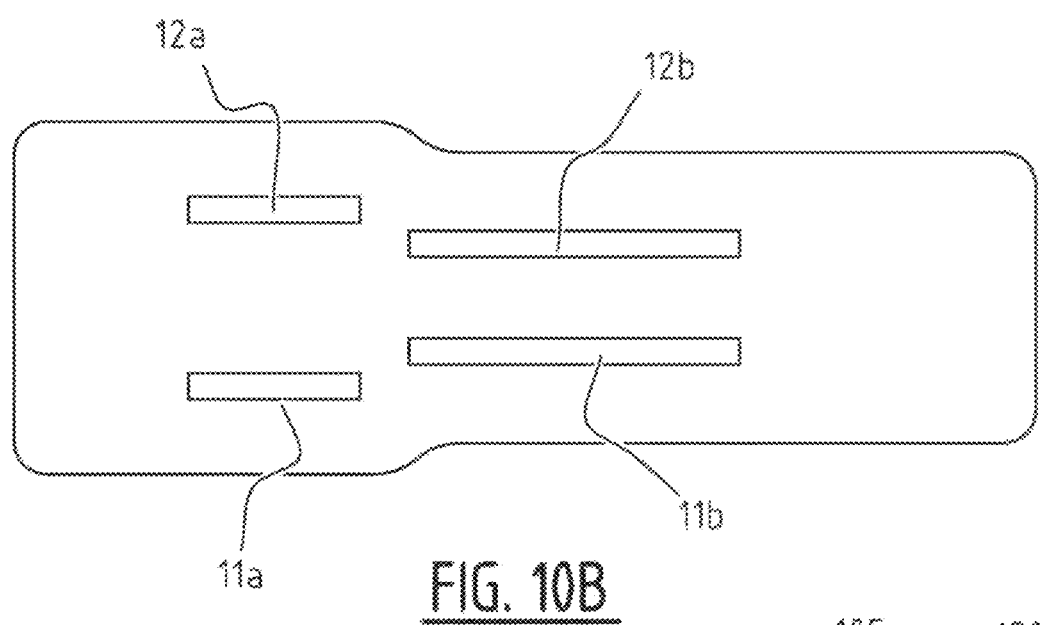
FIG. 10B shows a top view indicating how inserts may be positioned in order to create non-suction zones for the exemplary embodiment of FIG. 10.
Figure 10C:
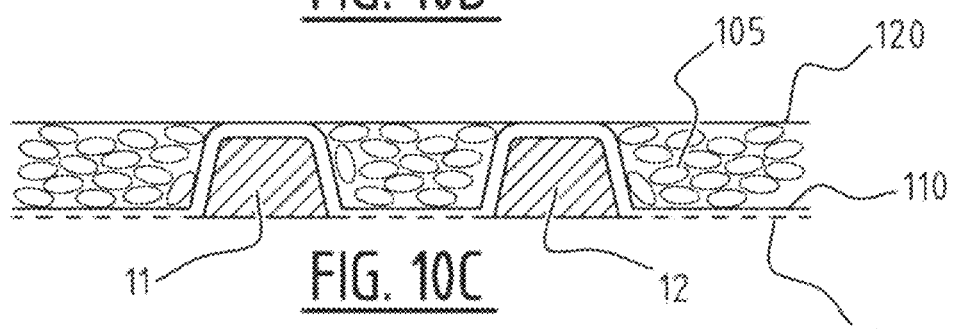
FIG. 10C shows a cross section of the absorbent core when the second sheet 120 is being applied.
Figure 10D:
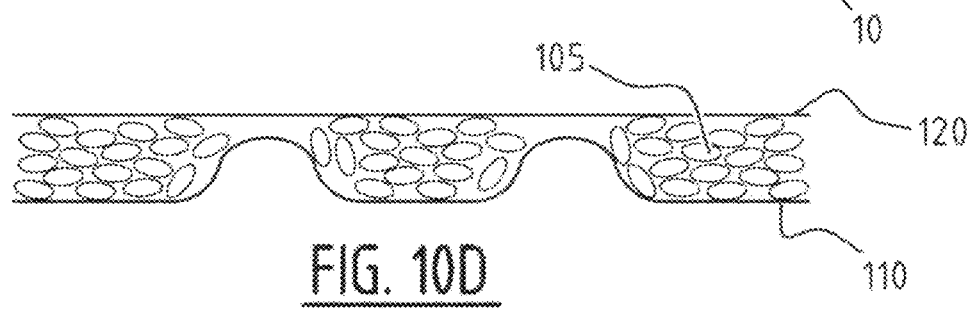
FIG. 10D shows a cross section of the absorbent core before attaching the first sheet 110 to the second sheet 120.

FIG. 10 illustrates an embodiment of a method for manufacturing an absorbent article according to the invention. The method comprises in a first step guiding a first sheet material 110 along an optional guide roller 5, and further along a rotating member 10, wherein a surface 15 of said rotating member 10 is provided with a pattern with suction zones 13, 13' and non-suction zones 11, 12; 11', 12'. The first sheet material 110 is shown in a transparent manner to reveal the suction and non-suction zones of the rotating member 10. The suction zones 13, 13' may be provided with holes, and the non-suction zones 11, 12; 11', 12' are formed of closed material. For example, the non-suction zones 11, 12; 11', 12' may be provided with inserts as shown in FIG. 10A. As shown in FIG. 1A, the inserts 11, 12; 11', 12', may have a trapezoidal cross section. FIG. 10B shows an insert pattern with four non-suction zones 11a, 11b, 12a, 12b per absorbent core. The inserts may be fixed e.g. with screws on the rotating member 10. At an inner area of the rotating member 10 a vacuum is applied, see VACUUM 1. The non-suction zones 11, 12; 11', 12' comprise at least a first elongate zone 11, 11' and a second elongate zone 12, 12' extending in a circumferential direction of the rotating member 10. In a second step an absorbent material F is applied via a hopper 40 on said first sheet material 110 on the rotating member 10 such that the suction zones 13, 13' are covered with absorbent material and substantially no absorbent material is present on the non-suction zones 11, 12; 11', 12'. In a third step a second sheet material 120 is applied on top of the absorbent material on the first sheet material 110. e.g. using a further rotating member 20. This is shown also in FIG. 10C where a cross section through the absorbent core is shown during the application of the second sheet material 120. FIG. 10D shows the cross section of the absorbent core downstream of rotating member 10. One of said first and second sheet material is a top core wrap sheet material, and the other one is a back core wrap sheet material. In the illustrated embodiment it is assumed that the first sheet material 110 is the top core wrap sheet material. In a fourth step the first sheet material 110 is attached to the second sheet material 120 at least in the areas where substantially no absorbent material is present, and such that at least a first and a second channel 140, 150 are formed in said top core wrap sheet material 110. The attaching may be done by applying pressure and heat on the top core wrap sheet material 110 and/or on the back core wrap sheet material 120 in the areas where substantially no absorbent material is present, e.g. by a rotating member 30 and/or opposite rotating member 30' which is provided with at least a first and a second seal rib 31, 32 dimensioned for applying pressure and heat on the top core wrap sheet material 110 in the areas where substantially no absorbent material is present in order to create the first and second channel 140, 150, respectively.

While the above-described method of manufacturing absorbent articles has good results, the top core wrap sheet and the back core wrap sheet may not be sufficiently strongly attached to one another, especially in cases where a significant amount of liquid is absorbed. Therefore, it may be desirable to additionally use a binder, such as glue, to strengthen the bond between the top and back core wrap sheets.

It is however inadvisable to apply this binder to the entire surface area of the wrap sheet being guided over rotating member 10, since this may lead to the absorbent material and/or binder contaminating the attachments zones 140, 150, 160, 170, and therefore hindering the formation of channels.

Therefore it is advantageous to use a specific method to apply the glue to the back and/or top wrap sheets. In FIGS. 10E-10H, a manufacturing method including application of a binder is demonstrated which does not have this drawback.

In particular, taking as an example the possible manufacturing process for the embodiment of FIGS. 1A and 1B, while the first sheet material 110 is being guided along an optional guide roller and further along a rotating member a binder, such as glue, may first be applied to the first sheet material, but only in substantially parallel stripes which do not overlap with the intended locations of the attachment zones 140, 150, 160, 170. Note that in this embodiment, the first sheet material forms the bottom core wrap, but in other embodiments this can also be the top core wrap. The skilled person will be aware of various method of binder/glue application, such as spraying, contact application and so on.

Figure 10E:
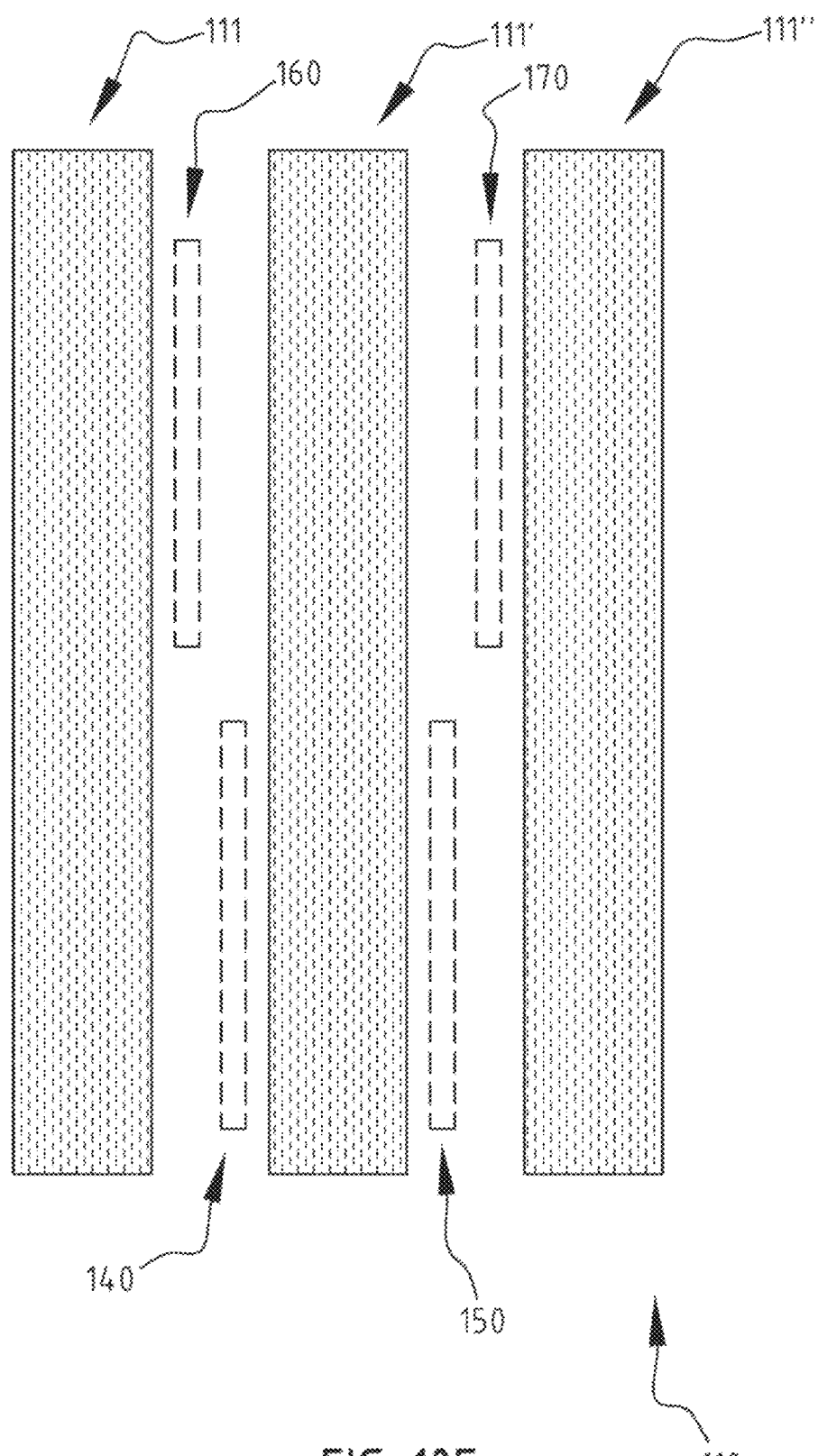
FIGS. 10E-10H illustrate an alternate method for manufacturing an absorbent article, wherein 10E shows glue application to the bottom core wrap. IOF shows glue application to the top core wrap, 10G shows the combined bottom and top core wraps, and IOF shows the absorbent article after the manufacturing steps.

FIG. 10E shows a possible pattern for the application of glue to the first sheet material, which will be the back core wrap. In particular, in this example there are three stripes 111, 111', 111", but a different number of substantially parallel stripes, either continuous, intermittent and/or discontinuous in the longitudinal direction, may also be chosen depending on the shape and locations of the attachment zones 140, 150, 160, 170, which preferably cover a substantial portion of the surface of the bottom core wrap while not overlapping with the intended location of the attachment zones, and preferably while keeping some distance from the intended location of the attachment zones. Although. FIG. 10E illustrates an application pattern of stripes, it is clear to the skilled person that the application pattern can be adapted and tuned depending on the intended shape, configuration and location of the one or more attachment zones. Moreover, the skilled person will know how to best adapt the binder application zones on the first and second sheet materials 110, 120 for other configurations of attachments zones, such as the ones described in the present application. Preferably, the application of the glue to the bottom core wrap takes place while the bottom core wrap is moved towards the rotating number, and before the absorbent material is added to it. In such a way, the sheet material on the rotating member is already provided with binder, and may subsequently have absorbent material attached thereto via the hopper.

Please note that the dotted line indicating the intended location of the attachment zones is there for illustrative purposes only; it does not correspond to anything on the first sheet material 110.

Figure 10F:
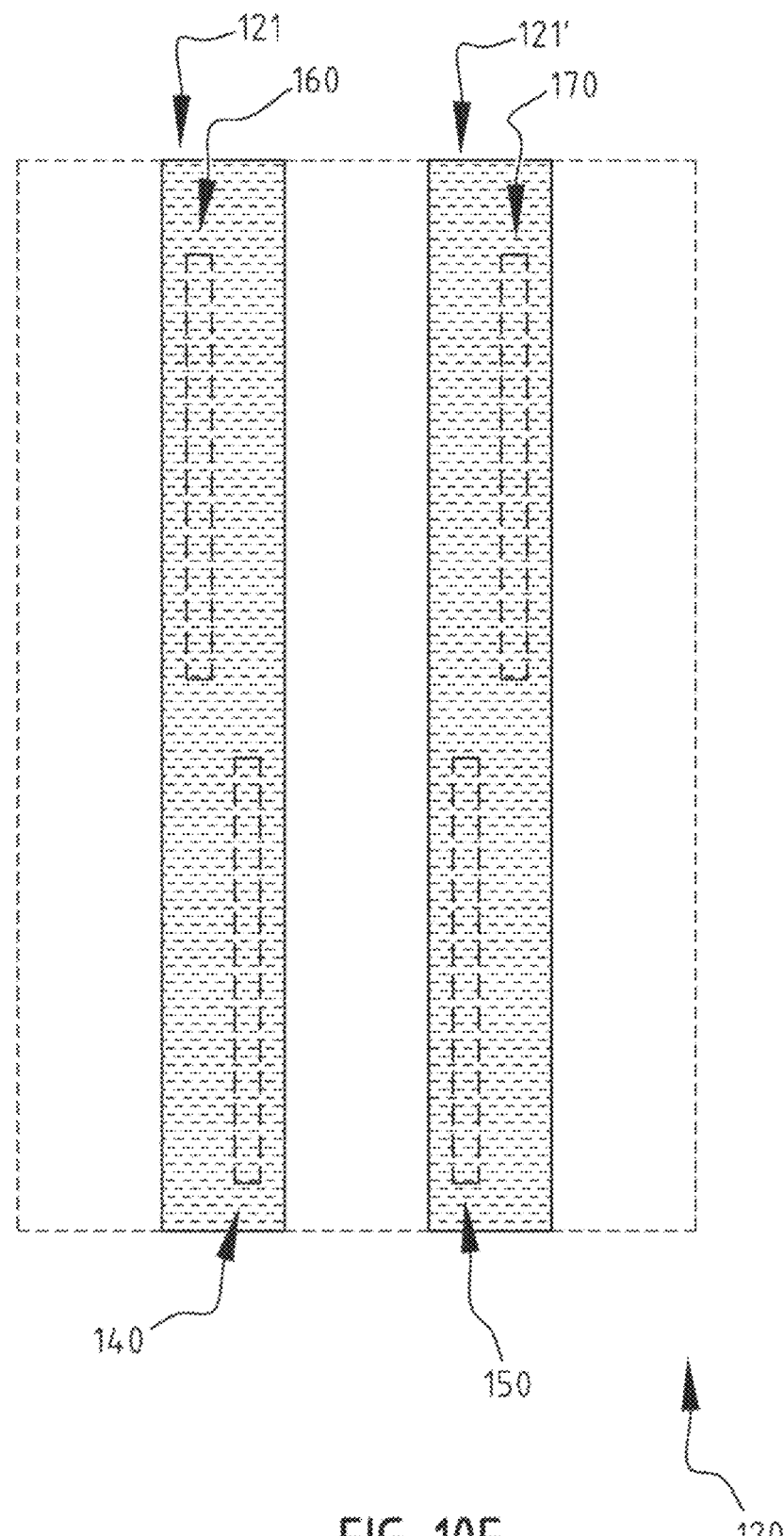

FIG. 10F shows application of glue to the second sheet material 120, which in this case will become the top core wrap. In this case too the application of the binder preferably happens along substantially parallel stripes 121, 121', which preferably are complementary to the stripes on the first sheet material 110. Preferably, the application of glue to the top core wrap sheet happens at a distance from hopper 40, to minimize the chance of contamination, i.e. absorbent material sticking to the areas that are to become attachment zones 140, 150, 160, 170. For instance, the binder may be applied before or while the sheet material is guided along further rotating member 20. Note that here, too, the dotted lines merely indicate the intended position of the attachment zones 140, 150, 160, 170; they do not indicate any interruption or change in the binder application. As before, the skilled person will be aware of various method of binder/glue application, such as spraying, contact application and so on.

Figure 10G:
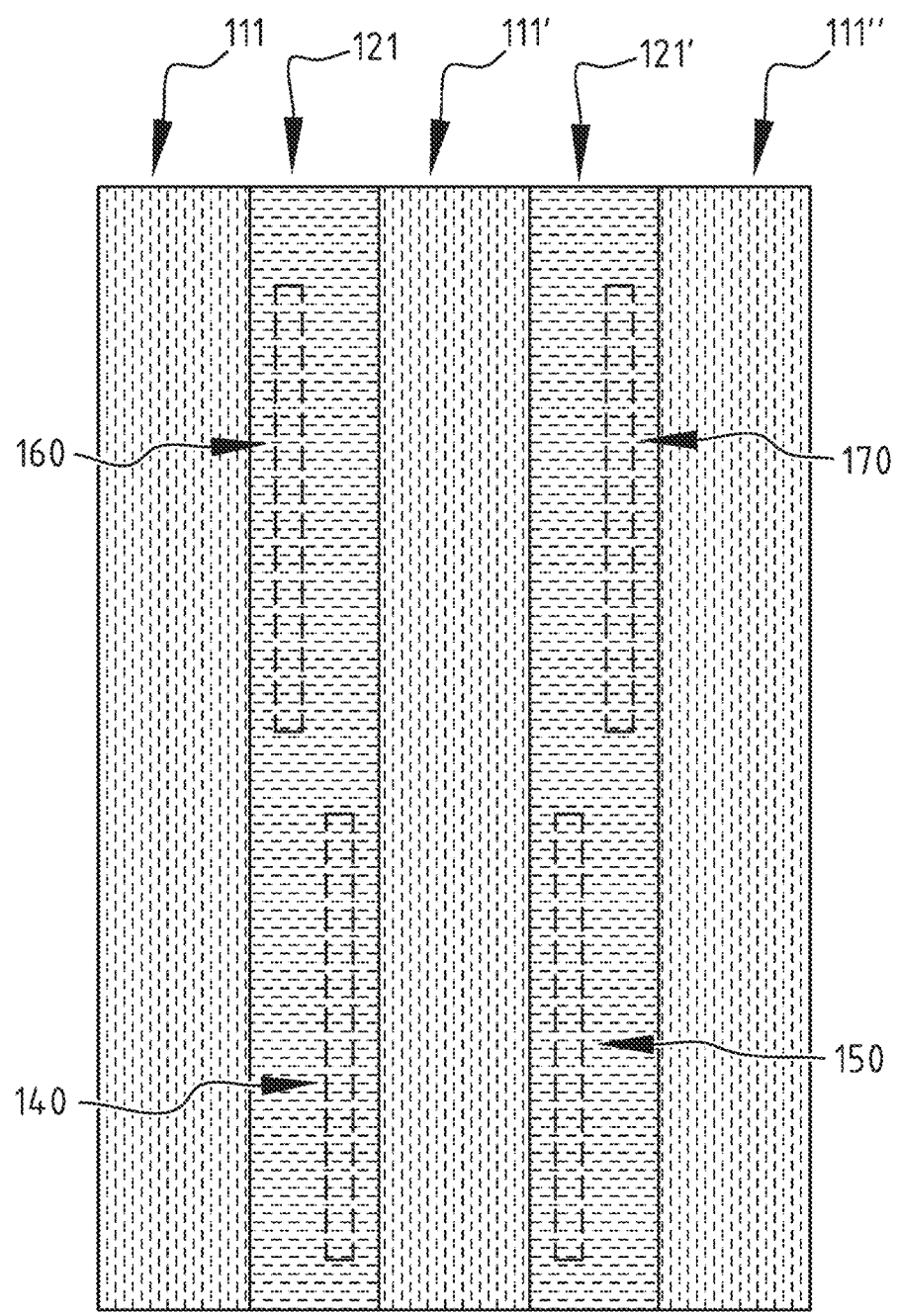

FIG. 10G shows the result after the third step described above has taken place, i.e. after the second sheet material 120, which here is the top core wrap sheet, is applied on top of the absorbent material on the first sheet material 110, e.g. using a further rotating member 20. Note that the pattern fill indicates the presence of binder, and not the presence of absorbent material, since the absorbent material will not be present in the areas indicated by the dotted lines. These areas will be bonded together in a fourth step such as described above, such that channels 140, 150, 160 and 170 are formed in said back core wrap sheet materials 110 and/or 120, for instance by applying pressure and heat on the back core wrap sheet material 110 and/or on the top core wrap sheet material 120 in the areas where substantially no absorbent material is present, e.g. by a rotating member 30 and/or opposite rotating member 30' which is provided with at least a first and a second seal rib 31, 32 dimensioned for applying pressure and heat in between the core wrap sheet materials 110 and 120 in the areas where substantially no absorbent material is present in order to create the channels 140, 150, 160 and 170.

Figure 10H:
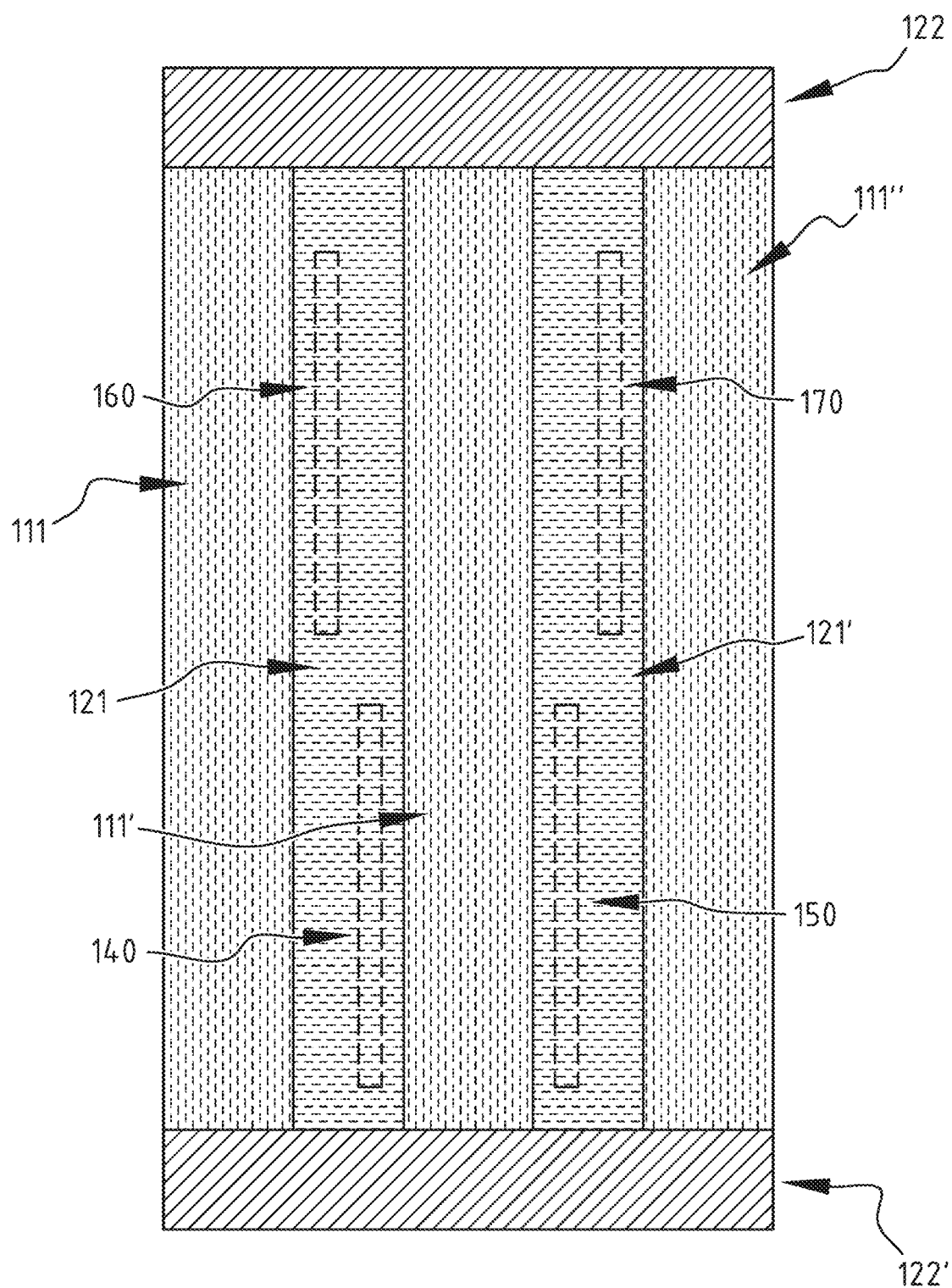

Finally, FIG. 10H shows the absorbent article resulting from the above-described method, in which a further step has taken place of traversal sealing in bands 122, 122' by chemical, thermal or physical binding such as for in stance glue, heat and/or pressure, which prevents the core from opening up and the front and the back. Note that this step of transversal sealing may also take place prior to the fourth step.

The above-described method may yield an absorbent article with higher dry and especially wet integrity and which avoids unwanted migration of absorbent material, while avoiding the risk of contamination in the attachment zones 140, 150, 160 and 170 which may impede the formation of channels. The skilled person will understand that this method is not limited to this particular configuration of attachment zones and will know how to best adapt the binder application zones on the first and second sheet materials 110, 120 for other configurations, such as the ones described in the present application. More in particular the skilled person understands that the method is also useful for absorbent cores with only one attachment zone or with more than two attachment zones.

FIGS. 11A-11E

Figure 11A:
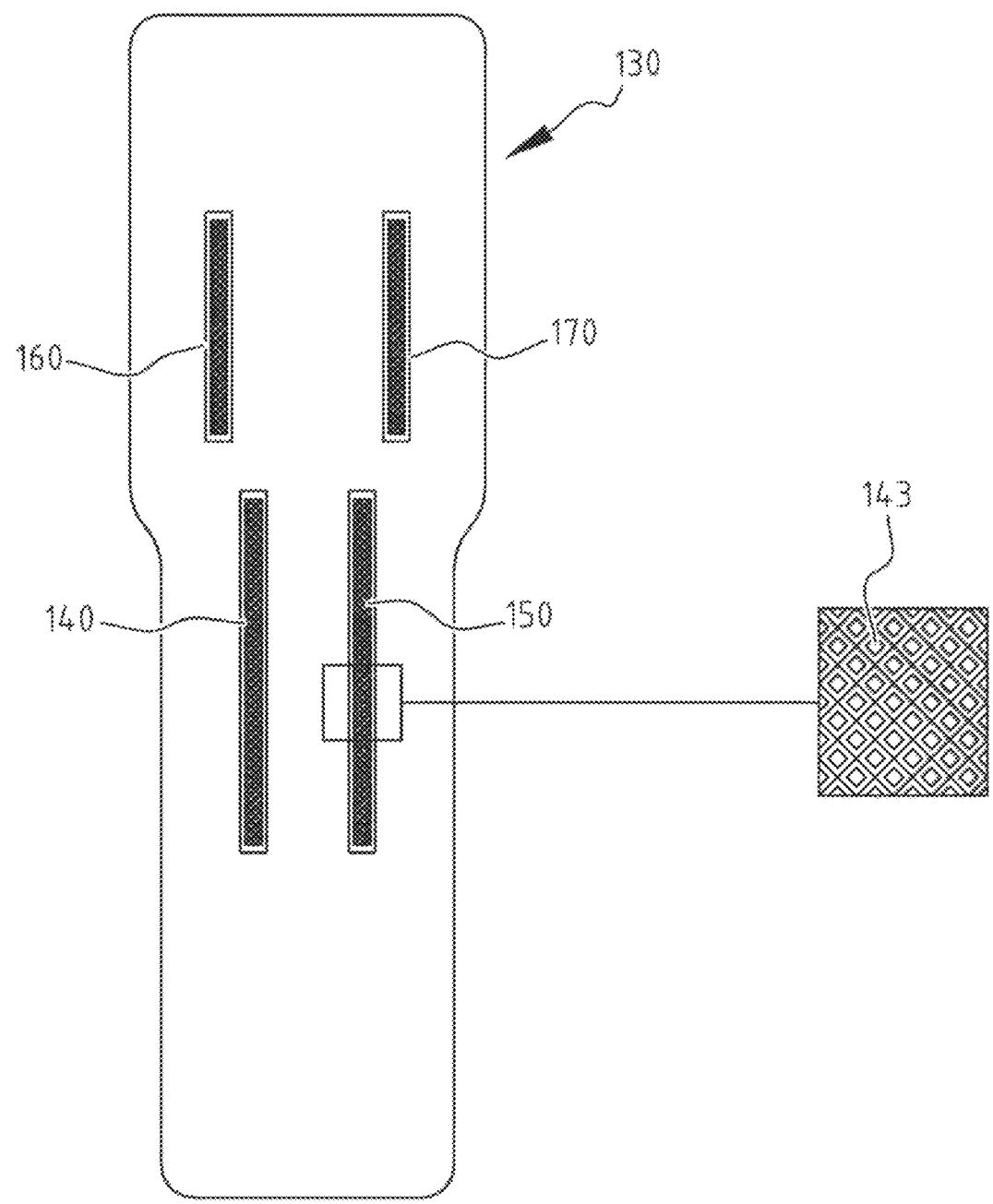
FIG. 11A shows a top view of an exemplary embodiment of an absorbent core with four attachment zones using a first exemplary embodiment of a sealing pattern.

FIG. 11A illustrates an exemplary embodiment of an absorbent core 130 with four attachment zones creating channels 140, 150, 160, 170. In the embodiment of FIG. 11A, the attachment zones are formed by welding the top core wrap sheet 110 to the back core wrap sheet 112. This welding may be done according to a predetermined sealing pattern. In the embodiment of FIG. 11A, the pattern consists of a plurality of discrete shapes 143, here a plurality of squares. Preferably, the discrete shapes 143 have dimensions smaller than 2 mm. Preferably, the distance between adjacent discrete shapes is between 0.5 and 3 mm.

Figure 11B:
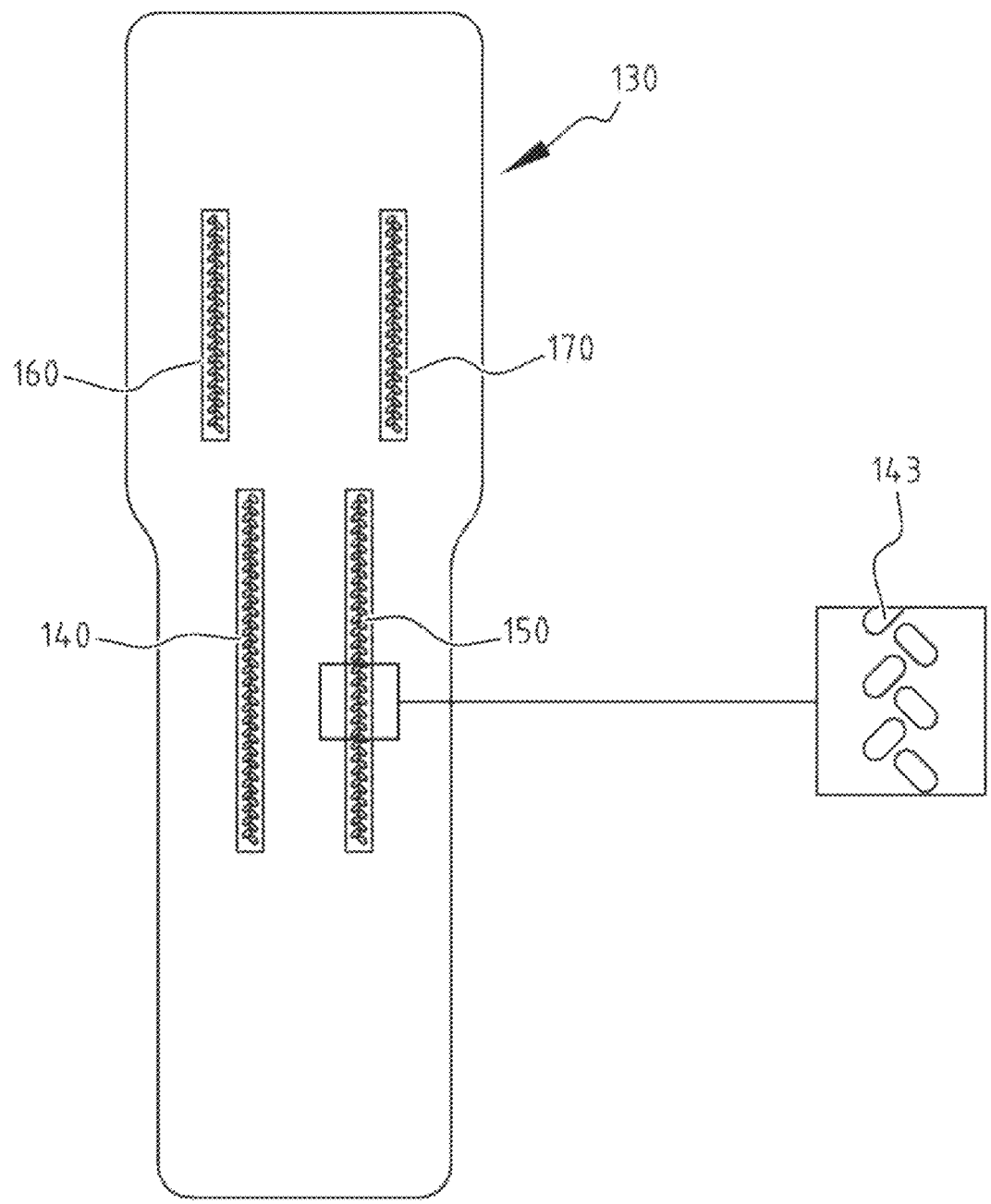
FIG. 11B shows a top view of an exemplary embodiment of an absorbent core with four attachment zones using a second exemplary embodiment of a sealing pattern.

FIG. 11B illustrates another exemplary embodiment of a sealing pattern that may be used in an embodiment of the invention. Here the pattern consists of a plurality of discrete shapes in the form of rounded elements 143. The rounded elements may have a length dimension between 0.5 mm and 5 mm, and a width dimension between 0.5 mm and 5 mm. Preferably, the discrete shapes are equally distributed in the attachment zones.

Figure 11C:
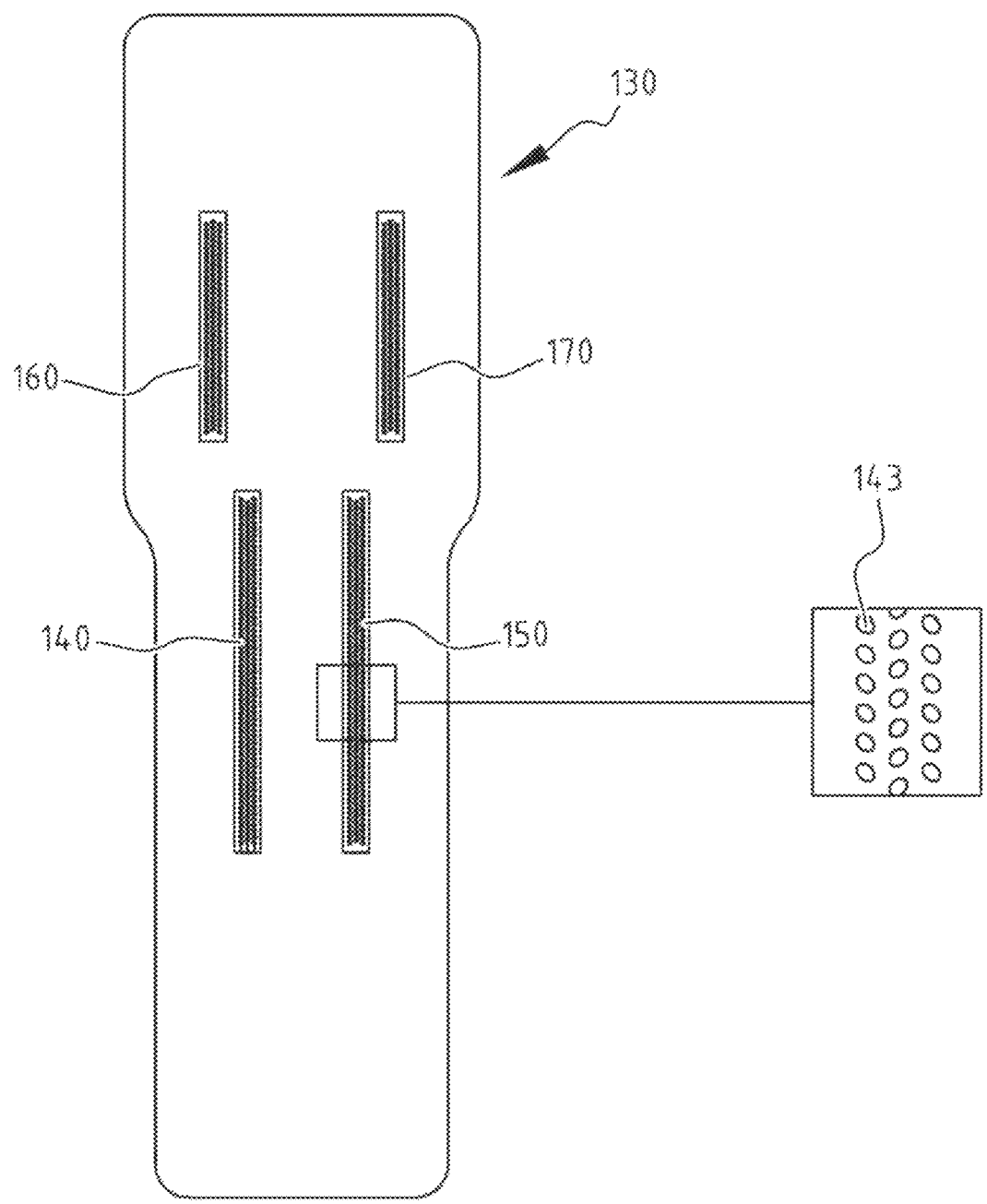
FIG. 11C shows a top view of an exemplary embodiment of an absorbent core with four attachment zones using a third exemplary embodiment of a scaling pattern.

FIG. 11C illustrates yet another embodiment where the sealing pattern consists of discrete shapes which are rounded. In this embodiment, three columns of rounded discrete elements 143 are used for each attachment zone 140, 150, 160, 170.

Figure 11D:
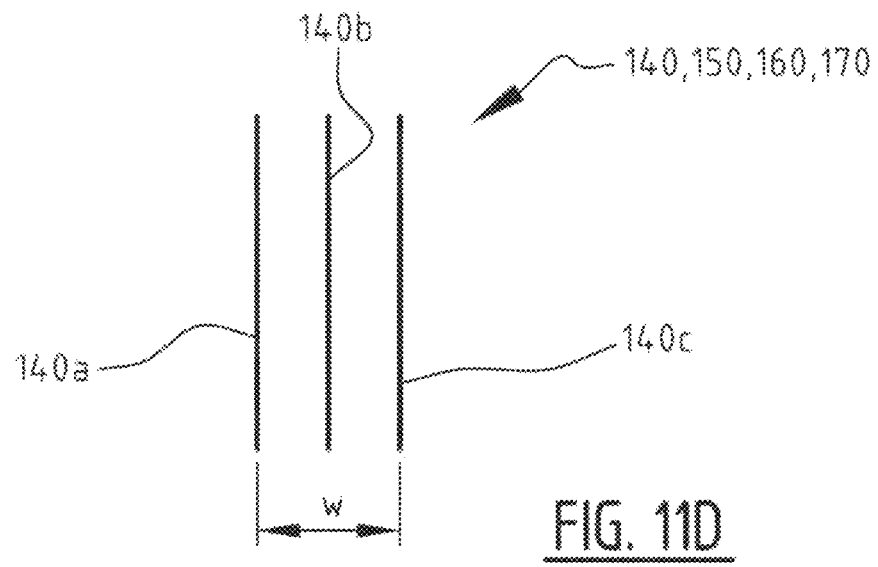
FIG. 11D illustrates a fourth exemplary embodiment of a possible sealing pattern.

FIG. 11D illustrates another exemplary embodiment of an attachment zone for creating a channel 140, 150, 160, 170. In this embodiment, the attachment zone is formed by a plurality of continuous line-shaped attachments 140a, 140b, 140c. The number of lines used may vary, and may be e.g. two lines or more than three adjacent lines. Preferably, the distance w between a first line 140a and a last line 140c is at least 1 mm, more preferably at least 2 mm, even more preferably more than 4 mm.

Figure 11E:
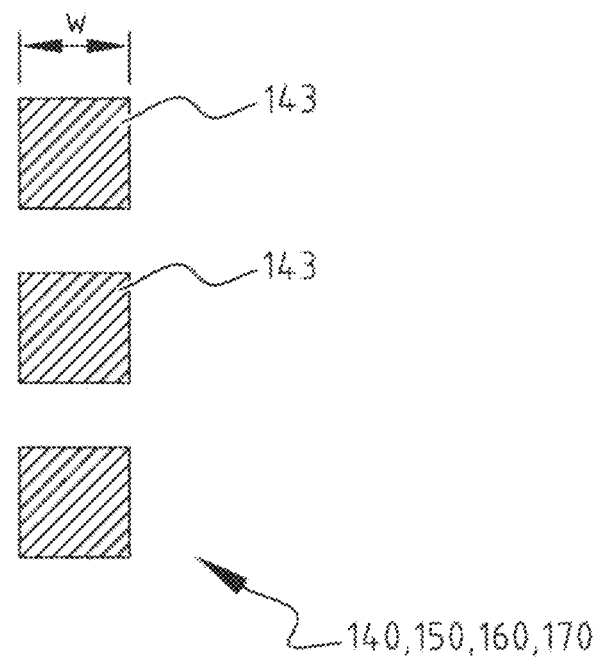
FIG. 11E illustrates a fifth exemplary embodiment of a possible sealing pattern.

In the exemplary embodiment of FIG. 11E, the attachment zones creating channels 140, 150, 160, 170 may be formed of a plurality of discrete elements 143, wherein each discrete element has a width w which covers the entire width w of the attachment zone.

Figure 12:
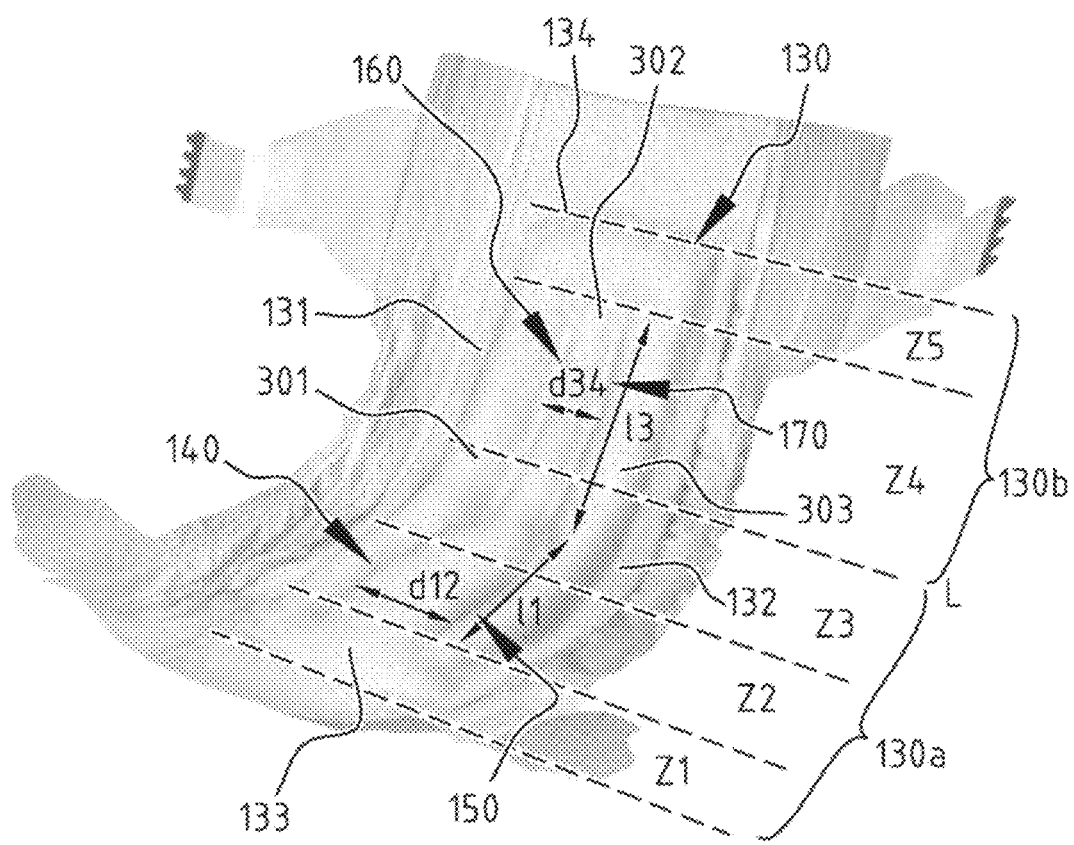
FIG. 12 is a perspective view of an exemplary embodiment of a diaper in a wetted state.
Figure 13A:
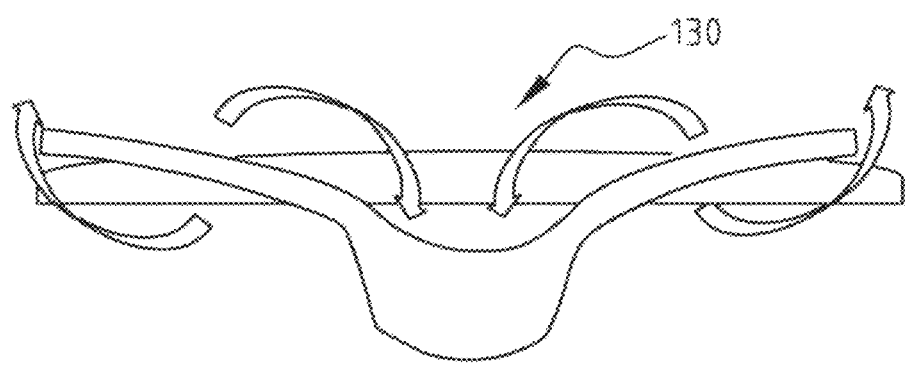
FIGS. 13A and 13B are cross-sectional views illustrating the effect of liquid being absorbed by a traditional absorbent core and liquid being absorbed by an absorbent core according to an exemplary embodiment of the invention, respectively.
Figure 13B:
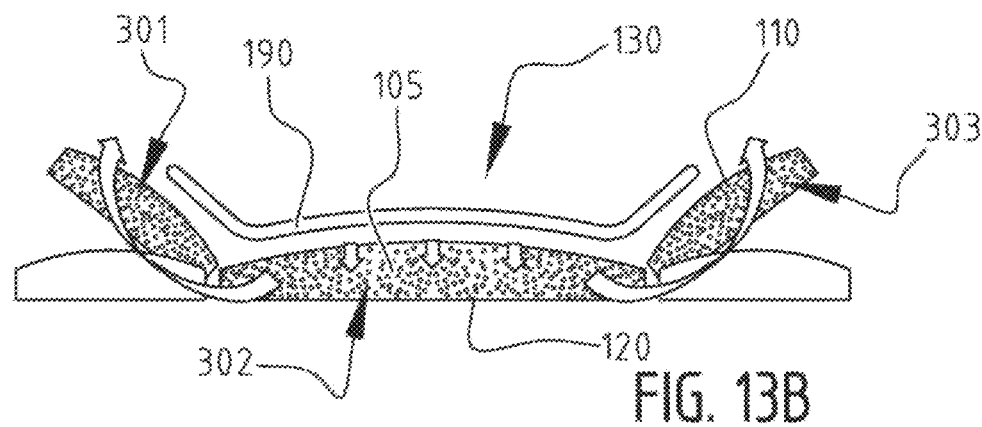

FIGS. 13A-B and 12

FIG. 13A illustrates an exemplary embodiment of a traditional absorbent core. When a traditional absorbent core absorbs liquid, the core becomes bulky such that the diaper is no longer well adapted to the body. The liquid does not spread evenly but remains in the center of the absorbent core. FIG. 13B illustrates an exemplary embodiment of an absorbent core of the invention. Thanks to the attachment zones and associated channels 140, 150, 160, 170, the liquid is evenly spread, resulting in the formation of tubes 301, 302, 303 which provide a tub shape to the absorbent core 130. Such a tub shape adapts perfectly to the body. Further, compared to prior art solutions, the liquid is kept in an improved manner absorbed in the absorbent core 130, and the risk on leakage is reduced. Also, because of the creation of the channels 140, 150, 160, 170, the liquid is absorbed faster. FIG. 12 shows a perspective view of a diaper in the wetted state. FIG. 12 clearly illustrates the formation of three tubes 301, 302, 303 giving the diaper a tub shape which is well adapted to the body. Preferably absorbent core 130 is provided with a plurality of attachment zones 140, 150, 160, 170 where the top core wrap sheet is attached to the back core wrap sheet, and where preferably substantially no absorbent material is present. Seen in a longitudinal direction of the absorbent core 130, looking from the front edge 133 to the rear edge 134, the absorbent core 130 comprises subsequently a first, second, third, fourth and fifth zone Z1, Z2, Z3, Z4, Z5.

The absorbent core 130 comprises a front portion 130a extending between the front edge 133 and a transverse crotch line L of the absorbent core, and a rear portion 130b extending between the rear edge 134 and the transverse crotch line L of the absorbent core 130. The first, second and third zone Z1, Z2, Z3 extend in the front portion 130a of the absorbent core and the fourth and fifth zone Z4, Z5 extend in the rear portion 130b. Preferably, in said first and fifth zone Z1, Z5 substantially no permanent attachment zones are present. However the first and/or fifth zone Z1, Z5 may comprise temporary secondary attachments that loosen upon wetting. The second zone Z2 comprises a first and a second permanent elongate front attachment zone 130, 140, said first and second front attachment zones 130, 140 extending from an edge of the first zone Z1 in the direction of the third zone Z3.

The fourth zone Z4 comprises a first and second rear elongate attachment zone 160, 170, said first and second rear attachment zone extending from an edge of the fifth zone Z5 in the direction of the third zone Z3.

The first and second rear elongate attachment zones 160, 170 extend from the fourth zone into the third zone Z3 so that an absorbent article is formed that fits well to the body of the wearer. Preferably a distance between the transverse crotch line L and a transverse center line T extending perpendicular on the longitudinal direction of the absorbent core, through the middle of the absorbent core, is smaller than 10%, more preferably smaller than 5% of the length of the absorbent core.

The first zone Z1 extends over a length corresponding with at least 5%, preferably at least 10% of the length la of the absorbent core seen in the longitudinal direction, e.g. between 10% and 20%. The fifth zone Z5 extends over a length corresponding with at least 10% of the length la of the absorbent core seen in the longitudinal direction, preferably at least 20%, more preferably at least 25%, e.g. between 20% and 40%.

Preferably the second, the third and/or the fourth zone Z1, Z2, Z3 each extends over a length corresponding with at least 10% of the length la of the absorbent core seen in the longitudinal direction, preferably at least 15%, e.g. between 10% and 20% of the length of the absorbent core. Preferably the first front attachment zone 140 and the second front attachment zone 150 are arranged symmetrically with respect to a longitudinal center axis CL of the absorbent core 130. Preferably a minimum distance d12 between the first and the second front attachment zone is between 20 mm and 70 mm, more preferably between 30 mm and 60 mm, even more preferably between 40 mm and 55 mm. As explained in the summary, such a configuration is especially suitable for male persons.

Preferably the first rear attachment zone 160 and the second rear attachment zone 170 are arranged symmetrically with respect to the longitudinal center axis CL of the absorbent core. Preferably the distance d34 between the first and the second rear attachment zone 160, 170 is between 10 mm and 50 mm, more preferably between 15 mm and 40 mm, even more preferably between 20 mm and 30 mm.

A first smallest distance d12 between the first and the second front attachment zone 140, 150 is bigger than a second smallest distance d34 between the first and the second rear attachment zone 160, 170. The first and the second front attachment zone 140, 150 extend in a longitudinal direction of the absorbent core over a length l1 which is less than the length l3 of the first and second rear attachment zone. Preferably, the length l1 of the first and second front attachment zone 140, 150 is larger than 30 mm, more preferably larger than 40 mm, even more preferably larger than 50 mm.

The plurality of attachment zones 140, 150, 160, 170 may be permanent attachment zones which remain attached when wetted. The plurality of attachment zones may extend, seen in the transverse direction of the absorbent core, over the transverse distance which is at least 1 mm, preferably at least 3 mm, more preferably at least 4 mm, even more preferably at least 5 mm, most preferably at least 6 mm.

FIG. 14

Figure 14:
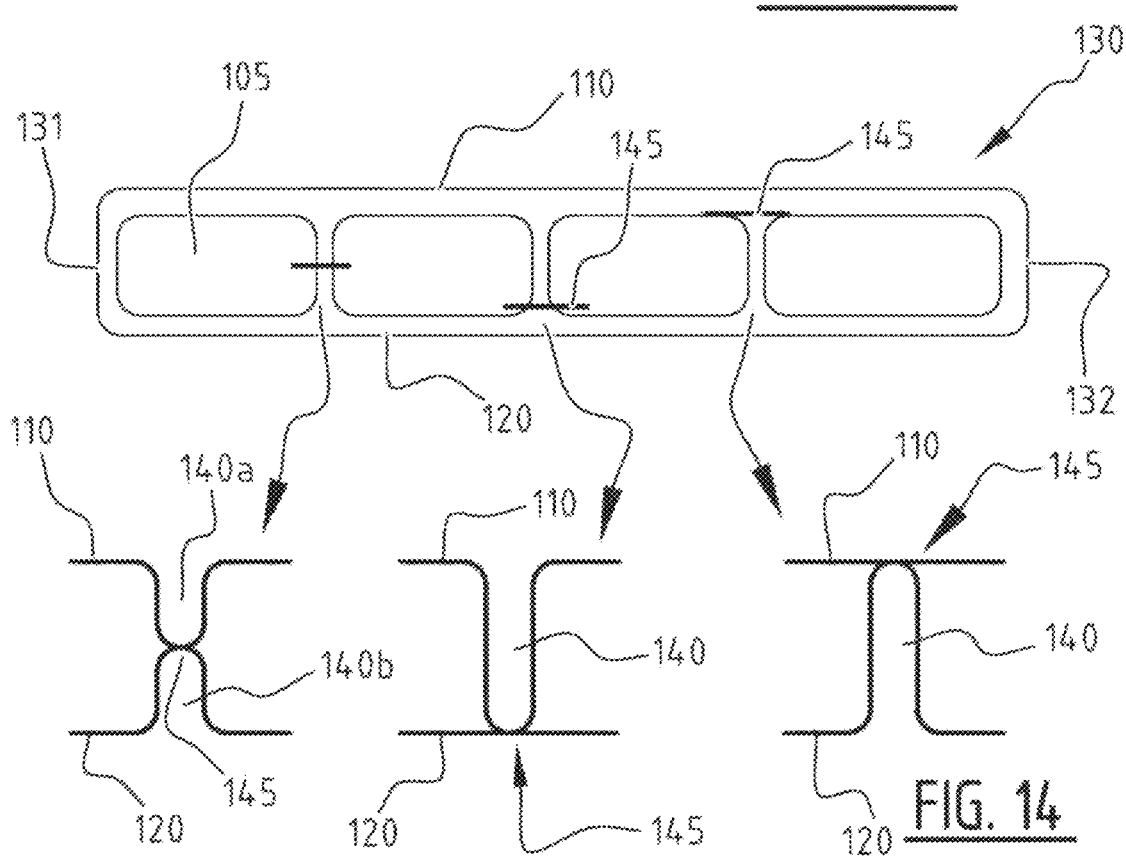
FIG. 14 illustrates a schematic cross-section of an absorbent core, wherein three possible locations are indicated for the attachment zones.

FIG. 14 illustrates an absorbent core 130 comprising an absorbent material 105 between a top core wrap sheet 110 and a back core wrap sheet 120. The absorbent core has a first and second longitudinal edge 131, 132. The absorbent core 130 is provided with a plurality of attachment zones 145. FIG. 14 illustrates that the attachment zones 145 may be positioned at different locations. As illustrated on the left in FIG. 14, the attachment zone may be positioned more or less centrally such that an upper channel portion 140*a* and a lower channel portion 140*b* is formed. In an alternative embodiment, the attachment zone 145 may be positioned at the bottom such that an upper channel 140 is created, see the example in the middle of FIG. 14. According to yet another embodiment, the attachment zone 145 may be located at the top, such that the channel 140 is formed below top core wrap sheet 110. The skilled person understands that any variants thereof are also possible, as long as the attachment zones allow the formation of channels upon wetting of the absorbent core 130.

Although the method is illustrated for two channels, the skilled person understands that the method can be adapted for forming three, four or more channels, and in particular for manufacturing any one of the absorbent articles disclosed in the present application.

FIGS. 15A-15X, 16A-16S, 17A-17V and 18A-G

FIGS. 15A-15X, 16A-16S, 17A-17V and 18A-F illustrate multiple advantageous positions for the attachment zones in an absorbent core according to the invention. Preferably the absorbent core of those examples is provided with a plurality of attachment zones where the top core wrap sheet is attached to the back core wrap sheet, and where preferably substantially no absorbent material is present. Seen in a longitudinal direction of the absorbent core, looking from the front edge to the rear edge, the absorbent core comprises subsequently a first, second, third, fourth and fifth zone Z1, Z2, Z3, Z4, Z5, as illustrated. The principles about the zones set out above for various embodiments may also be applied in the embodiments of FIGS. 15A-15X, 16A-16S, 17A-17V and 18A-F. In possible embodiments, although not illustrated, small portions of the attachment zones of FIGS. 15A-15X, 16A-16S, 17A-17V may be unattached to create one or more bridging zones. More generally, the bridging zone may comprise one or more temporary attachments between the top and back core wrap sheet which are configured to detach when wetted; and/or at one or more permanent attachment zones in a direction from the first to the second side edge; and/or absorbent material in order to make a transverse capillary flow and/or mass flow possible. According to the exemplary embodiment of FIG. 15A the plurality of attachment zones comprises a first attachment zone 140, a second attachment zone 150, a third attachment zone 160 and a fourth attachment zone 170, and a central attachment zone 180. The first and second attachment zones 140 diverge from the central attachment zone 180 in the crotch region in the direction of a rear transverse edge of absorbent core. The third and fourth attachment zone 160, 170 diverge from the central attachment zone 180 in the crotch region in the direction of a front transverse edge of absorbent core.

Figure 15A:
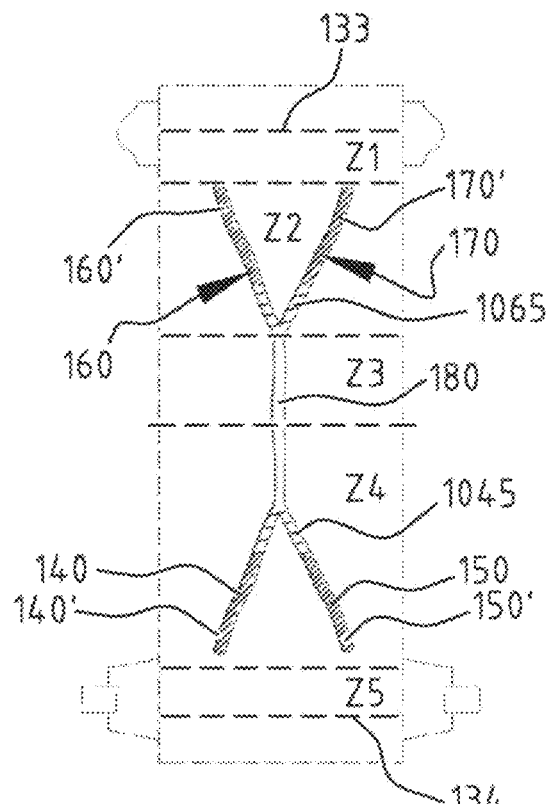
FIGS. 15A-15X illustrate exemplary embodiments of an absorbent core according to the invention.

The embodiment of FIG. 15A can be used for both male and female. In the embodiment of FIG. 15A the first attachment zone 140 and the second attachment zone 150 form together a substantially V-shaped zone. This substantially V-shaped zone comprises a first elongate attachment zone 140' (indicated as a solid fill area), a second elongate attachment zone 150' (indicated as a solid fill area), and a V-shaped connecting attachment zone 1045 (indicated as a hatched area). The first and second elongate attachment zone 140', 150' extend next to each other from the crotch region in the direction of the rear transverse edge 134. The connecting attachment zone 1045 connects said first elongate attachment zone 140' with said second attachment zone 150'. The connecting attachment zone 1045 is a front connecting attachment zone which connects a front end portion of the first attachment zone 140' to a corresponding front end portion of the second attachment zone 150'. Similarly, the third attachment zone 160 and the fourth attachment zone 170 form together a substantially V-shaped zone. This substantially V-shaped zone 160, 170 comprises a third elongate attachment zone 160', a fourth elongate attachment zone 170', and a V-shaped connecting attachment zone 1065. The third and fourth elongate attachment zone 160'. 170' extend next to each other from the crotch region in the direction of the front transverse edge 133. The connecting attachment zone 1065 connects said third elongate attachment zone 160' with said fourth elongate attachment zone 170'. The connecting attachment zone 1065 is a rear connecting attachment zone which connects a rear end portion of the third attachment zone 160' to a corresponding rear end portion of the fourth attachment zone 170. The V-shaped zone 160, 170 guides the liquid from left and right parts of the front portion. As illustrated the first interconnecting attachment zone 1065 may be arranged in the front portion, and more in particular in the second zone Z2, and the second interconnecting attachment zone 1045 may be arranged in the rear portion, and in particular in the fourth zone Z4. By connecting the first interconnecting attachment zone 1065 with the second interconnecting attachment zone 1045 in the crotch region with a central longitudinal attachment zone 180 a convenient liquid distribution channel network is created allowing the liquid to be distributed rapidly throughout the absorbent core.

Figure 15B:
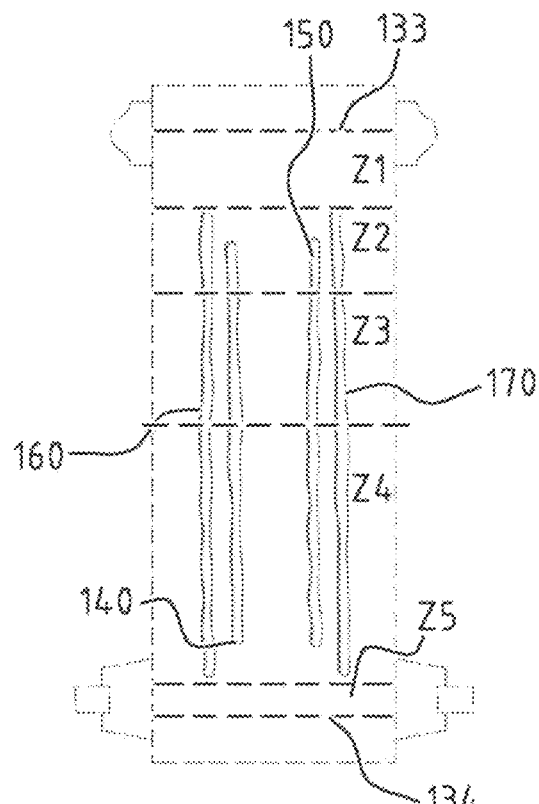

According to the exemplary embodiment of FIG. 15B the plurality of attachment zones comprises a first attachment zone 140, a second attachment zone 150, a third attachment zone 160 and a fourth attachment zone 170. This embodiment is similar to the embodiment of FIG. 2A-2B, with this difference that the outer attachment zones 160, 170 are longer than the inner attachment zones 140, 150. The embodiment of FIG. 15B can be used for both male and female.

Figure 15C:
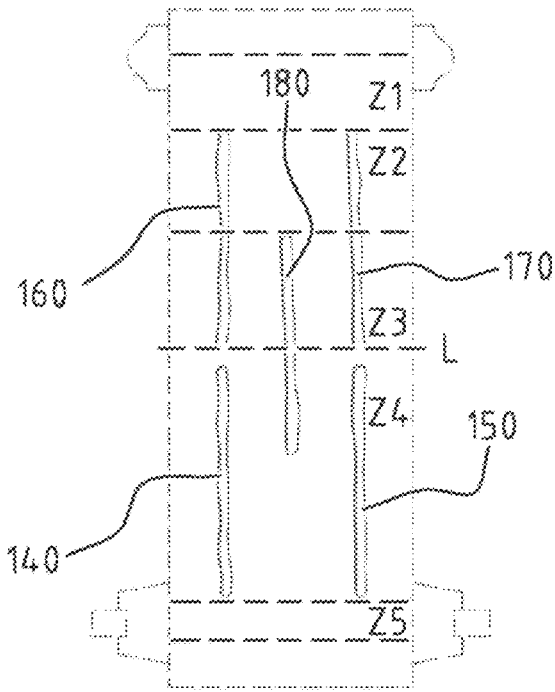

According to the exemplary embodiment of FIG. 15C the plurality of attachment zones comprises a first attachment zone 140, a second attachment zone 150, a third attachment zone 160 and a fourth attachment zone 170, and a central attachment zone 180. The first and third attachment zones 140, 160 are aligned in the longitudinal direction. Also, the second and fourth attachment zones 150, 170 are aligned and extend substantially parallel to the first and third attachment zones 140, 160. The embodiment of FIG. 15C can be used for both male and female.

Figure 15D:
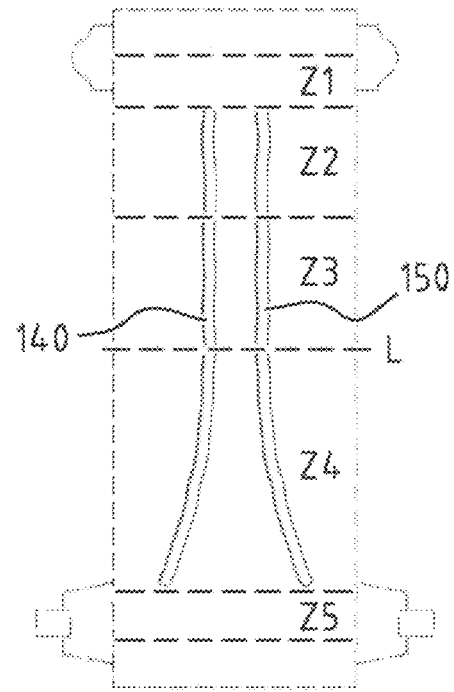

According to the exemplary embodiment of FIG. 15D the plurality of attachment zones comprises a first attachment zone 140 and a second attachment zone 150. The first and second attachment zones 140 are substantially parallel in the crotch region and diverge in the direction of a front transverse edge of absorbent core. The embodiment of FIG. 15D is preferable for female.

Figure 15E:
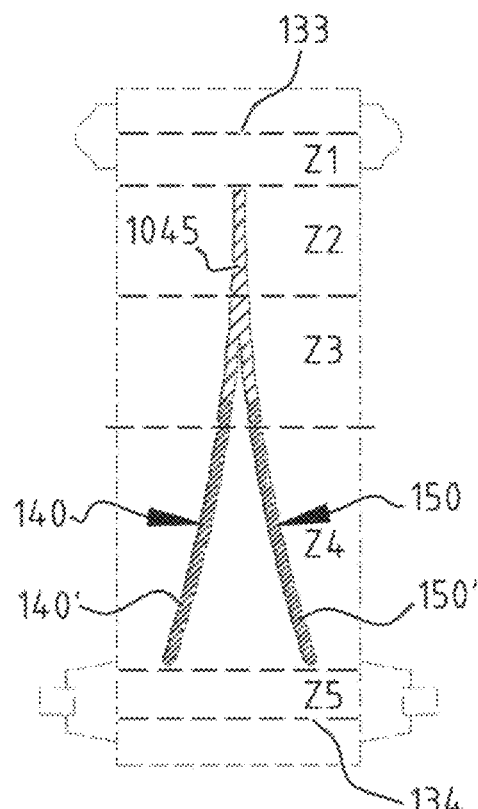

According to the exemplary embodiment of FIG. 15E the plurality of attachment zones comprises a first attachment zone 140 and a second attachment zone 150. The first and second attachment zones 140 partially overlap in the crotch region and diverge in the direction of a rear transverse edge of absorbent core. The embodiment of FIG. 15E is preferable for a female. The embodiment of FIG. 15E is preferable for female.

In the embodiment of FIG. 15E the first attachment zone 140 and the second attachment zone 150 form together a substantially V-shaped zone. This substantially V-shaped zone comprises a first elongate attachment zone 140' (indicated as a solid fill area), a second elongate attachment zone 150' (indicated as a solid fill area), and a V-shaped connecting attachment zone 1045 (indicated as a hatched area). The first and second elongate attachment zone 140', 150' extend next to each other from the crotch region in the direction of the rear transverse edge 134, and more particularly in the fourth and third zone Z4 and Z3. The connecting attachment zone 1045 connects said first elongate attachment zone 140' with said second attachment zone 150'. The connecting attachment zone 1045 is a front connecting attachment zone which connects a front end portion of the first attachment zone 140' to a corresponding front end portion of the second attachment zone 150'. The V-shaped zone 140, 150 guides the liquid from the front portion to the left and right parts of the rear portion. As illustrated the first interconnecting attachment zone 1045 may be arranged in the front portion and more in particular in the second zone Z2. In that manner a convenient liquid distribution channel network is created allowing the liquid to be distributed rapidly throughout the absorbent core.

Figure 15F:
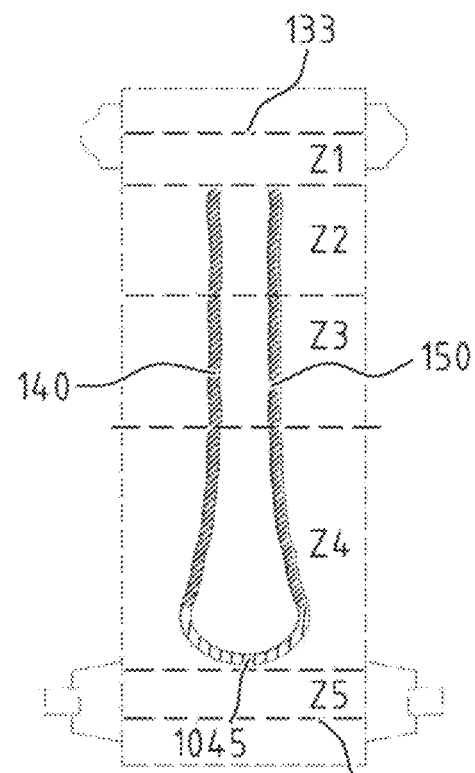

According to the exemplary embodiment of FIG. 15F the plurality of attachment zones comprises a first longitudinal attachment zone 140 and a second longitudinal attachment zone 150 which are interconnected by an attachment portion 1045 in a rear portion of the absorbent core. In that manner any leakage via the rear portion can be reduced or avoided. The embodiment of FIG. 15F is preferable for female.

In the embodiment of FIG. 15F the first attachment zone 140, the second attachment zone 150 and the connecting attachment zone 1045 form together a substantially U-shaped zone. This substantially U-shaped zone comprises a first elongate attachment zone 140 (indicated as a solid fill area), a second elongate attachment zone 150 (indicated as a solid fill area), and a curved connecting attachment zone 1045 (indicated as a hatched area). The first and second elongate attachment zone 140, 150 extend next to each other from the crotch region in the direction of the front transverse edge 133 and in the direction of the rear transverse edge 134, and more particularly in the fourth, third and second zone Z4, Z3 and Z2. The connecting attachment zone 1045 connects said first elongate attachment zone 140 with said second attachment zone 150. The connecting attachment zone 1045 is a rear connecting attachment zone which connects a rear end portion of the first attachment zone 140 to a corresponding rear end portion of the second attachment zone 150. The U-shaped zone 140, 150, 1045 guides the liquid from the left and right parts of the front portion to the rear portion. As illustrated the first interconnecting attachment zone 1045 may be arranged in the rear portion and more in particular in the fourth zone Z4. In that manner a convenient liquid distribution channel network is created allowing the liquid to be distributed rapidly throughout the absorbent core.

Figure 15G:
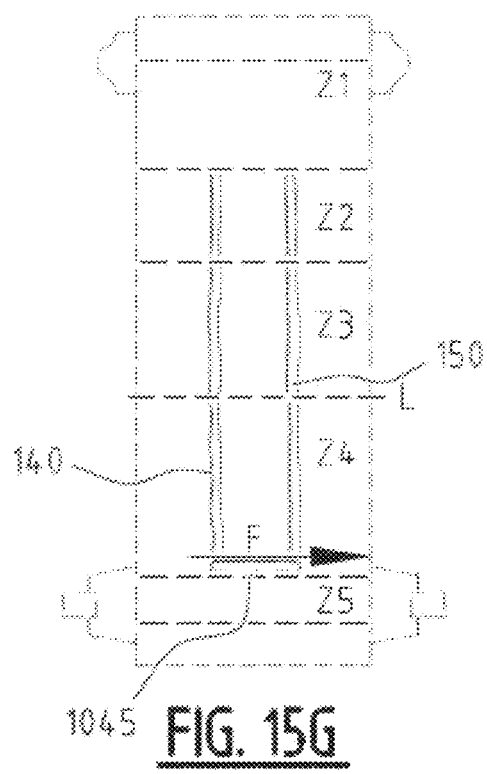

According to the exemplary embodiment of FIG. 15G the plurality of attachment zones comprises a first longitudinal attachment zone 140, a second longitudinal attachment zone 150, and a transverse attachment zone 1045 in a front portion of the absorbent core. The transverse attachment zone 1045 substantially connects a front end of first longitudinal attachment zone 140 and a front end of second longitudinal attachment zone 150. As illustrated the first interconnecting attachment zone 1045 may be arranged in the rear portion and more in particular in the fourth zone Z4.

Figure 15H:
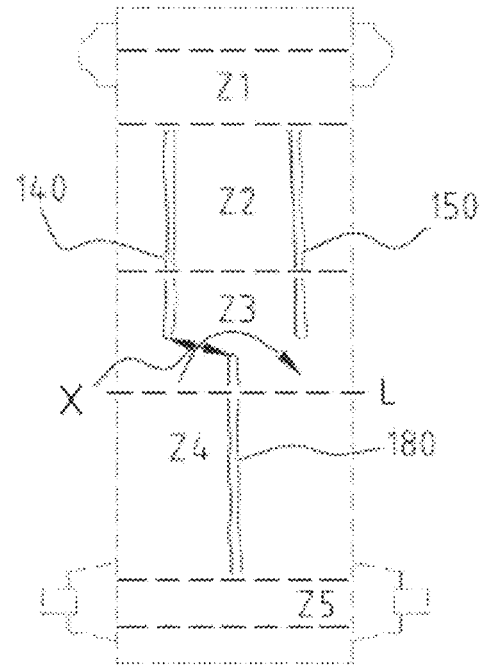
Figure 15I:
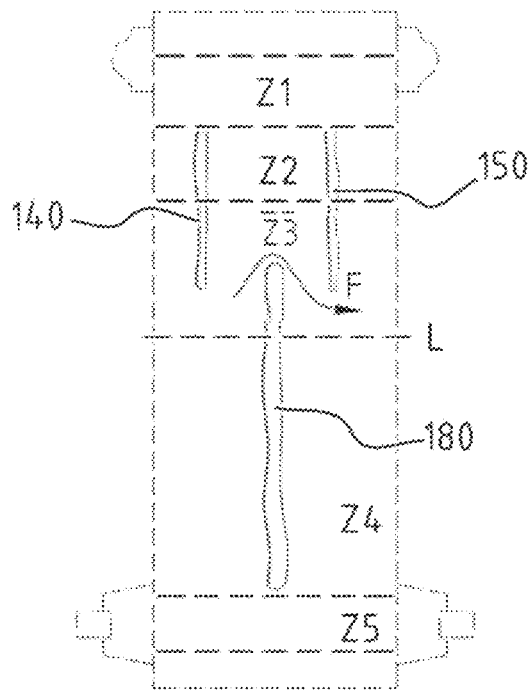

According to the exemplary embodiment of FIG. 15H the plurality of attachment zones comprises a first longitudinal attachment zone 140, a second longitudinal attachment zone 150, a central longitudinal attachment zone 180. The first and second longitudinal attachment zones 140, 150 extend adjacent to each other from the crotch region to a rear transverse edge of the absorbent core. The central longitudinal attachment zone 180 extends from the crotch region in the direction of the front transverse edge of the absorbent core. The embodiment of FIG. 15H is preferable for male. The first and a second attachment zone 140, 150 extend next to each other from a crotch region in the direction of the front edge, and the third attachment zone 180 extends from the crotch region in the direction of the rear edge, wherein seen in a projection on a transverse direction the third attachment zone 180 is located between the first and the second attachment zone 140, 150. Seen in a projection on a longitudinal direction of the absorbent article 130, a projection of the first and second attachment zone 140, 150 does not overlap with a projection of the third attachment zone. The exemplary embodiment of FIG. 15I is similar to the embodiment of FIG. 15H, with this difference that the central attachment zone 180 extends also from the crotch region in the direction of the rear transverse edge, partially in between the first and second attachment zone 140, 150. The embodiment of FIG. 15I is preferable for male. The first and a second attachment zone 140, 150 extend next to each other from a crotch region in the direction of the front edge, and the third attachment zone 180 extends from the crotch region in the direction of the rear edge, wherein seen in a projection on a transverse direction the third attachment zone 180 is located between the first and the second attachment zone 140, 150. Seen in a projection on a longitudinal direction of the absorbent article 130, a projection of the first and second attachment zone 140, 150 partially overlaps with a projection of the third attachment zone 180.

Figure 15J:
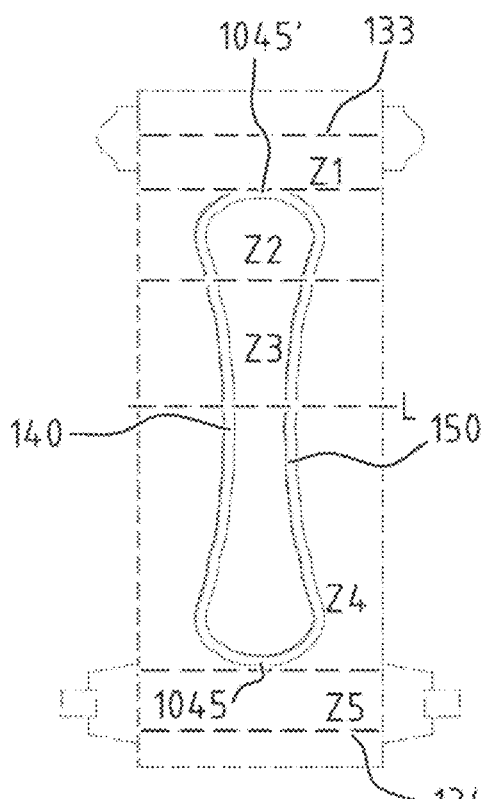

According to the exemplary embodiment of FIG. 15J the plurality of attachment zones comprises a first longitudinal attachment zone 140 and a second longitudinal attachment zone 150 which are interconnected by an attachment portion 1045' in a front portion of the absorbent core and an attachment portion 1045 in a rear portion of the absorbent core. In that manner any leakage via the front and rear portion can be reduced or avoided. The embodiment of FIG. 15I can be used for both male and female.

In the embodiment of FIG. 15J the first attachment zone 140, the second attachment zone 150 and two connecting attachment zones 1045, 1045' form together a substantially rectangular attachment zone. This substantially rectangular attachment zone comprises a first elongate attachment zone 140, a second elongate attachment zone 150, and two curved connecting attachment zones 1045, 1045'. The first and second elongate attachment zone 140, 150 extend next to each other from the crotch region in the direction of the front transverse edge 133 and in the direction of the rear transverse edge 134, and more particularly in the fourth, third and second zone Z4, Z3 and Z2. The connecting attachment zone 1045 is a rear connecting attachment zone which connects a rear end portion of the first attachment zone 140 to a corresponding rear end portion of the second attachment zone 150. The connecting attachment zone 1045 is located in the fourth zone Z4. The connecting attachment zone 1045' is a front connecting attachment zone which connects a front end portion of the first attachment zone 140 to a corresponding front end portion of the second attachment zone 150. The connecting attachment zone 1045' is located in the second zone Z2. In that manner a convenient liquid distribution channel network is created allowing the liquid to be distributed rapidly throughout the absorbent core.

Figure 15K:
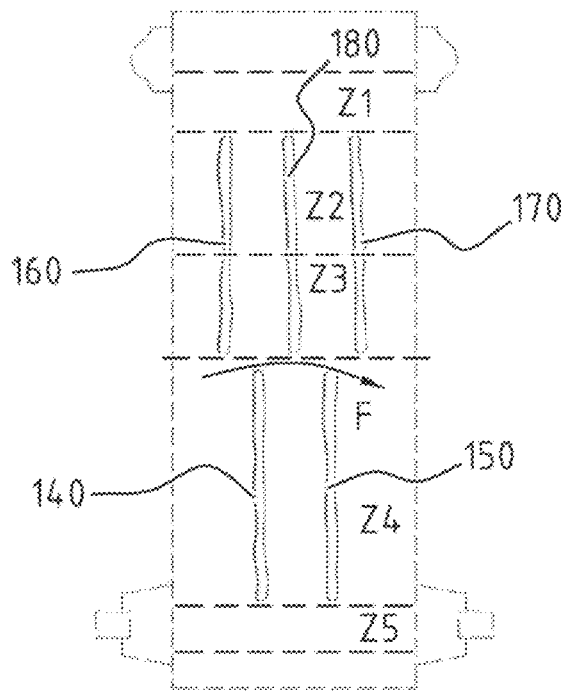

According to the exemplary embodiment of FIG. 15K the plurality of attachment zones comprises a first attachment zone 140, a second attachment zone 150, a third attachment zone 160 and a fourth attachment zone 170, and a central attachment zone 180. The first and second attachment zones 140, 150 extend adjacent to each other from a crotch region in the direction the rear transverse edge. Also, the third and fourth attachment zones 160, 170, as well as the central attachment zone 180 extend adjacent to each other from a crotch region in the direction the front transverse edge. In that manner the distribution of liquid in the front portion of the absorbent core can be further enhanced. The embodiment of FIG. 15K is preferable for male. The first and a second elongate attachment zone 140, 150 extend next each other, at least in the rear portion of the absorbent core in the direction of the rear transverse edge, and the third and fourth elongate attachment zone 160, 170 extend next to each other, at least in the front portion of the absorbent core, in the direction of the front edge. Measured in a transverse direction, a first maximum distance between the first and the second attachment zone 140, 150 is smaller than a second maximum distance between the third and the fourth attachment zone 160, 170.

Figure 15L:
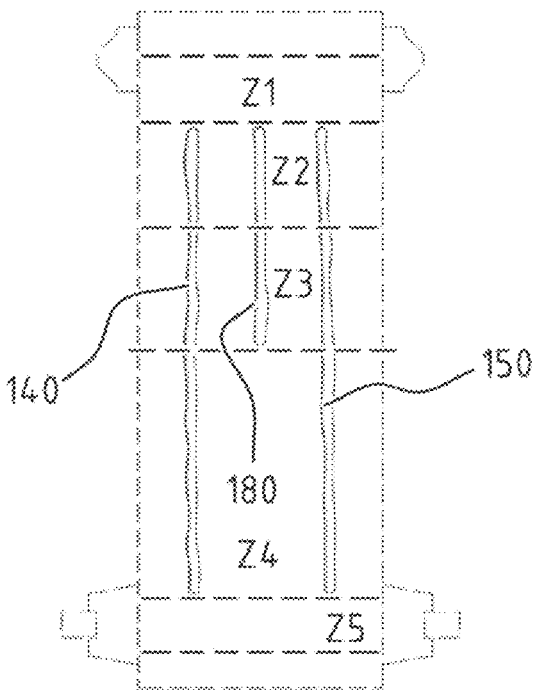

According to the exemplary embodiment of FIG. 15L the plurality of attachment zones comprises a first longitudinal attachment zone 140, a second longitudinal attachment zone 150, and a central longitudinal attachment zone 180. The first and second longitudinal attachment zones 140, 150 extend adjacent to each other over at least 60% of the length of the absorbent core. The central longitudinal attachment zone 180 extends between the first and second attachment zones 140, 150, from the crotch region in the direction of the rear transverse edge of the absorbent core. The embodiment of FIG. 15L can be used for both male and female.

Figure 15M:
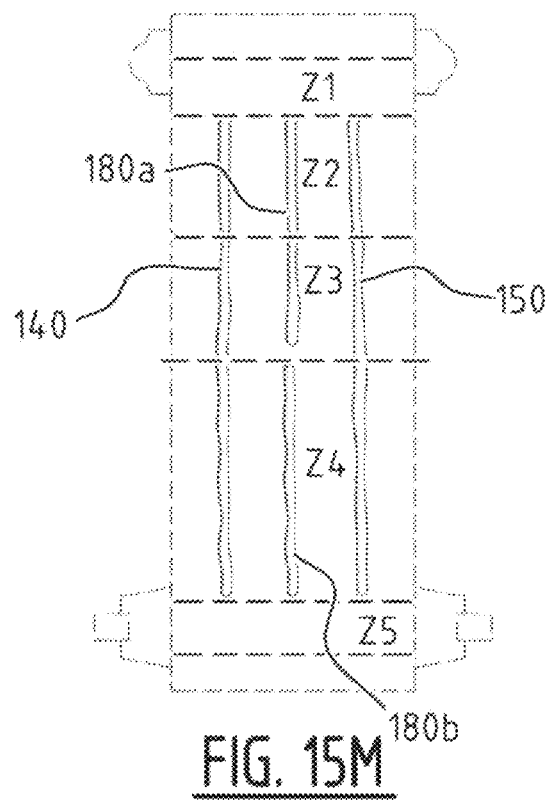

According to the exemplary embodiment of FIG. 15M the plurality of attachment zones comprises a first longitudinal attachment zone 140, a second longitudinal attachment zone 150, a central rear longitudinal attachment zone 180a, and a central front longitudinal attachment zone 180b. The first and second longitudinal attachment zones 140, 150 extend adjacent to each other over at least 60% of the length of the absorbent core. The central rear and front longitudinal attachment zones 180a, 180b extends between the first and second attachment zones 140, 150, in a rear and front portion of the absorbent core, respectively. The embodiment of FIG. 15M can be used for both male and female.

Figure 15N:
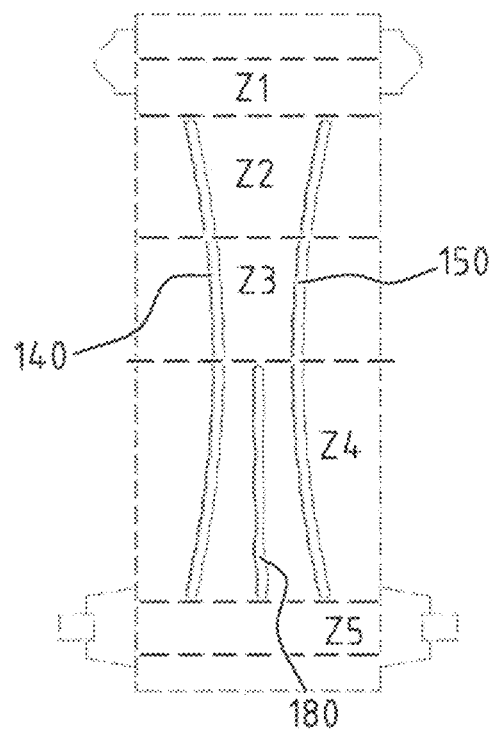

According to the exemplary embodiment of FIG. 15N the plurality of attachment zones comprises a first attachment zone 140, a second attachment zone 150, and a central attachment zone 180. The first and second attachment zones 140 diverge from the crotch region in the direction of a front and rear transverse edge of absorbent core. The central attachment zone is provided in between the first and second attachment zone 140, 150, mainly in a front portion of the absorbent core. The embodiment of FIG. 15N can be used for both male and female.

Figure 15O:
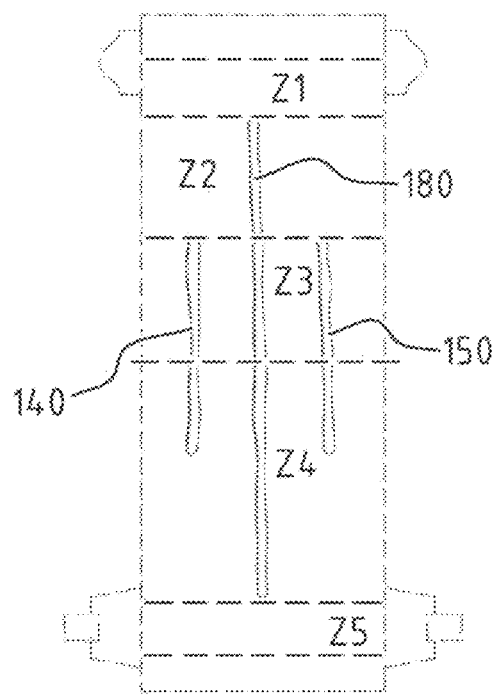

According to the exemplary embodiment of FIG. 15O the plurality of attachment zones comprises a first longitudinal attachment zone 140, a second longitudinal attachment zone 150, and a central longitudinal attachment zone 180. The first and second longitudinal attachment zones 140, 150 extend adjacent and parallel to each other in the crotch region. The central longitudinal attachment zone 180 extends between the first and second attachment zones 140, 150, over at least 60% of the length of the absorbent core. The embodiment of FIG. 15O can be used for both male and female. According to the exemplary embodiment of FIG. 15P the plurality of attachment zones comprises a first attachment zone 140 and a second attachment zone 150. The first and second attachment zones 140, 150 extend from the crotch region in the direction of a front and rear transverse edge of absorbent core, and are curved such that the first and second attachment zones 140, 150 cross each other at a first crossing point in a front portion of the absorbent core and in a second crossing point in the rear portion of the absorbent core. The embodiment of FIG. 15P can be used for both male and female.

Figure 15P:
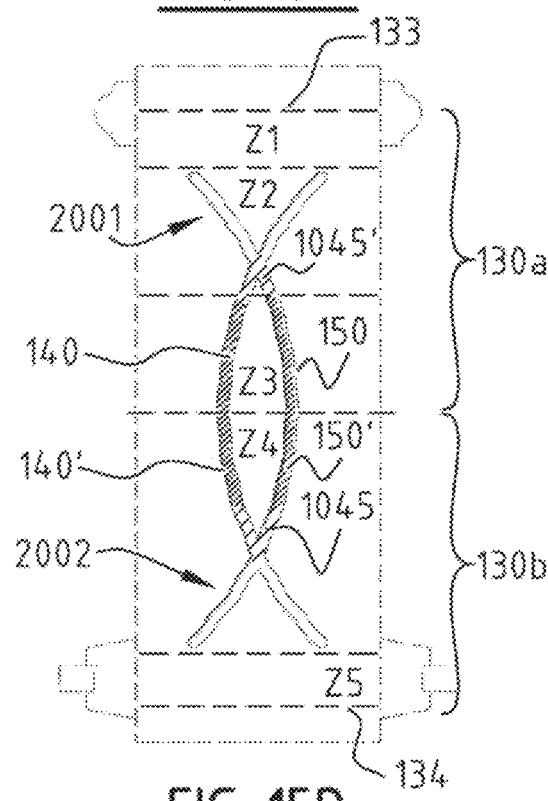

In the embodiment of FIG. 15P a first elongate attachment zone 140', a second elongate attachment zone 150' and two connecting attachment zones 1045, 1045' form together a substantially 0-shaped attachment zone. This substantially 0-shaped attachment zone comprises the first elongate attachment zone 140', the second elongate attachment zone 150', and two V-shaped connecting attachment zones 1045, 1045'. The first and second elongate attachment zone 140', 150' extend next to each other from the crotch region in the direction of the front transverse edge 133 and in the direction of the rear transverse edge 134, and more particularly in the fourth, and third zone Z4, Z3. The connecting attachment zone 1045 is a rear connecting attachment zone which connects a rear end portion of the first attachment zone 140' to a corresponding rear end portion of the second attachment zone 150'. The connecting attachment zone 1045 is located in the fourth zone Z4. The connecting attachment zone 1045' is a front connecting attachment zone which connects a front end portion of the first attachment zone 140' to a corresponding front end portion of the second attachment zone 150'. The connecting attachment zone 1045' is located in the second zone Z2. Further a first and second V-shaped attachment zone 2001, 2002 may be provided at a rear side and front side of the substantially 0-shaped attachment zone 140', 150', 1045, 1045'. In that manner a convenient liquid distribution channel network is created allowing the liquid to be distributed rapidly throughout the absorbent core.

Figure 15Q:
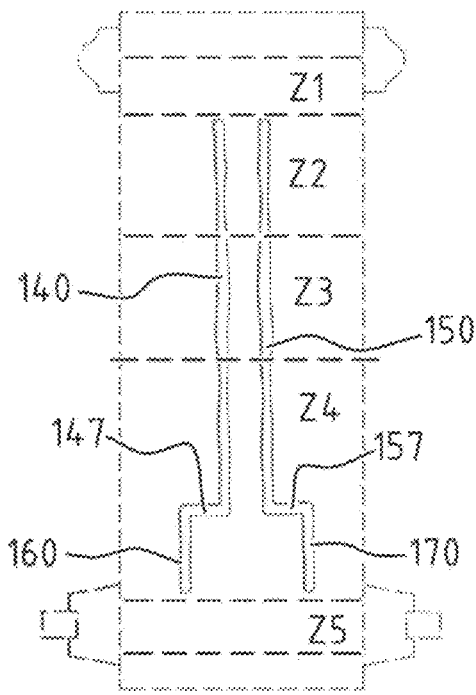

According to the exemplary embodiment of FIG. 15Q the plurality of attachment zones comprises a first longitudinal attachment zone 140, a second longitudinal attachment zone 150, a third attachment longitudinal zone 160 and a fourth longitudinal attachment zone 170. The first and second attachment zones 140, 150 extend from the crotch region in the direction of the rear transverse edge, and are interconnected via transverse attachment portions 147, 157 to third and fourth attachment zone 160, 170 extending from the crotch region to the front transverse edge, respectively. The embodiment of FIG. 15Q is preferable for female.

Figure 15R:
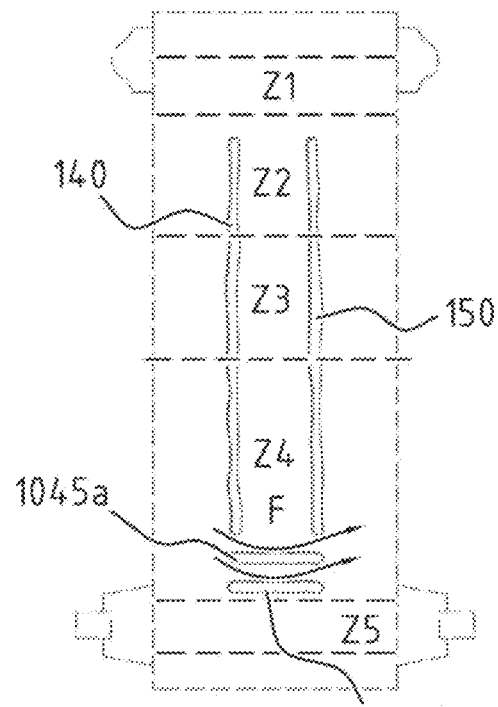
Figure 15S:
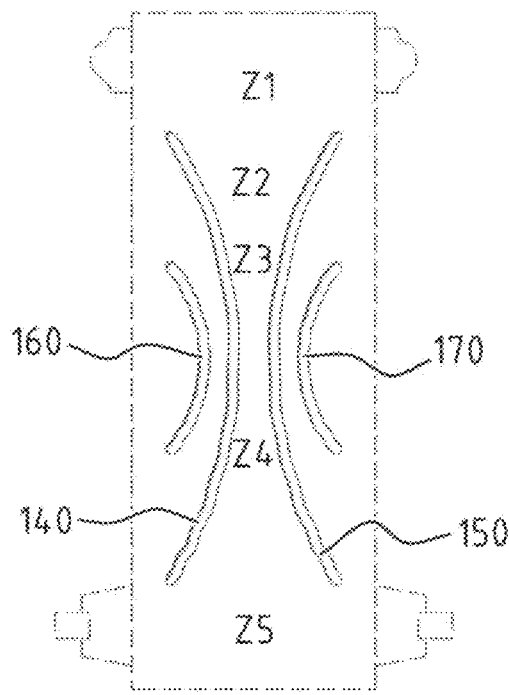

The exemplary embodiment of FIG. 15R is similar to the embodiment of FIG. 15G with this difference that two parallel transverse attachment zones 1045a and 1045b are provided in the front region of the absorbent core. The embodiment of FIG. 15R can be used for both male and female. According to the exemplary embodiment of FIG. 15S the plurality of attachment zones comprises a first attachment zone 140, a second attachment zone 150, a third attachment zone 160 and a fourth attachment zone 170. The first and second attachment zones 140, 150 diverge from the crotch region in the direction of a front and rear transverse edge of absorbent core. The third and fourth attachment zones 160, 170 are located outwardly of the first and second attachment zones 140, 150, are shorter than the first and second attachment zones 140, 150, and also diverge from the crotch region in the direction of a front and rear transverse edge of absorbent core. In that manner, in the wetted state, a plurality of tubes is created, wherein the tubes are smaller in a center of the crotch region and gradually widen in the direction of the front and rear transverse edge of the absorbent core. In that manner the shape of the tub which is formed in the wetted state can be further improved to fit well to the body. The embodiment of FIG. 15S can be used for both male and female.

Figure 15T:
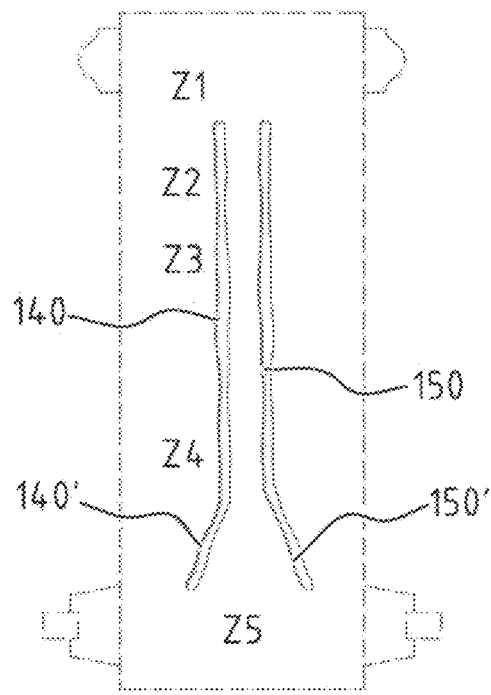

According to the exemplary embodiment of FIG. 15T the plurality of attachment zones comprises a first longitudinal attachment zone 140 and a second longitudinal attachment zone 150, wherein front end portions 140', 150' thereof diverge in the direction of the front transverse edge of the absorbent core. The embodiment of FIG. 15T is preferable for female.

Figure 15U:
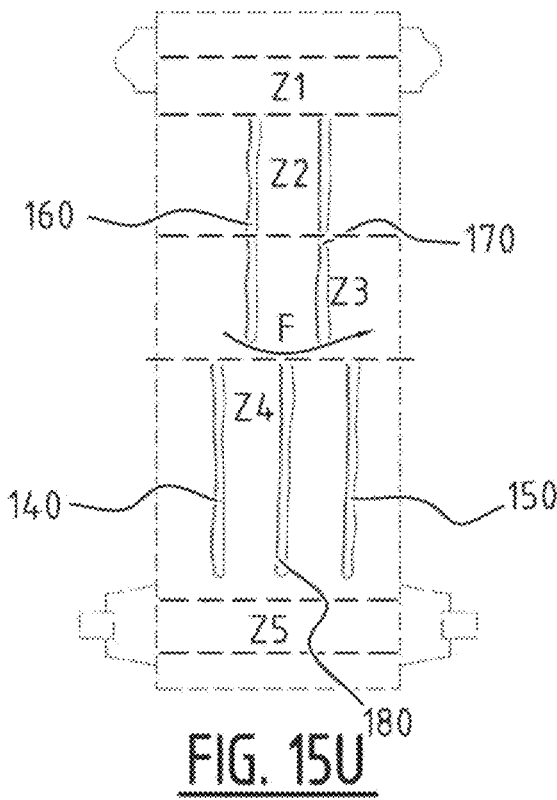

According to the exemplary embodiment of FIG. 15U the plurality of attachment zones comprises a first longitudinal attachment zone 140, a second longitudinal attachment zone 150, a third longitudinal attachment zone 160 and a fourth longitudinal attachment zone 170, and a central longitudinal attachment zone 180. The first and second attachment zones 140, 150, as well as the central attachment zone 180 extend adjacent to each other from a crotch region in the direction the front transverse edge. Also, the third and fourth attachment zones 160, 170 extend adjacent to each other from a crotch region in the direction the rear transverse edge. In that manner the distribution of liquid in the front portion of the absorbent core can be further enhanced. The embodiment of FIG. 15U is preferable for female.

Figure 15V:
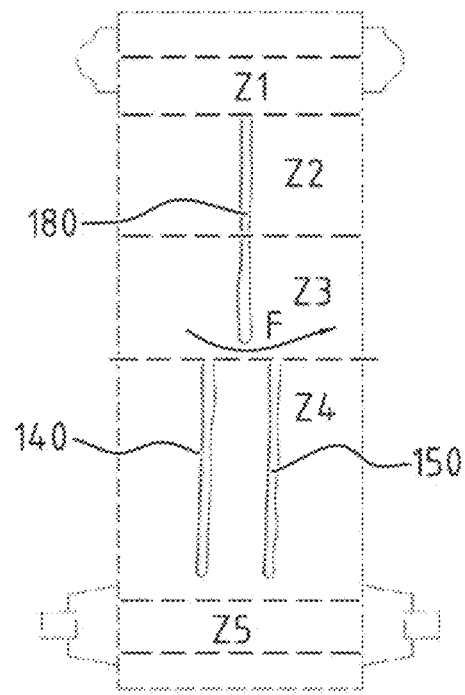

According to the exemplary embodiment of FIG. 15V the plurality of attachment zones comprises a first longitudinal attachment zone 140, a second longitudinal attachment zone 150, and a central longitudinal attachment zone 180. The first and second attachment zones 140, 150 extend adjacent to each other from a crotch region in the direction the front transverse edge. The central attachment zone 180 extends from a crotch region in the direction the rear transverse edge. The embodiment of FIG. 15V can be used for both male and female.

Figure 15W:
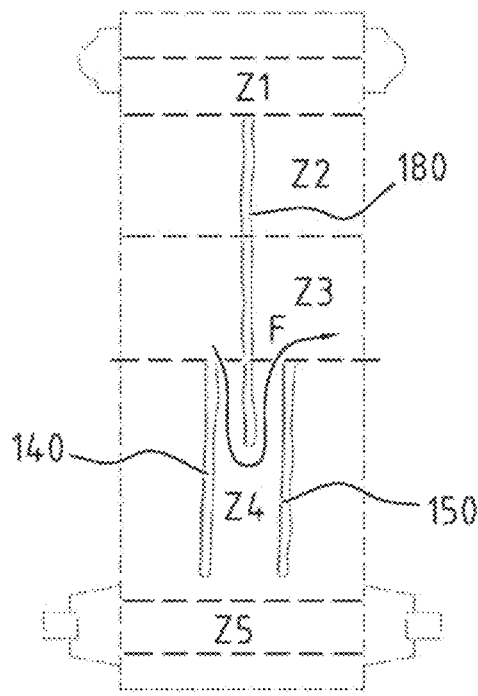
Figure 15X:
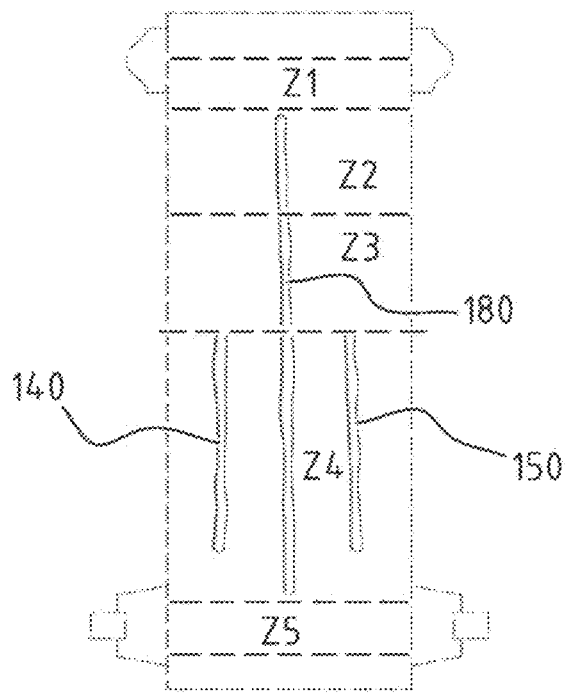

The exemplary embodiment of FIG. 15W is similar to the embodiment of FIG. 15V with this difference that the central attachment zone 180 extends partially in between the first and the second attachment zone 140, 150. The embodiment of FIG. 15W can be used for both male and female. The exemplary embodiment of FIG. 15X is similar to the embodiment of FIG. 15V with this difference that the central attachment zone 180 extends all the way in between the first and the second attachment zone 140, 150 in the direction of the front transverse edge. The embodiment of FIG. 15X can be used for both male and female.

Figure 16A:
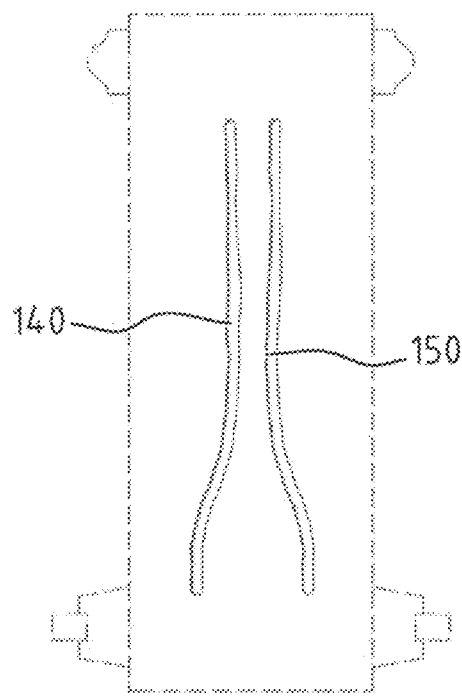
FIGS. 16A-16S illustrate other exemplary embodiments of an absorbent core according to the invention.

According to the exemplary embodiment of FIG. 16A the plurality of attachment zones comprises a first attachment zone 140 and a second attachment zone 150. The first and second attachment zones 140 are substantially parallel in a rear part of the crotch region, whilst the transverse distance between the first and second attachment zones gradually increases in the direction of a front transverse edge of absorbent core. The embodiment of FIG. 16A is preferable for female.

Figure 16B:
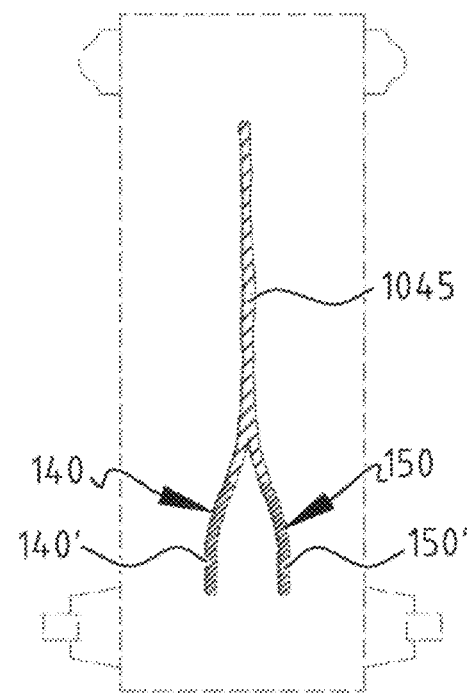

According to the exemplary embodiment of FIG. 16B the plurality of attachment zones comprises a first attachment zone 140 and a second attachment zone 150. The first and second attachment zones 140 partially overlap in a front part of the crotch region, whilst the transverse distance between the first and second attachment zones gradually increases in the direction of a rear transverse edge of absorbent core. The embodiment of FIG. 16B is preferable for female. FIG. 16B is similar to the embodiment of FIG. 15E with this difference that the elongate attachment zones 140', 150' are shorter and that the connecting zone 1045 comprises a longer longitudinal section extending from the second zone Z2 to the third zone Z3 into the fourth zone Z4 where the elongate attachment zones 140', 150' are located.

Figure 16C:
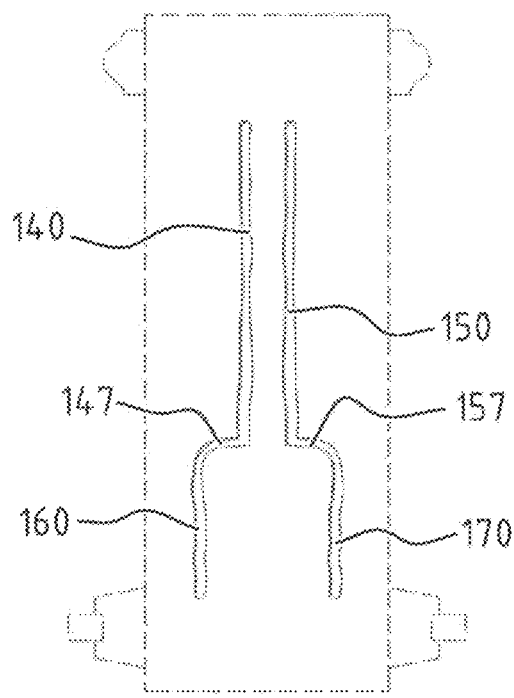
Figure 16D:
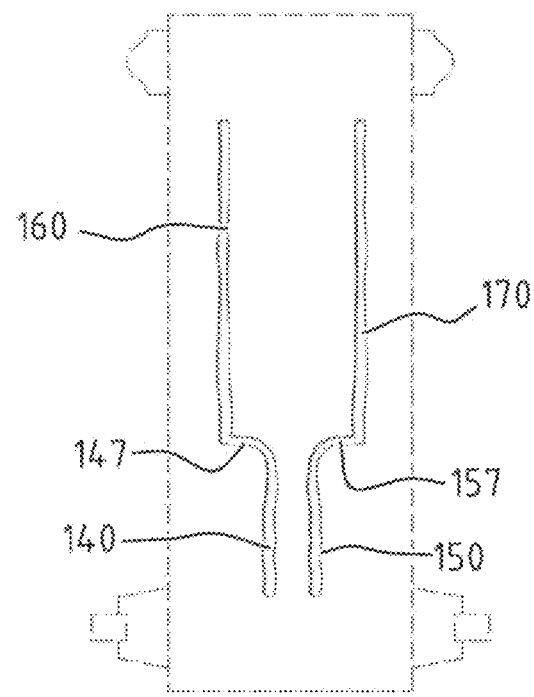
Figure 16E:
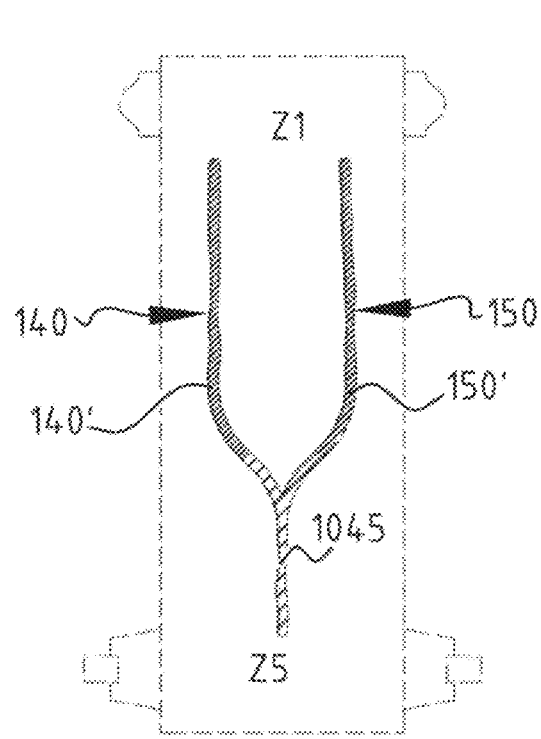

According to the exemplary embodiment of FIGS. 16C and 16D the plurality of attachment zones comprises a first longitudinal attachment zone 140, a second longitudinal attachment zone 150, a third attachment longitudinal zone 160 and a fourth longitudinal attachment zone 170. The first and second attachment zones 140, 150 extend from the crotch region in the direction of the rear transverse edge (FIG. 16D) or in the direction of the front transverse edge (FIG. 16C), and are interconnected via transverse attachment portions 147, 157 to third and fourth attachment zone 160, 170 extending from the crotch region to the front transverse edge (FIG. 16D) or in the direction of the rear transverse edge (FIG. 16C), respectively. In FIG. 16C the distance between the first and second attachment zones is smaller than the distance between the third and fourth attachment zones, whilst in FIG. 16D the distance between the first and second attachment zones is bigger than the distance between the third and fourth attachment zones. The embodiment of FIG. 16E is similar to the embodiment of FIG. 16D with this difference that the third and fourth attachment zones overlap in a front portion of the absorbent core. The embodiments of FIGS. 16C and 16E are preferable for female. The embodiment of FIG. 16D is preferable for male. The first and a second elongate attachment zone 140, 150 extend next to each other in the rear portion of the absorbent core in the direction of the rear transverse edge, and the third and fourth elongate attachment zone 160, 170 extend next to each other in the front portion of the absorbent core, in the direction of the front edge. Measured in a transverse direction, a first maximum distance between the first and the second attachment zone 140, 150 is smaller than a second maximum distance between the third and the fourth attachment zone 160, 170.

Figure 16F:
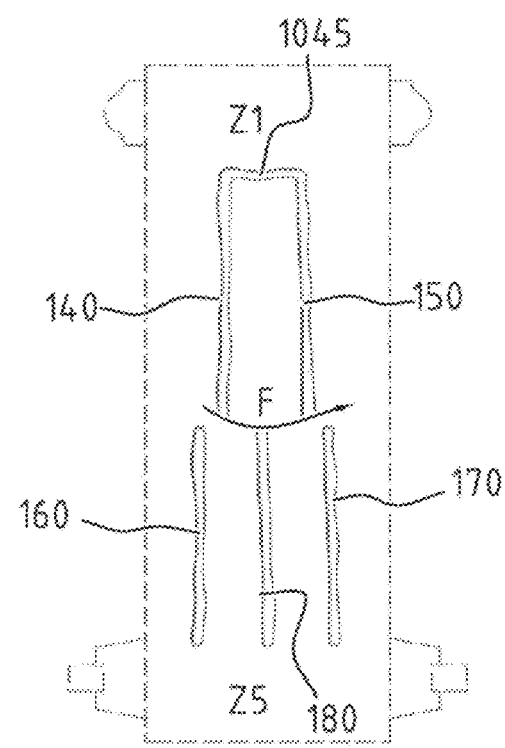

FIG. 16E is similar to the embodiment of FIG. 15E with this difference that the connecting zone 1045 is a rear connecting zone extending in the fourth zone Z4, whilst the elongate attachment zones 140', 150' are located mainly in the second and third zone Z2 and Z3. The embodiment of FIG. 16F is similar to the embodiment of FIG. 15U with this difference that the third and fourth longitudinal attachment zones 160, 170 are interconnected at their rear end by a transverse attachment zone 1045. The embodiment of FIG. 16F is preferable for female.

Figure 16G:
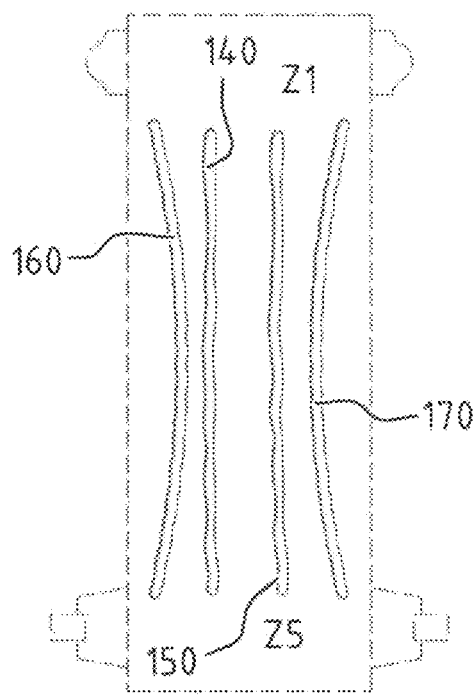

The embodiment of FIG. 16G is similar to the embodiment of FIG. 15B with this difference that the third and fourth longitudinal attachment zones 160, 170 have end portions which diverge outwardly in the direction of the front transverse edge and the rear transverse edge of the absorbent core. The embodiment of FIG. 16G can be used for both male and female.

Figure 16H:
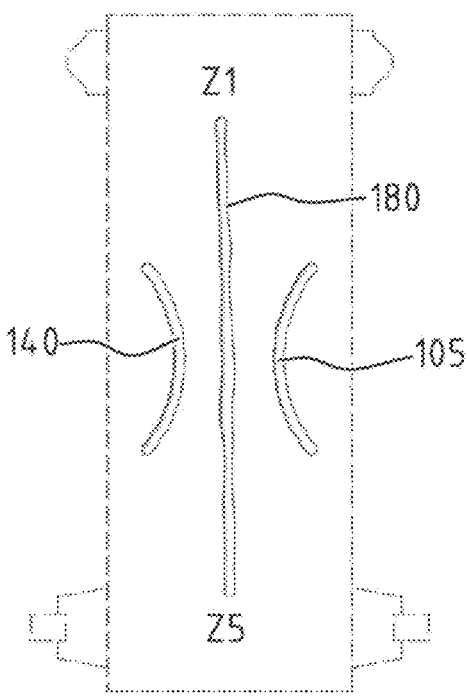

The embodiment of FIG. 16H is similar to the embodiment of FIG. 15O with this difference that the first and second attachment zones 140, 150 have end portions which diverge outwardly in the direction of the front transverse edge and the rear transverse edge of the absorbent core. The embodiment of FIG. 16H can be used for both male and female.

Figure 16I:
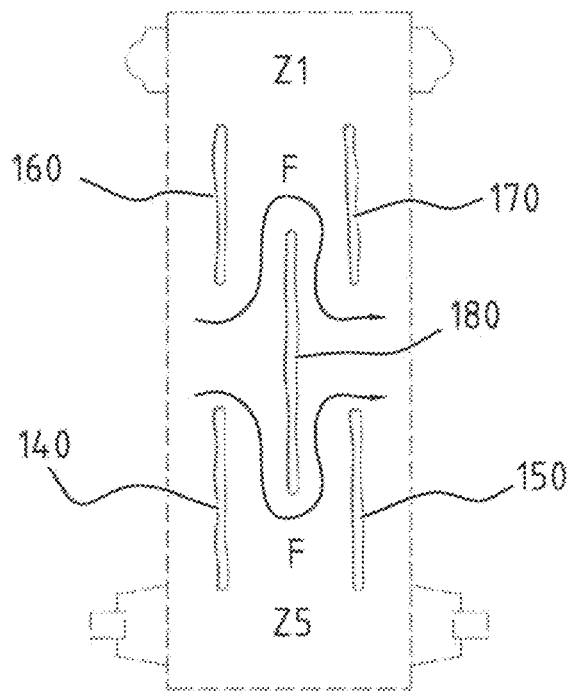

The embodiment of FIG. 16I is similar to the embodiment of FIG. 15C with this difference that the first, second, third and fourth attachment zones 140, 150, 160, 170 are shorter such that in a central part of the crotch region only central attachment zone 180 is present. The embodiment of FIG. 16I can be used for both male and female.

Figure 16J:
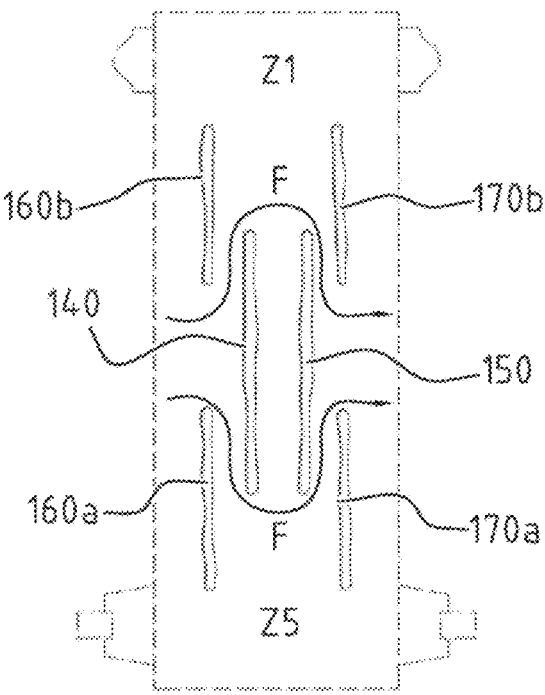

The embodiment of FIG. 16J is similar to the embodiment of FIG. 16I with this difference that the two central attachment zones 180 are provided between first and third attachment zones 140, 160 and second and fourth attachment zones 150, 170. The embodiment of FIG. 16J can be used for both male and female.

Figure 16K:
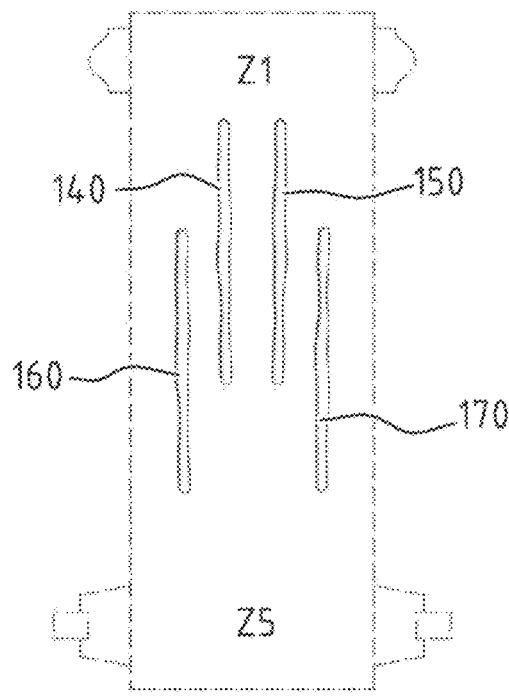
Figure 16L:
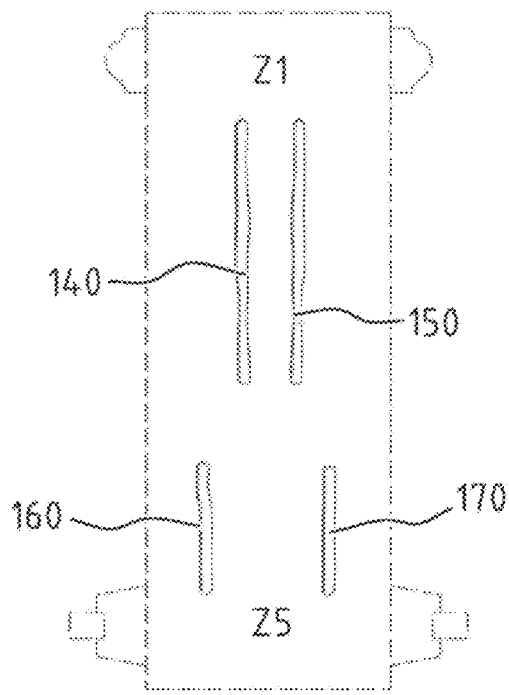

The embodiments of FIGS. 16K and 16L the plurality of attachment zones comprises a first longitudinal attachment zone 140, a second longitudinal attachment zone 150, a third attachment longitudinal zone 160 and a fourth longitudinal attachment zone 170. The first and second attachment zones 140, 150 extend from the crotch region in the direction of the front transverse edge. The third and fourth attachment zone 160, 170 extend from the crotch region to the rear transverse edge. The distance between the first and second attachment zones 140, 150 is bigger than the distance between the third and fourth attachment zones 160, 170. In FIG. 16K the third and fourth attachment zones 160, 170 extend partially between the first and second attachment zones 140, 150, whilst in FIG. 16L, seen in the longitudinal direction, the third and fourth attachment zones 160, 170 are at a distance of the first and second attachment zones 140, 150. The embodiments of FIG. 16K and FIG. 16L are preferable for female.

Figure 16M:
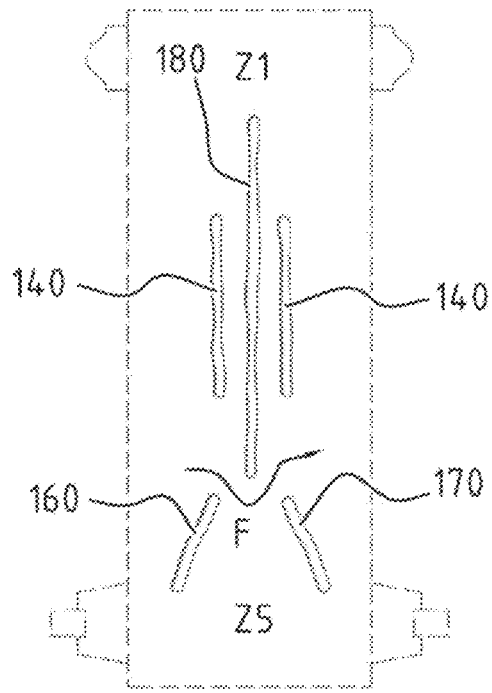
Figure 16N:
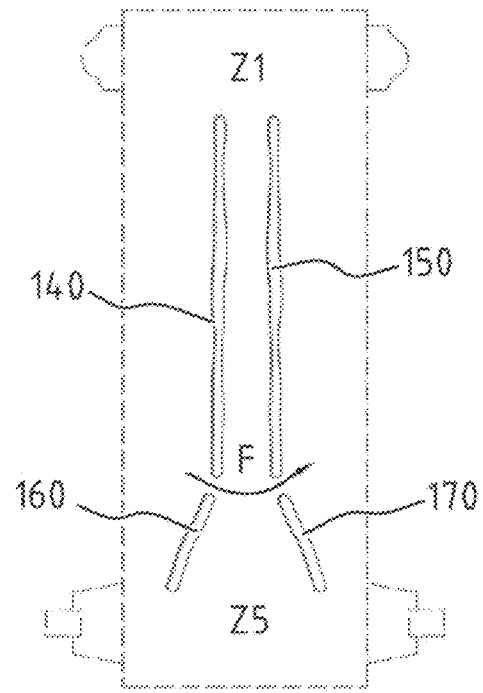
Figure 16O:
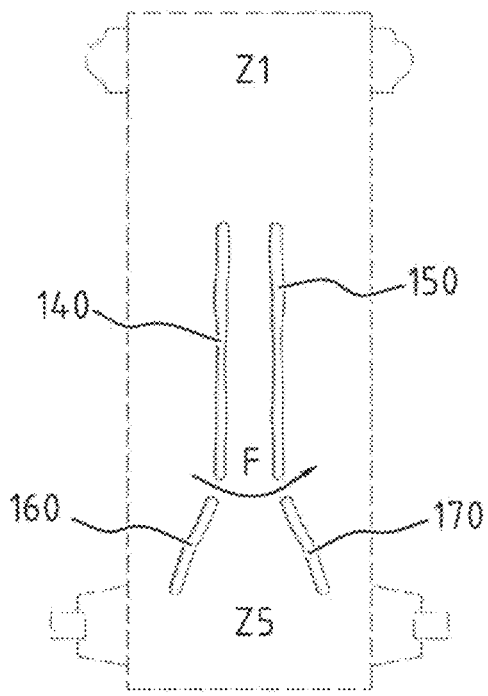

In the embodiments of FIGS. 16M, 16N and 16O the plurality of attachment zones comprises a first longitudinal attachment zone 140, a second longitudinal attachment zone 150, and outwardly diverging attachment zones 160, 170 in a front portion of the absorbent core. In FIG. 16M, additionally a central attachment zone 180 is provided between the first longitudinal attachment zone 140 and the second longitudinal attachment zone 150. The embodiments of FIGS. 16M, 16N and 16O are preferable for female.

Figure 16P:
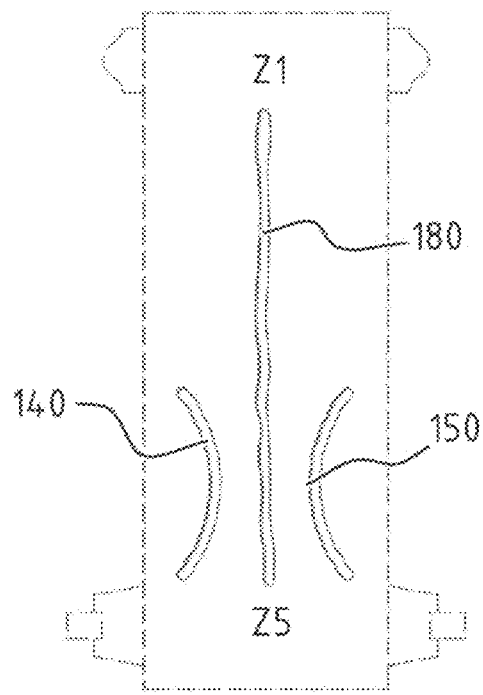

FIG. 16P is similar to the embodiment of FIG. 16H with this difference that first and second attachment zones are provided more to the front of absorbent core. The embodiment of FIG. 16P can be used for both male and female.

Figure 16Q:
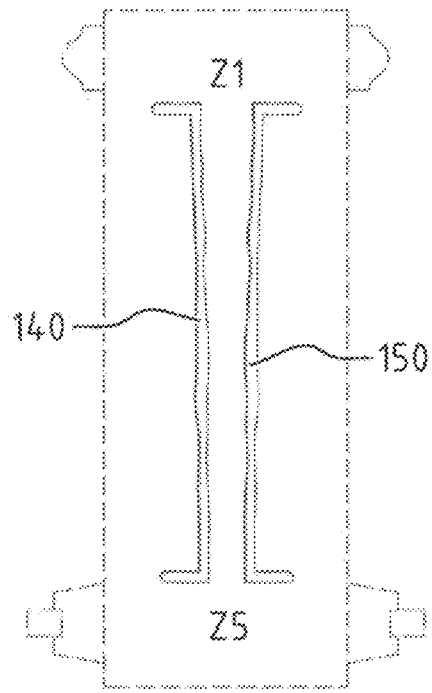

In the embodiment of FIG. 16Q the plurality of attachment zones comprises a first longitudinal attachment zone 140 and a second longitudinal attachment zone 150 which extend over at least 60° % of the length of the absorbent core. The first longitudinal attachment zone 140 and the second longitudinal attachment zone 150 are each provided at a front end and at a rear end with an outwardly directed transverse portion. In that manner leakage risks at the front and rear portions of the absorbent core can be further reduced. The embodiment of FIG. 16Q can be used for both male and female.

Figure 16R:
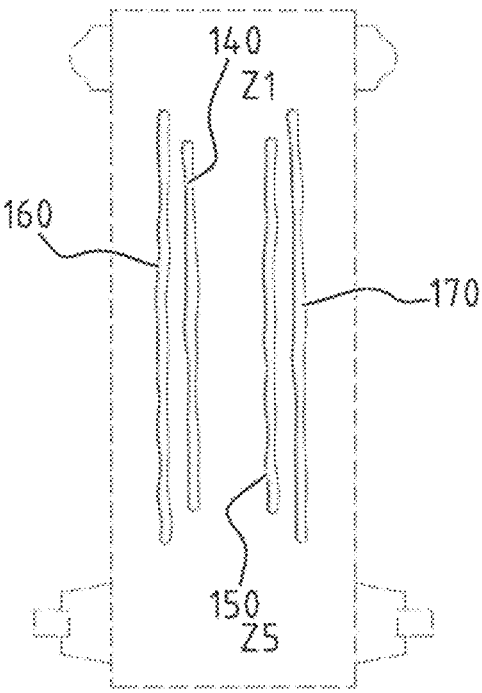

FIG. 16R is similar to the embodiment of FIG. 15B. The embodiment of FIG. 16R can be used for both male and female.

Figure 16S:
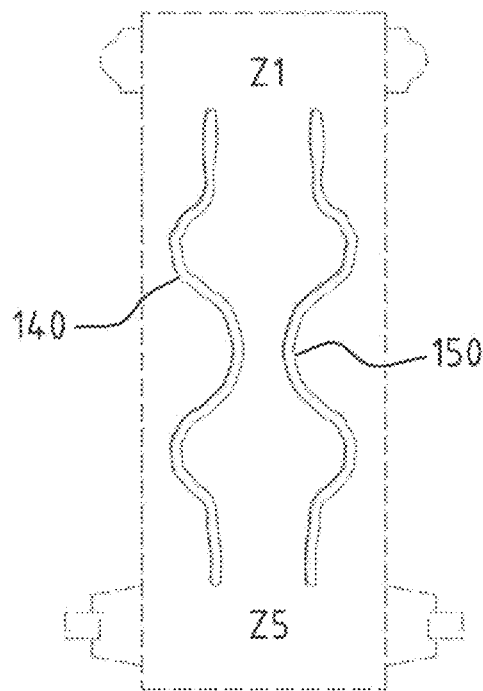

In the embodiment of FIG. 16S the plurality of attachment zones comprises a first undulated attachment zone 140 and a second undulated attachment zone 150 each extending over at least 60% of the length of the absorbent core. The undulations will increase the length of the channels 140, 150, further improving the liquid distribution in the absorbent core. The embodiment of FIG. 16S can be used for both male and female.

FIGS. 17A-17V and FIGS. 18A-18G illustrate yet other exemplary embodiments of an absorbent core according to the invention.

Figure 17A:
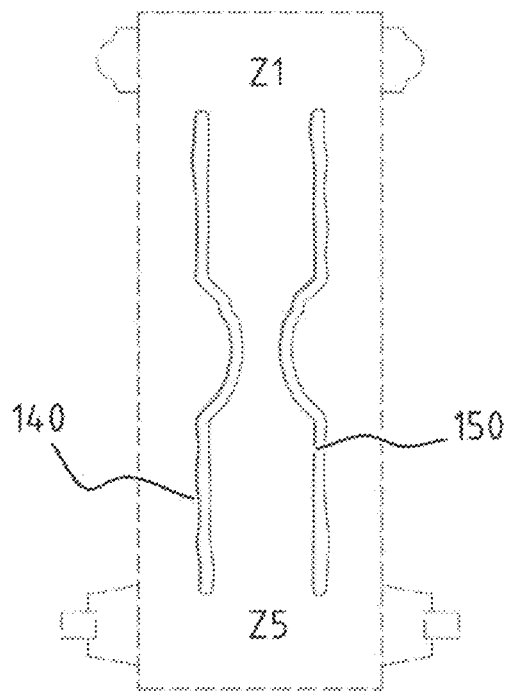
FIGS. 17A-17V illustrate yet other exemplary embodiments of an absorbent core according to the invention.
Figure 17B:
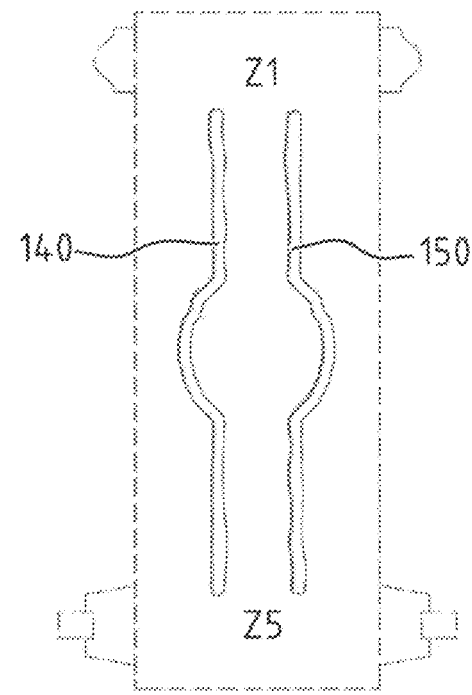
Figure 17C:
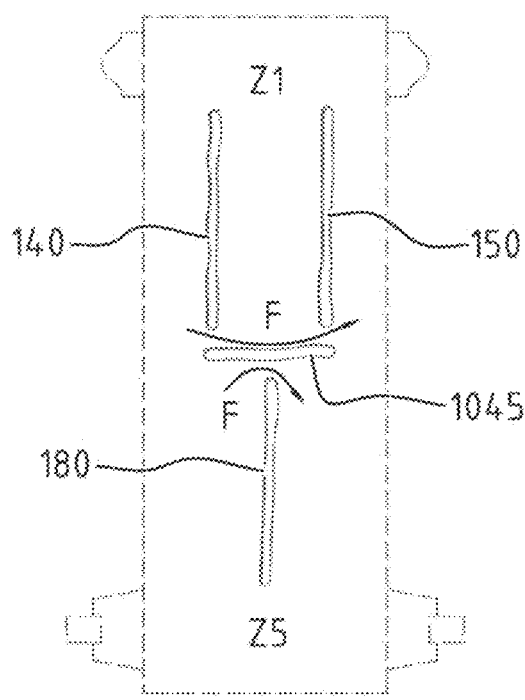
Figure 17D:
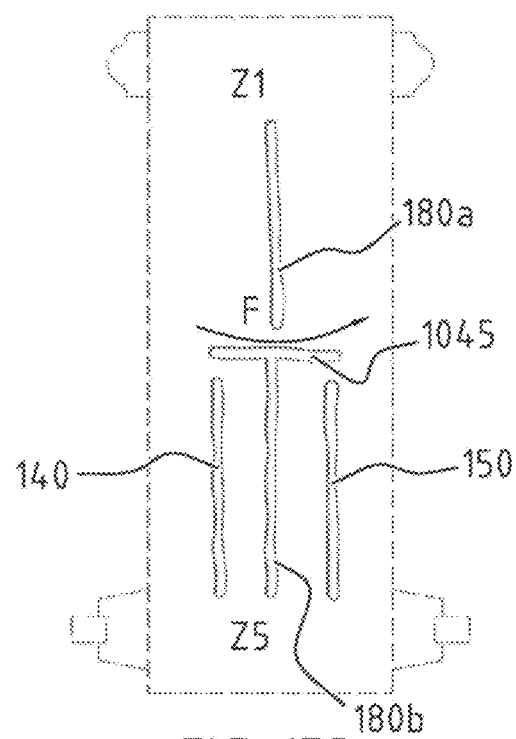
Figure 17E:
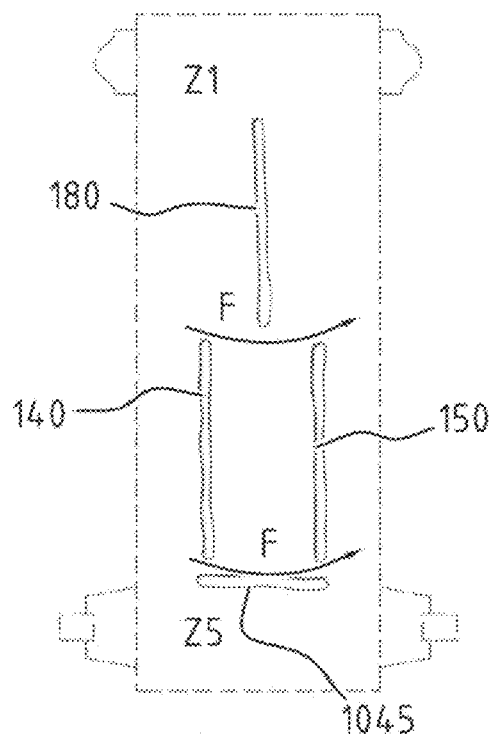
Figure 17F:
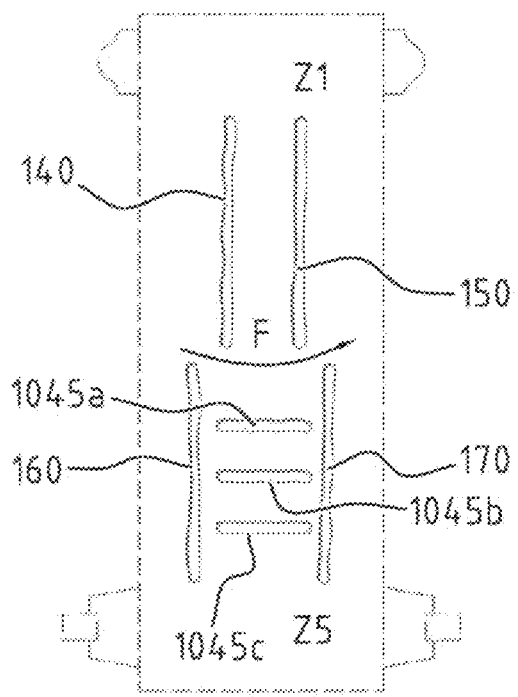
Figure 17G:
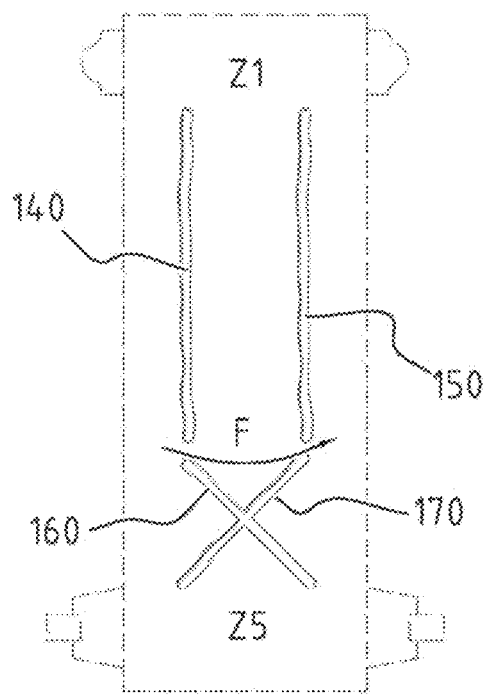

FIGS. 17A, 17B, 17H and 17K illustrate that the first and second attachment zones 140, 150 may comprise curved portions. FIGS. 17C, 17D, 17E, 17F, 17G, 17J, 17L, 17M, 17N, 17O, 17P, 17Q, 17R, 17S, 17T, 17U, 17V illustrate that various patterns are possible with one or more longitudinal sections 140, 150, 160, 170, 180, and/or one or more inclined sections 160, 170, 160a, 160b, 170a, 170b and/or one or more transverse sections 1045, 1045a, 1045b, 1045c. FIG. 17I illustrates that also curved transverse sections 1045a, 1045b may be used. The embodiments of FIGS. 17A, 17B, 17D, 17G, 17E, 17G, 17H, 17I, 17G, 17K, 17L, 17M, 17O, 17Q, 17R and 17S can be used for both male and female. The embodiments of FIGS. 17C, 17N and 17P are preferable for male. The embodiments of FIGS. 17F, 17T, 17U and 17V are preferable for female. These embodiments illustrate that the liquid distribution may be further enhanced using transverse permanent or semi-permanent attachment zones and/or additional longitudinal attachment zones.

Figure 17H:
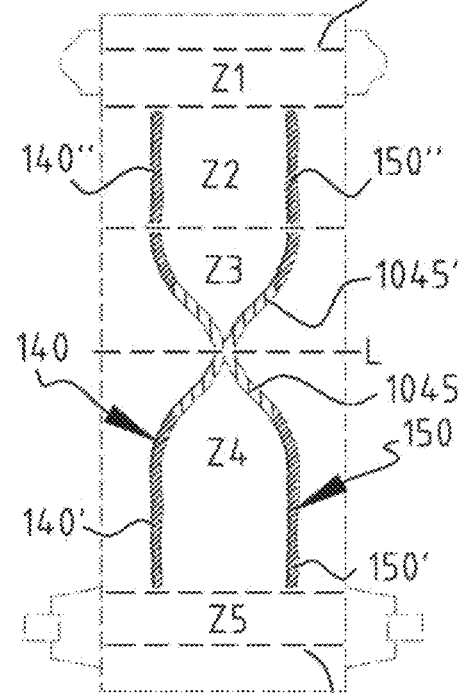
Figure 17I:
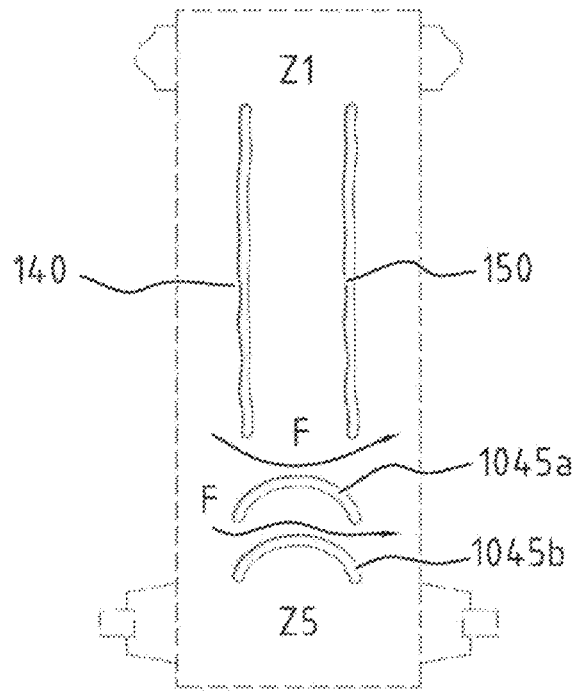
Figure 17J:
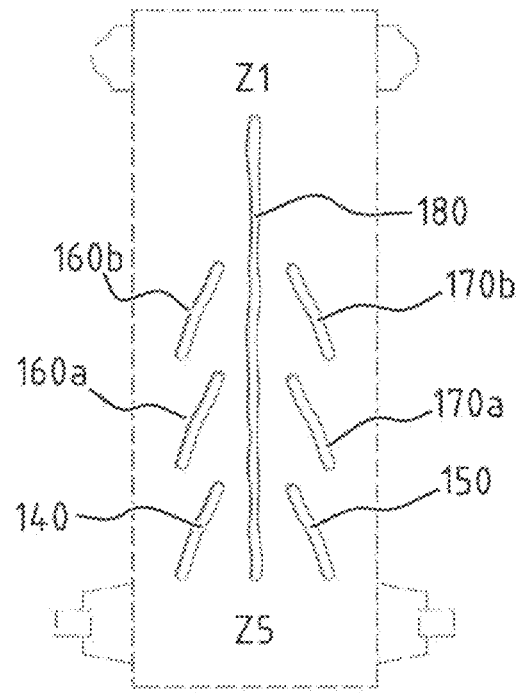

In the embodiment of FIG. 17H the first attachment zone 140 and the second attachment zone 150 form together two substantially V-shaped zones. A first substantially V-shaped zone is located in a rear portion (and in particular in the fourth zone Z4) and comprises a first elongate attachment zone 140' (indicated as a solid fill area), a second elongate attachment zone 150' (indicated as a solid fill area), and a V-shaped connecting attachment zone 1045 (indicated as a hatched area). The first and second elongate attachment zone 140'. 150' extend next to each other from the crotch region in the direction of the rear transverse edge 134 and diverge in the direction of the rear transverse edge 134. The connecting attachment zone 1045 connects said first elongate attachment zone 140' with said second elongate attachment zone 150'. The connecting attachment zone 1045 is a front connecting attachment zone which connects a front end portion of the first attachment zone 140' to a corresponding front end portion of the second attachment zone 150'. Similarly, a third elongate attachment zone 140", a fourth elongate attachment zone 150" and a connecting attachment zone 1045' form together a second substantially V-shaped zone located in a front portion of the absorbent core and more in particular in the second and third zone Z2, Z3. This second substantially V-shaped zone 140", 150", 1045' may be joined to the first substantially V-shaped zone 104', 150', 1045. In the illustrated embodiment the connecting attachment zones 1045, 1045' are connected at or near the transverse crotch line L. The third and fourth elongate attachment zone 140", 150" extend next to each other from the crotch region in the direction of the front transverse edge 133 and diverge in this direction. The connecting attachment zone 1045' connects said third elongate attachment zone 140" with said fourth elongate attachment zone 150". The connecting attachment zone 1045' is a rear connecting attachment zone which connects a rear end portion of the third attachment zone 140" to a corresponding rear end portion of the fourth attachment zone 150". The first and second V-shaped zones guide the liquid from left and right parts of the front portion towards the rest of the absorbent core. As illustrated the first interconnecting attachment zone 1045' may be arranged in the front portion, and more in particular in the third zone Z3, and the second interconnecting attachment zone 1045 may be arranged in the rear portion, and in particular in the fourth zone Z4. By connecting the first interconnecting attachment zone 1045 with the second interconnecting attachment zone 1045' in the crotch region a convenient liquid distribution channel network is created allowing the liquid to be distributed rapidly throughout the absorbent core.

Figure 17K:
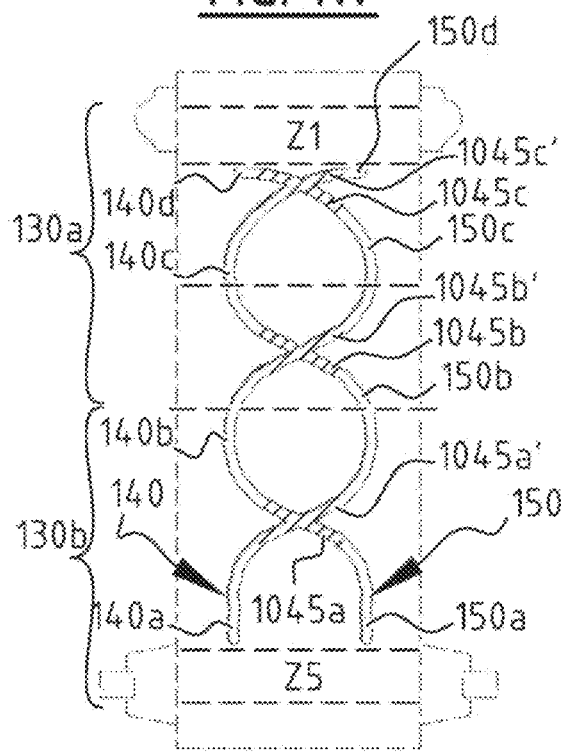
Figure 17L:
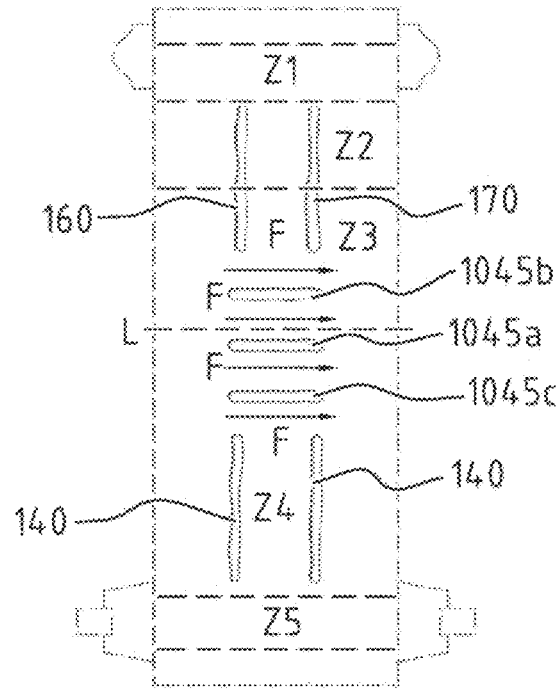
Figure 17M:
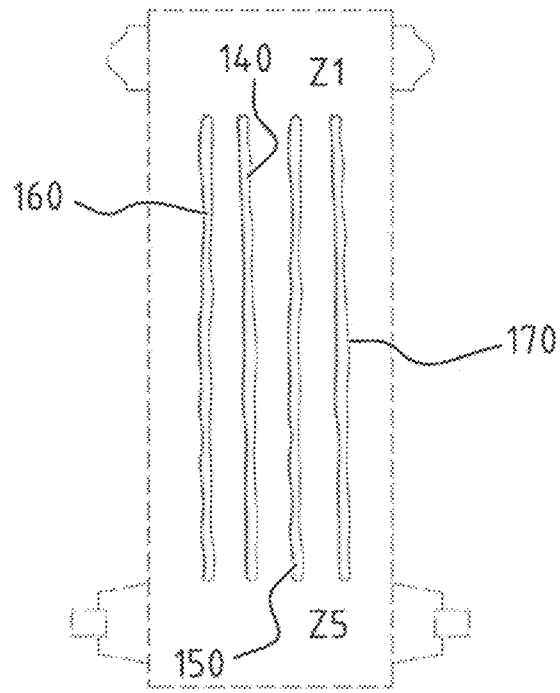
Figure 17N:
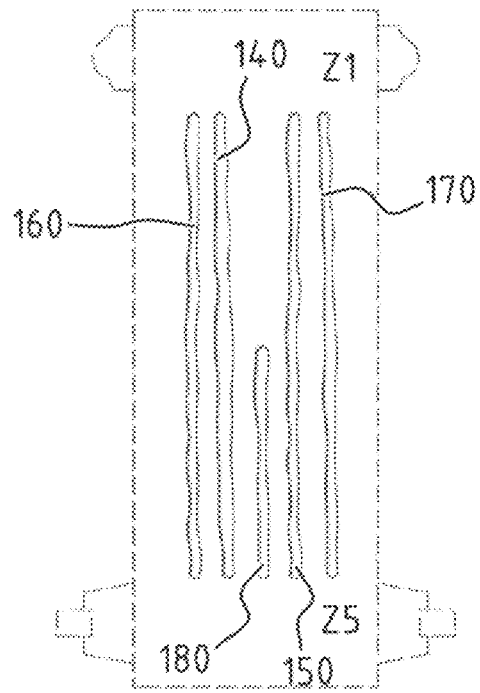
Figure 17O:
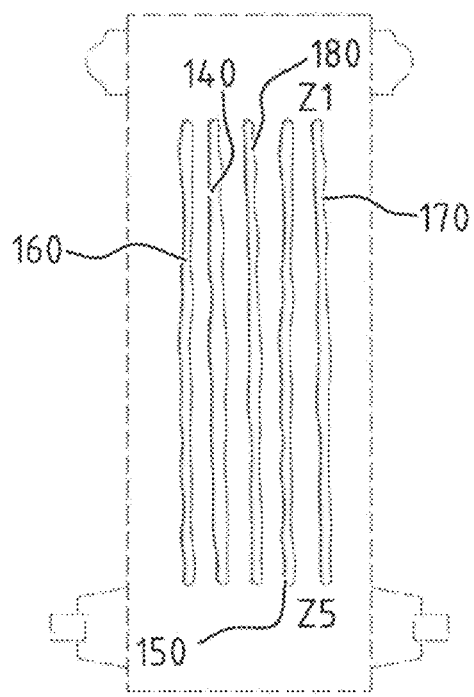
Figure 17P:
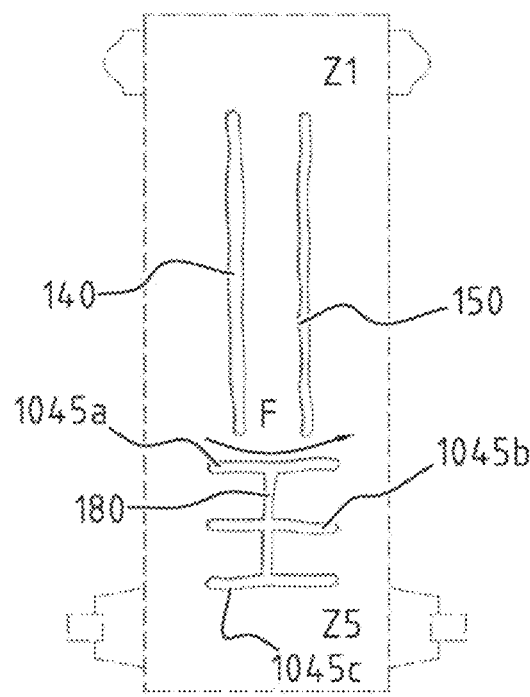
Figure 17Q:
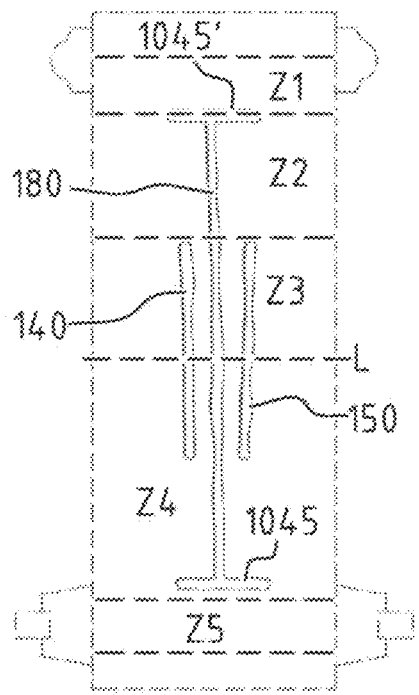
Figure 17R:
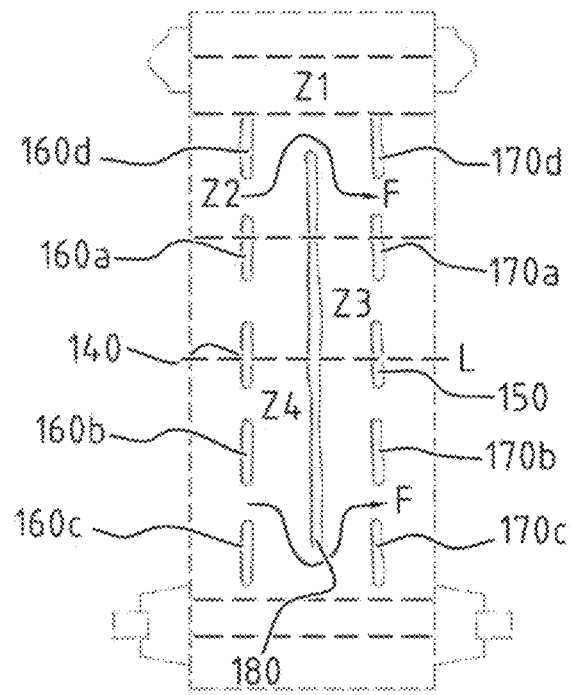
Figure 17S:
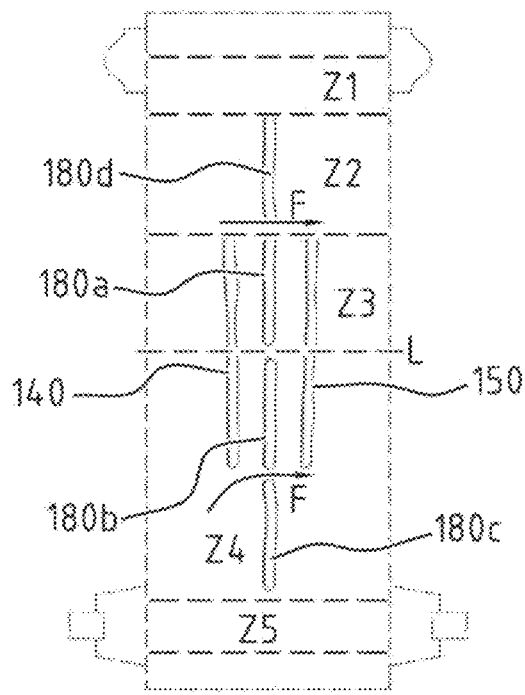
Figure 17T:
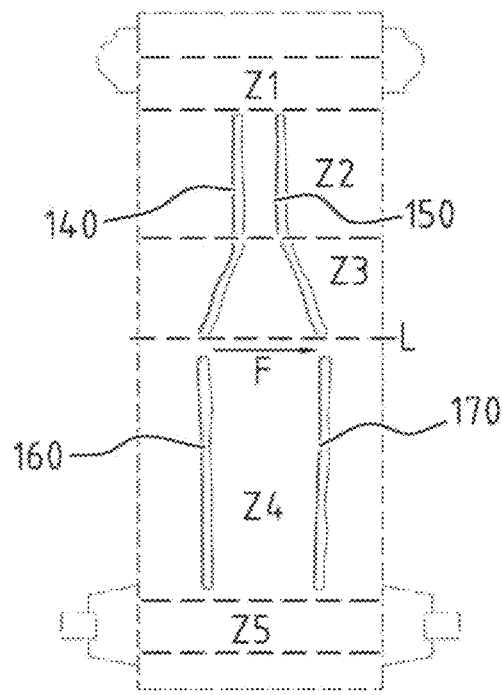
Figure 17U:
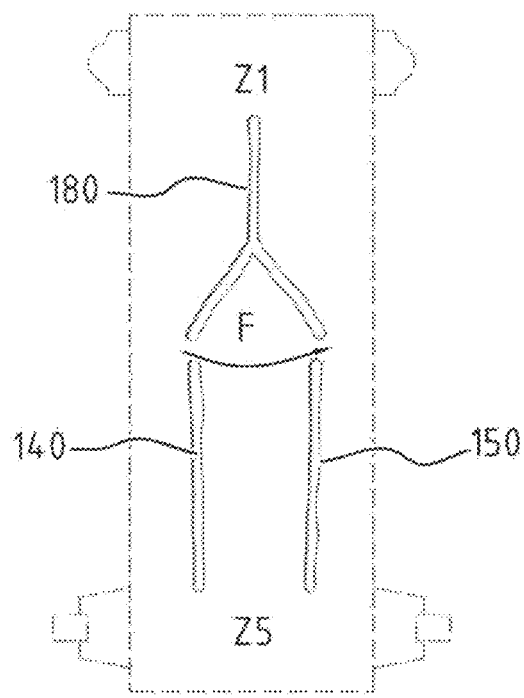
Figure 17V:
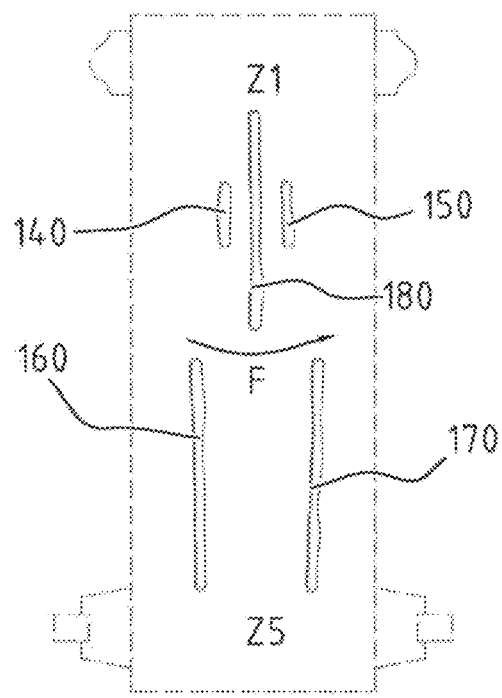

In the embodiment of FIG. 17K the first attachment zone 140 and the second attachment zone 150 form together two "O"-shaped zones between a first and a second substantially V-shaped zone. The first V-shaped zone comprises elongate attachment zones 140*a*, 150*a* interconnected by a connecting attachment zone 1045*a*. The first O-shaped zone comprises elongate attachment zones 140*b*, 150*b* interconnected by connecting attachment zones 1045*a*', 1045*b*. The second O-shaped zone comprises elongate attachment zones 140*c*, 150*c* interconnected by connecting attachment zones 1045*b*', 1045*c*. The second V-shaped zone comprises elongate attachment zones 140*d*, 150*d* interconnected by a connecting attachment zone 1045*c*'.

Figure 18A:
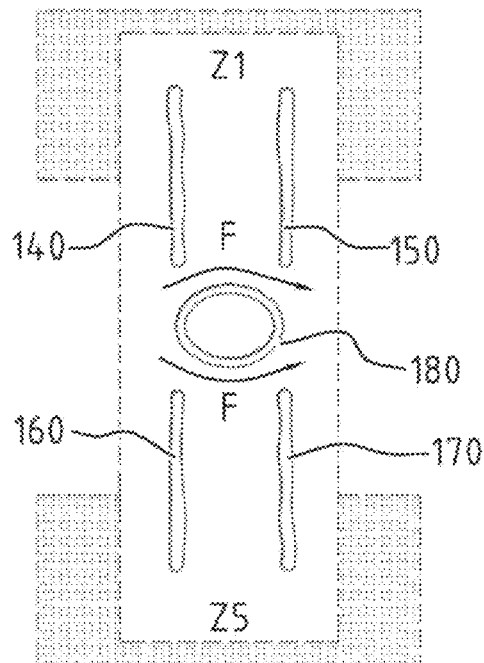
FIGS. 18A-18G illustrate yet other exemplary embodiments of an absorbent core according to the invention.

FIGS. 18A-18G illustrate further embodiments. In FIG. 18A the first to fourth attachment zones are similar to the first to fourth attachment zones of FIG. 16I, but instead of a central rectilinear attachment zone, there is provided an oval attachment zone 180 in the crotch region, between the first and second attachment zone 140, 150 and the third and fourth attachment zone 160, 170.

Figure 18B:
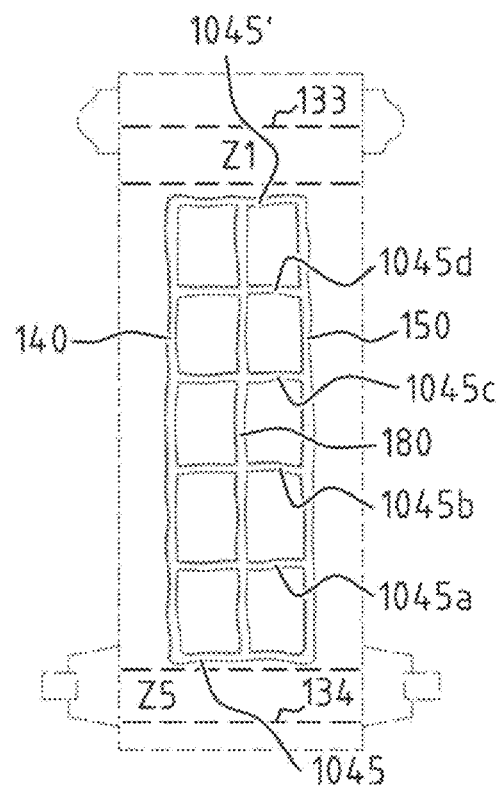
Figure 18C:
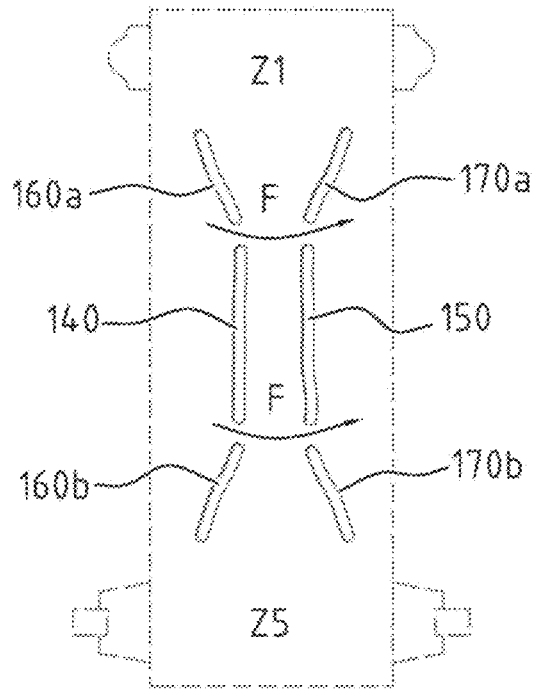
Figure 18D:
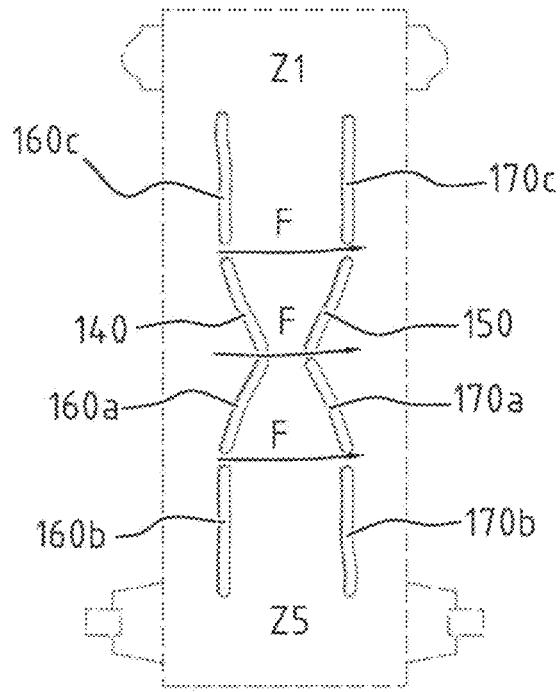
Figure 18E:
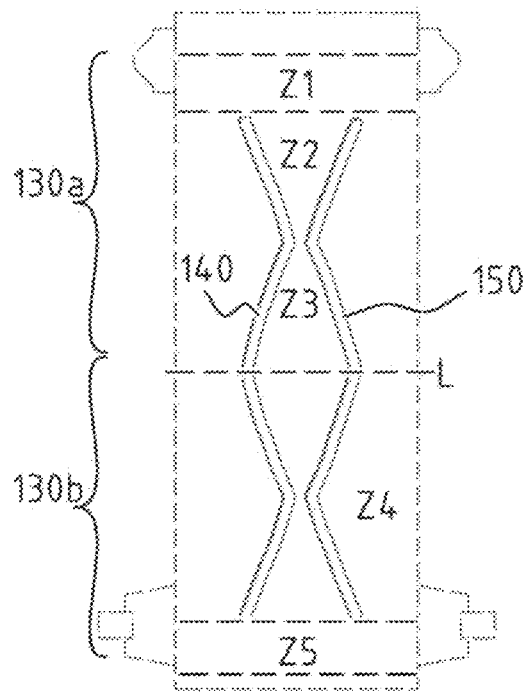
Figure 18F:
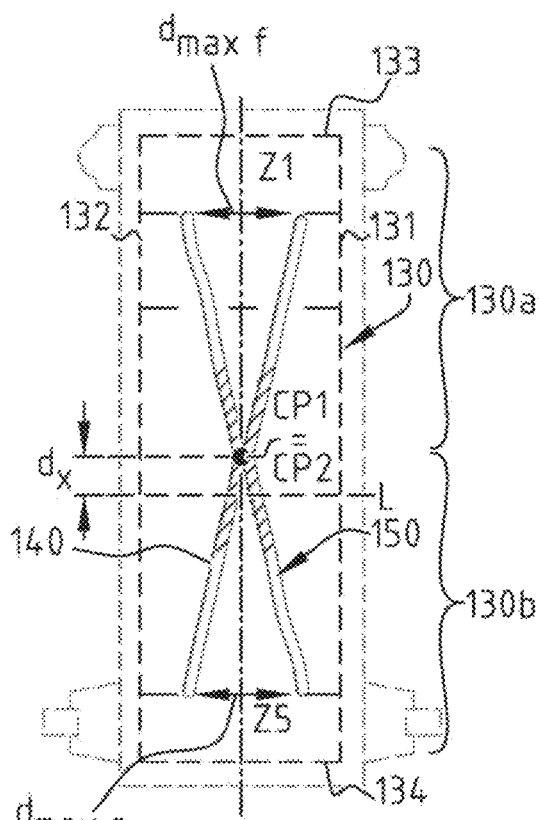
Figure 18G:
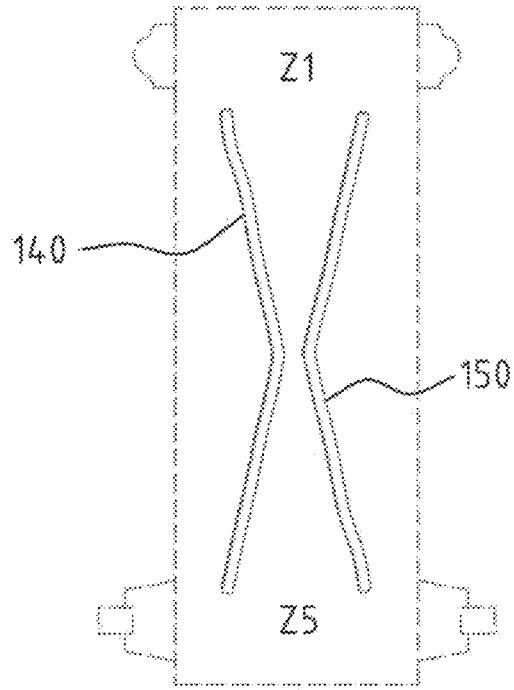

FIGS. 18B, 18C, 18D illustrate that various patterns are possible with one or more longitudinal sections and/or one or more inclined sections and/or one or more transverse sections as described before. FIGS. 18E, 18F, 18G illustrate that the first and second attachment zones 140, 150 may comprise various rectilinear sections which are oriented at an angle with respect to the longitudinal direction of the absorbent core. The embodiments of FIGS. 18A, 18B, 18C, 18D, 18E, 18F and 18G can be used for both male and female.

In the embodiment of FIG. 18B the first attachment zone 140 and the second attachment zone 150 are interconnected by a plurality of transverse connecting attachment zones comprising a front connecting attachment zone 1045', a rear connecting attachment zone 1045, and a plurality of intermediate connecting attachment zones 1045*a*, 1045*b*, 1045*c*, 1045*d*. The number of intermediate connecting attachment zones may be dependent on the size of the absorbent core. Preferably the first and second elongate attachment zone extend from the fourth to the second zone. Optionally one or more longitudinal intermediate attachment zones 180 may be provided. In the embodiment of FIG. 18B the first attachment zone 140 and the second attachment zone 150 form two V-shaped attachment zones, similar to the embodiment of FIG. 17H but with straight zones 140, 150.

In the embodiment of FIG. 18F the absorbent core 130 comprises an absorbent material between a top core wrap sheet and a back core wrap sheet, said absorbent core 130 being positioned in between the topsheet and the backsheet of the absorbent article. The absorbent core 130 has a first and second longitudinal edge 131, 132 and a first and second transverse edge 133, 134. The absorbent core 130 has a longitudinal center line CL dividing the absorbent core 130 in a first longitudinal portion and a second longitudinal portion on either side of the longitudinal center line. The absorbent core 130 has a transverse crotch line L dividing the absorbent core 130 in a front portion 130*a* and a rear portion 130*b* on either side of the transverse crotch line L. The absorbent core 130 is provided with a plurality of attachment zones 140, 150 where the top core wrap sheet is attached to the back core wrap sheet.

The plurality of attachment zones 140, 150 comprises a first elongate attachment zone 140 crossing the longitudinal center line CL in a first crossing point CP1, in said front portion 130*a* and/or in said rear portion 130*b*, from the first longitudinal portion to the second longitudinal portion. In the illustrated embodiment the first crossing point is located at a distance dx of the transverse crotch line L, here in the front portion 130*a*. However, in other embodiments the first crossing point CP1 may be located in the rear portion 130*b* of the absorbent core 130. In yet other embodiments, the first crossing point CP1 may also be located on the transverse crotch line L, i.e. at the border of the front portion 130*a* and the rear portion 130*b*. The plurality of attachment zones 140, 150 comprises a second elongate attachment zone 150 crossing said longitudinal center line CL in a second crossing point CP2, in said front portion 130*a* and/or in said rear portion 130*b*, from the second longitudinal portion to the first longitudinal portion. In the illustrated embodiment of FIG. 18F, the first and second crossing point CP1, CP2 are the same point. The position of the first and second crossing point CP1, CP2 (and in particular the distance dx) may be optimized in function of whether the absorbent article is intended for a male or female.

Preferably, the distance between the first and/or second crossing point CP1. CP2 and the transverse crotch line is larger than 1% of the length of the absorbent core, more preferably larger than 2%, even more preferably larger than 3%. Preferably, the distance between the first and/or second crossing point CP1, CP2 and the transverse crotch line is smaller than 20% of the length of the absorbent core, more preferably smaller than 10%.

A distance between the transverse crotch line L and a transverse center line T extending perpendicular on the longitudinal direction of the absorbent core, through the middle of the absorbent core, is smaller than 10%, more preferably smaller than 5% of the length of the absorbent core. The transverse center line T is not shown in FIG. 18F but is drawn in FIG. 27B.

Preferably, the first elongate attachment zone 140 extends both in the front portion 130*a* and in the rear portion 130*b* and the second elongate attachment zone 150 extends both in the front portion 130*a* and in the rear portion 130*b*. Preferably, the first elongate attachment zone 140 and the second elongate attachment zone 140 are arranged symmetrically with respect to the longitudinal center line CL of the absorbent core 130.

Preferably, a maximum distance dmaxf, dmaxr between the first and the second elongate attachment zone 140, 150 is between 15 and 70% of the width of the absorbent core, more preferably between 20 and 50%. A maximum distance dmaxf between the first and the second attachment zone 140, 150 in the front portion 130*a* may be different from a maximum distance dmaxr between the first and the second attachment zone 140, 150 in the rear portion 130*b*. Preferably, the length of the first and second attachment zone is larger than 10% of the length of the absorbent core, more preferably larger than 30%, even more preferably larger than 50%. Preferably, the attachment zones 140, 150 are permanent attachment zones which remain attached when wetted. Preferably, said first and second attachment zone 140, 150 each extend, seen in the transverse direction of the absorbent core, over the transverse distance which is at least 1 mm, preferably at least 3 mm, more preferably at least 4 mm, even more preferably at least 5 mm, most preferably at least 6 mm.

A front end of the first attachment zone 140 is preferably located in the second zone Z2, and a rear end of the first attachment zone 140 is preferably located in the fourth zone Z4. Similarly, a front end of the second attachment zone 150 is preferably located in the second zone Z2 or in the third zone, and a rear end of the second attachment zone 150 is preferably located in the fourth zone Z4, wherein the zone may be defined as described in the summary.

Figure 26A:
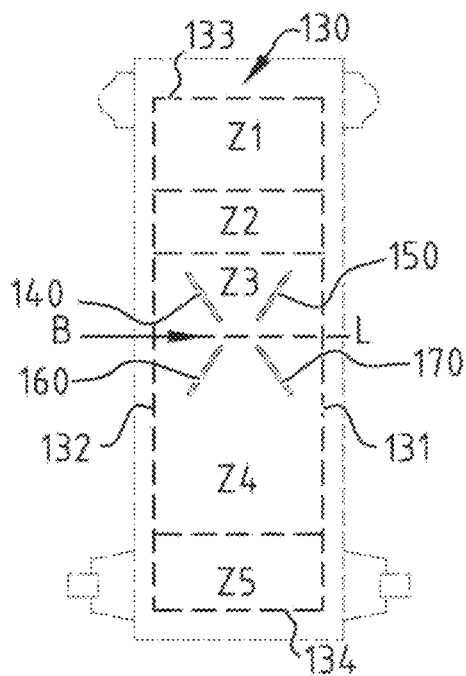
FIGS. 26A-26T illustrate yet other exemplary embodiments of an absorbent core according to the invention.
Figure 26B:
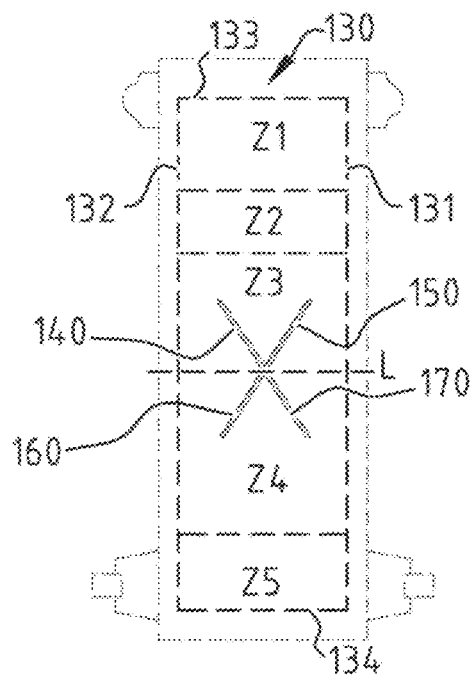
Figure 26C:
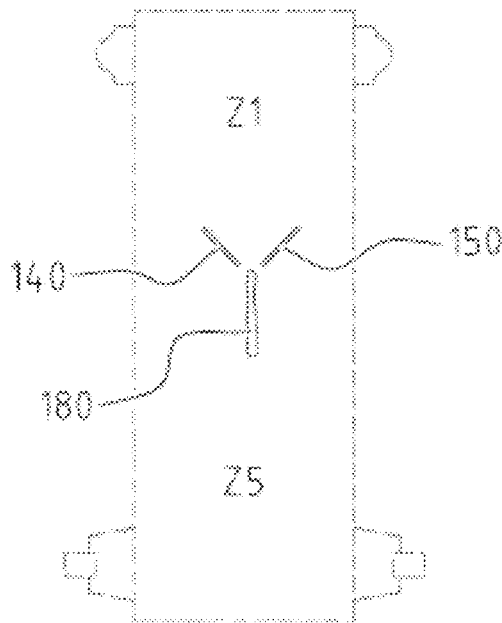
Figure 26D:
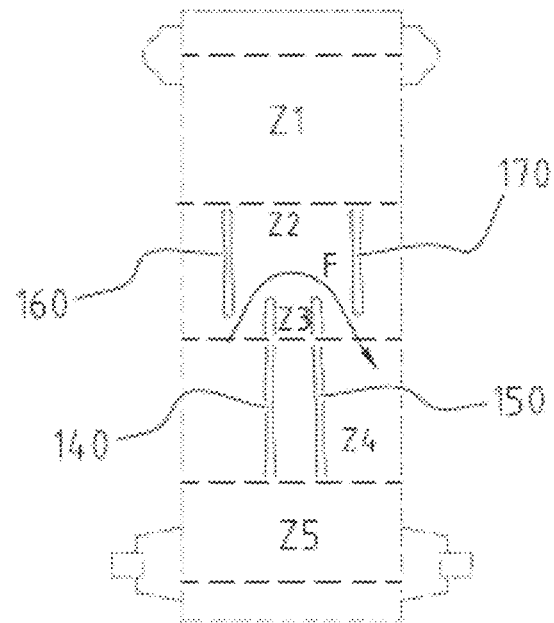
Figure 26E:
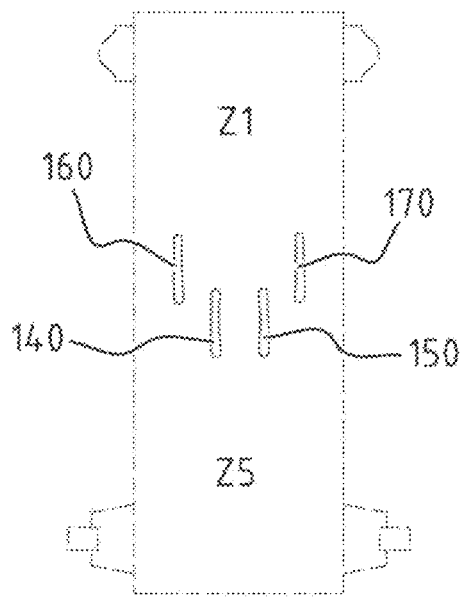
Figure 26F:
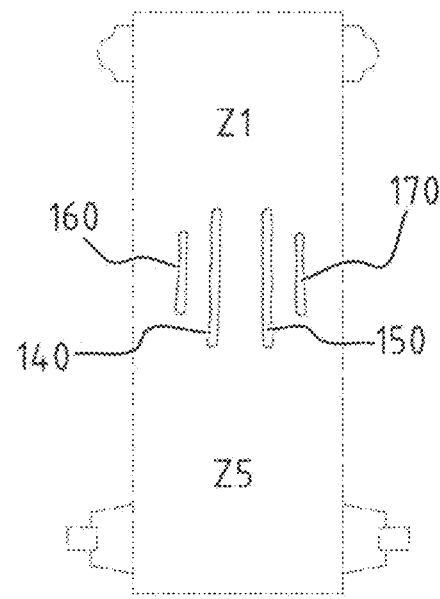

A similar embodiment is illustrated in FIG. 26B, where the first elongate attachment zone comprises portions 140, 160, and the second elongate attachment zone comprises portions 150, 170.

Figure 26G:
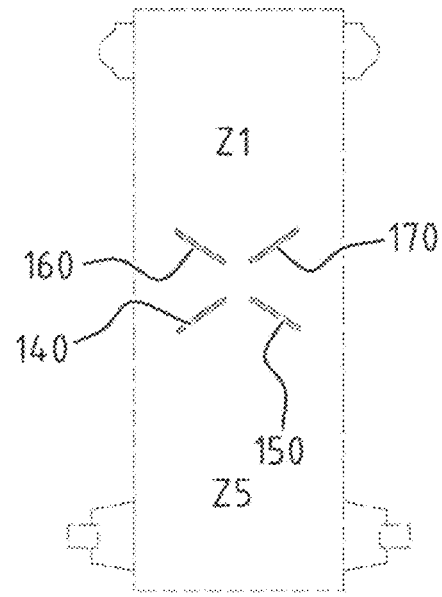
Figure 26H:
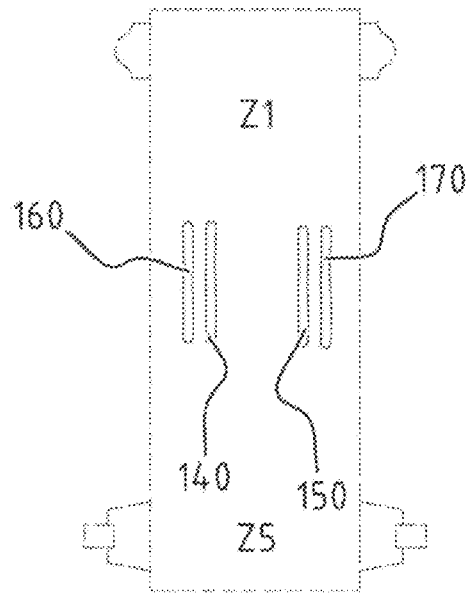
Figure 26I:
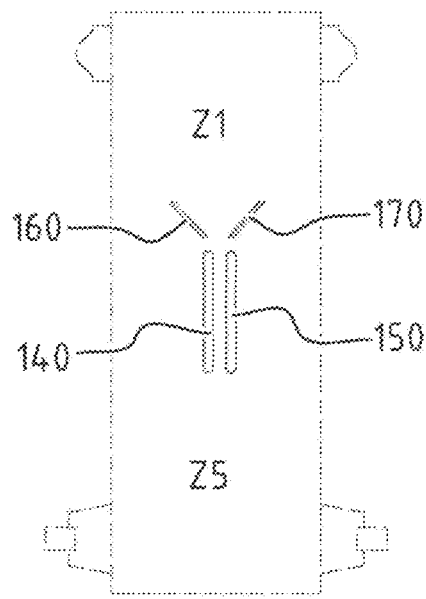
Figure 26J:
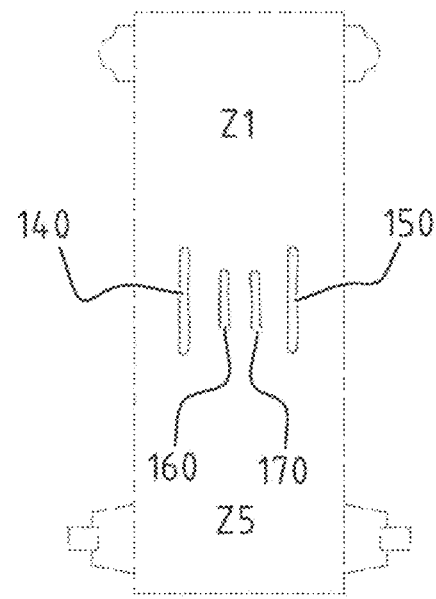
Figure 26K:
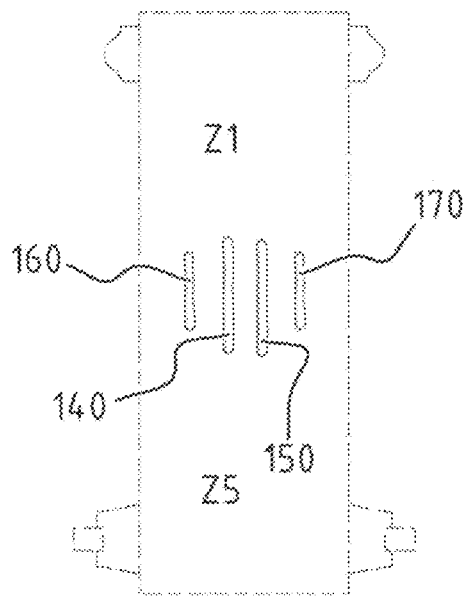
Figure 26L:
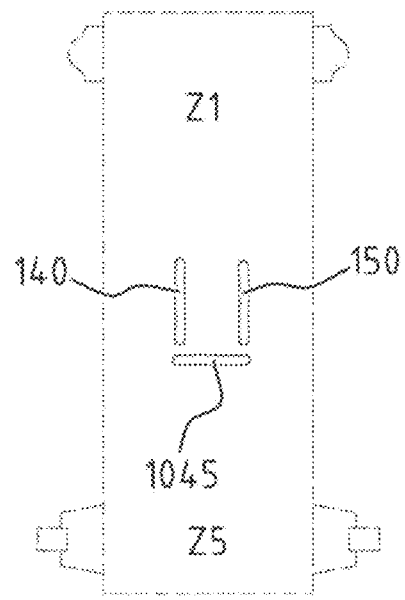
Figure 26M:
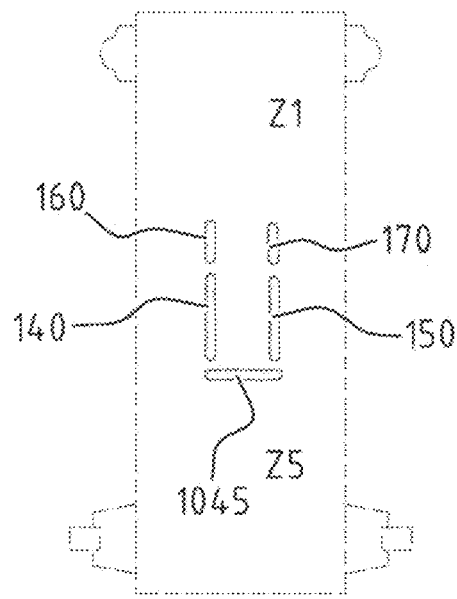
Figure 26N:
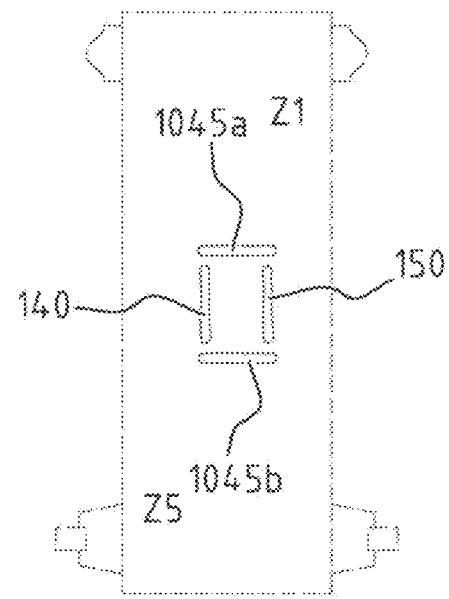
Figure 26O:
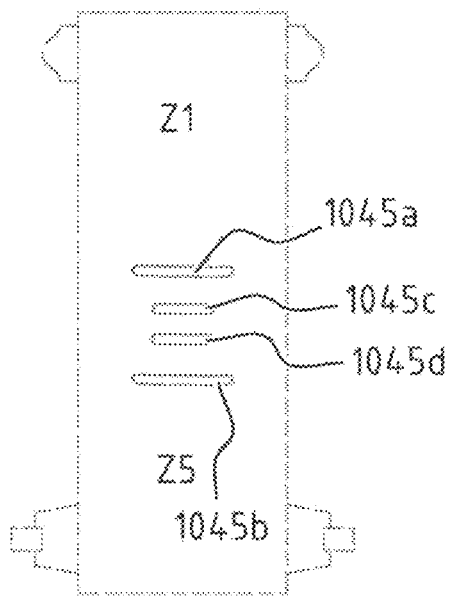
Figure 26P:
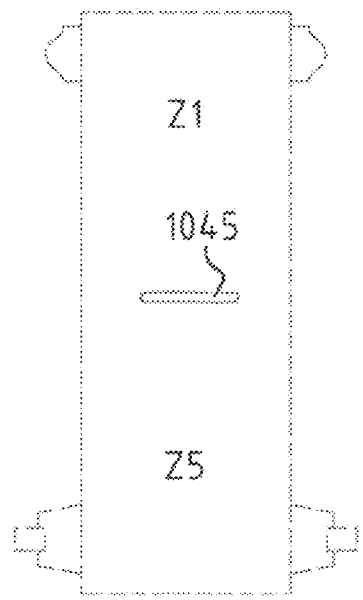
Figure 26Q:
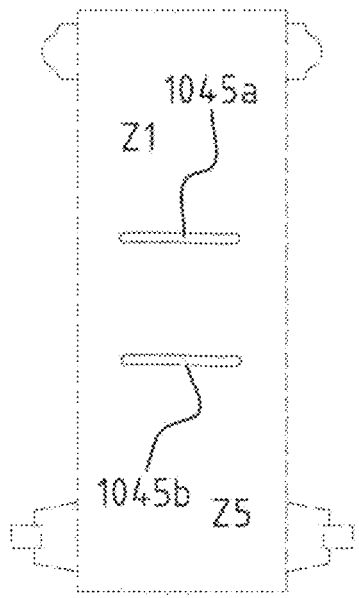
Figure 26R:
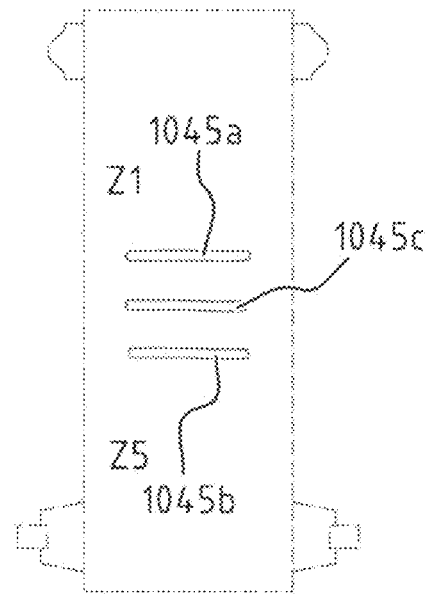
Figure 26S:
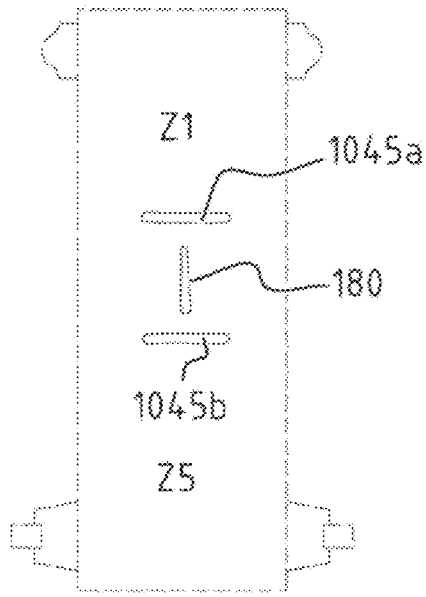
Figure 26T:
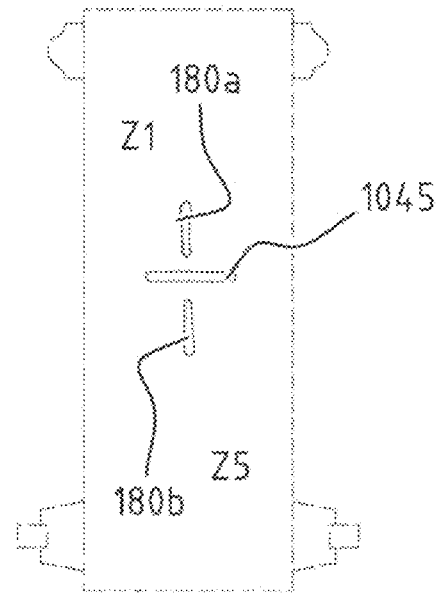

In the embodiments of FIGS. 26A and 26G, the first and second elongate attachment zone 140, 160; 150, 170 may comprise a bridging zone B allowing a liquid flow between the first and the second longitudinal edge 131, 132 by capillary action through the absorbent material and/or by mass flow, such that upon wetting of the absorbent material, front channels 140, 150 and rear channels 160, 170 are created, wherein the bridging zone B extends between said front and rear channels; wherein a minimum distance between said front and rear channel is preferably larger than 3 mm more preferably larger than 5 mm. The bridging zone B may extend from a first portion of the absorbent core to a second portion of the absorbent core, wherein the first portion is defined between the first longitudinal edge 131 and the longitudinal center axis CL of the absorbent core 130 and the second portion is defined between the second longitudinal edge 132 and the longitudinal center axis CL of the absorbent core. The bridging zone B may comprise one or more temporary attachments between the top and back core wrap sheet which are configured to detach when wetted; and/or the bridging zone B may comprise at least one permanent attachment zone in a direction from the first to the second longitudinal edge 131, 132; and/or the said bridging zone B may comprise absorbent material. Preferably, the absorbent material comprises cellulosic fluff pulp and/or superabsorbent particles.

In the embodiments of FIGS. 18F, 18G, 26A, 26B and 26G, the first and second attachment zone together for a substantially X-shaped zone arranged symmetrically with respect to the longitudinal center line CL. In other embodiments, an X-shaped zone may be combined with differently shaped zones, see e.g. FIG. 17G. Also, the X-shaped zone may comprised curved portions, see e.g. the embodiments of FIGS. 17H, 21N, 22P, 23U, 23V.

In yet other embodiments, multiple X-shaped zones may be combined, see e.g. the embodiments of FIGS. 15P, 17K, 18E. In the embodiment of FIGS. 15P and 18E a first X-shaped attachment zone (including V-shaped portion 2001 and a front portion of 140', 150') is located in the front portion 130a, and a second X-shaped attachment zone (including V-shaped portion 2002 and a rear portion of 140', 150') is located in the rear portion 130b. The first X-shaped attachment zone is connected to the second X-shaped attachment zone at the transverse crotch line L. In the embodiment of FIG. 17K a first X-shaped attachment zone (including portion 1045c, 1045c') is located in the second zone Z2 of the front portion 130a, a second X-shaped attachment zone (including portions 1045b, 1045b) is located in the third zone Z3 of the front portion 130a, and a third X-shaped attachment zone (including portions 1045a, 1045a') is located in the fourth zone Z4 of the rear portion 130b. The first X-shaped attachment zone is connected to the second X-shaped attachment zone, and the second X-shaped attachment zone is connected to the third X-shaped attachment zone.

FIGS. 19A-19D

FIGS. 19A-19D illustrate further embodiments wherein the absorbent core is provided with at least a first attachment zone 140, wherein in said first attachment zone 141 said top core wrap sheet is attached to said back core wrap sheet along an attachment which extends, seen in a transverse and/or longitudinal direction of the absorbent core, over a transverse and/or longitudinal distance which is at least 1 mm, preferably at least 2 mm, more preferably at least 3 mm, most preferably at least 4 mm; and/or said top core wrap sheet is attached to said back core wrap sheet along a discontinuous attachment at a plurality of locations at a distance of each other, seen in the transverse and/or longitudinal direction of the absorbent core; such that upon wetting of the absorbent material, a first channel is created at said first attachment zone 140. The embodiments of FIGS. 19A, 19B. 19C and 19D can be used for both male and female.

Figure 19A:
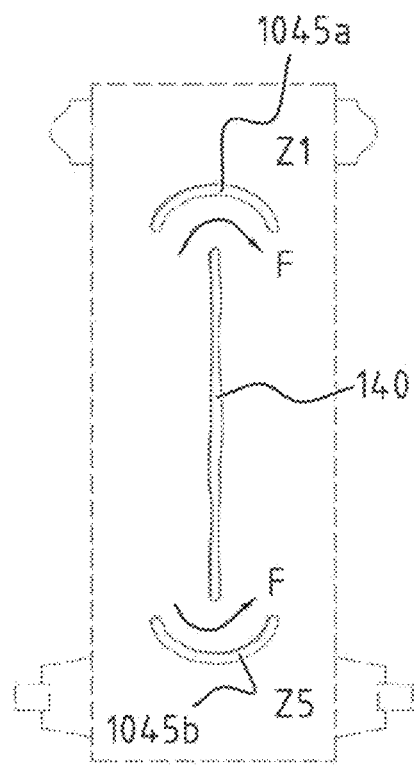
FIGS. 19A-19D illustrate yet other exemplary embodiments of an absorbent core according to the invention.
Figure 19B:
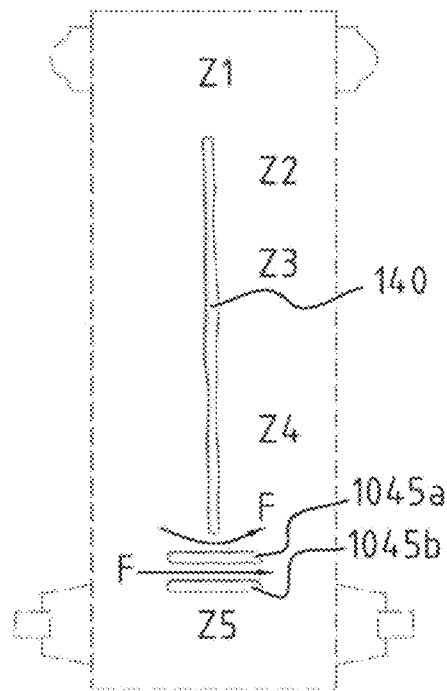
Figure 19C:
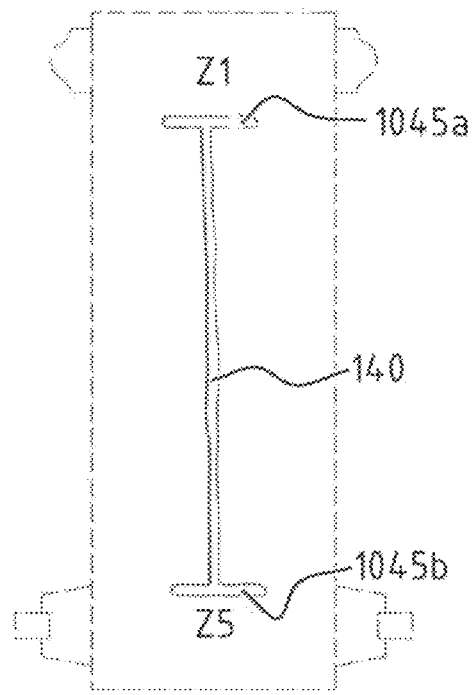
Figure 19D:
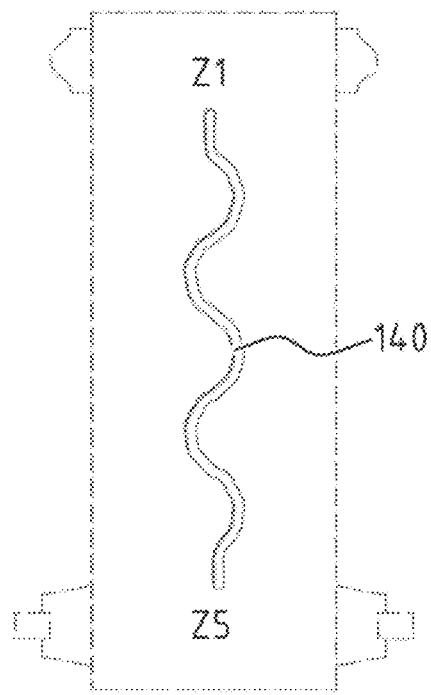

In the embodiment of FIG. 19A, a single longitudinal attachment zone 140 is illustrated, along with a first and second transversal attachment zone 1045a, 1045b which are positioned at either end of the longitudinal attachment zone 140. The first and second transversal attachment zone 1045a, 1045b are illustrated as curved zones, but it is clear to the skilled person that the first and/or second transversal attachment zone may also be provided as straight zones. In the embodiment of FIG. 19B, a single longitudinal attachment zone 140 is illustrated, along with a first and second transversal attachment zone 1045a, 1045b which are positioned between the attachment zone 140 and the first transversal edge of the absorbent core. In addition to, or alternative to the embodiment of FIG. 19B the first and second transversal attachment zones 1045a. 1045b may be positioned between the attachment zone 140 and the second transversal edge of the absorbent core. In other words, it is clear to the skilled person that e.g. a third and/or fourth transversal attachment zone may be added. In the embodiment of FIG. 19C, a single longitudinal attachment zone 140 is illustrated, along with a first and second transversal attachment zone 1045a, 1045b which are positioned at either side of the longitudinal attachment zone 140. Although the transversal attachment zones 1045a. 1045b are illustrated to be connected to the longitudinal attachment zone 140, it is clear to the skilled person that other embodiments exist wherein the transversal attachment zones 1045a, 1045b are not connected to the longitudinal attachment zone 140. In the embodiment of FIG. 19D, a single longitudinal attachment zone 140 is illustrated. The illustrated longitudinal attachment zone 140 comprises curved sections, however, in addition or alternatively the longitudinal attachment zone 140 may comprise straight sections. It is clear to the skilled person that any of the earlier described embodiments related to at least two longitudinal attachment zones, or any combination thereof may be applied to the embodiments wherein the absorbent core comprises a single longitudinal attachment zone.

Since liquid may in many cases not be distributed evenly or symmetrically, it may be advantageous to include at least one attachment zone through which liquid may go from the first and second channels 140, 150 and vice-versa. This will allow a good distribution over the entire absorbent core as well as an improved formation of the channels and the tub-shape upon swelling of the absorbent core.

FIGS. 20A-20Z, 21A-21Z, 22A-22Z, 23A-23V

In the embodiments of FIGS. 20A-20W, 20Z, 21G-21M, 21O-21T, 21V-21X, 21Z, 22D-22M, 22R-22Z, 23A-23L, this is achieved with a transversal attachment zone 1045 connecting the rear ends of longitudinal attachment zones 140, 150. As will be clear from the figures, the presence of such a transversal attachment zone 1045 does not preclude the elements mentioned in conjunction with the previous figures, such as the presence of a central attachment zone 180 and/or variations of the length, position and/or shape of longitudinal attachment zones 140, 150. The figures furthermore show that the presence of such a transversal attachment also does not preclude the presence of third and fourth longitudinal attachment zones 160, 170, or of transversal attachment zones 147, 157 which connect the longitudinal attachment zones 140, 150 to the further longitudinal attachment zones 160, 170. Furthermore, the figures show that the transversal attachment zone 1045 need not be straight: it may be rounded as in for example FIGS. 20A-20D, rounded at the edges only as for example in FIGS. 20E-20H, or take another shape. In the embodiments of FIGS. 20A-20Z, 21G-Z, 22D-22N, 22R-Z. 23A-23L, 23U-V the first attachment zone 140, 160 (where present; in some embodiments the zone is indicated with one reference number 140 and in other embodiments with two reference numbers 140, 160), the second attachment zone 150, 170 (where present) and the connecting attachment zone 1045 form together a substantially U-shaped zone. The substantially U-shaped zone may extend from the rear portion to the front portion (and in particular from the fourth zone Z4 to the second zone Z2). The first and second elongate attachment zone 140, 150, 160, 170 (where present) extend next to each other from the crotch region in the direction of the rear transverse edge 134 and/or the front transverse edge 133. Optionally the first and second elongate attachment zone 140, 150, 160, 170 (where present) may diverge in the direction of the front transverse edge 133. The connecting attachment zone 1045 connects said first elongate attachment zone 140, 160 (where present) with said second elongate attachment zone 150, 170 (where present). The connecting attachment zone 1045 may be a front connecting attachment zone which connects a front end portion of the first attachment zone to a corresponding front end portion of the second attachment zone (FIG. 20X-Y); or a rear connecting attachment zone which connects a rear end portion of the first attachment zone to a corresponding rear end portion of the second attachment zone (FIGS. 20A-W, and 20Z, 21G-21Z). It is noted that also two U-shaped attachment zones may be provided, see FIGS. 21N and 22N, 23U, 23V. The presence of a central attachment zone 180, especially in the front portion may further enhance the liquid distribution. The length of the central attachment zone 180 is preferably at least 20% of the length of the first and second elongate attachment zone 140, 150, and is preferably located at least partially between the first and second elongate attachment zone 140, 150.

Figure 20A:
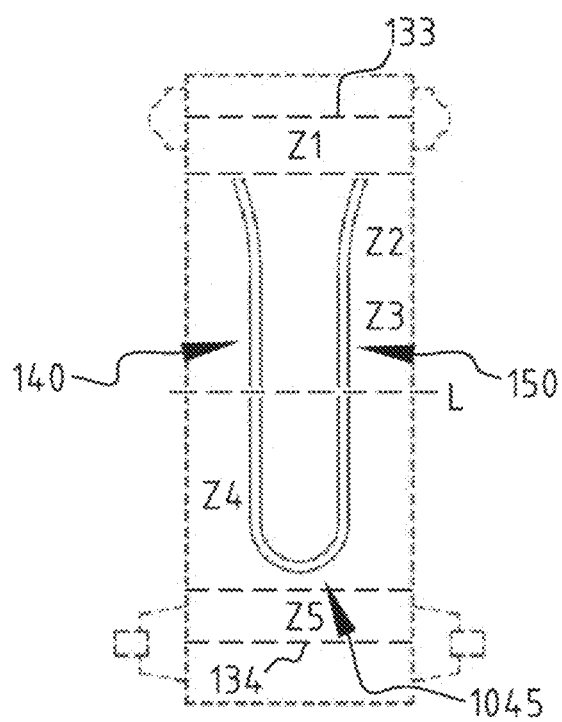
FIGS. 20A-20Z illustrate yet other exemplary embodiments of an absorbent core according to the invention.
Figure 20B:
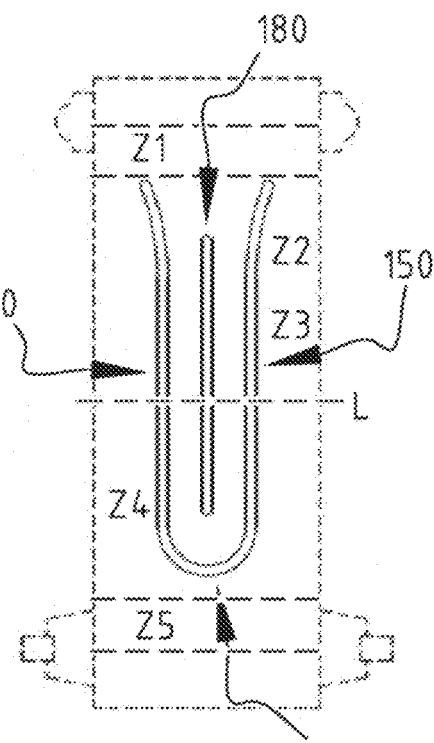
Figure 20C:
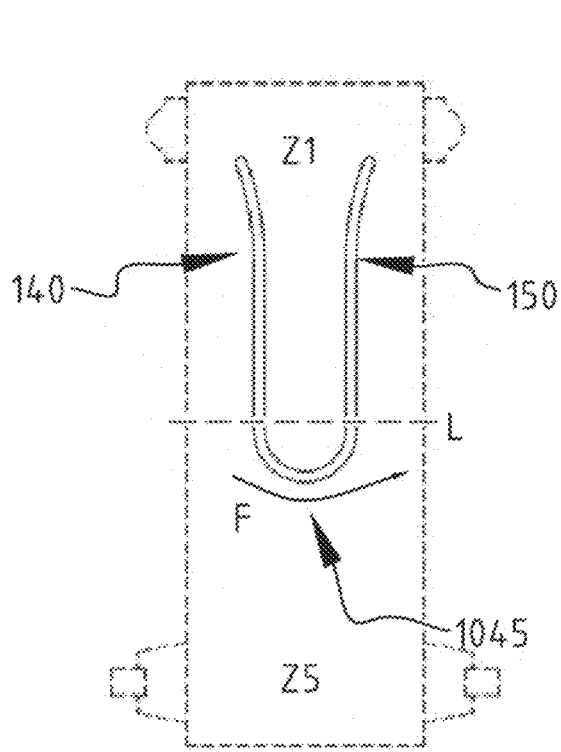
Figure 20D:
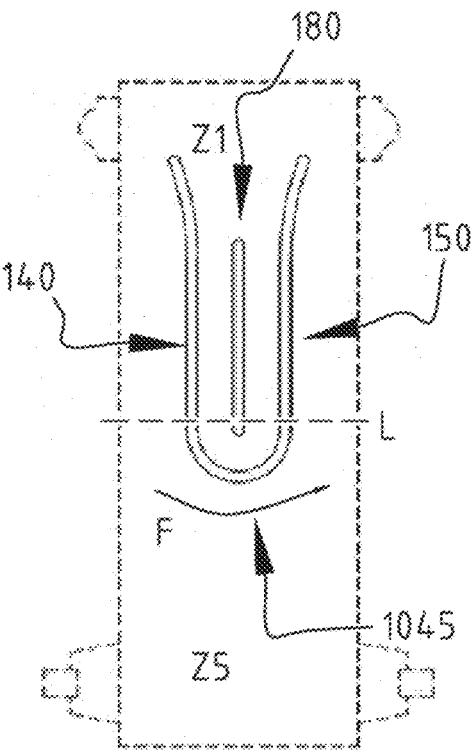
Figures 20E, 20F:
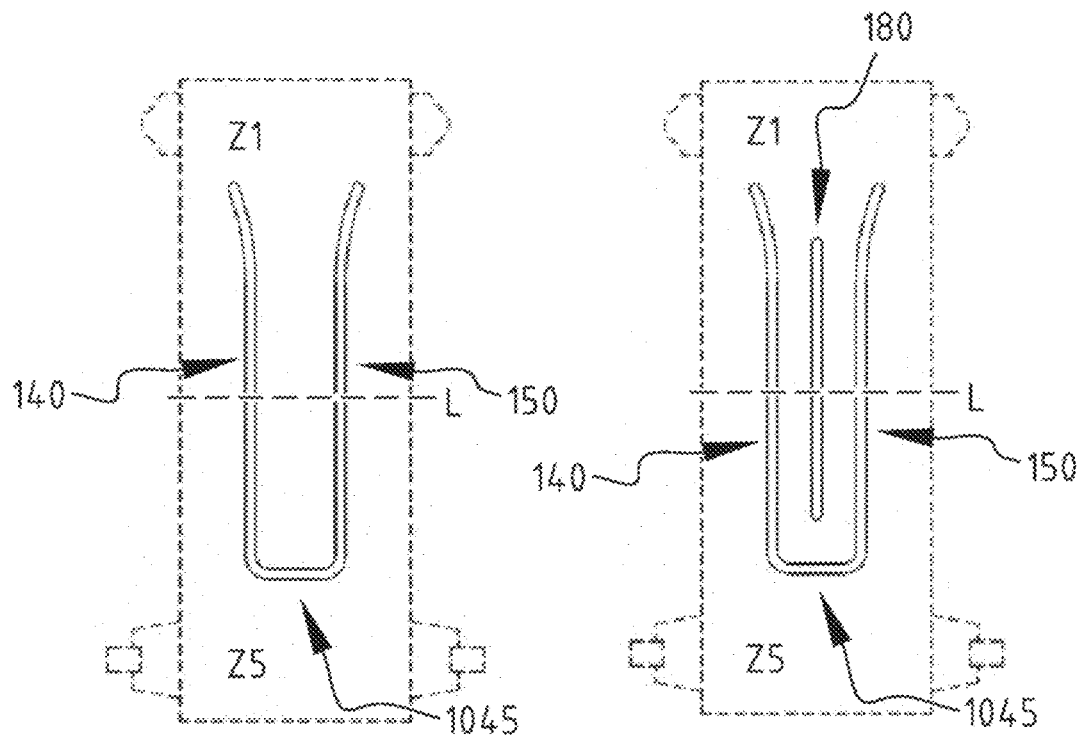
Figures 20G, 20H:
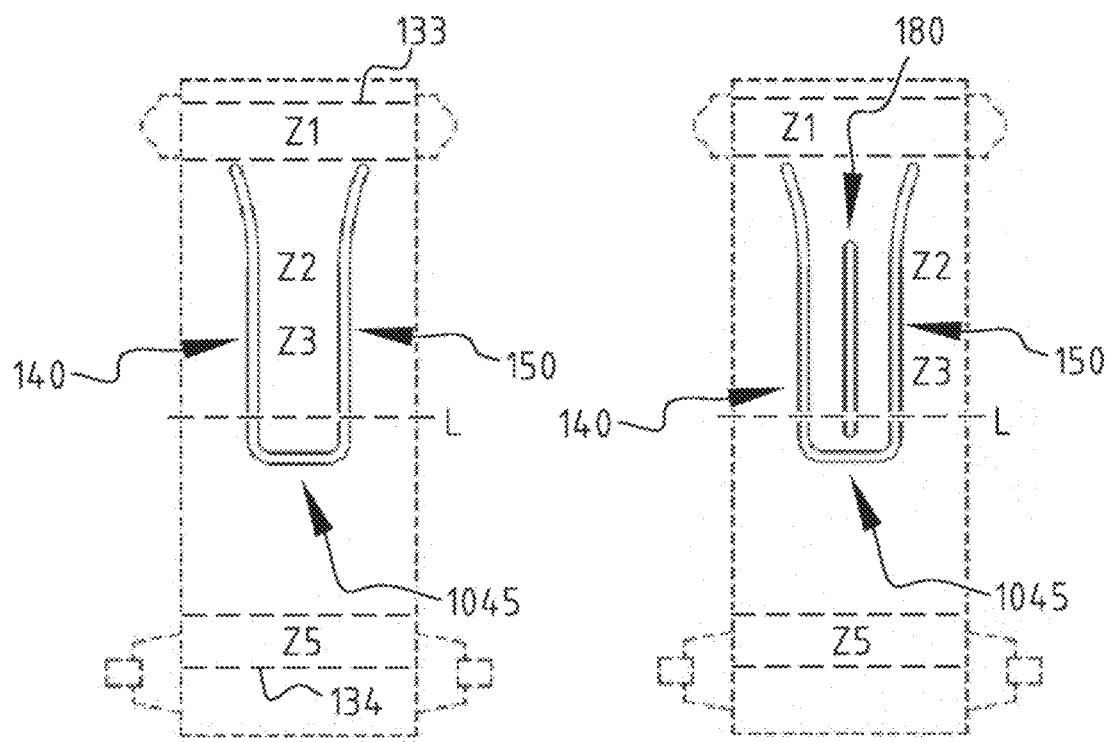
Figure 20U:
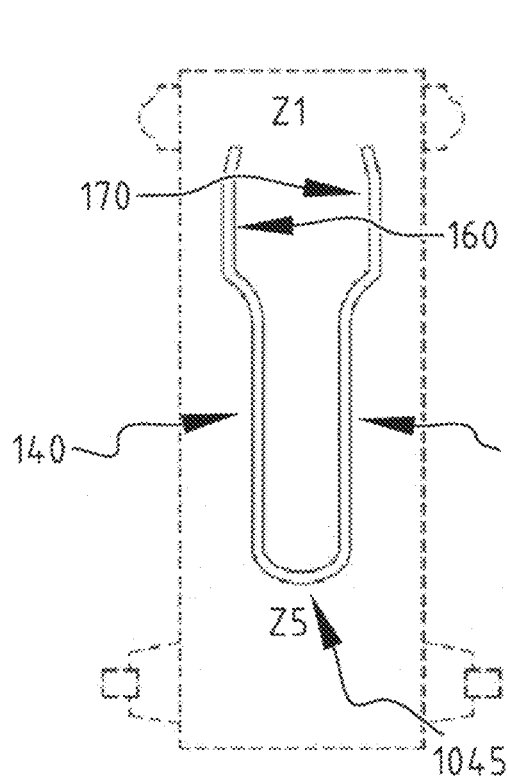
Figure 20V:
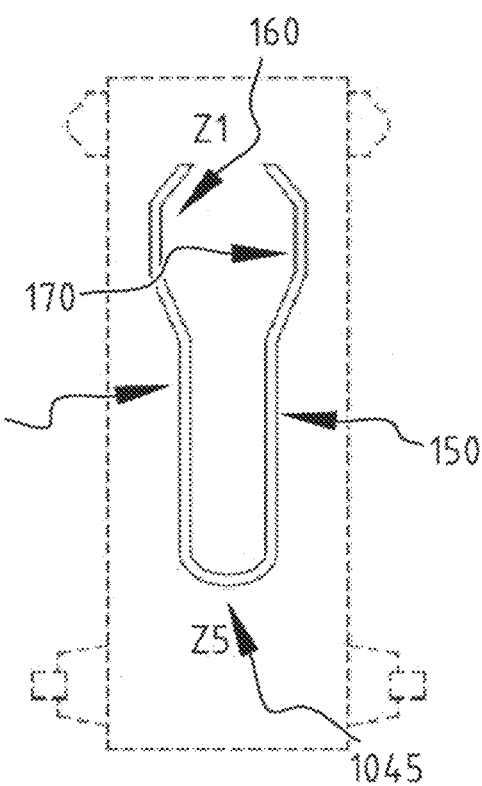
Figure 20W:
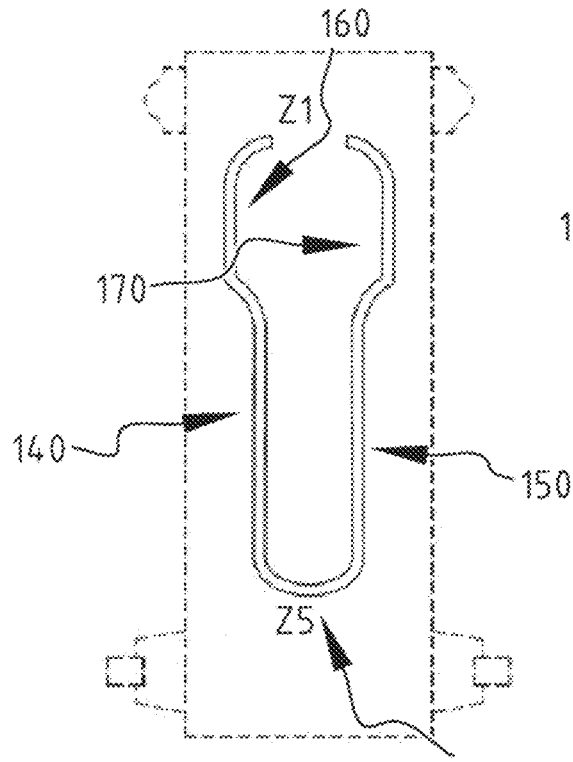
Figure 20X:
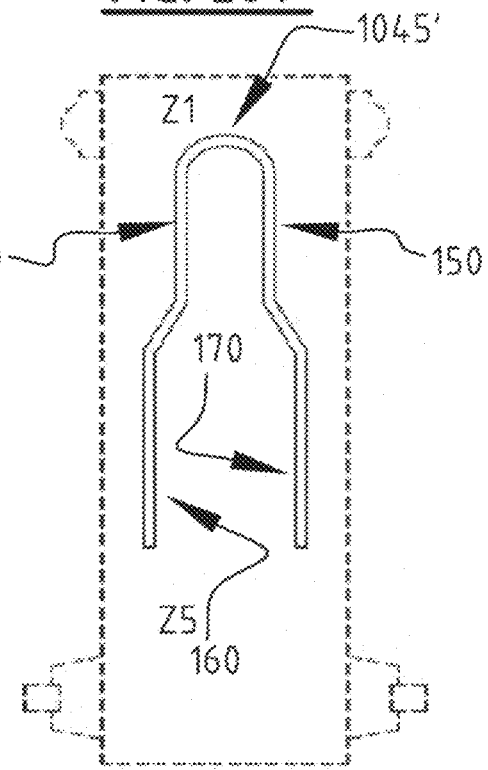
Figure 20Y:
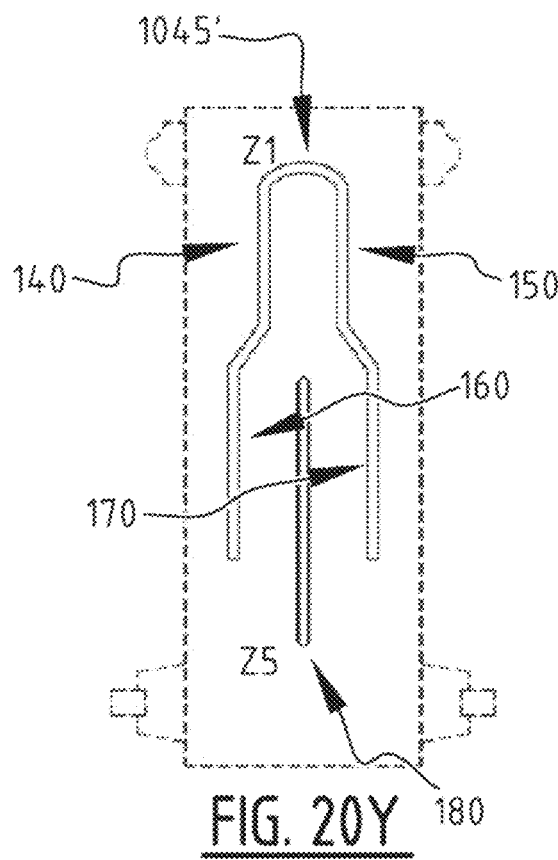
Figure 20Z:
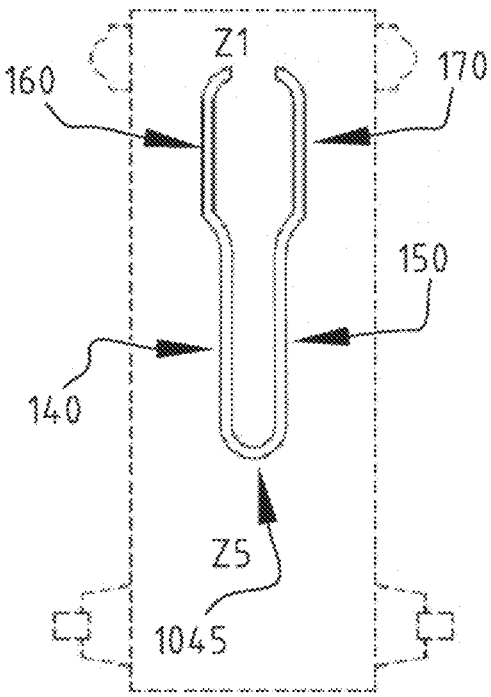
Figure 21A:
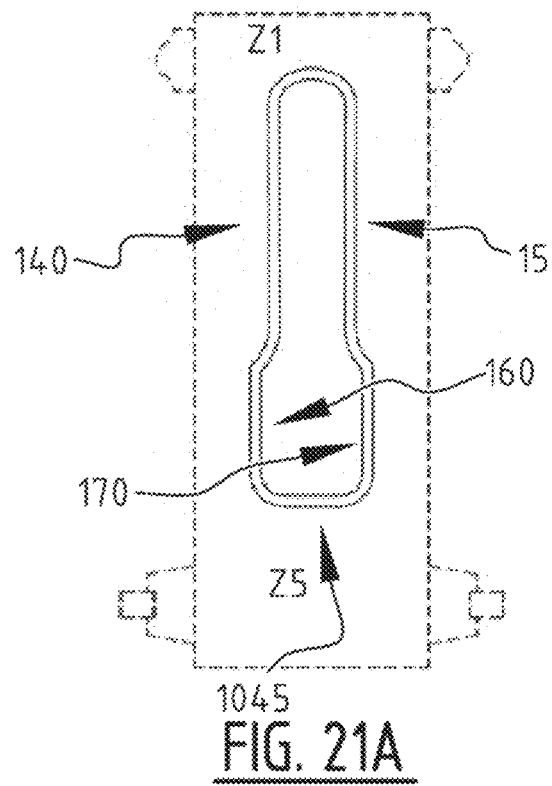
FIGS. 21A-21Z illustrate yet other exemplary embodiments of an absorbent core according to the invention.
Figure 21B:
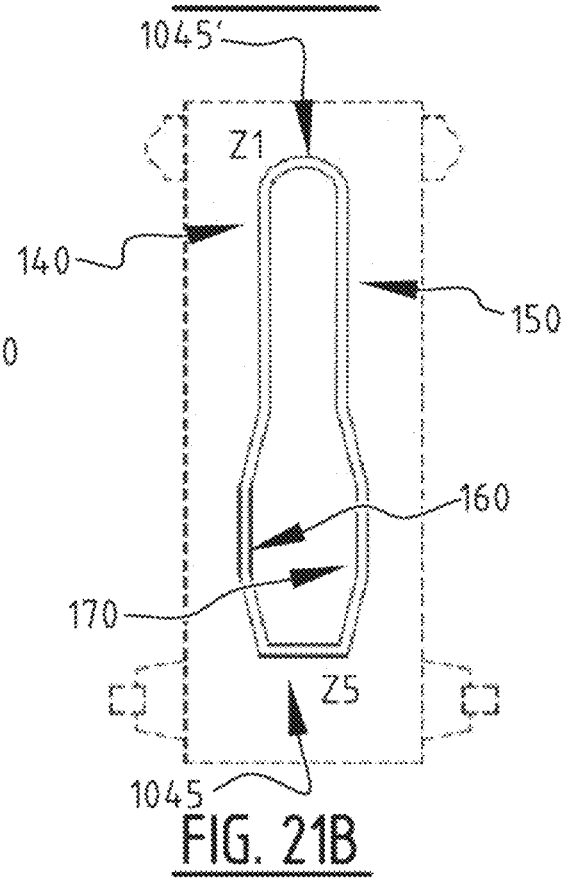
Figure 21C:
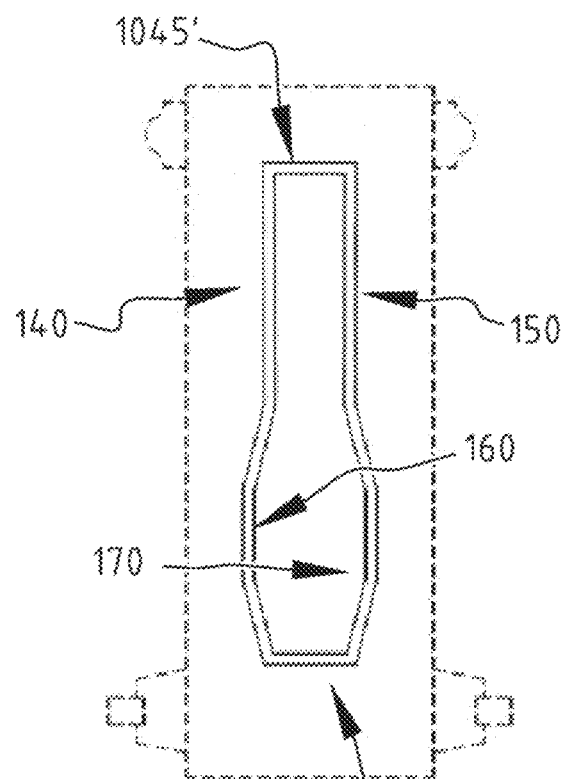
Figure 21D:
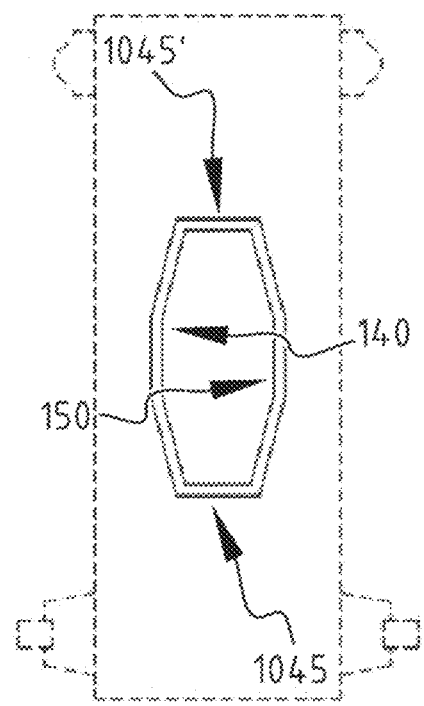
Figure 21E:
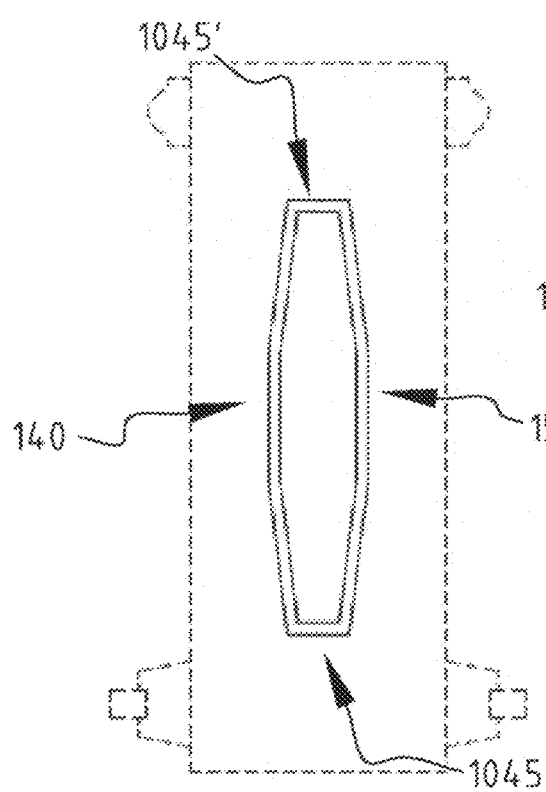
Figure 21F:
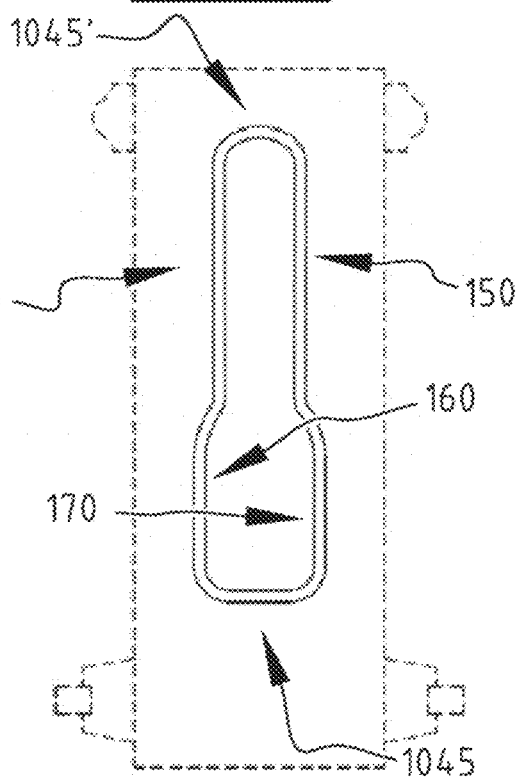
Figure 21K:
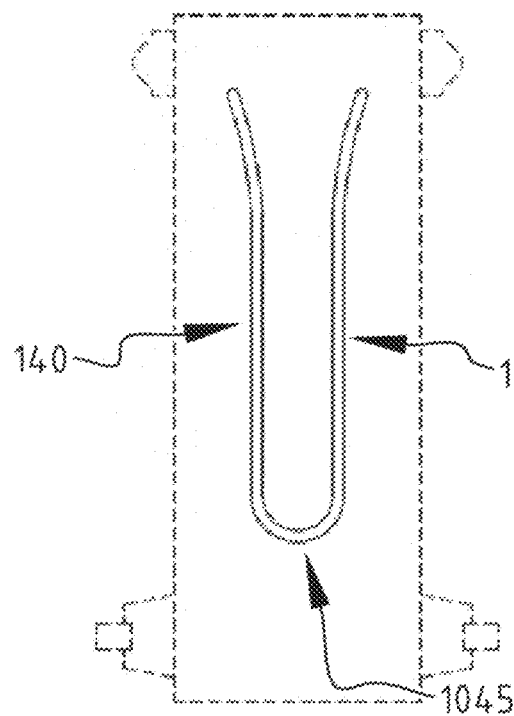
Figure 21L:
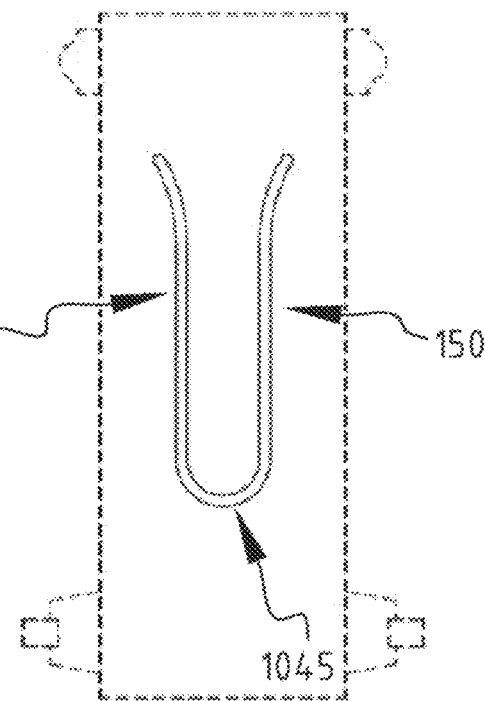
Figure 21M:
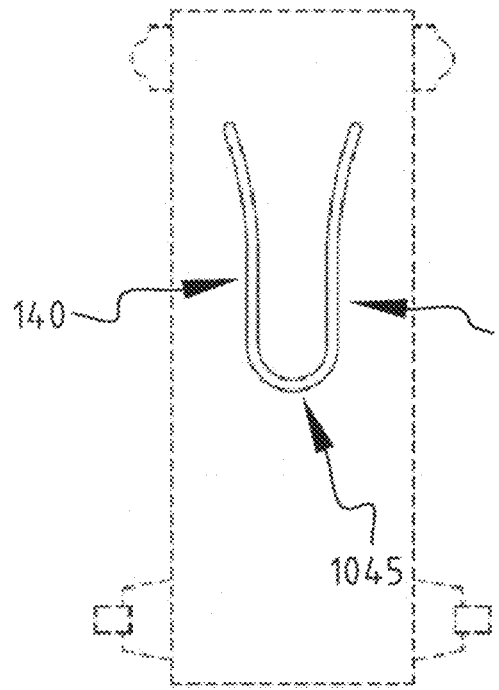
Figure 21N:
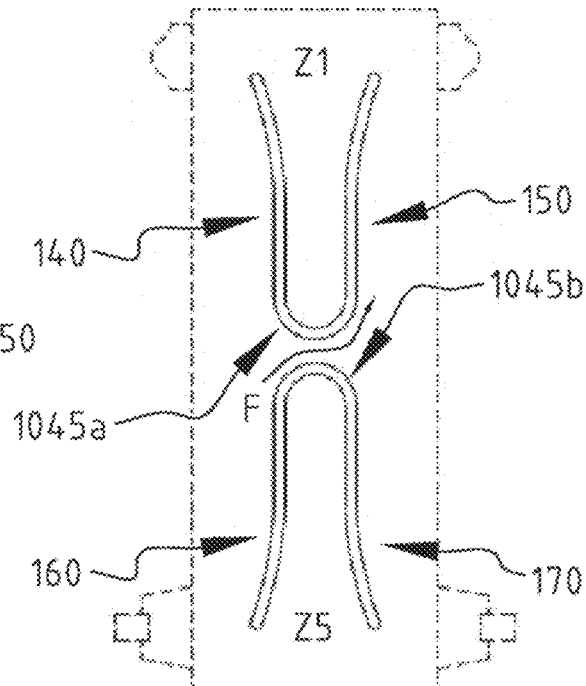
Figure 21O:
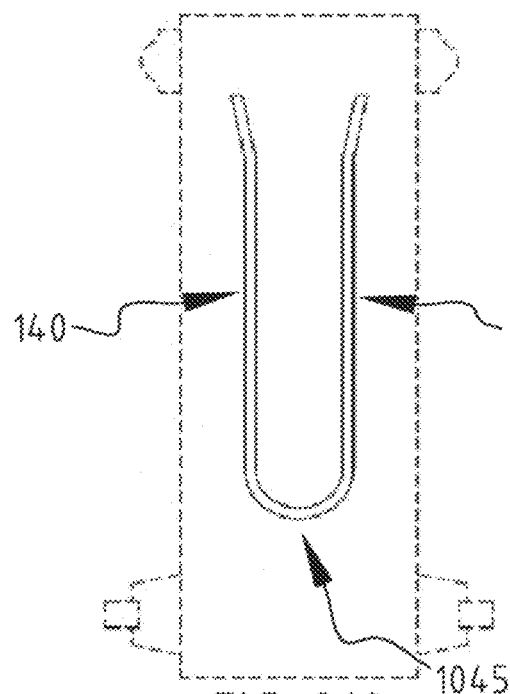
Figure 21P:
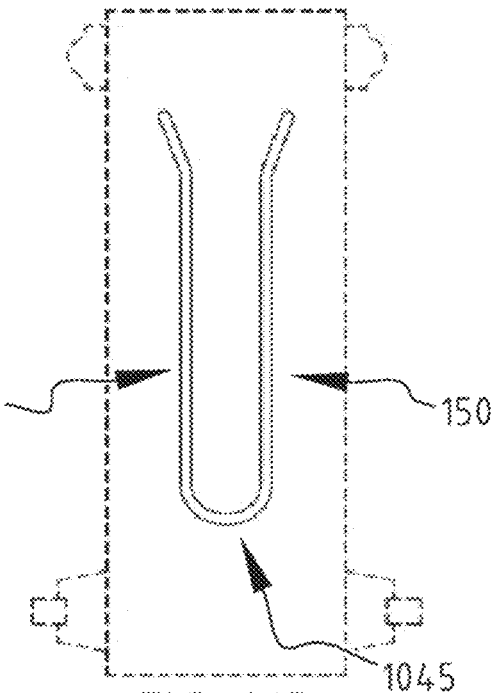
Figure 21Q:
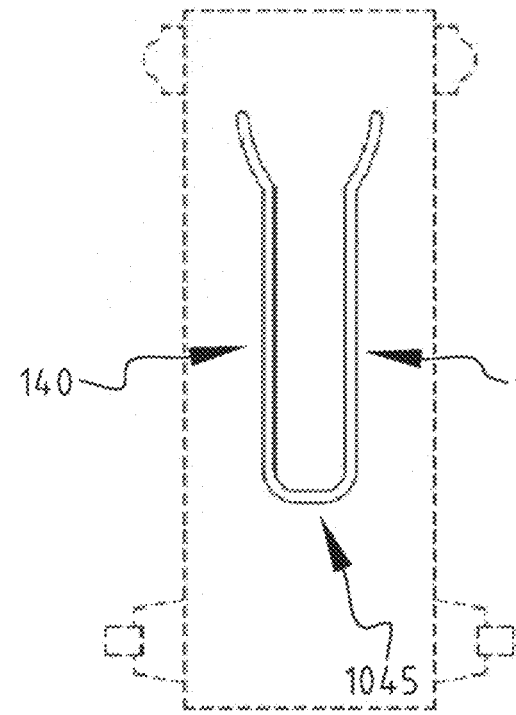
Figure 21R:
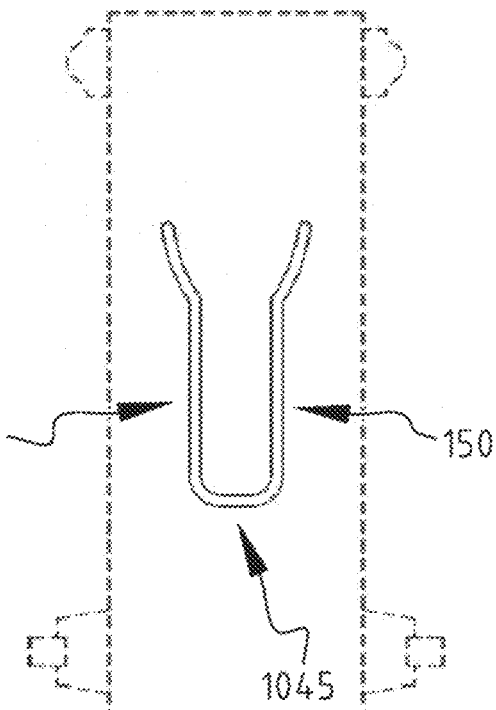
Figure 21W:
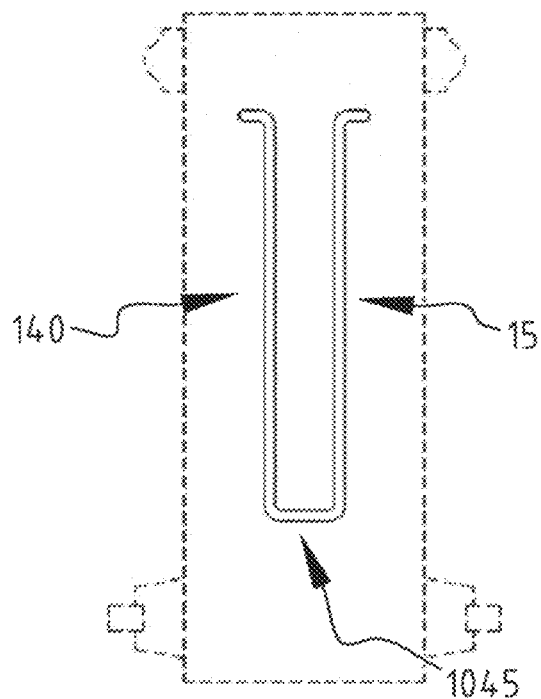
Figure 21X:
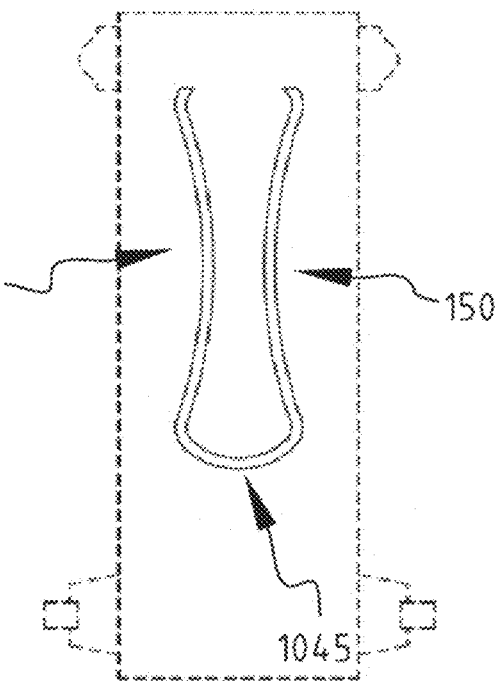
Figure 21Y:
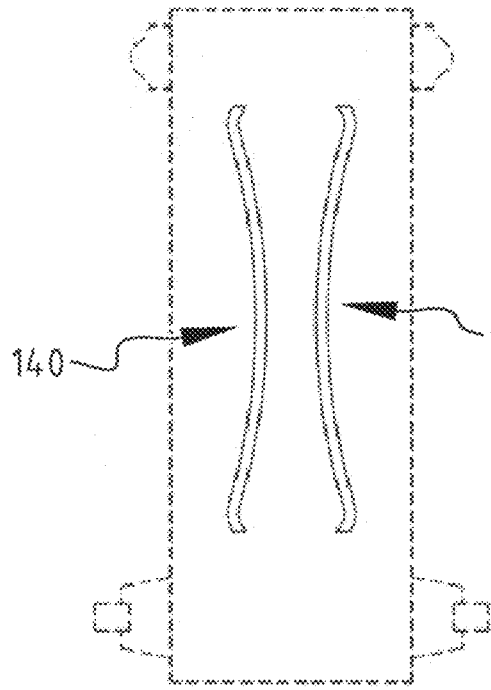
Figure 21Z:
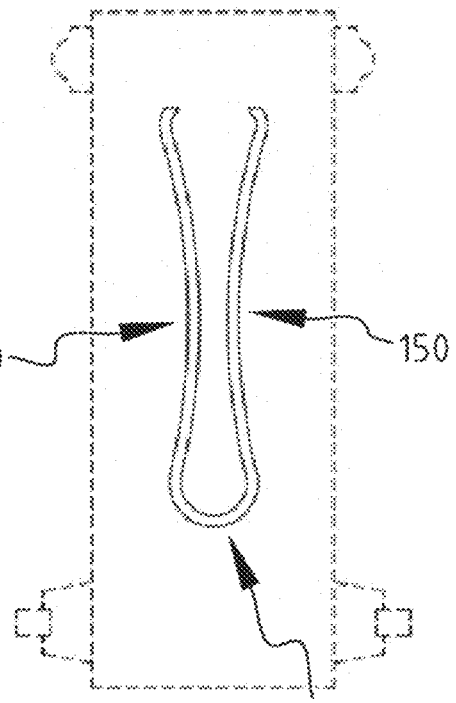
Figure 22A:
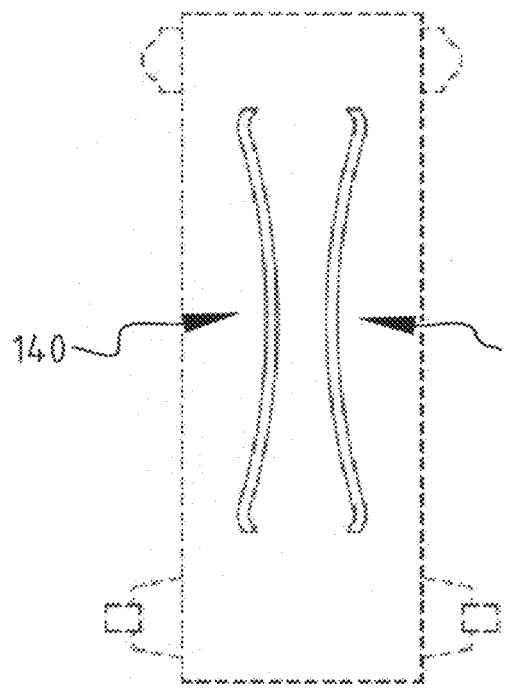
FIGS. 22A-22Z illustrate yet other exemplary embodiments of an absorbent core according to the invention.
Figure 22B:
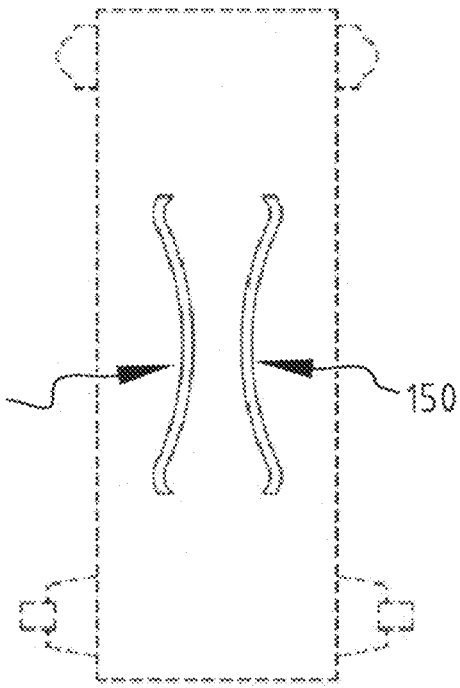
Figure 22C:
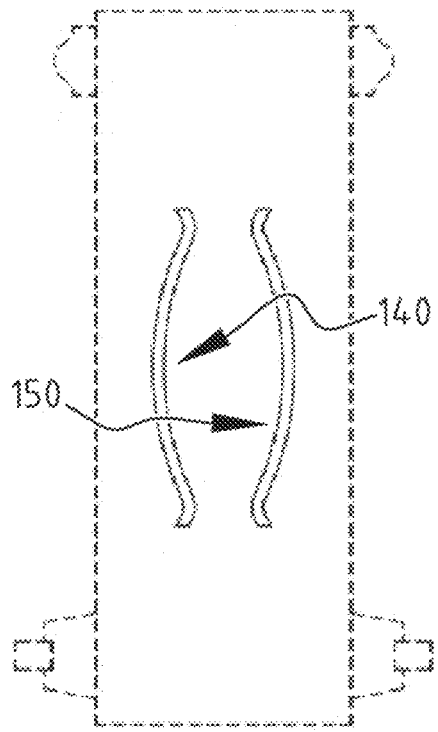
Figure 22D:
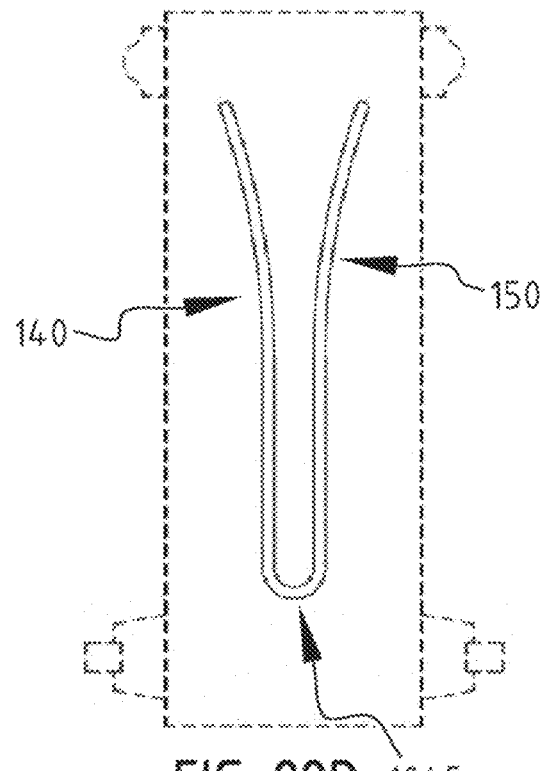
Figure 22E:
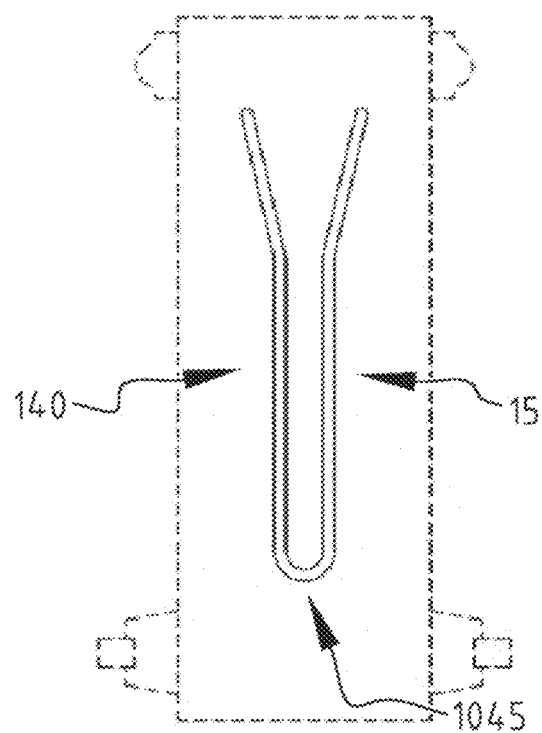
Figure 22F:
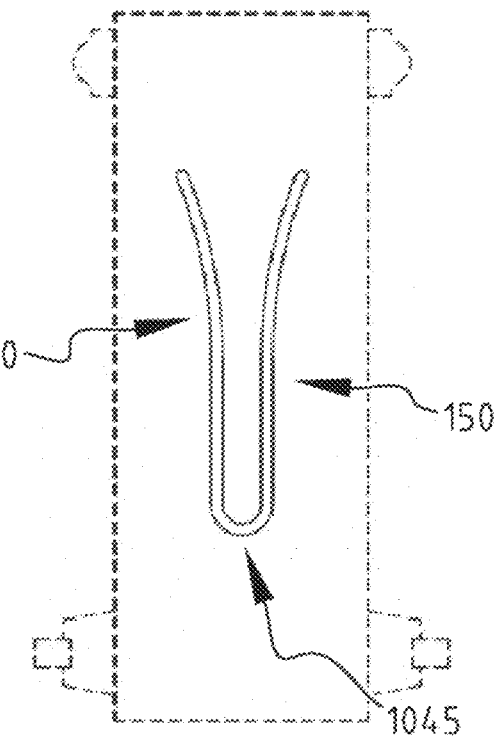
Figure 22G:
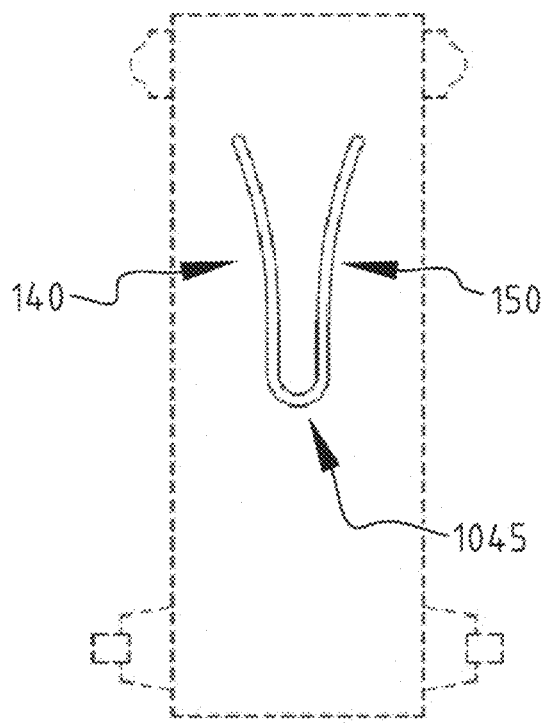
Figure 22H:
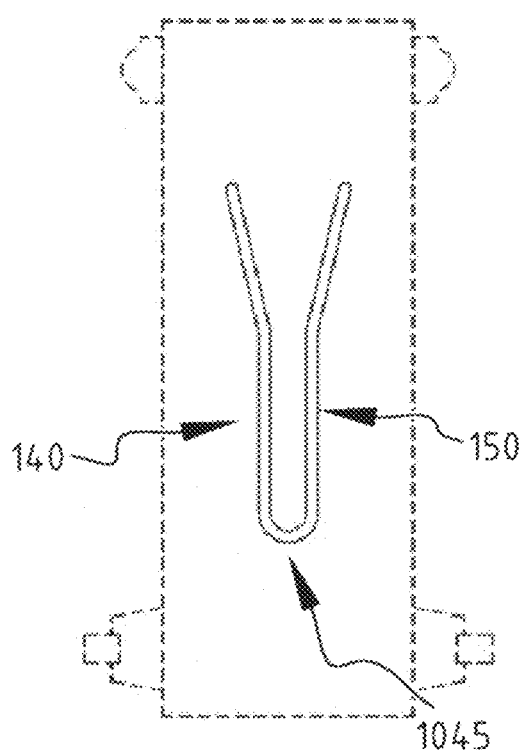
Figures 22I, 22J:
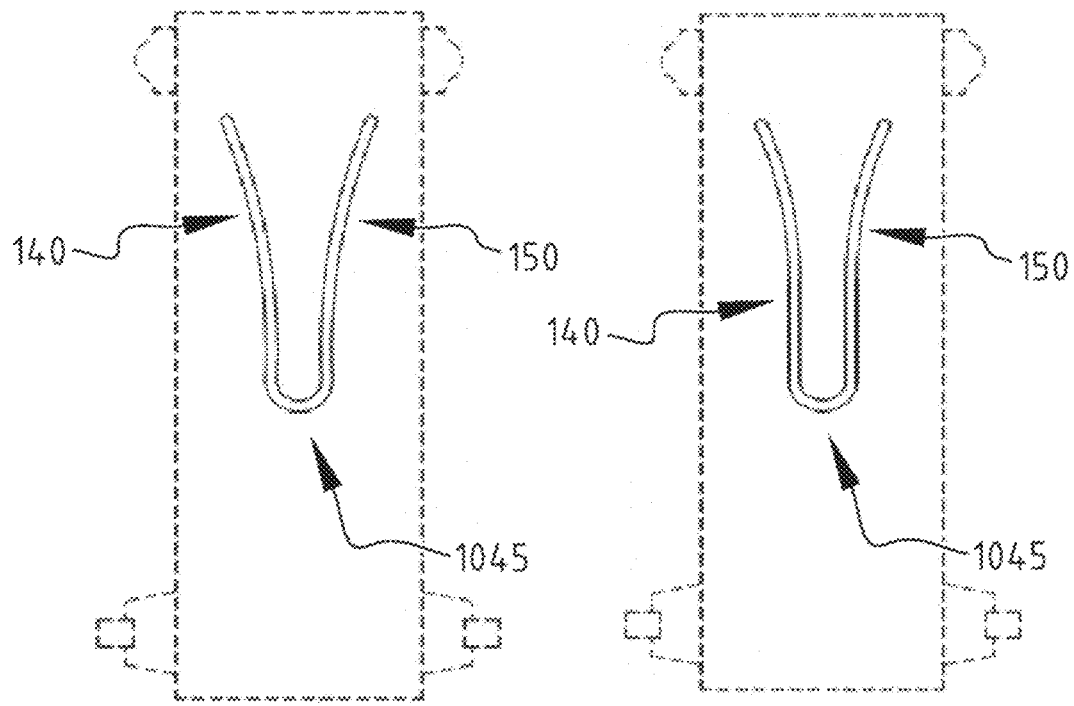
Figures 22K, 22L:
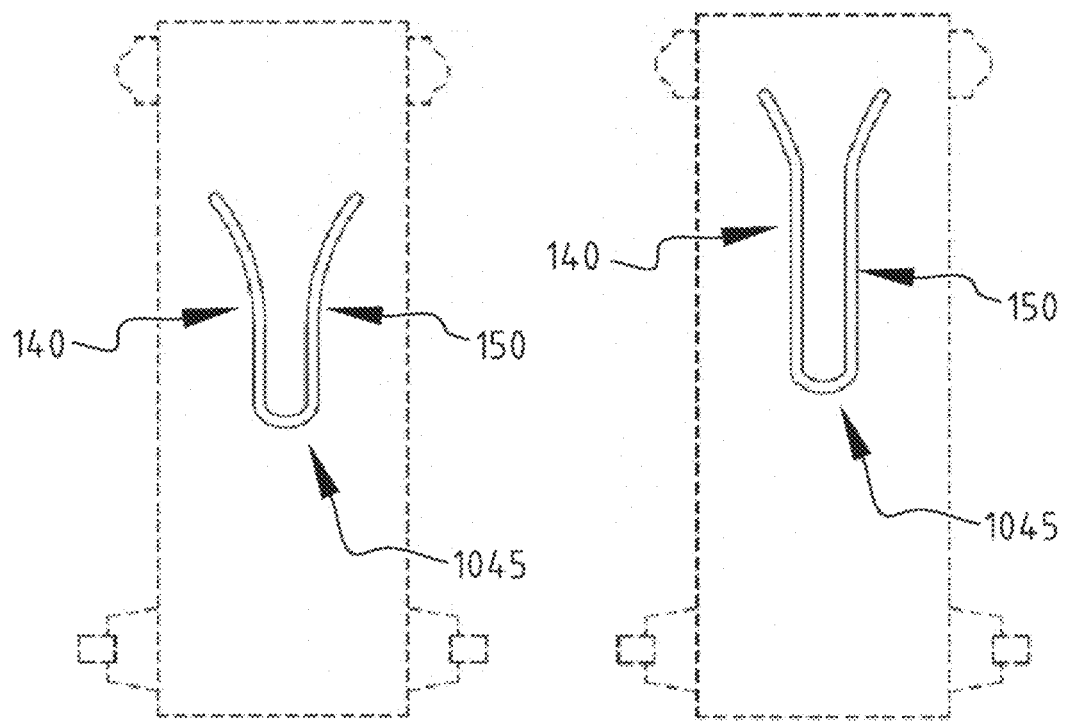
Figure 22M:
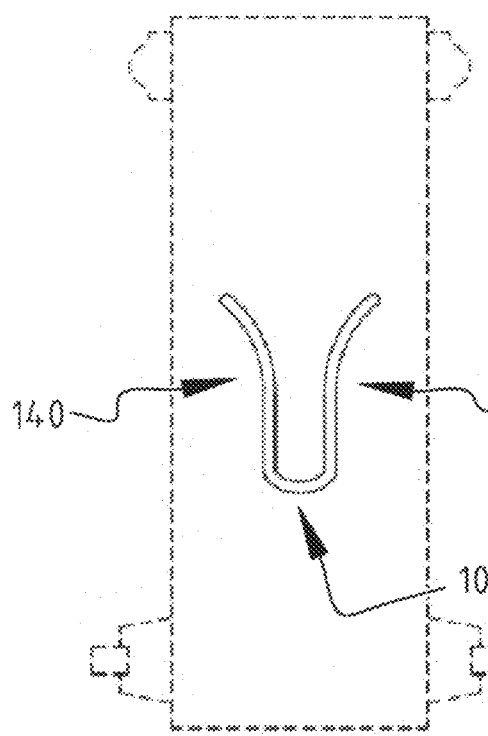
Figure 22N:
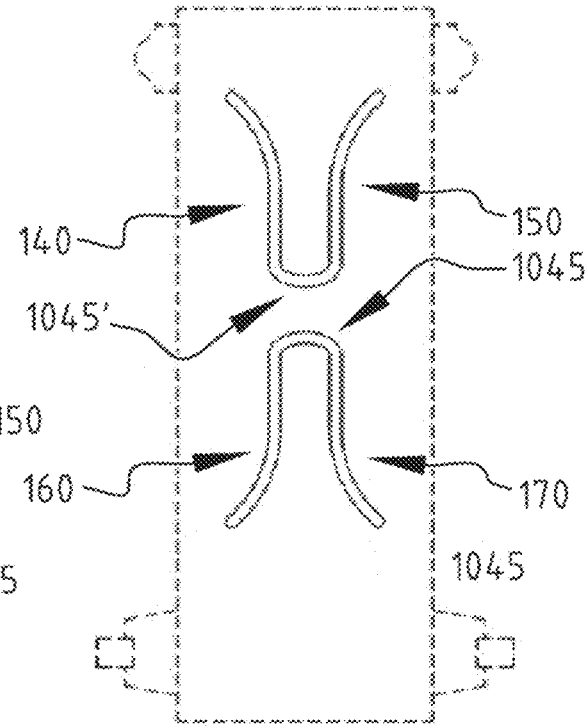
Figure 22O:
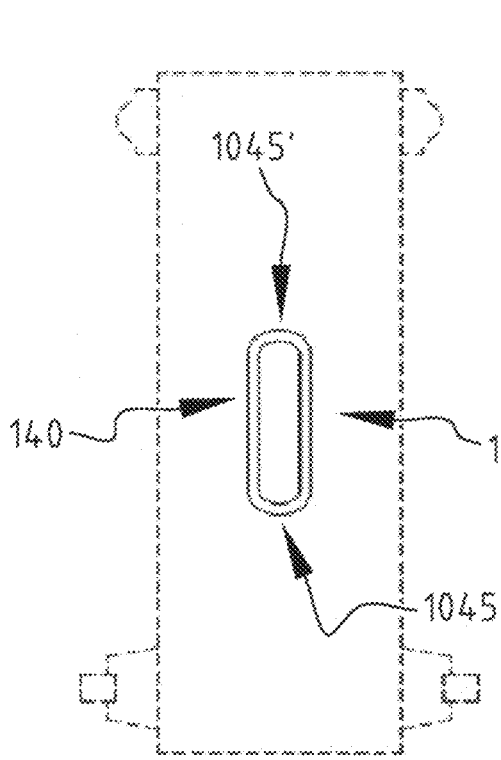
Figure 22P:
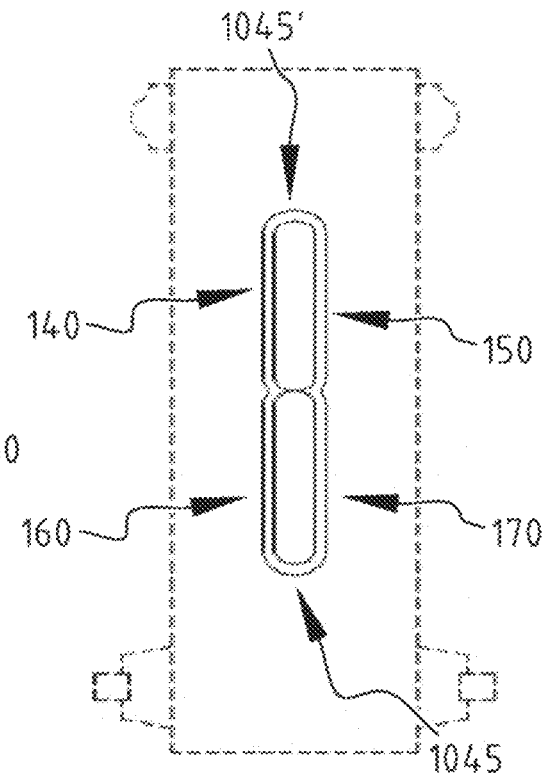
Figures 22Q, 22R:
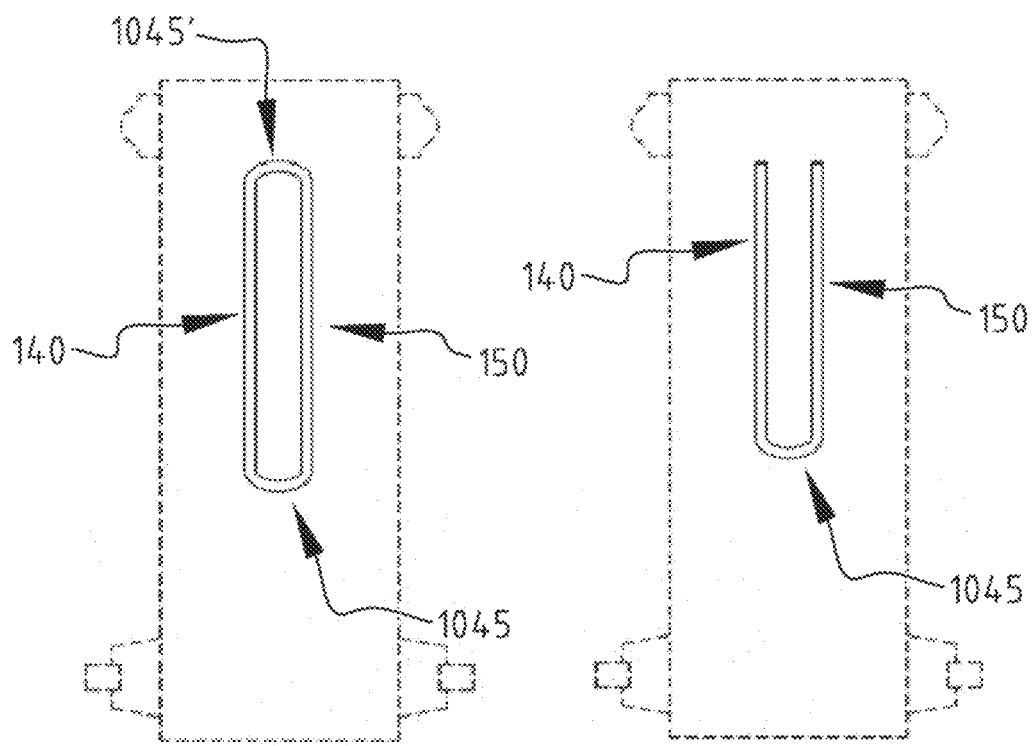
Figures 22S, 22T:
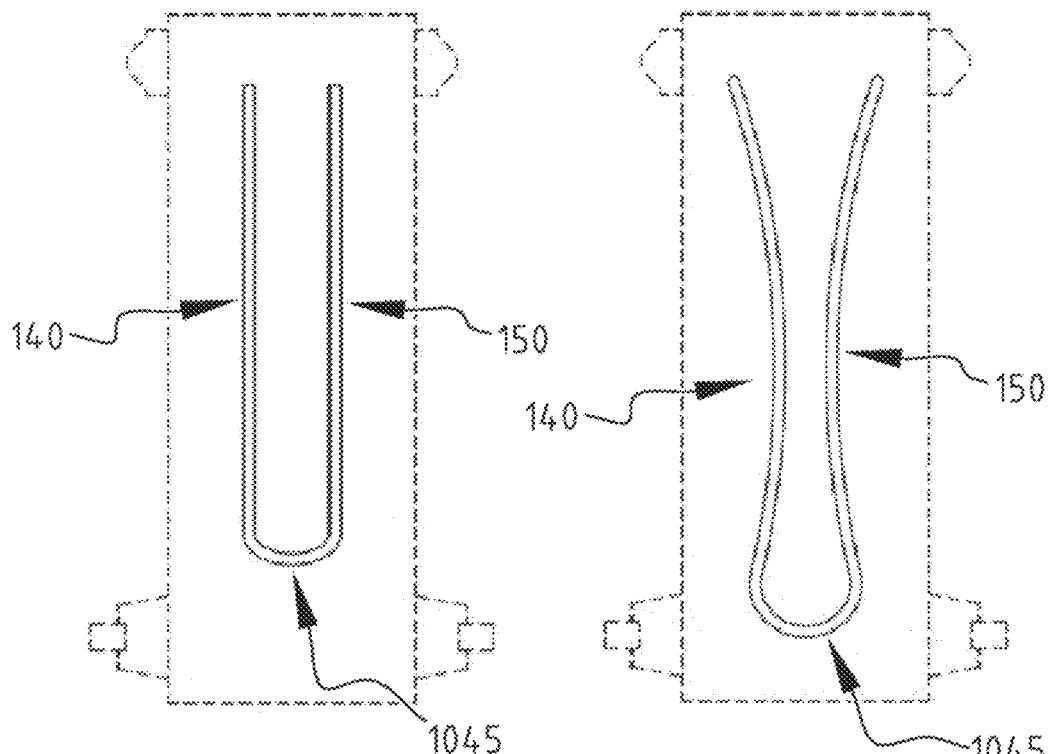
Figures 22U, 22W:
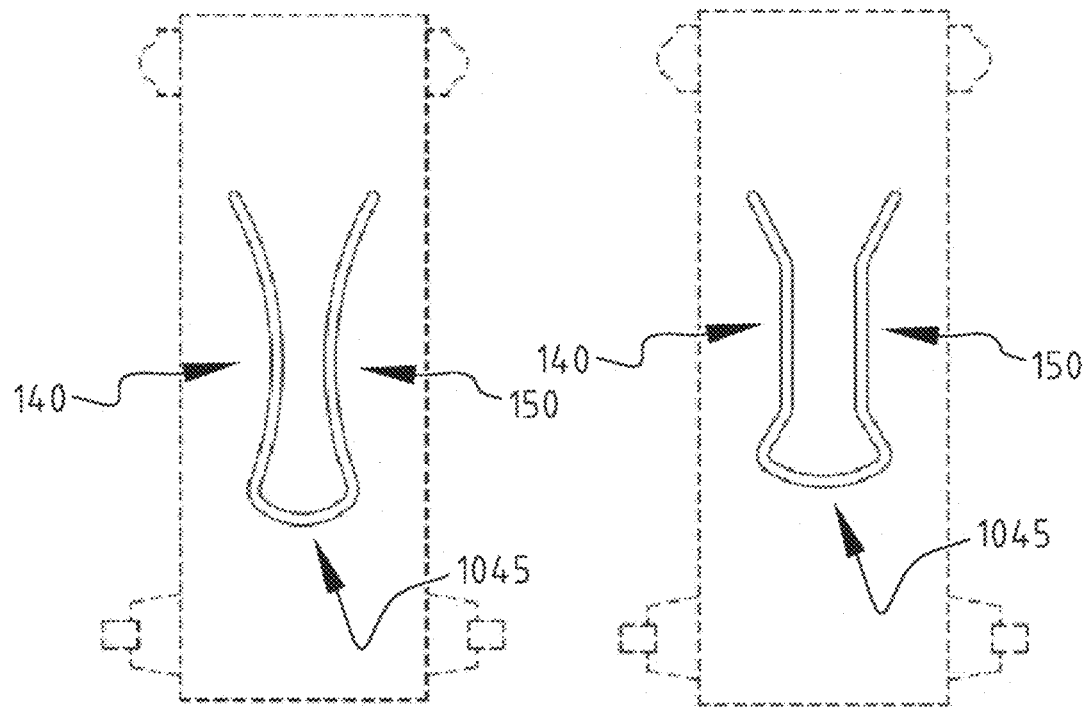
Figures 22V, 22X:
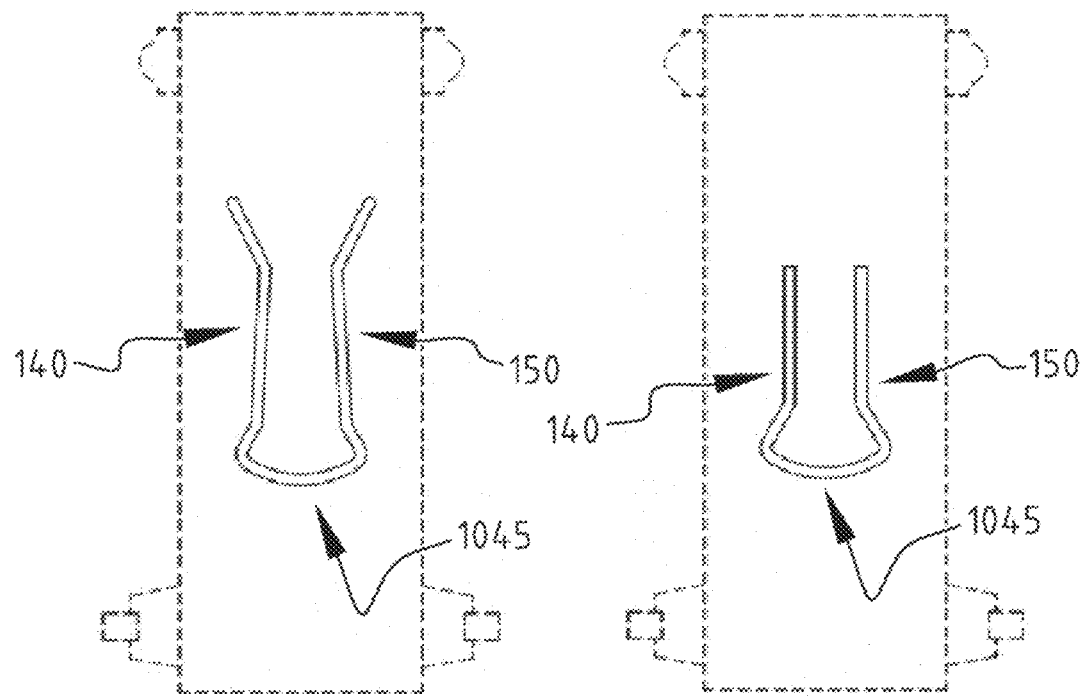
Figures 22Y, 22Z:
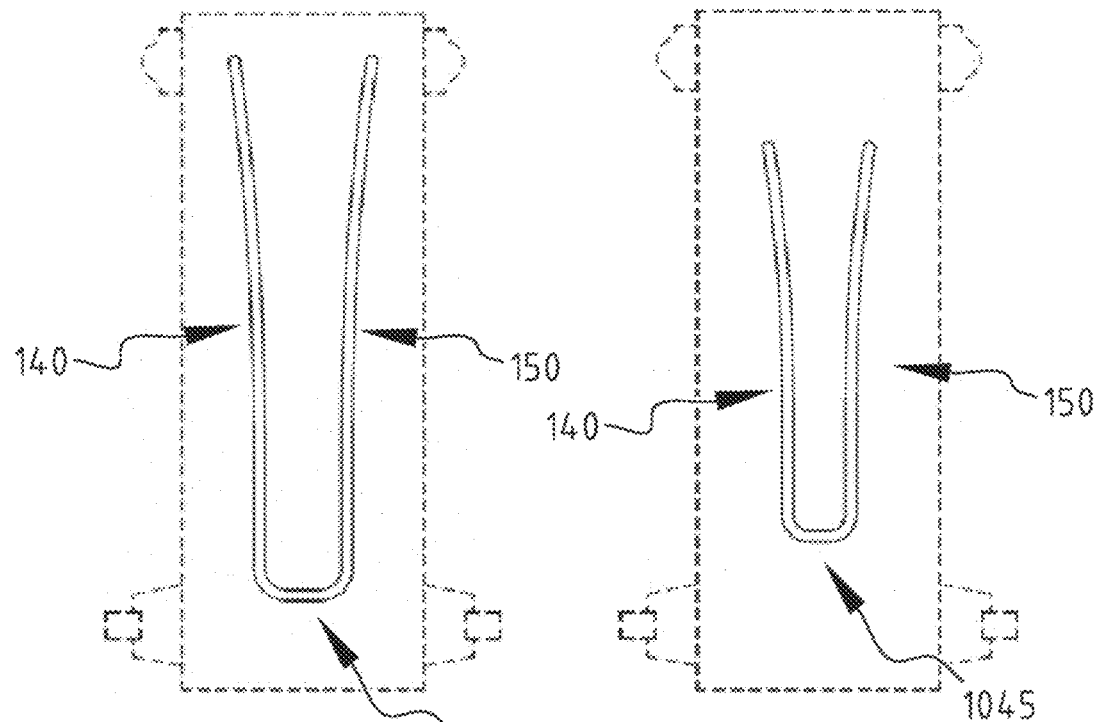

In the embodiments of FIGS. 20X-20Y, a transversal attachment zone 1045' connects the back ends of longitudinal attachment zones 140, 150. In the embodiments of FIGS. 21A-21F, 22O-22Q. 23M-23P, there are two transversal attachment zones 1045 and 1045', respectively connecting the front and back ends of the longitudinal attachment zones 140, 150, 160, 170. In the embodiments of FIGS. 21N, 22N, 23U and 23V, there are two longitudinal attachment zones 140, 150 positioned toward the front side of the absorbent core which are connected by a transversal attachment zone 1045', 1045a at their rear ends, as well as two longitudinal attachment zones 160, 170 positioned toward the rear side of the absorbent core which are connected by a transversal attachment zone 1045, 1045b at their front ends.

In the embodiment of FIGS. 21A-21F. 22O-22Q. 23M-23P the first attachment zone 140, 160 (where present), the second attachment zone 150, 170 (where present) and two connecting attachment zones 1045, 1045' form together a substantially rectangular or O-shaped attachment zone. This substantially rectangular attachment zone comprises a first elongate attachment zone 140, 160 (where present), a second elongate attachment zone 150, 170 (where present), and two straight or curved connecting attachment zones 1045, 1045'. The first and second elongate attachment zone 140, 150, 160, 170 (where present) extend next to each other from the crotch region in the direction of the front transverse edge 133 and/or in the direction of the rear transverse edge 134, and more particularly in the fourth, third and second zone Z4, Z3 and Z2. The connecting attachment zone 1045 is a rear connecting attachment zone which connects a rear end portion of the first attachment zone 140, 160 (where present) to a corresponding rear end portion of the second attachment zone 150, 170 (where present). Preferably, he connecting attachment zone 1045 is located in the fourth zone Z4. The connecting attachment zone 1045' is a front connecting attachment zone which connects a front end portion of the first attachment zone 140 to a corresponding front end portion of the second attachment zone 150. Preferably, the connecting attachment zone 1045' is located in the second zone Z2. In that manner a convenient liquid distribution channel network is created allowing the liquid to be distributed rapidly throughout the absorbent core.

Figures 23A, 23B:
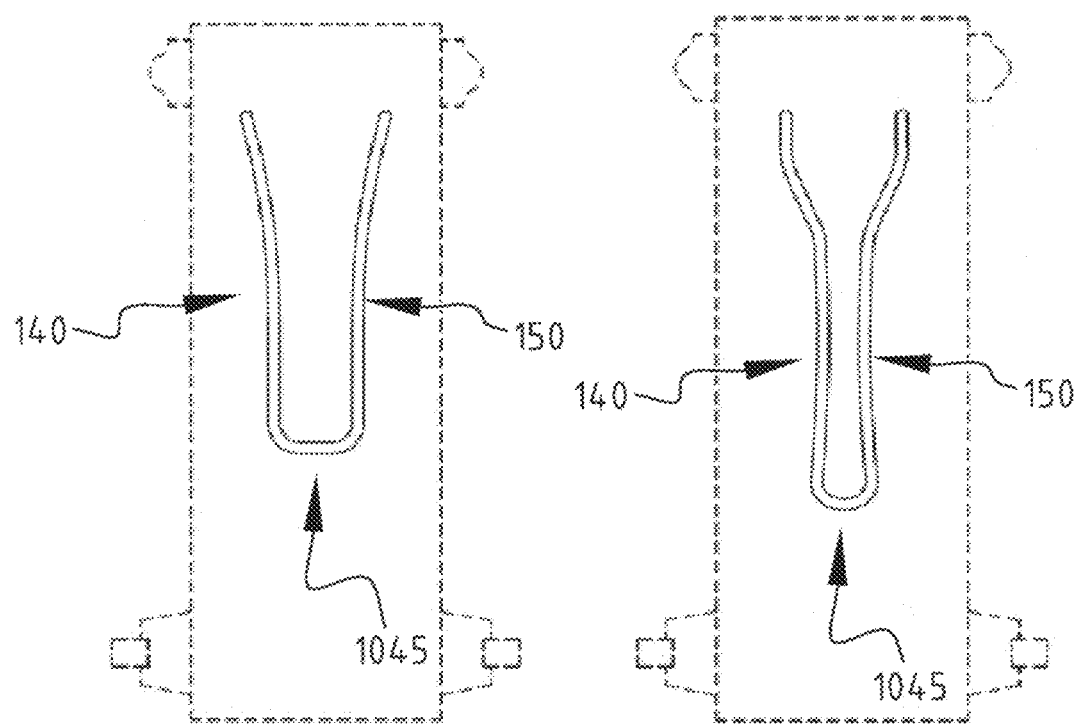
FIGS. 23A-23V illustrate yet other exemplary embodiments of an absorbent core according to the invention.
Figure 23G:
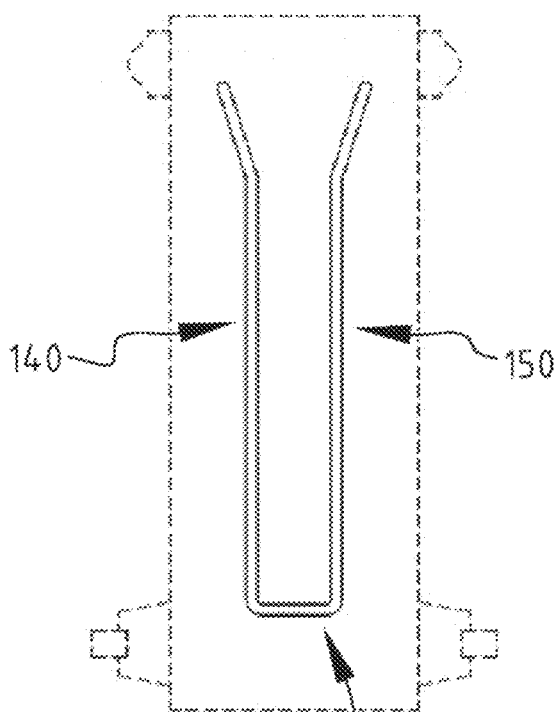
Figure 23H:
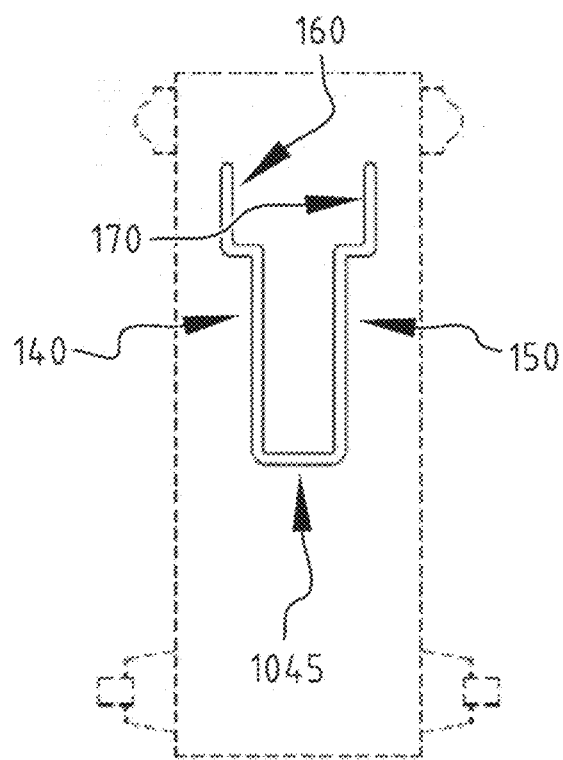
Figure 23I:
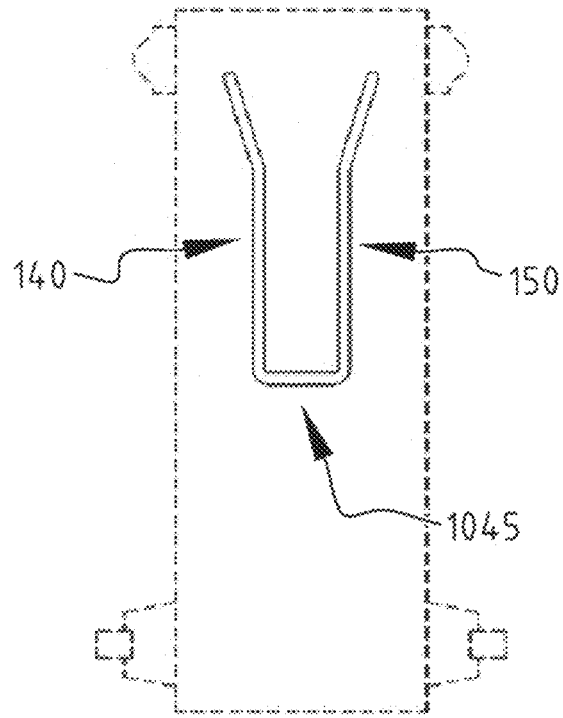
Figure 23J:
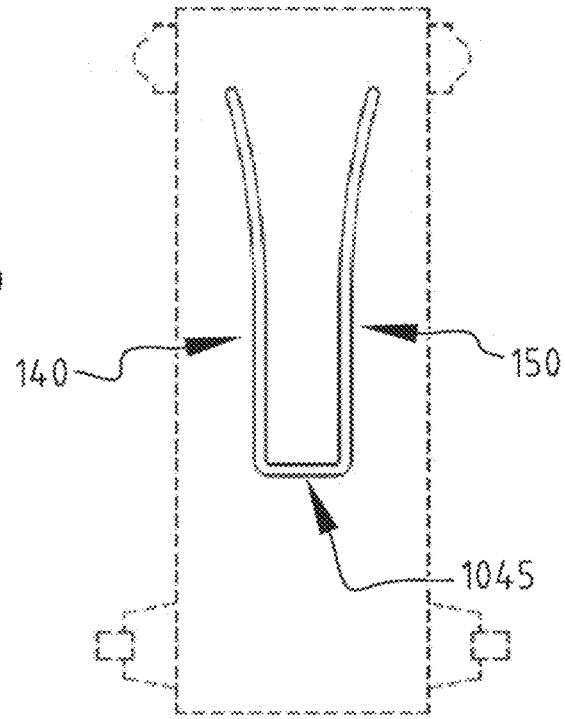
Figures 23K, 23L:
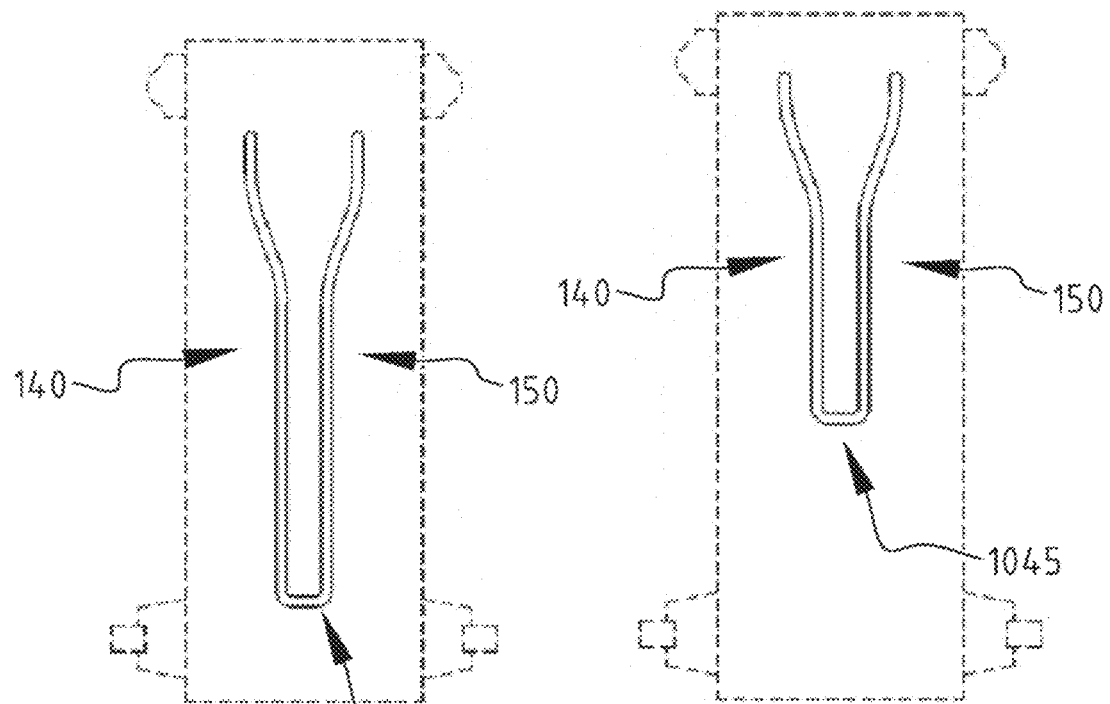
Figures 23M, 23N:
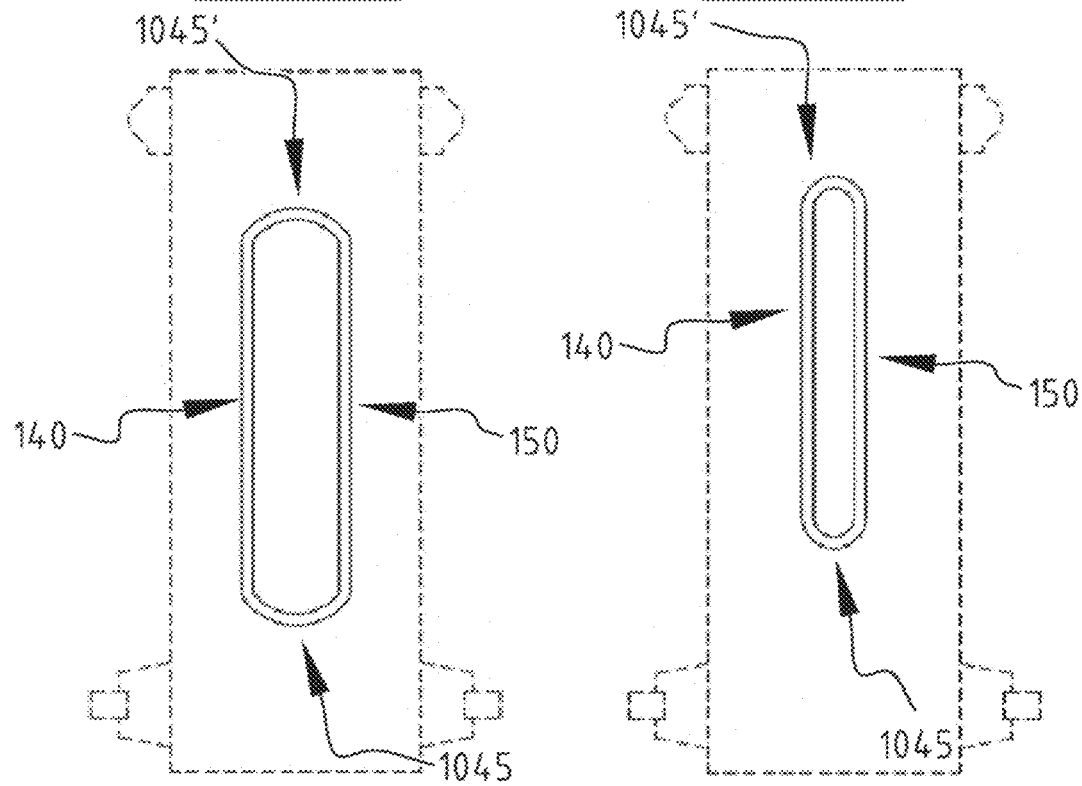
Figure 23O:
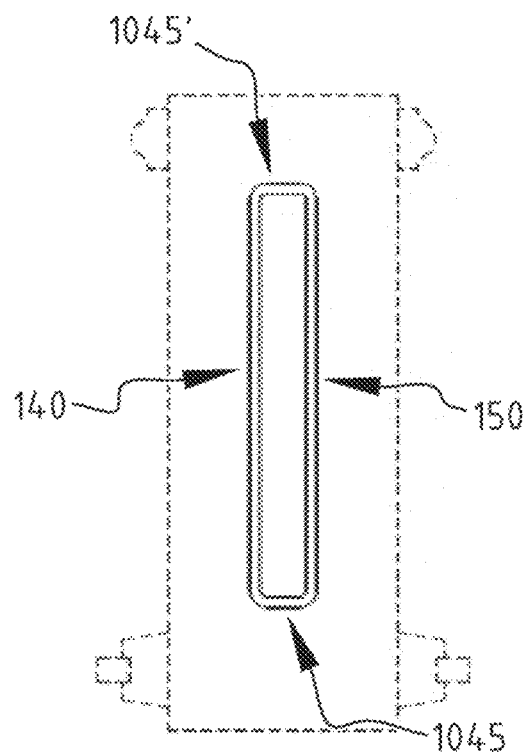
Figure 23P:
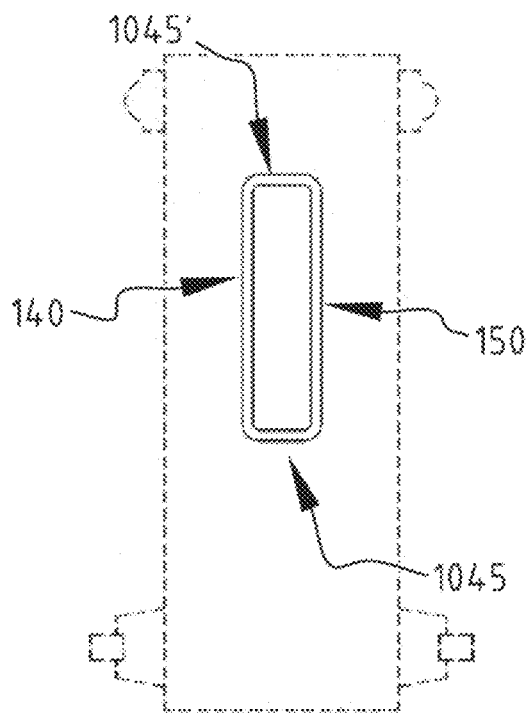
Figure 23Q:
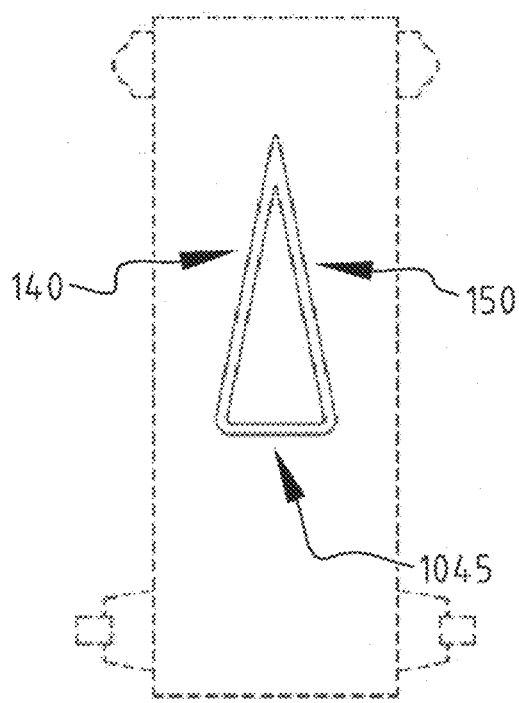
Figure 23R:
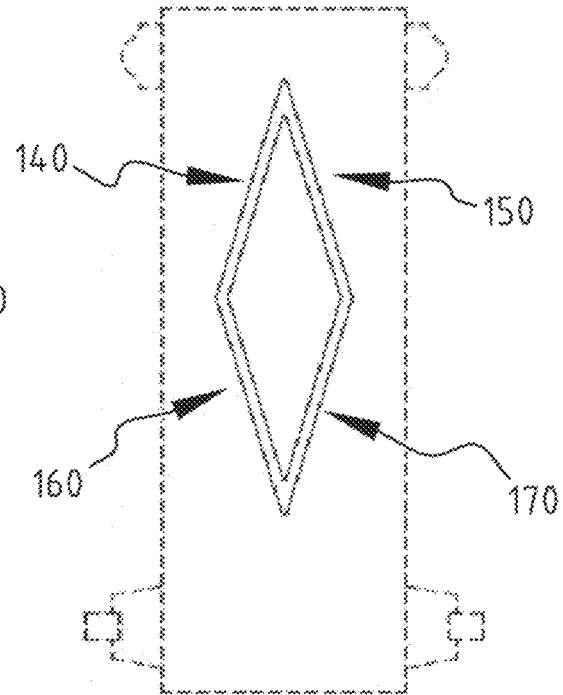
Figures 23S, 23T:
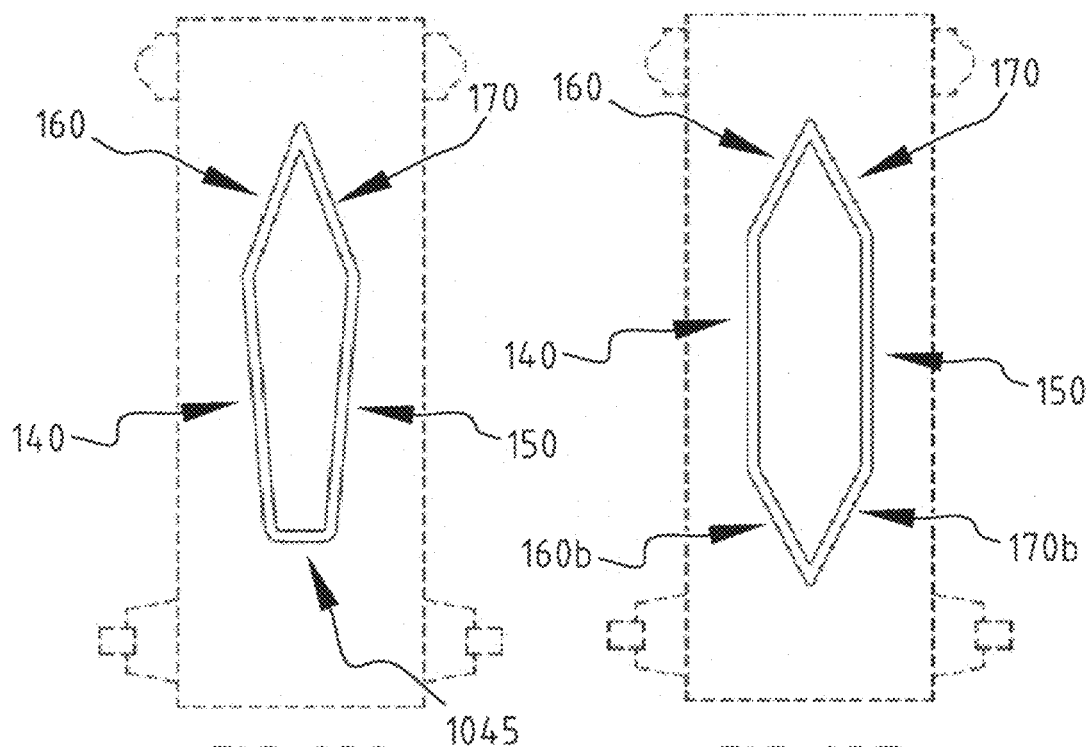
Figures 23U, 23V:
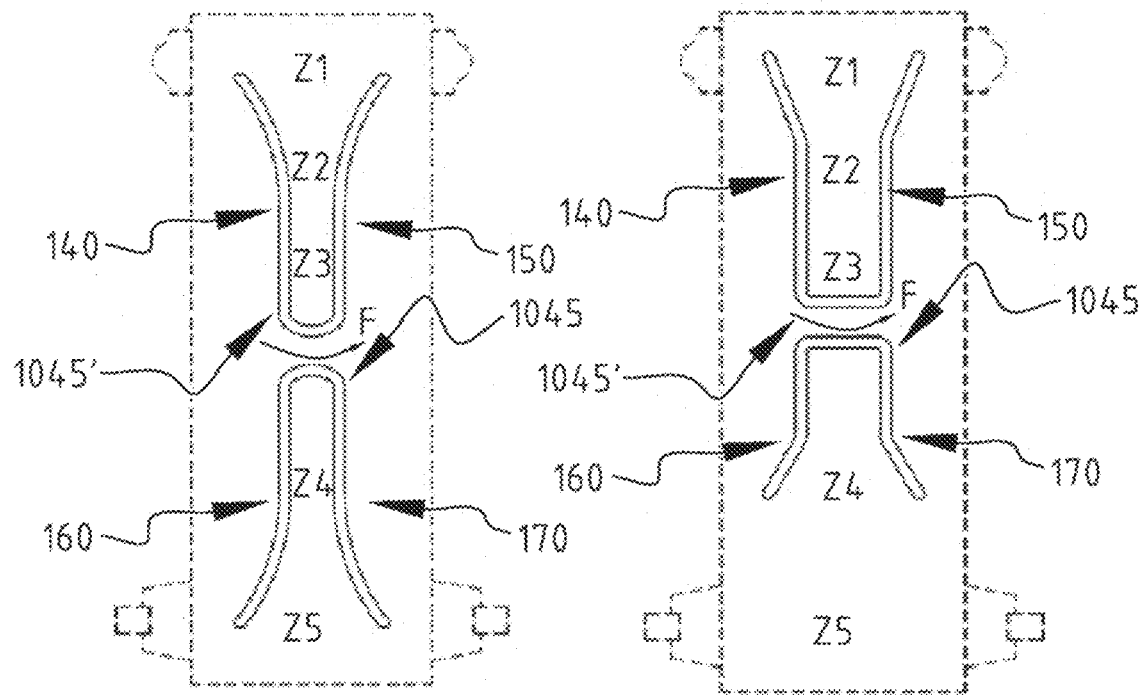

The connecting between the longitudinal channels need not be done with a transversal channel, but may also be achieved by shaping the longitudinal channels in a specific way. For example, in the embodiment of FIG. 23R, the four longitudinal attachment zones 140, 150, 160, 170 collectively form a diamond shape. Likewise, in the embodiment of FIG. 23T, six longitudinal attachment zones 140, 150, 160a, 170a, 160b, 170c are so connected as to form an elongated hexagon shape. Combinations of these two methods of connecting channels are also possible. In the embodiment of FIG. 23Q, the longitudinal attachment zones 140, 150 are connected at their rear ends by a transversal attachment zone 1045 and converge to meet at their front ends. In the embodiment of FIG. 23S, longitudinal attachment zones 140 and 150 are connected by a transversal attachment zone 1045, while longitudinal attachment zones 160, 170, which are connected to zones 140, 150 respectively, converge at their front ends. The skilled person will be capable of envisaging other combinations and variations of the depicted embodiments.

The advantageous effect may be achieved even in cases wherein the longitudinal attachment zones are not directly connected, but merely approach each other in certain places. For example, in the embodiments of FIG. 20Z, 21J, 21T, the rear ends of longitudinal attachment zones 140, 150 are connected by transversal attachment zone 1045, and the front ends of longitudinal attachment zones 160, 170 are shaped such that they approach one another. In other embodiments, such as the ones of FIG. 21U, 21Y, 22A-22C, the longitudinal attachment zones 140, 150, 160, 170 approach one another either at the ends or along their path, and this may, depending on the specific configuration, be sufficient to allow for liquid to go from one channel to another.

The embodiments of FIGS. 21D, 21E, 21N, 21T, 21U, 21X, 21Y, 22A, 22B, 22C, 22N, 22O, 22P, 22Q, 22R, 22S, 23D, 23E, 23M, 23N, 23O, 23P, 23R, 23T, 23U and 23V can be used for both male and female. The embodiments of FIGS. 20A, 20B, 20C, 20D, 20E, 20F, 20G, 20H, 20I, 20J, 20K, 20L, 20M, 20N, 20O, 20P, 20Q, 20R, 20S, 20T, 20U, 20V, 20W, 20Z, 21K, 21L, 21M, 21O, 21P, 21Q, 21R, 21S, 21V, 21W, 21Z, 22D, 22E, 22F, 22G, 22H, 22I, 22J, 22K, 22L, 22M, 22T, 22U, 22V, 22W, 22Y, 22Z, 23A, 23B, 23C, 23F, 23G, 23H, 23I, 23J, 23K, 23L and 23S are preferable for male. The embodiments of FIGS. 20X, 20Y, 21A, 21B, 21C, 21F, 21G, 21H, 21I, 21J, 22X and 23Q preferable for female.

FIGS. 24A-C, 25A-25Z and FIGS. 26A-26T

Figure 24A:
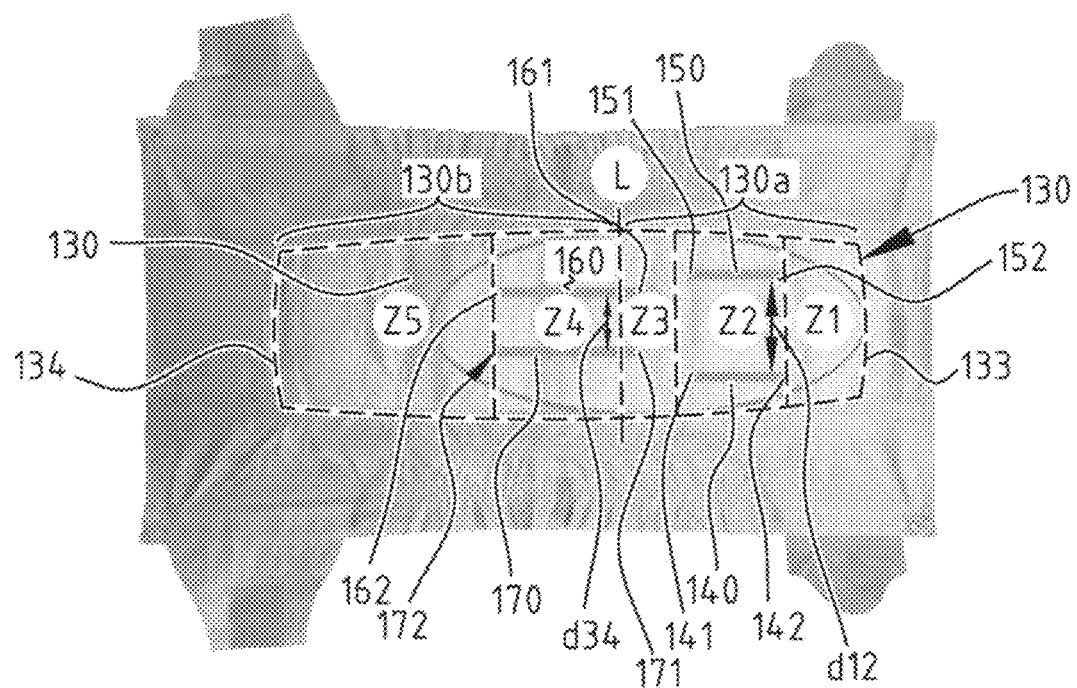
FIGS. 24A-24C are photographs of an exemplary embodiment of a diaper in a dry and wetted state.
Figure 24B:
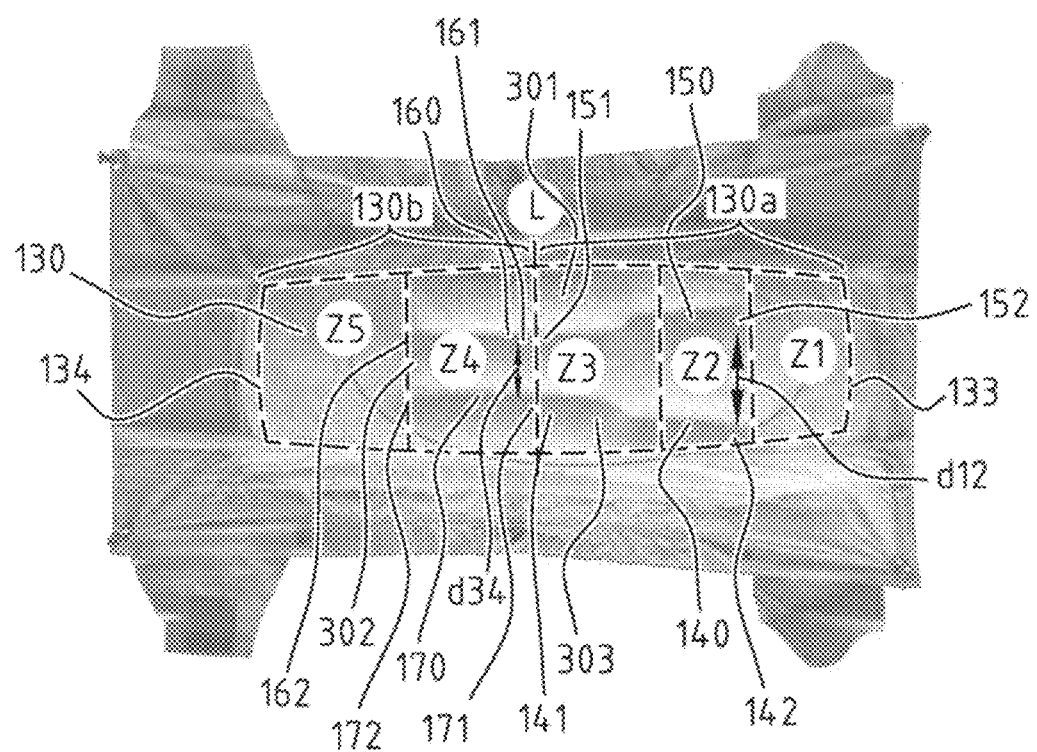
Figure 24C:
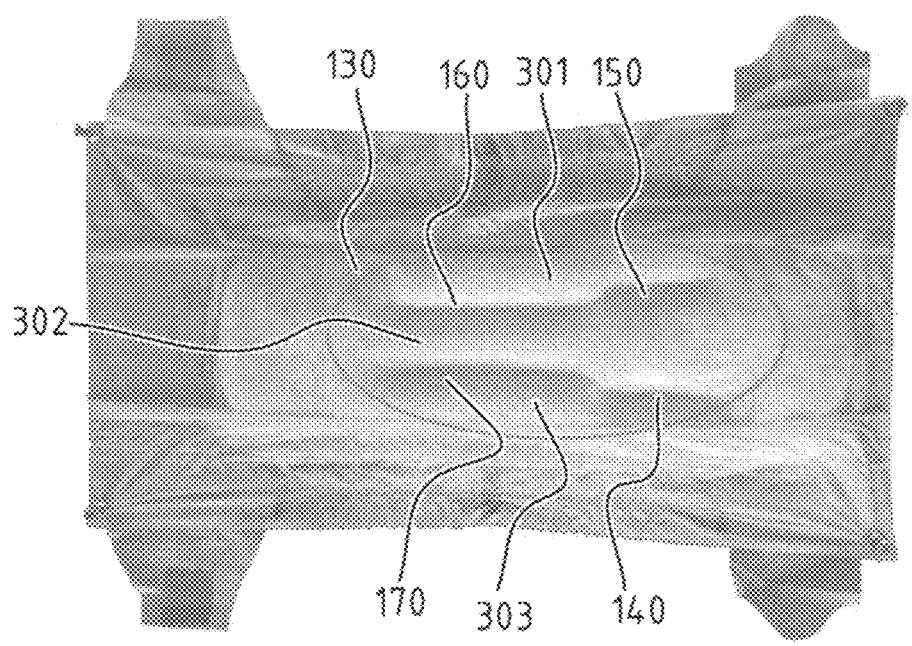

In addition to the perspective view as shown in FIG. 12, FIGS. 24A-C are photographs representing an absorbent article comprising an exemplary embodiment of an absorbent core of the invention. FIG. 24A illustrates the absorbent article when the absorbent core is in a dry state, whereas FIGS. 24B and 24C illustrate the absorbent article when the absorbent core is in a wetted state. In FIG. 24A attachments zones 140, 150, 160 and 170 wherein substantially no absorbent material is present, can be distinguished. However, in the illustrated photograph 24A the attachment zones 140, 150, 160 and 170 have been slightly darkened in order to better illustrate the position thereof, since due to quality restraints of the photograph 24A a part of this visual information has been lost. FIGS. 24B and 24C are photographs of the absorbent article in a wetted state, wherein tubes 301, 302, 303 have formed, which leads to the attachment zones 140, 150, 160 and 170 becoming more visible as channels. Thanks to the attachment zones and associated channels 140, 150, 160 and 170 the liquid is evenly spread, resulting in the formation of tubes 301, 302, 303 which provide a tub shape to the absorbent core 130. Such a tub shape adapts perfectly to the body and can be seen, at least partially, in FIG. 24C where the absorbent article is not attached to a bottom surface at the corners of the absorbent article, which is the case in FIGS. 24A and 24B. Further, compared to prior art solutions, the liquid is kept in an improved manner absorbed in the absorbent core 130, and the risk on leakage is reduced. Also, because of the creation of the channels 140, 150, 160, 170, the liquid is absorbed faster. Seen in a longitudinal direction of the absorbent core 130, looking from the front edge 133 to the rear edge 134, the absorbent core 130 comprises subsequently a first, second, third, fourth and fifth zone Z1, Z2, Z3, Z4, Z5. The zones may have the features of any one of the embodiments above.

The embodiments of FIGS. 24A, 24B and 24C are advantageous for a male person. Indeed, the first and a second elongate attachment zone 140, 150 extend next each other, at least in the front portion of the absorbent core in the direction of the front edge 133 of the absorbent core, and a third and a fourth elongate attachment zone 160, 170 extend next to each other, at least in the rear portion 130b of the absorbent core, in the direction of the second transverse edge 134. Measured in a transverse direction, a first maximum distance d12 between the first and the second attachment zone 140, 150 is bigger than a second maximum distance d34 between the third and the fourth attachment zone 160, 170, the first distance d12 between the first and the second attachment zone is at least 5%, preferably at least 10% bigger, even more preferably at least 15% bigger than a second distance d34 between the third and the fourth attachment zone. In the embodiment of FIG. 24A, the first and the second elongate attachment zone 140, 150 each have a front end 142, 152 adjacent to absorbent material and a rear end 141, 151 adjacent to absorbent material. The third and the fourth elongate attachment zone 160, 170 each have a rear end 162, 172 adjacent to absorbent material and a front end 161, 171 adjacent to absorbent material. In the embodiment of FIG. 24B, the first and the second elongate attachment zone 140, 150 each have a front end 142, 152 adjacent to absorbent material and a rear end 141, 151 connected on the crotch line L to a front end 171, 161 of the third and the fourth elongate attachment zone 160, 170. The third and the fourth elongate attachment zone 160, 170 each have a rear end 162, 172 adjacent to absorbent material. In the embodiment of FIG. 24A, seen in a projection on the longitudinal direction of the absorbent core, the first and the second attachment zone 140, 150 extend over a length which is less than the length of the third and fourth attachment zone 160, 170. The distance (d12) between the first and the second attachment zone 140, 150 is preferably between 15 and 70% of the width of the absorbent core, more preferably between 20 and 50%; wherein preferably the distance (d12) between the first and the second attachment zone is between 10 mm and 100 mm, more preferably between 20 mm and 80 mm, even more preferably between 30 mm and 70 mm. Preferably, the distance (d34) between the third and the fourth attachment zone is between 5 and 60% of the width of the absorbent core, more preferably between 10 and 40%; wherein preferably the distance (d34) between the third and the fourth attachment zone is between 5 mm and 60 mm, more preferably between 10 mm and 50 mm, even more preferably between 15 mm and 40 mm. Preferably, the length of the first and the second attachment zone 140, 150 is larger than 5% of the length of the absorbent core 130; more preferably larger than 10%, even more preferably larger than 15%. Also, preferably the length of the third and the fourth attachment zone is larger than 5% of the length of the absorbent core; more preferably larger than 10%, even more preferably larger than 15%. Preferably, the length of the third and the fourth attachment zone 160, 170 is larger than the length of the first and the second attachment zone 130, 140, preferably at least 10% larger, more preferably at least 20% larger. Preferably, seen in a projection on a longitudinal direction, the first and second attachment zone 140, 150 do not overlap with the third and fourth attachment zone 160, 170.

In the embodiment of FIG. 24B the first attachment zone 140 may be connected to the third attachment zone 170 through a permanent or semi-permanent attachment zone and the second attachment zone 150 may be connected to the fourth attachment zone 160 through a permanent or semi-permanent attachment zone, wherein a semi-permanent attachment zone may loosen upon wetting to allow for a liquid flow in a transverse direction.

FIGS. 25A-25Z and FIGS. 26A-26T illustrate embodiments in which the dimensions of the longitudinal attachments zones 140, 150, 160, 170, 180 in the longitudinal direction have been reduced as compared to previously illustrated embodiments. Regarding the illustrated configurations of the shorter longitudinal attachments zones 140, 150, 160, 170, central attachments zones 180, 180a, 180b, 180c and transversal attachment zones 1045, 1045a, 1045b, 1045c as illustrated in FIGS. 25A-25Z and FIGS. 26A-26T, it is clear to the skilled person that the above described technical considerations and advantages in view of longer longitudinal attachments zones 140, 150, 160, 170, central attachments zones 180, 180a, 180b, 180c and transversal attachment zones 1045, 1045a, 1045b, 1045c as illustrated in the previous figures apply in a similar way, mutatis mutandis.

Figure 25A:
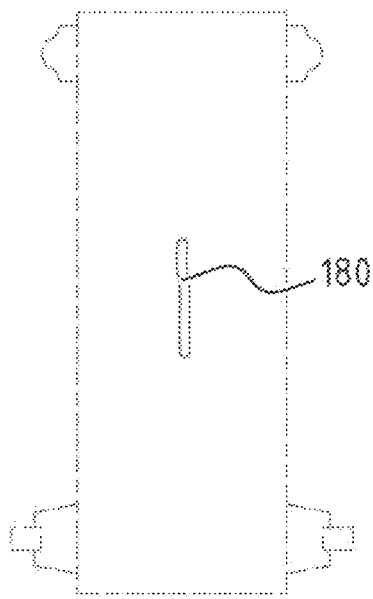
FIGS. 25A-25Z illustrate yet other exemplary embodiments of an absorbent core according to the invention.
Figure 25B:
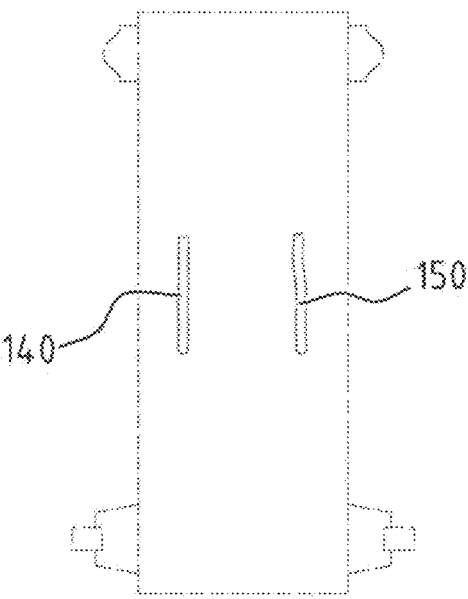
Figure 25C:
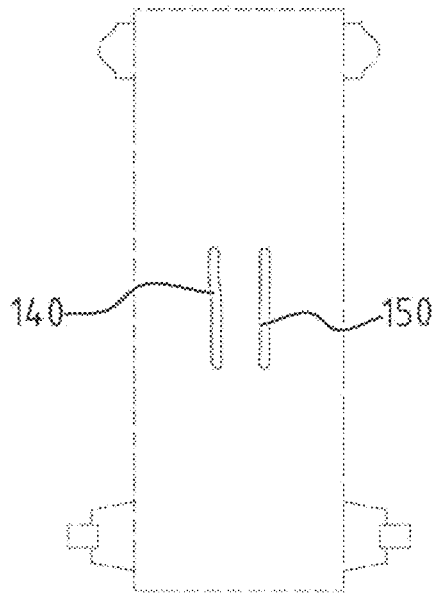
Figure 25D:
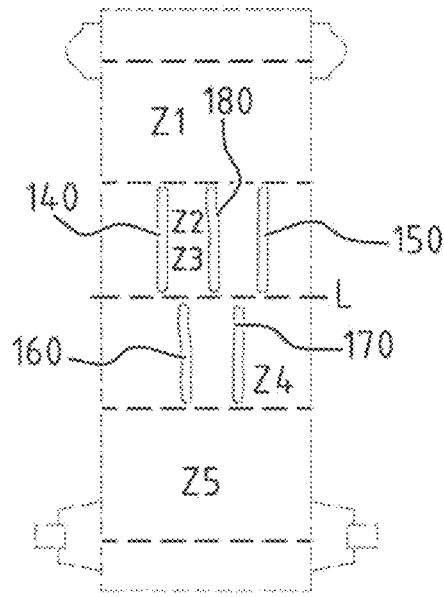
Figure 25E:
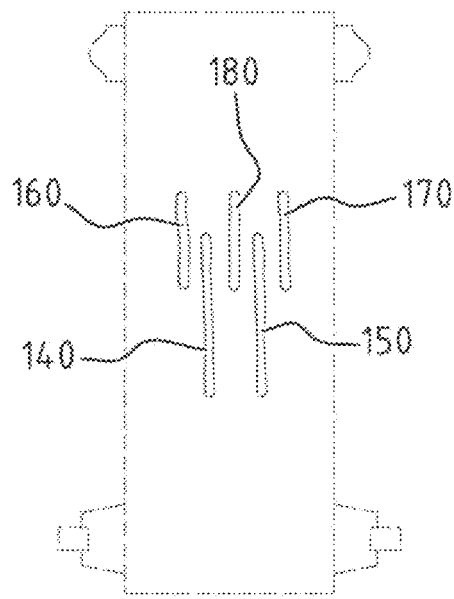
Figure 25F:
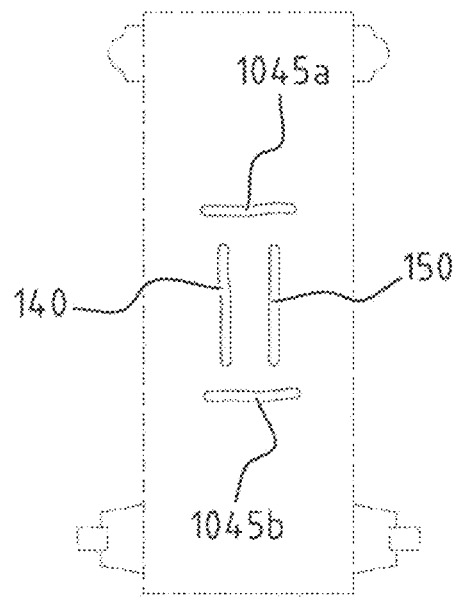
Figure 25G:
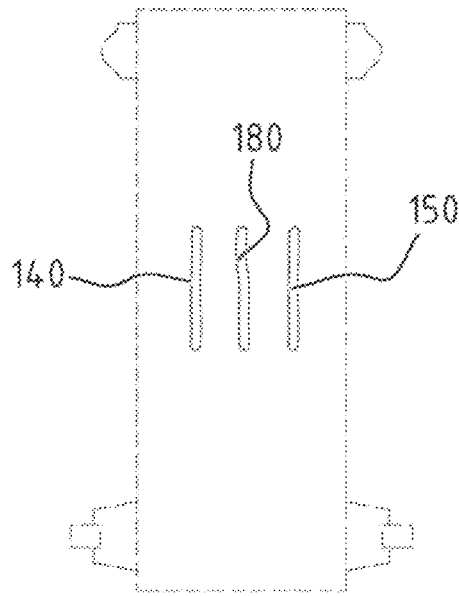
Figure 25H:
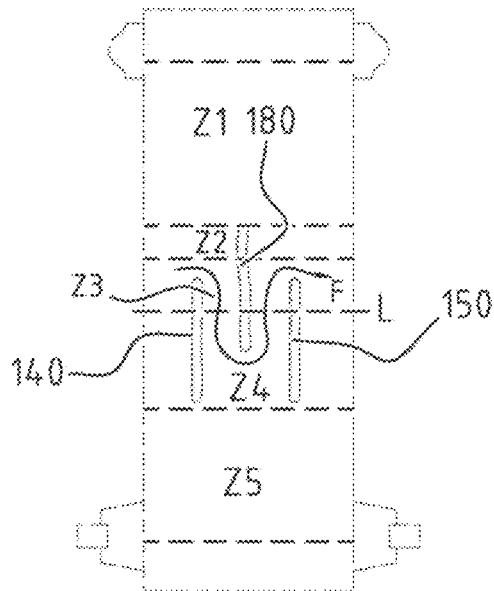
Figure 25I:
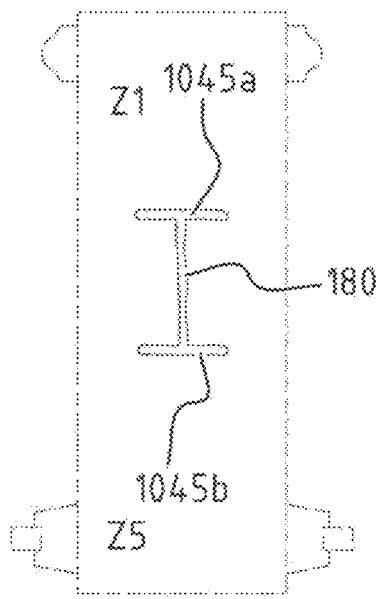
Figure 25J:
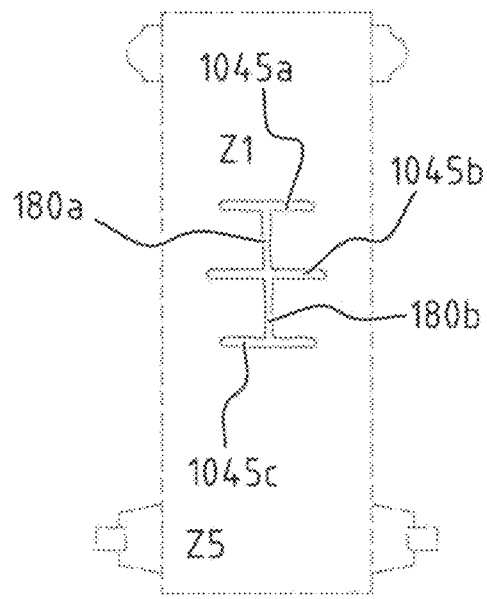
Figure 25K:
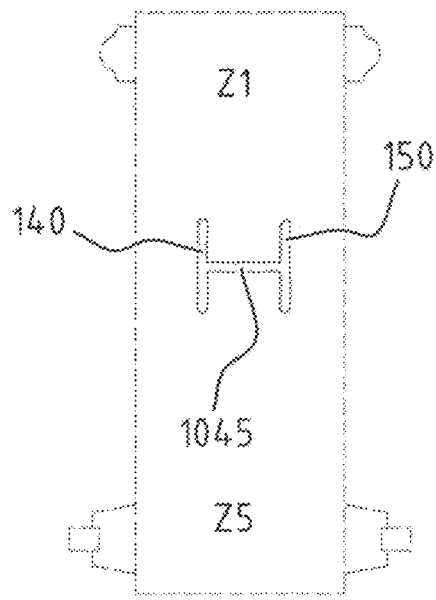
Figure 25L:
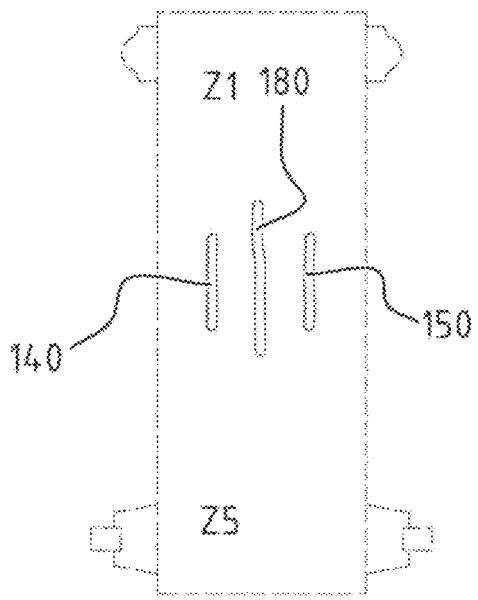
Figure 25M:
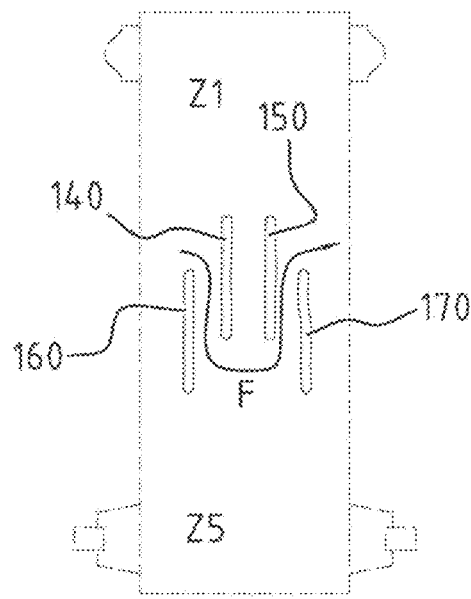
Figure 25N:
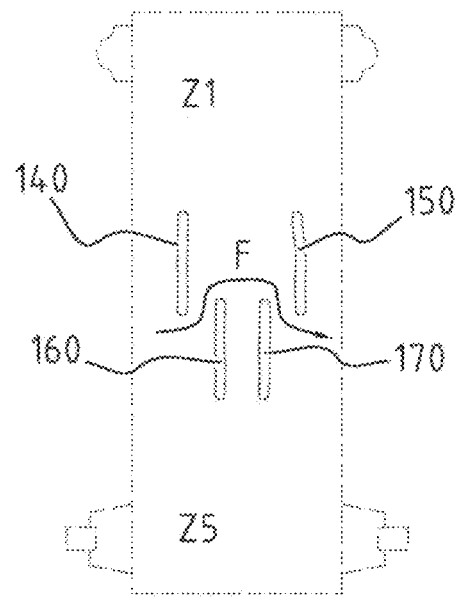
Figure 25O:
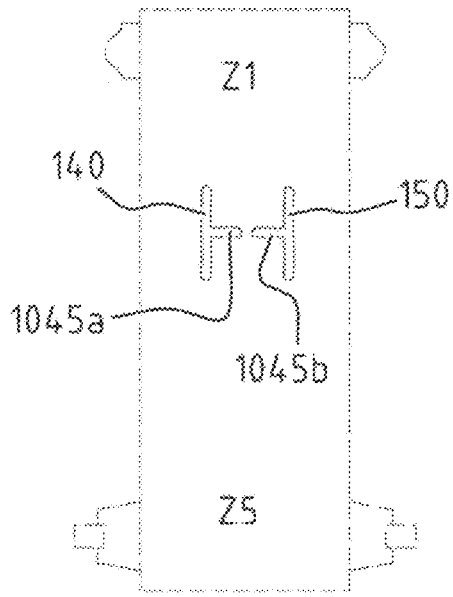
Figure 25P:
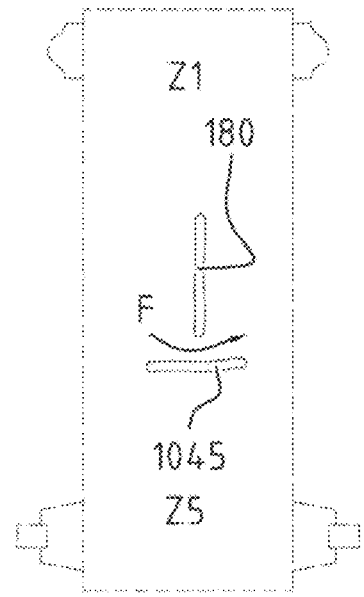
Figure 25Q:
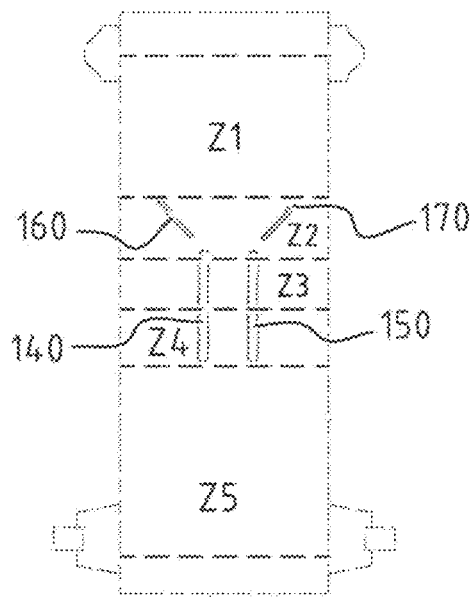
Figure 25R:
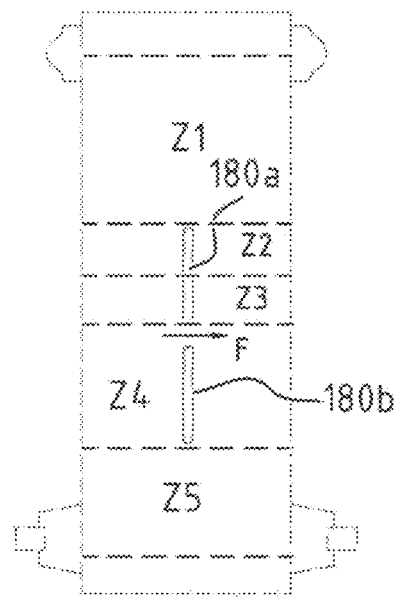
Figure 25S:
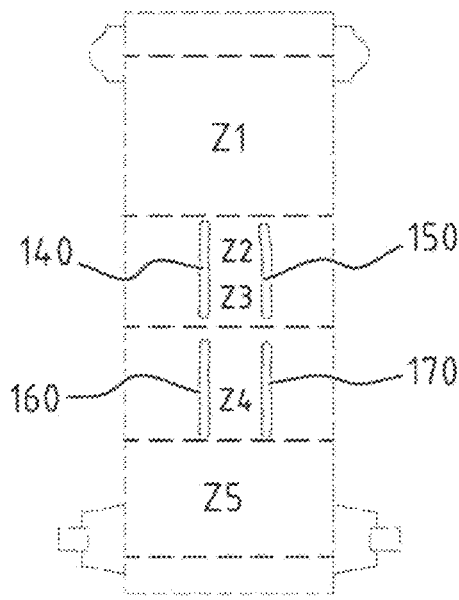
Figure 25T:
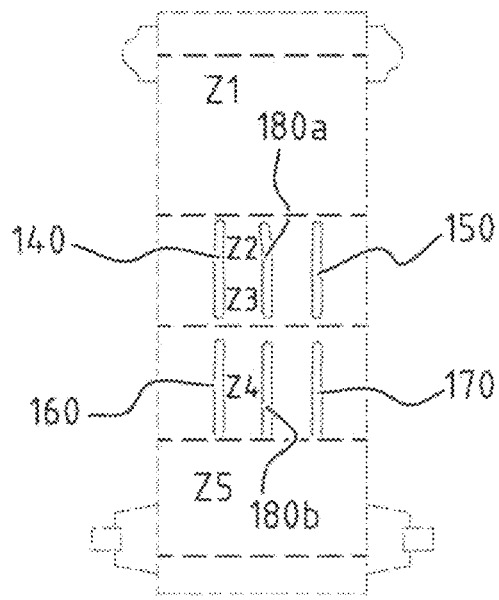
Figure 25U:
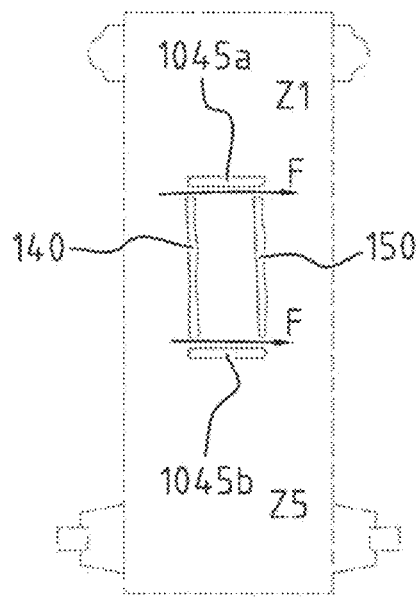
Figure 25V:
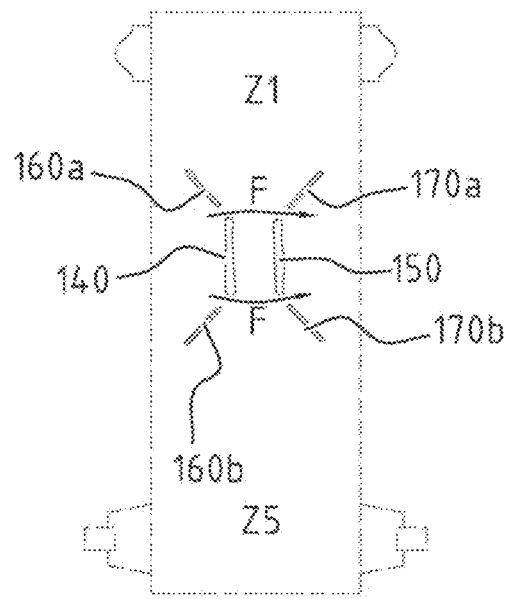
Figure 25W:
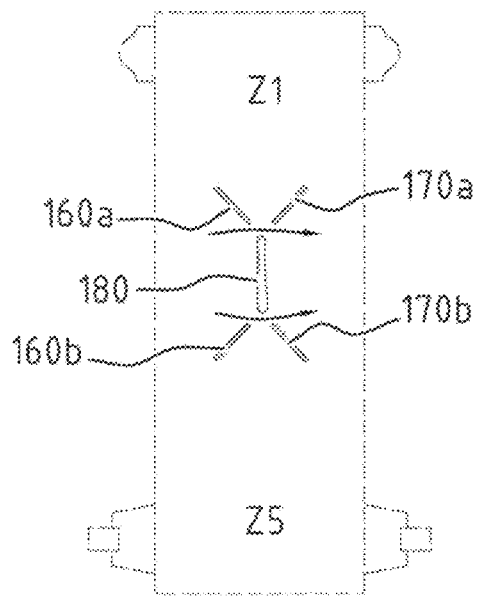
Figure 25X:
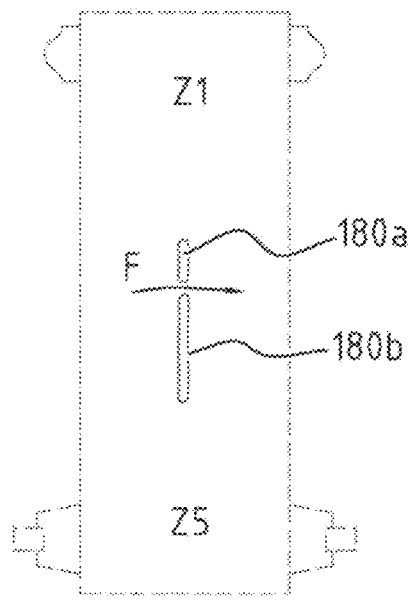
Figure 25Y:
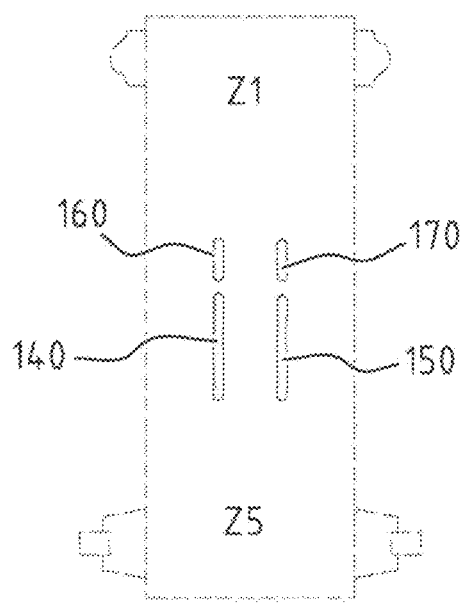
Figure 25Z:
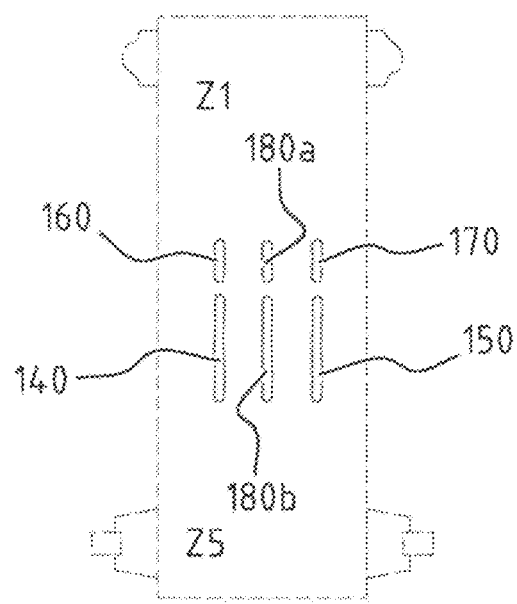

The embodiments of FIGS. 25A, 25B, 25C, 25F, 25G, 25H, 25I, 25J, 25K, 25L, 25O, 25P, 25R, 25S, 25T, 25U, 25V, 25W, 25X, 25Y, 25Z, 26A, 26B, 26F, 26G, 26H, 26J, 26K, 26L, 26M, 26N, 26O, 26P, 26Q, 26R, 26S and 26T can be used for both male and female. The embodiments of FIGS. 25D, 25E, 25N, 25Q, 26C, 26D, 26E and 26I are preferable for male. The embodiments of FIG. 25M is preferable for female.

FIG. 27A-B

Figure 27A:
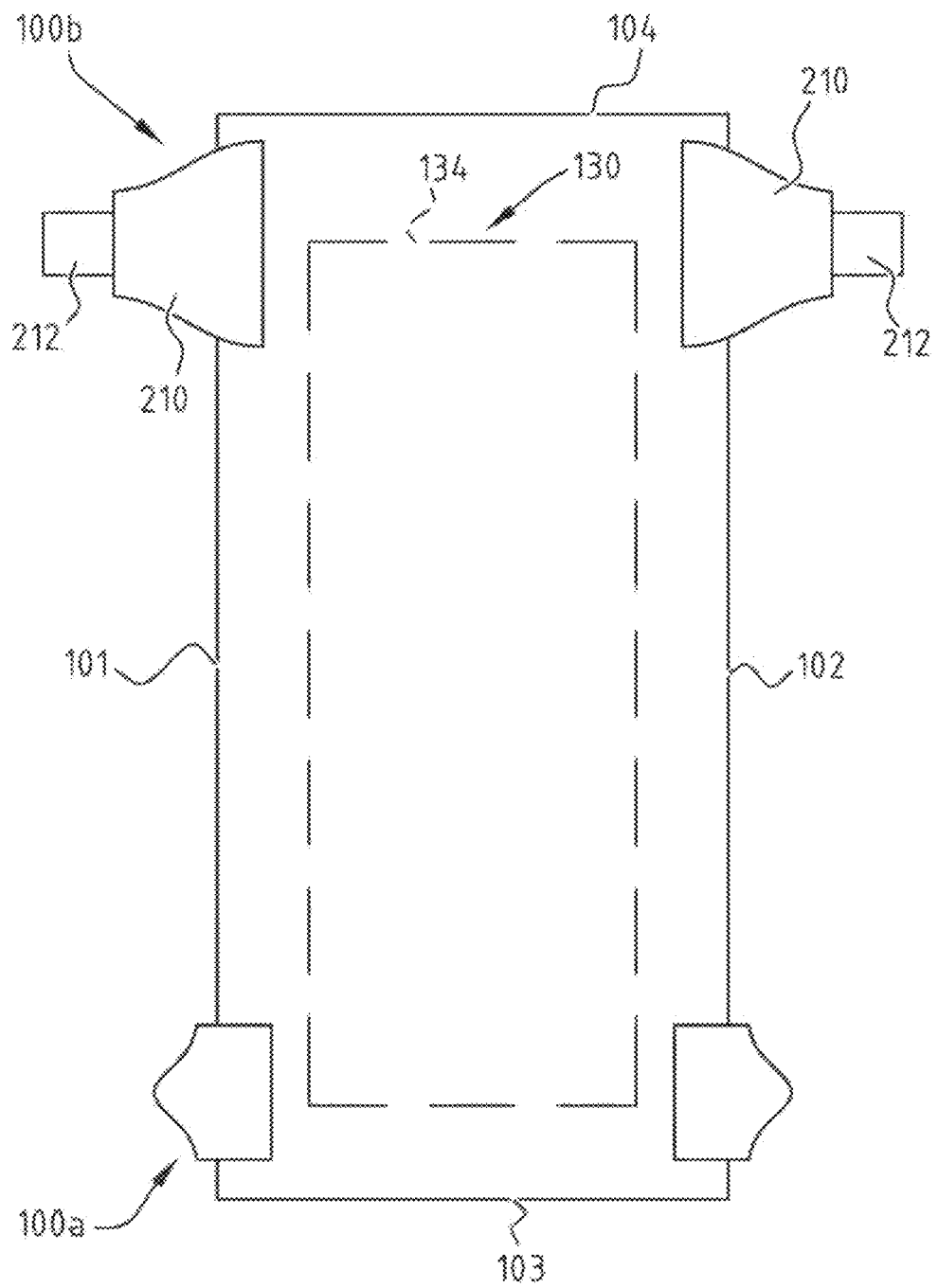
FIGS. 27A and 27B illustrate another exemplary embodiment of an absorbent article according to the invention.

FIG. 27A illustrates a top view of an absorbent article, here a diaper 100, in its flat out, un-contracted state with the wearer side facing the viewer. The skilled person understands that the absorbent article may also be a pant or an adult incontinence garment or the like. Preferably the chassis includes side panels or ears 210, elasticized leg cuffs and elastic waist elements. A front end portion of diaper 100 is configured as a front waist region 100a. The opposite rear end portion is configured as a back waist region 100b of diaper 100. Waist regions 100a and 100b may include elastic waist elements such that they gather about the waist of the wearer to provide improved fit and containment. The periphery of diaper 100 is defined by the outer edges of the diaper 100 in which longitudinal edges 101, 102 run generally parallel to a longitudinal axis of diaper 100 and transverse end edges 103, 104 run between the longitudinal edges 101, 102 generally parallel to a transverse axis of diaper 100. The chassis also comprises a fastening system, which may include at least one fastening or securing member 212 and at least one landing zone (not visible). The various components within diaper 100 may be bound, joined or secured by any method known in the art, for example by adhesives in uniform continuous layers, patterned layers or arrays of separate lines, spirals or spots. Top core wrap sheet, topsheet, back core wrap sheet, backsheet, absorbent material and other components may be assembled in a variety of well-known configurations and are well known in the art.

Figure 27B:
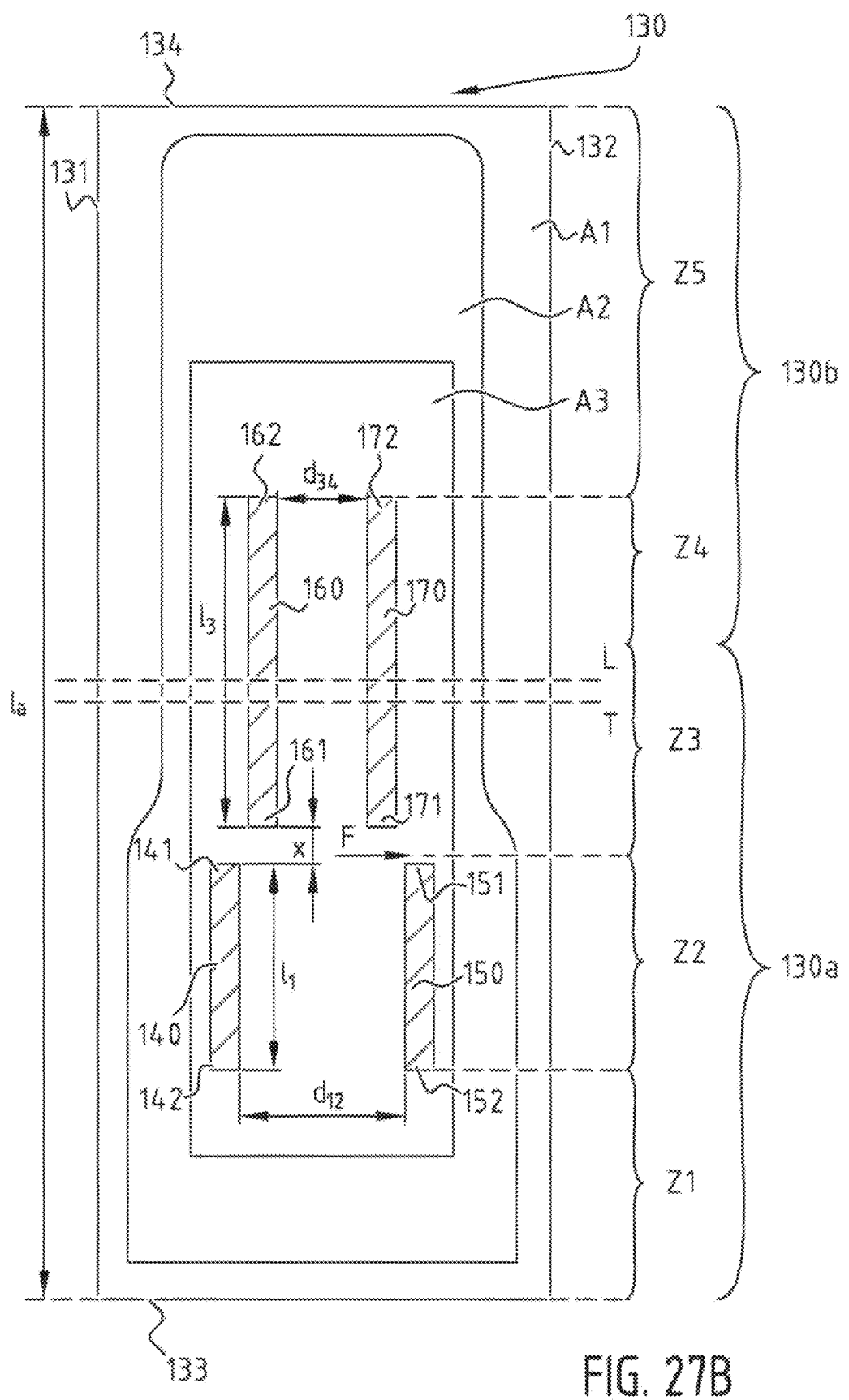

FIG. 27B illustrates the absorbent core 130 of the absorbent article of FIG. 27A. The absorbent article 100 comprises a liquid pervious topsheet, a liquid impervious backsheet, and the absorbent core 130 positioned in between the topsheet and the backsheet. The absorbent core 130 comprises absorbent material between a top core wrap sheet and a back core wrap sheet, in a similar manner as described in the other embodiments. Absorbent core 130 has a first and second side edge 131, 132, a front edge 133 and a rear edge 134, wherein the absorbent core is provided with a plurality of attachment zones 140, 150, 160, 170 where the top core wrap sheet is attached to the back core wrap sheet, and where preferably substantially no absorbent material is present. Seen in a longitudinal direction of the absorbent core 130, looking from the front edge 133 to the rear edge 134, the absorbent core 130 comprises subsequently a first, second, third, fourth and fifth zone Z1, Z2, Z3, Z4, Z5.

The absorbent core 130 comprises a front portion 130a extending between the front edge 133 and a transverse crotch line L of the absorbent core, and a rear portion 130b extending between the rear edge 134 and the transverse crotch line L of the absorbent core 130. The first, second and third zone Z1, Z2, Z3 extend in the front portion of the absorbent core and the fourth and fifth zone Z4, Z5 extend in the rear portion. Preferably, in said first and fifth zone substantially no permanent attachment zones are present. The second zone Z2 comprises a first and a second permanent elongate front attachment zone 130, 140, said first and second front attachment zones 130, 140 extending from an edge of the first zone Z1 in the direction of the third zone Z3.

The fourth and third zone comprises a first and second rear elongate attachment zone 160, 170, said first and second rear attachment zone extending from an edge of the fifth zone Z5 in the direction of the third zone Z3. At least one of said second, third and fourth zone comprises a bridging zone B allowing a liquid flow F between the first and the second side edge 131, 132 by capillary action through the absorbent material. The bridging zone B extends between the first front attachment zone 140 and the first rear attachment zone 160, such that upon wetting of the absorbent material, a front and rear channel are created at said first front and rear attachment zone 140, 160, respectively, wherein the bridging zone B extends between said front and rear channel. Preferably a minimum distance x between the first front attachment zone 140 and the first rear attachment zone 160 is larger than 3 mm more preferably larger than 5 mm. The bridging zone B further extends between the second front attachment zone 150 and the second rear attachment zone 170, such that upon wetting of the absorbent material, a front and rear channel are created at said second front and rear attachment zone 150, 170, respectively, wherein the bridging zone B further extends between said front and rear channel. Preferably a minimum distance x between the second front attachment zone 150 and the second rear attachment zone 170 is larger than 3 mm more preferably larger than 5 mm.

The first and second rear elongate attachment zones 160, 170 extend from the fourth zone into the third zone Z3 so that an absorbent article is formed that fits well to the body of the wearer. Preferably a distance between the transverse crotch line L and a transverse center line T extending perpendicular on the longitudinal direction of the absorbent core, through the middle of the absorbent core, is smaller than 10%, more preferably smaller than 5% of the length of the absorbent core.

The first zone Z1 extends over a length corresponding with at least 5%, preferably at least 10% of the length la of the absorbent core seen in the longitudinal direction, e.g. between 10% and 20%. The fifth zone Z5 extends over a length corresponding with at least 10% of the length la of the absorbent core seen in the longitudinal direction, preferably at least 20%, more preferably at least 25%, e.g. between 20% and 40%.

Preferably the second, the third and/or the fourth zone Z1, Z2, Z3 each extends over a length corresponding with at least 10% of the length la of the absorbent core seen in the longitudinal direction, preferably at least 15%. e.g. between 10% and 20% of the length of the absorbent core. Preferably the first front attachment zone 140 and the second front attachment zone 150 are arranged symmetrically with respect to a longitudinal center axis CL of the absorbent core 130. Preferably the distance d12 between the first and the second attachment zone is between 20 mm and 70 mm, more preferably between 30 mm and 60 mm, even more preferably between 40 mm and 55 mm. As explained in the summary, such a configuration is especially suitable for male persons.

Preferably the first rear attachment zone 160 and the second rear attachment zone 170 are arranged symmetrically with respect to the longitudinal center axis CL of the absorbent core. Preferably the distance d34 between the first and the second rear attachment zone 160, 170 is between 10 mm and 50 mm, more preferably between 15 mm and 40 mm, even more preferably between 20 mm and 30 mm.

The bridging zone B extends from a first portion of the absorbent core, in the second and/or third zone Z2, Z3, to a second portion of the absorbent core, in the second and/or third zone, wherein the first portion is defined between the first side edge 131 and the longitudinal center axis CL of the absorbent core 130 and the second portion is defined between the second side edge 132 and the longitudinal center axis CL of the absorbent core 130. The bridging zone B may comprise temporary attachments between the top and back core wrap sheet which are configured to detach when wetted.

A first smallest distance d12 between the first and the second front attachment zone 140, 150 is bigger than a second smallest distance d34 between the first and the second rear attachment zone 160, 170. The first and the second front attachment zone 140, 150 extend in a longitudinal direction of the absorbent core over a length l1 which is less than the length l3 of the first and second rear attachment zone. Preferably, the length of the first and second front attachment zone 140, 150 is larger than 30 mm, more preferably larger than 40 mm, even more preferably larger than 50 mm.

The plurality of attachment zones 140, 150, 160, 170 may be permanent attachment zones which remain attached when wetted. The plurality of attachment zones may extend, seen in the transverse direction of the absorbent core, over the transverse distance which is at least 1 mm, preferably at least 3 mm, more preferably at least 4 mm, even more preferably at least 5 mm, most preferably at least 6 mm.

Preferably, the length of the first/second front attachment zone 140, 150 is larger than 5% of the length of the absorbent core: preferably larger than 10%, more preferably larger than 15%; and/or wherein the length of the first/second rear attachment zone 160, 170 is larger than 5% of the length of the absorbent core, preferably larger than 10%, more preferably larger than 15%. Preferably the length of the first/second front attachment zone is at least 10%, more preferably at least 25%, even more preferably at least 35%, or even at least 50 or 75% of the length of the first rear attachment zone.

Preferably the distance between the first and the second front attachment zone 140, 150 is between 15 and 70% of the width of the absorbent core (measured perpendicular on the length la), more preferably between 20 and 50%. Preferably the distance between the first and the second rear attachment zone 160, 170 is between 5 and 60% of the width of the absorbent core, more preferably between 10 and 40%.

The plurality of attachment zones comprise at least a first and a second elongate attachment zone 140, 150 extending next each other, at least in the front portion of the absorbent core in the direction of the first transverse edge 133, and a third and a fourth elongate attachment zone 160, 170 extending next to each other, at least in the rear portion 130b of the absorbent core 130, in the direction of the second transverse edge 134. Measured in a transverse direction, a first largest distance d12 between the first and the second attachment zone 140, 150 is bigger than a second largest distance d34 between the third and the fourth attachment zone 160, 170. Preferably the first distance d12 between the first and the second attachment zone 140, 150 is at least 5%, more preferably at least 10% bigger, even more preferably at least 20% bigger than a second distance d34 between the third and the fourth attachment zone 160, 170. The distance d12 between the first and the second attachment zone may be between 15 and 70% of the width of the absorbent core, more preferably between 20 and 50%; wherein preferably the distance d12 between the first and the second attachment zone is between 10 mm and 100 mm, more preferably between 20 mm and 80 mm, even more preferably between 30 mm and 70 mm. The distance d34 between the third and the fourth attachment zone is between 5 and 60% of the width of the absorbent core, more preferably between 10 and 40%; wherein preferably the distance d34 between the third and the fourth attachment zone is between 5 mm and 60 mm, more preferably between 10 mm and 50 mm, even more preferably between 15 mm and 40 mm. Due to the specific physiological structure of male at the genital region, such a pattern has the advantage that liquid can be distributed over substantially the entire absorbent core, and that any leakage risks in various positions of the male wearer can be reduced.

It is clear to the skilled person that the first largest distance d12 between the first and the second attachment zone 140, 150 may also be smaller than a second largest distance d34 between the third and the fourth attachment zone 160, 170. Such embodiment is particularly advantageous for female, due to the specific physiological structure of female at the genital region, as liquid can be distributed over substantially the entire absorbent core and leakage risks in various positions of the female wearer can be reduced. There may also be embodiments wherein d12 and d34 are substantially equal, which embodiments can be used for both male and female.

The absorbent core 130 comprises a front portion 130a extending between the front edge 133 and a transverse crotch line L of the absorbent core 130, and a rear portion 130b extending between the rear edge 134 and the transverse crotch line L of the absorbent core 130. Preferably a distance between the transverse crotch line L and a transverse center line T extending perpendicular on the longitudinal direction of the absorbent core 130, through the middle of the absorbent core 130, is smaller than 10%, more preferably smaller than 5% of the length of the absorbent core 130. The first and the second elongate attachment zone 140, 150 each have a front end 142, 152 adjacent to absorbent material and a rear end 141, 151 adjacent to absorbent material; and the third and the fourth elongate attachment zone 160, 170 each have a rear end 162, 172 adjacent to absorbent material and a front end 161, 171 adjacent to absorbent material. In other embodiments the first zone 140 may be connected to the third zone 160 at the transverse crotch line L, and the second zone 150 may be connected to the fourth zone 170 at the transverse crotch line.

Seen in a projection on the longitudinal direction of the absorbent core, preferably the first and the second attachment zone 140, 150 extend over a length which is less than the length of the third and fourth attachment zone 160, 170. The length of the first and the second attachment zone 140, 150 may be larger than 30 mm, preferably larger than 40 mm, more preferably larger than 50 mm. The length of the third and the fourth attachment zone may be larger than 30 mm, preferably larger than 40 mm, more preferably larger than 50 mm. The first attachment zone 140 and the second attachment zone 150 may be arranged symmetrically with respect to a longitudinal center axis of the absorbent core 130 extending between the front edge 133 and rear edge 134. Seen in a projection on a longitudinal direction, the first and second attachment zone 140, 150 do not overlap with the third and fourth attachment zone 160, 170. However, in other embodiments there may be some overlap.

The first attachment zone 140 may be separated from the third attachment zone 160 by absorbent material, and the second attachment zone 150 may be separated from the fourth attachment zone 170 by absorbent material. The absorbent material may comprise cellulosic fluff pulp and/or superabsorbent particles. In some embodiments the absorbent material may be substantially fluffless.

In other non-illustrated embodiments, the first attachment zone 140 may also be connected to the third attachment zone 160 through a first semi-permanent attachment zone and the second attachment zone 150 may also be connected to the fourth attachment zone 170 through a second semi-permanent attachment zone. The semi-permanent attachment may be configured to release after having been in contact with urine for a predetermined period of time, and the predetermined period of time is preferably smaller than 30 s.

The first and second attachment zone 140, 150 extend, seen in the transverse direction of the absorbent core 130, over the transverse distance which may be at least 1 mm, preferably at least 3 mm, more preferably at least 4 mm, even more preferably at least 5 mm, most preferably at least 6 mm. The first attachment zone 140 and the second attachment zone 150 may be substantially parallel and extend in a longitudinal direction of the absorbent core 130, as shown in FIG. 27B; or an angle between the first attachment zone 140 and a longitudinal direction of the absorbent core 130 and an angle between the second attachment zone 150 and the longitudinal direction of the absorbent core 130 may be smaller than 5° (not illustrated). The third attachment zone 160 and the fourth attachment zone 170 may be substantially parallel and extend in a longitudinal direction of the absorbent core 130, as shown in FIG. 27B; or an angle between the third attachment zone 160 and a longitudinal direction of the absorbent core 130 and an angle between the fourth attachment zone 170 and the longitudinal direction of the absorbent core 130 may be smaller than 5° (not illustrated). Seen in a projection on a longitudinal direction of the absorbent core 130, the plurality of attachment zones together may cover at least 30%, preferably at least 40% of a length of the absorbent core 130.

Preferably the plurality of attachment zones comprise substantially no absorbent material, and may be permanent attachment zones which remain attached when wetted. In other embodiments, in the first and second attachment zone 140, 150, the top core wrap sheet may be attached to the back core wrap sheet through permanent and semi-permanent attachment portions, said semi-permanent portions may be being configured to release after having been in contact with liquid whilst said permanent portions may be configured not to release after having been in contact with liquid.

A position and/or shape of one or more attachment zones of the plurality of attachment zones may be indicated by means of a distinguishable color and/or colored pattern. The position and/or shape of one or more of the plurality of attachment zones may also be indicated by means of a printed ink layer. The distinguishable color and/or colored pattern may be provided on at least one of the topsheet, the top core wrap sheet, the backsheet and the back core wrap sheet.

The areas A1, A2, A3 indicated in FIG. 27B may have a different amount of absorbent material/absorbent capacity per surface area. Preferably the central area A3 has a larger amount of absorbent material/capacity per surface area than the intermediate area A2. Preferably, the intermediate area A2 has a larger amount of absorbent material/capacity per surface area than a circumferential area A1.

Features described above for other embodiments described above may apply in a similar manner for the embodiment of FIGS. 27A and 27B.

FIGS. 28A-E

Figure 28A:
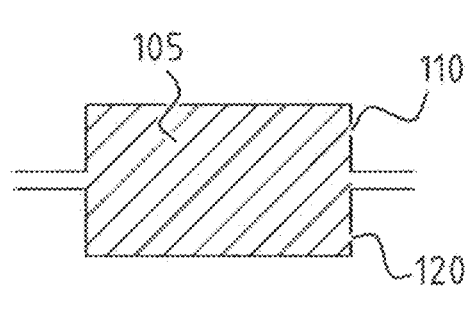
FIGS. 28A-28F illustrate different embodiments of a top core wrap sheet 110 and/or bottom core wrap sheet 120 of an absorbent core.
Figure 28B:
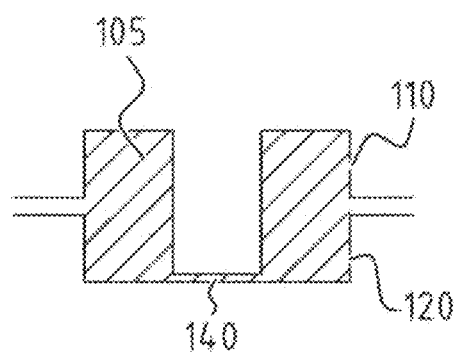
Figure 28C:
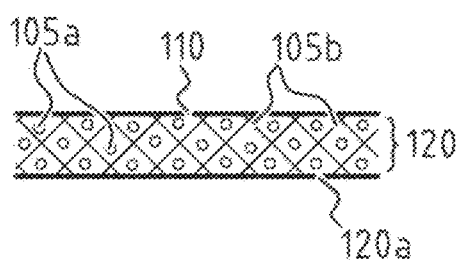
Figure 28D:
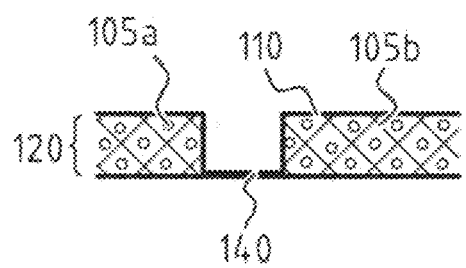
Figure 28E:
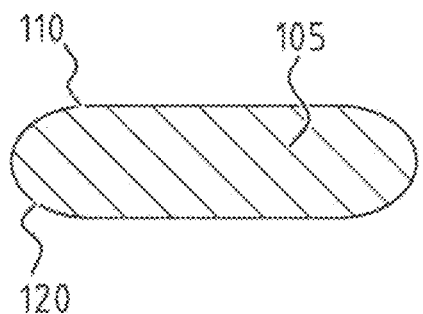
Figure 28F:
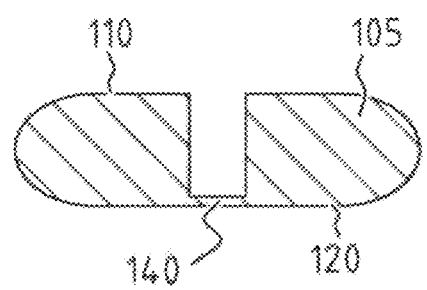

FIGS. 28A, 28C and 28E illustrate different embodiments of a top core wrap sheet 110 and/or bottom core wrap sheet 120 of an absorbent core. FIGS. 28B, 28D and 28F illustrate schematically how attachment zones may be provided by attaching the top core wrap sheet 110 to the bottom core wrap sheet 120 in the corresponding embodiments of FIGS. 28A, 28C and 28E. FIG. 28A illustrates an embodiment wherein a separate top core wrap sheet 110 and separate bottom core wrap sheet 120 are provided and wherein between the top core wrap sheet 110 and bottom core wrap sheet 120 absorbent material 105 is present. FIG. 28B illustrates the embodiment of FIG. 28A wherein the top core wrap sheet 110 is attached to the bottom core wrap sheet 120 at attachment 140. This corresponds with the embodiments as illustrated in FIGS. 1C and 1D. FIG. 28C illustrates an embodiment wherein first core wrap sheet 110 is used in combination with a second core wrap sheet 120 wherein the second core wrap sheet 120 comprises a fibrous substrate layer 120a and absorbent material 105a embedded within the fibers 105b of substrate layer 120a. In other words, in the embodiment of FIG. 28B the absorbent material is an integral part of the second core wrap sheet 120. It is clear to the skilled person that the first core wrap sheet 110 may correspond to the top core wrap sheet and the second core wrap sheet 120 may correspond to the bottom core wrap sheet, or vice versa. FIG. 28D illustrates the embodiment of FIG. 28C wherein the top core wrap sheet 110 is attached to the bottom core wrap sheet 120 at attachment 140. FIG. 28E illustrates an embodiment wherein the top core wrap sheet 110 and bottom core wrap sheet 120 are made of one piece of sheet material. In other words, the top core wrap sheet 110 is formed integrally with the bottom core wrap sheet 120. The piece of sheet material 110, 120 is wrapped around the absorbent material 105 such that an upper portion of the sheet material can be considered to be the top core wrap sheet 110 and a bottom portion of the sheet material can be considered to be the bottom core wrap sheet 120. FIG. 28F illustrates the embodiment of FIG. 28E wherein the top core wrap sheet 110 is attached to the bottom core wrap sheet 120 at attachment 140. Preferably the attachment 140 between the top core wrap sheet 110 and the bottom core wrap sheet 120 is realized by any one of the following or a combination thereof: pressure bonding, thermo-bonding, sonic bonding, chemical bonding, adhesive, mechanical bonding. It is clear to the skilled person, that when attachment zones are described within this disclosure, the attachment between the top core wrap sheet and back core wrap sheet may be interpreted to be formed according to any one of the above described embodiments or combinations thereof.

FIG. 28

FIG. 28 illustrates a further embodiment of the absorbent core 130 of the absorbent article of FIG. 27A. According to the embodiment of FIG. 28, the plurality of attachment zones comprises a first and a second attachment zone 140, 150 extending next to each other from a crotch region in the direction of the front edge 133, and a third attachment zone 180 extending from the crotch region in the direction of the rear edge 134, wherein seen in a projection on a transverse direction the third attachment zone 180 is located between the first and the second attachment zone 140, 150. The first attachment zone 140 and the second attachment zone 150 are substantially parallel and extend in a longitudinal direction of the absorbent core 130. The largest distance between the first 140 and the second attachment zone 150 is d12. Seen in a projection on the longitudinal direction of the absorbent core, the first and the second attachment zone extend over a length which may be less than the length of the third attachment zone. The first and the second elongate attachment zone 140, 150 each have a front end 142, 152 adjacent to absorbent material and a rear end 141, 151 adjacent to absorbent material; and the third elongate attachment zone 180 has a rear end 182 adjacent to absorbent material and a front end 181 adjacent to absorbent material. In other embodiments, the first attachment zone and/or the second attachment zone 140, 150 may be connected to the third zone 180. This embodiment is particularly advantageous for male, due to the specific physiological structure of male at the genital region. It is clear to the skilled person that there may also be embodiments advantageous for female and/or can be used for both male and female, for example embodiments wherein the first and second attachment zone 140, 150 extending next to each other from the crotch region in the direction of the rear edge 134, and the third attachment zone 180 extending from the crotch region in the direction of the front edge 133.

FIGS. 29-35

The exemplary embodiment of FIG. 29 is similar to the embodiment of FIG. 27B, with the difference that the first attachment zone 140 and the second attachment zone 150 are not parallel, and diverge in the direction of a front edge 133 of absorbent core 130. The largest distance d12 between the first 140 and the second attachment zone 150 may be between a front end 142 of the first attachment zone 140 and a front end 152 of the second attachment zone 150.

The exemplary embodiment of FIG. 30 is similar to the embodiment of FIG. 29, with this difference that the first and second attachment zone 140 and 150 are substantially parallel in the crotch region and diverge in the direction of a front edge 133 of absorbent core 130. Further, the first attachment zone 140 may be connected to the third attachment zone 160 through a first semi-permanent attachment zone 135, and the second attachment zone 150 may be connected to the fourth attachment zone 170 through a second semi-permanent attachment zone 136. The plurality of attachment zones may be permanent attachment zones which remain attached when wetted. The exemplary embodiment of FIG. 31 is similar to the embodiment of FIG. 28, with this difference that the first attachment zone 140 and the second attachment zone 150 are not parallel as they start from a crotch region and diverge in the direction of a front edge 133 of absorbent core 130, and become substantially parallel as they extend further in the direction of a front edge 133 of absorbent core 130. The largest distance between the first 140 and the second attachment zone 150 d12 may be between a front end of the first attachment zone 140 and a front end of the second attachment zone 150.

Figure 32:
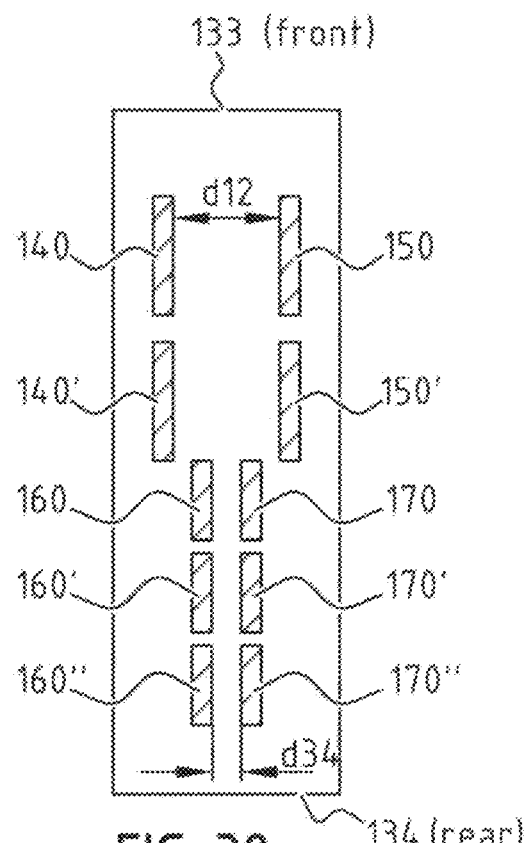

The exemplary embodiment of FIG. 32 illustrates that patterns are possible where each of the plurality of attachment zones comprise one or more sections. For example as shown in FIG. 32, the first attachment zone may comprise one or more sections 140, 140', and/or the second attachment zone may comprise one or more sections 150, 150', and/or the third attachment zone may comprise one or more sections 160, 160', 160', and/or the fourth attachment zone may comprise one or more sections 170, 170' 170".

Figure 33:
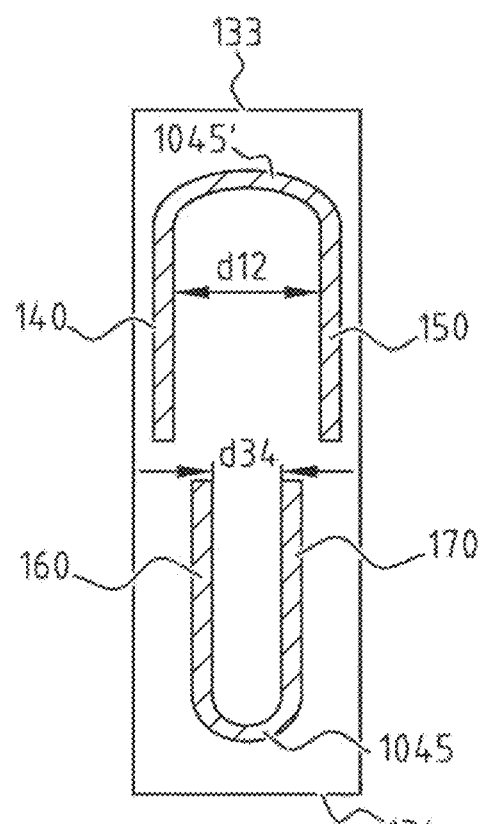

The exemplary embodiment of FIG. 33 illustrates that patterns are possible where the first attachment zone 140 and the second attachment zone 150 may be connected with a transversal attachment zone 1045', and/or the third attachment zone 160 and the fourth attachment zone 170 may be connected with a transversal attachment zone 1045. The transversal attachment zones 1045, 1045' may connect the front ends and/or rear ends of the first and the second attachment zones 140, 150 and/or the third and the fourth attachment zones 160, 170. Furthermore, the transversal attachment zone needs not to be straight: it may be rounded as in example of FIG. 33, or take another shape.

Figure 34:
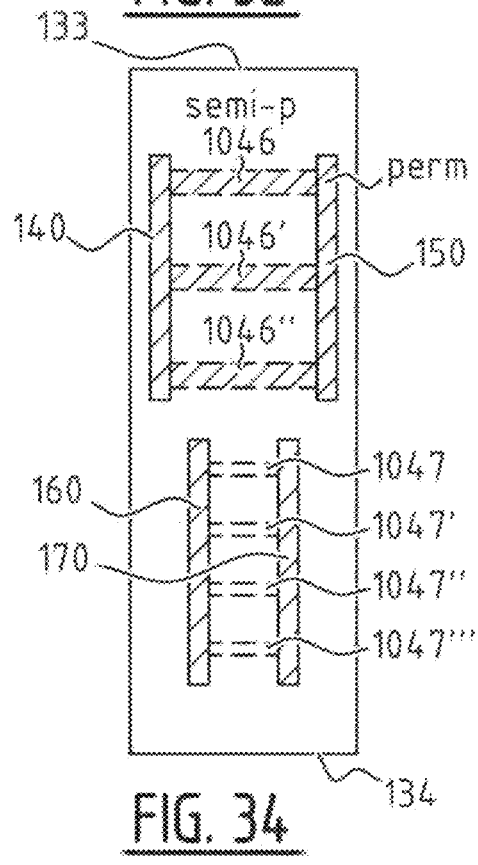

The exemplary embodiment of FIG. 34 illustrates that patterns are possible where the first attachment zone 140 and the second attachment zone 150 may be connected by at least one transversal semi-permanent attachment zone 1046, 1046', 1046", and the third attachment zone 160 and the fourth attachment zone 170 may also be connected with at least one transversal semi-permanent attachment zone 1047, 1047', 1047", 1047'''. The at least one transversal semi-permanent attachment zone may be configured to release after having been in contact with urine for a predetermined period of time, wherein said predetermined period of time is preferably smaller than 30 s. The at least one transversal semi-permanent attachment zone may be straight, or rounded, or take other shapes.

Figure 35:
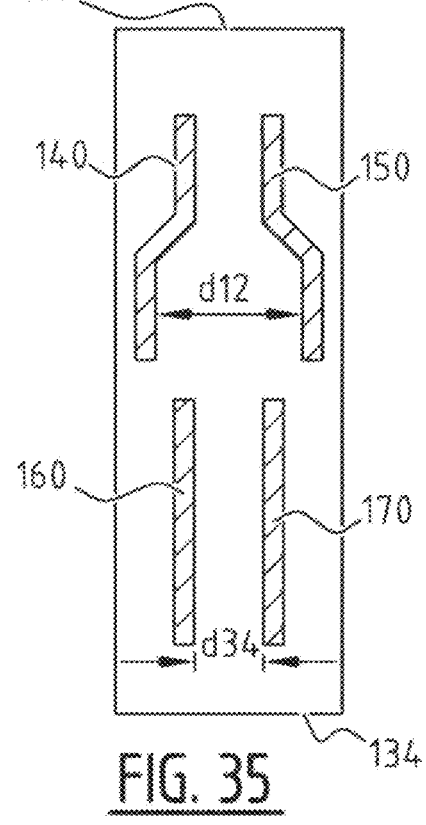

The exemplary embodiment of FIG. 35 illustrates that patterns are possible that the first and second attachment zones 140, 150 are substantially parallel in a part of the crotch region, whilst the transverse distance between the first and second attachment zones gradually decrease in the direction of a front edge 133 of absorbent core 130.

The exemplary embodiments shown in FIGS. 28 to 35 are particularly advantageous for male, due to the specific physiological structure of male at the genital region. However it is clear to the skilled person that how to best adapt this embodiment using other configurations, such as the ones described above, to make the embodiments advantageous for female, and/or suitable for both male and female. Features for other embodiments described above may apply in a similar manner for the embodiments of FIGS. 28 to 35.

FIGS. 36A-P

Figure 36A:
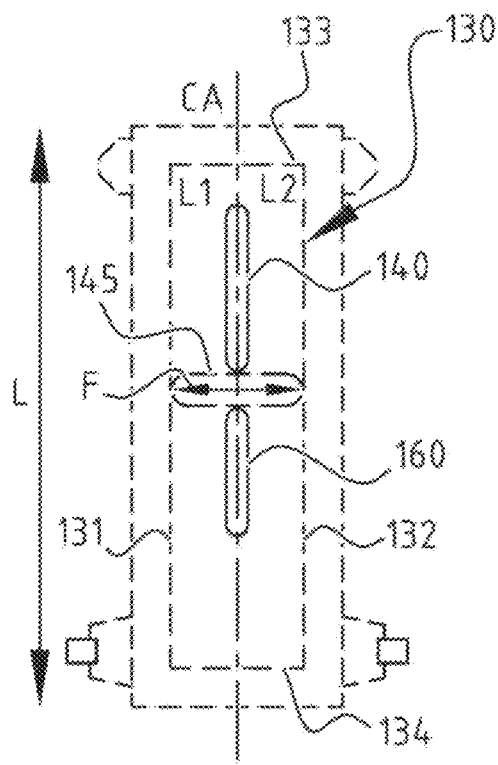
FIGS. 36A-36P illustrate yet other exemplary embodiments of an absorbent core according to the invention.
Figure 36B:
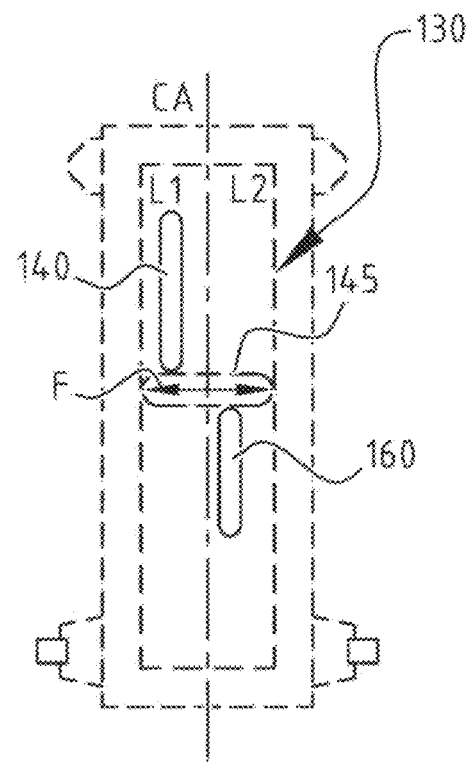
Figure 36C:
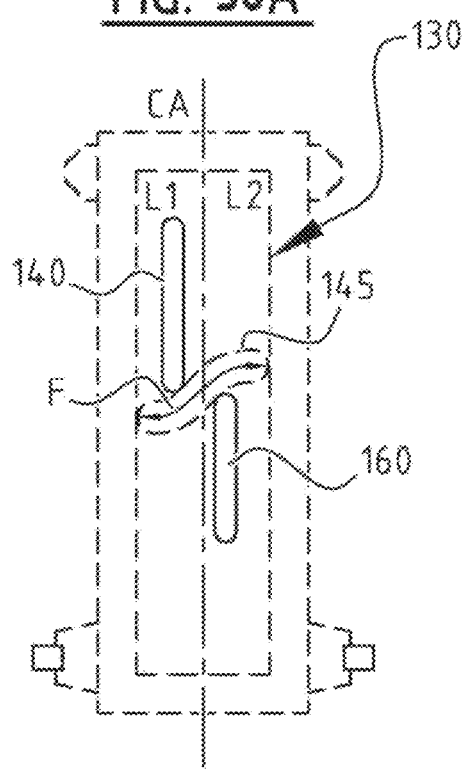
Figure 36D:
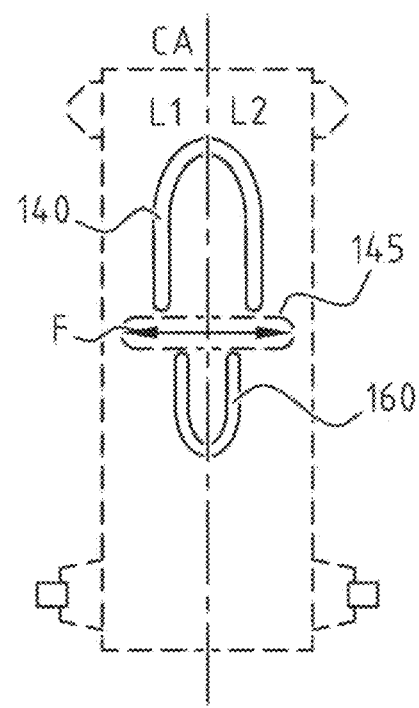
Figure 36E:
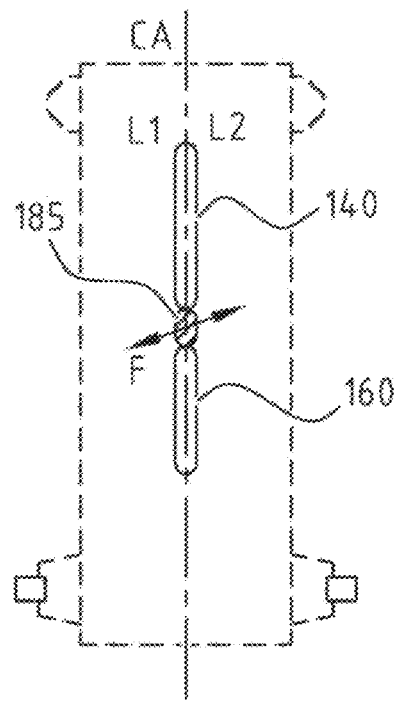
Figure 36F:
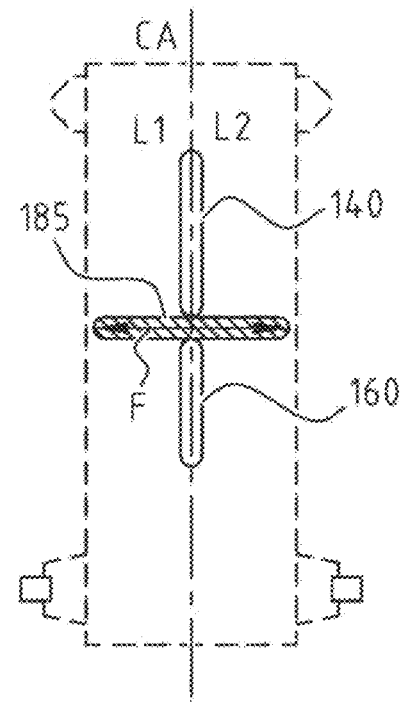
Figure 36G:
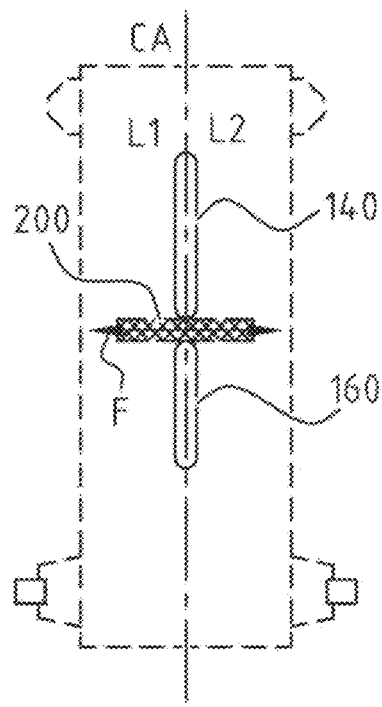
Figure 36H:
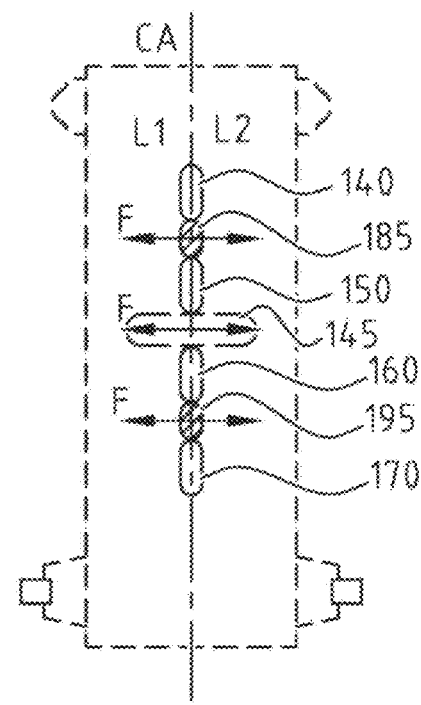
Figure 36I:
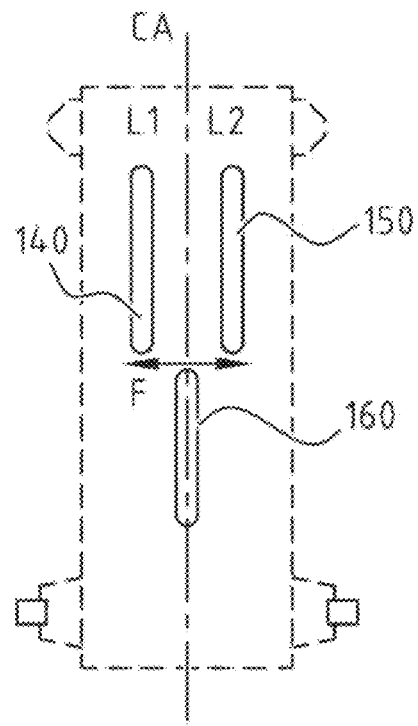
Figure 36J:
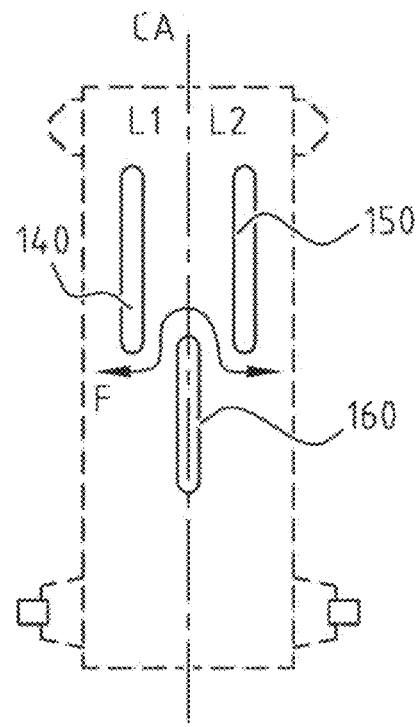
Figure 36K:
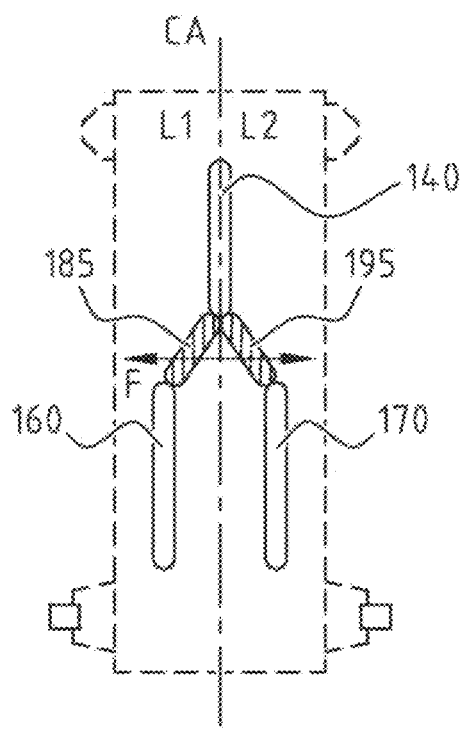
Figure 36L:
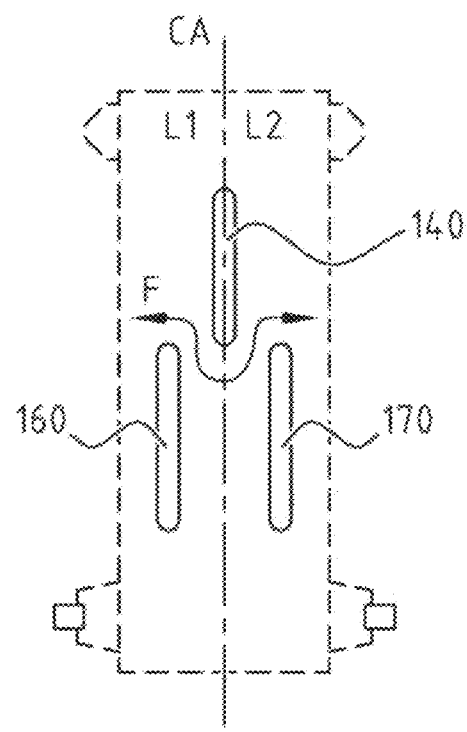
Figure 36M:
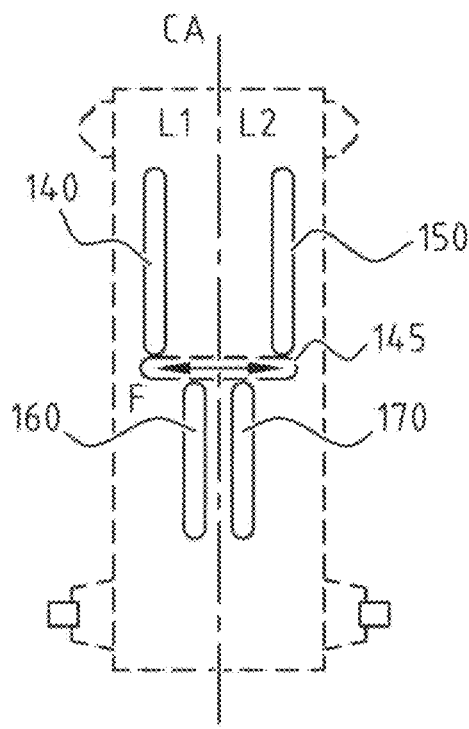
Figure 36N:
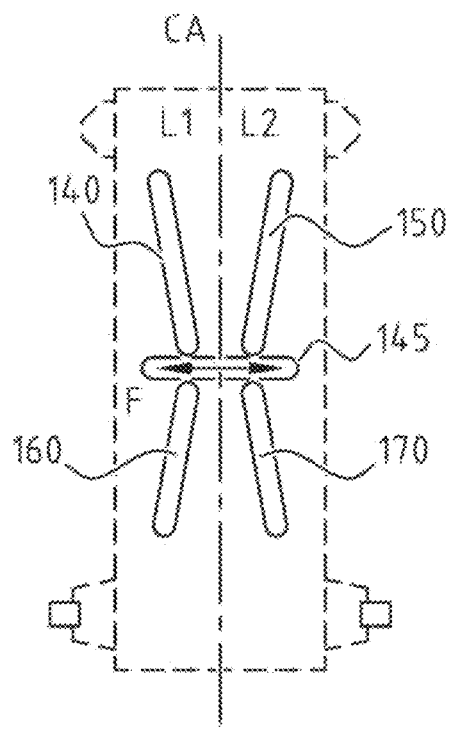
Figure 36O:
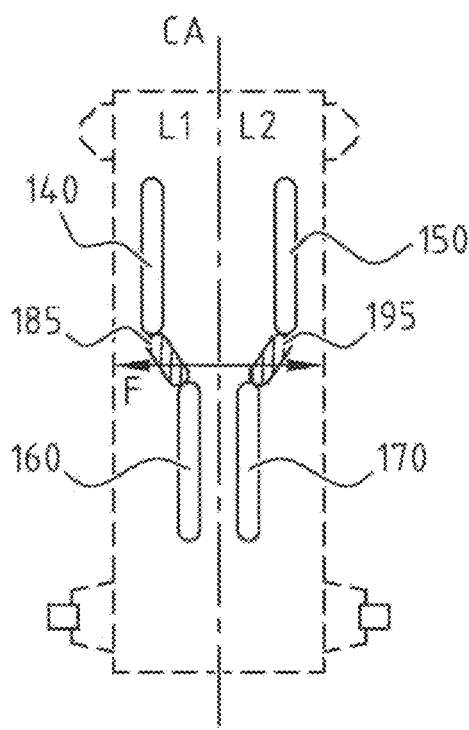
Figure 36P:
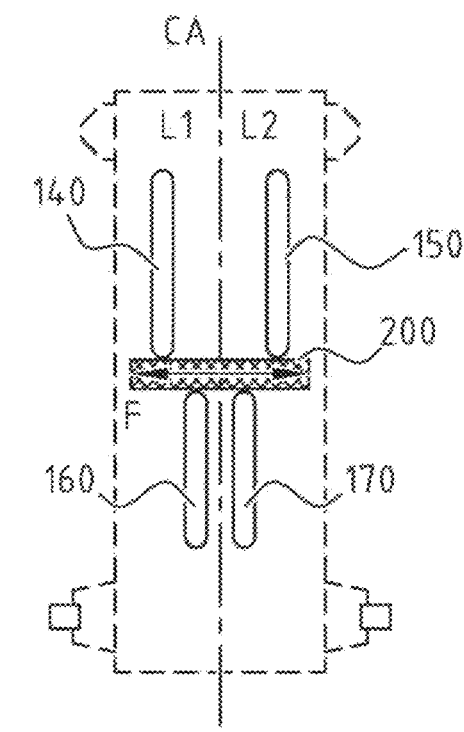

FIGS. 36A-36P are top views illustrating exemplary embodiment of an absorbent article comprising an absorbing core according to the invention. The absorbent core has a first and second longitudinal edge 131, 132 and a first and second transverse edge 133, 134. For the sake of clarity it is noted that the first longitudinal edge 131 corresponds with a left longitudinal edge, the second longitudinal edge 132 corresponds with a right longitudinal edge, the first transverse edge 133 corresponds with a front transverse edge, and the second transverse edge 134 corresponds with a rear transverse edge. For the sake of clarity, it is noted that in FIG. 36A the position of the absorbent core 130 within the absorbent articles is schematically illustrated, along with the above described edges 131, 132, 133 and 134 of the absorbent core. Also longitudinal portions L1, L2 of the absorbent core are illustrated, being separated by a longitudinal center axis CA. To reduce the complexity of the drawings, in FIGS. 36B and 36C merely the position of the absorbent core 130 is indicated, whereas this indication has been omitted in the rest of FIGS. 36D-36P. However, it is clear that for FIGS. 36D-36P a similar positioning of the absorbent core 130 and similar definition of longitudinal zones L1, L2 applies. The absorbent core 130 is provided with a plurality of attachment zones comprising at least one front attachment zone 140 and at least one rear attachment zone 160 and with at least one bridging zone 145 extending at least partially between said front and rear attachment zone. The front attachment zone 140 is positioned more to the front of the absorbent core as compared to the rear attachment zone 160. In other words, he front attachment zone 140 is positioned closer to the front transverse edge 133 of the absorbent core as compared to the rear attachment zone 160. Moreover, the front attachment zone 140 and rear attachment zone 150, when projected on a longitudinal direction L of the absorbent core, do not overlap or overlap only partially. For illustrative purposes the bridging zone 145 is delineated by dotted lines between the front attachment zone(s) 140, 150 and the rear attachment zone(s) 160, 170, thereby extending from a first longitudinal portion L1 of the absorbent core to a second longitudinal portion L2 of the absorbent core. It is clear that the dotted lines 145 are for illustrative purposes only and that an actual shape of the bridging zone 145 may deviate from the illustrated region surrounded by the dotted lines. Alternatively, or in addition to the dotted lines 145, the bridging zone may be indicated in the figures by an arrow F which corresponds to a flow of liquid through the bridging zone. The first longitudinal portion L1 may be defined between the first longitudinal edge 131 and a longitudinal center axis CA of the absorbent core and the second longitudinal portion L2 may be defined between the second longitudinal edge 132 and the longitudinal center axis CA of the absorbent core. Depending on embodiments the wording longitudinal center axis may have a different meaning. The wording longitudinal center axis may refer to an axis in the longitudinal direction of the absorbent core and running trough the middle of the absorbent core in the transverse direction of the absorbent core, thereby dividing the absorbent core in a first longitudinal portion L1 and a second longitudinal portion L2. Alternatively, or in addition the wording longitudinal center axis may refer to an axis in the longitudinal direction of the absorbent core positioned between two neighbouring longitudinal portions L1, L2. Upon wetting of the absorbent material, a front and rear channel are created at said front and rear attachment zone(s) 140, 150, 160, 170, respectively, wherein the bridging zone 145 allows a liquid flow, illustrated by arrow F, between the first longitudinal portion L1 and the second longitudinal portion L2, e.g. by capillary action and/or mass flow. It is clear that the arrow F is for illustrative purposes only and that an actual path of the liquid flowing through the bridging zone 145 may deviate from the illustrated arrow F.

FIGS. 36A-36G illustrate embodiments wherein the absorbent core comprises one front attachment zone 140, one rear attachment zone 160, and a bridging zone 145 at least partially between the front attachment zone 140 and rear attachment zone 160. In FIG. 36A the front attachment zone 140 and the rear attachment zone are aligned with each other and are oriented substantially along the longitudinal central axis CA of the absorbent core. Projections of the attachments zones 140 and 160 on the longitudinal direction L do not overlap. The attachment zones 140 and 160 divide the absorbent core into two longitudinal portions L1 and L2. The bridging zone 145 extends between the front attachment zone 140 and the rear attachment zone 160, from the first longitudinal portion L1 to the second longitudinal portion L2. The first longitudinal portion L1 may be defined between the first longitudinal edge 131 and the longitudinal center axis CA of the absorbent core and the second longitudinal portion L2 may be defined between the second longitudinal edge 132 and the longitudinal center axis CA of the absorbent core. Alternatively the first and second longitudinal portions L1 and L2 may be defined as being separated by the front and/or rear attachments zone 140, 160. However, because of the specific positioning and orientation of attachments zones 140, 160 in FIG. 36A, both definitions of the longitudinal portions L1 and L2 result in the same configuration of the absorbent core. When a liquid insult is received on either one of the longitudinal portions L1 or L2, the bridging zone 145 allows for liquid to travel to the other portion, where no liquid insult has been received. In this manner, although a liquid insult is received at one side (left or right) of the attachments zones 140, 150 absorbent material located at the other side (right or left) of the attachments zones 140, 150 can be utilized for absorbing the liquid. This results in improved overall absorbing capacity as compared to prior art absorbent articles wherein the absorbent core has no bridging zones which allow liquid communication through/over attachment zones wherein substantially no absorbent material is present. FIG. 36B illustrates a similar embodiment as FIG. 36A, with the difference that the front and rear attachments zones 140, 160 are not aligned in FIG. 36B, however the front and rear attachments zones 140, 160 are oriented substantially parallel to each other. Projections of the attachments zones 140 and 160 on the longitudinal direction L do not overlap. FIG. 36C illustrates a similar embodiment as FIG. 36B, with the difference that the front and rear attachments zones 140, 160 in FIG. 36C are positioned in such a way that projections of the attachments zones 140 and 160 on the longitudinal direction L do partially overlap. This results in a bridging zone 145 which allows for liquid to flow from one longitudinal portion to the other longitudinal portion along a curved path illustrated by the arrow F. It is clear to the skilled person that liquid may also flow along a straight angled path through the bridging zone 145, from a location more to the rear in longitudinal portion L1 to a location more to the front in longitudinal portion L2. In FIG. 36D, the front attachment zone 140 and rear attachment zone 160 are curved attachment zones. In this embodiment additional space for the bridging zone 145 is created by the curvature of the attachments zones 140 and 160. In FIG. 36E, a semi-permanent attachment 185 is provided between the front and rear attachments zones 140, 160. In this embodiment, the semi-permanent attachment 185 is aligned with the front and rear attachment zones 140, 160. In this manner, absorption capacity of the absorbent core may benefit from both capillary action and mass flow of liquid in order to enable liquid to be distributed quickly and adequately. In reaction to a first liquid insult the liquid will be distributed by mass flow by means of the channel(s) formed at the semi-permanent attachment(s). However, in reaction to further liquid insults, the semi-permanent attachment(s) will release, loosen and/or dissolve which will lead to the bridging zone allowing the liquid to pass through by capillary action. In other words, the bridging zone 145 may comprise a semi-permanent attachment 185 in a first stage of wetting, and may comprise substantially no attachments in a further stage of wetting. In FIG. 36F a similar configuration as illustrated in FIG. 36E is shown with the difference that the semi-permanent attachment 185 is oriented substantially in the transverse direction of the absorbent core. In this manner the functionality of the bridging zone via mass flow in the transverse direction is further enhanced. In FIG. 36G, the capillary bridge comprises a fluff fibers 200 which allow for liquid to flow between the front and rear attachment zones 140 and 160, respectively. Alternatively, or in addition a strip of airlaid fluff material may be provided at the bridging zone to further improve liquid carrying capacity of the bridging zone.

FIGS. 36H-36P illustrate embodiment wherein the absorbent core comprises an additional front attachment zone 150 and/or additional rear attachment zone 170. The absorbent core according to embodiments illustrated in FIGS. 36H-36P comprise one or more bridging zones. In FIG. 36H, three bridging zones may be distinguished, one bridging zone comprising no attachments between second front attachment zone 150 and rear attachment zone 160, one bridging zone comprising a semi-permanent attachment 185 between the first and second front attachment zones 140 and 150, and one bridging zone comprising a semi-permanent attachment 195 between the first and second rear attachment zones 160, 170. In FIG. 36I, a first and second front attachment zone 140, 150 are illustrated, wherein a bridging zone is formed between the first and second front attachment zones 140, 150 on the one hand and the rear attachment zone 160 on the other hand. Alternatively the skilled person understands that on the one hand a first (partial) bridging zone is formed between the first front attachment zone 140 and the rear attachment zone 160, and that on the other hand a second (partial) bridging zone is formed between the second front attachment zone 150 and the rear attachment zone 160. In FIG. 36J, a similar embodiment as illustrated in FIG. 36I is shown, with the difference that a projection of the rear attachment zone 160 on the longitudinal direction L now partially overlaps with the projection of the first front attachment zone 140 and/or projection of the second front attachment zone 150, which result in the bridging zone taking a curved form through which liquid can flow between and/or passed the front and rear attachment zones. In FIG. 36K, a first and second rear attachment zone 160, 170 are illustrated, wherein a bridging zone is formed between the first and second rear attachment zones 160, 170 on the one hand and the front attachment zone 140 on the other hand. Alternatively the skilled person understands that on the one hand a first (partial) bridging zone is formed between the first rear attachment zone 160 and the front attachment zone 140, and that on the other hand a second (partial) bridging zone is formed between the second rear attachment zone 170 and the front attachment zone 160. This is illustrated by semi-permanent attachments 185 and 195. In FIG. 36L, a first and second rear attachment zone 160, 170 are illustrated, wherein a bridging zone, comprising substantially no attachments, is formed between the first and second rear attachment zones 160, 170 on the one hand and the front attachment zone 140 on the other hand. Alternatively the skilled person understands that on the one hand a first (partial) bridging zone, comprising substantially no attachments, is formed between the first rear attachment zone 160 and the front attachment zone 140, and that on the other hand a second (partial) bridging zone, comprising substantially no attachments, is formed between the second rear attachment zone 170 and the front attachment zone 160. In FIGS. 36M-36P, a first and second front attachment zone 140, 150 are illustrated in combination with a first and second rear attachment zone 160, 170. In FIGS. 36M and 36N a bridging zone comprising substantially no attachments is formed between the front attachments zones 140, 150 and the rear attachment zones 160, 170. In FIG. 36O, the bridging zone comprises a semi-permanent attachment 185 between the first front attachment zone 140 and the first rear attachment zone 160, and a semi-permanent attachment 195 between the second front attachment zone 150 and the second rear attachment zone 170. In FIG. 36P, a bridging zone is provided between the front attachment zones 140, 150 and the rear attachment zones 160, 170 which bridging zone comprises fluff fibers and/or a strip of airlaid fluff material. In the embodiments of FIGS. 36M-36P, the first front attachment zone 140 and the second front attachment zone 150 are arranged symmetrically with respect to the longitudinal center axis of the absorbent core. Preferably the distance between the first and the second attachment zone is between 20 mm and 70 mm, more preferably between 30 mm and 60 mm, even more preferably between 40 mm and 55 mm. Especially for male persons, this distance is preferably sufficiently large such that urine is captured mainly in the area between the first front attachment zone 140 and the second front attachment zone 150.

The first front attachment zone 140 and the second front attachment zone 150 may be substantially parallel and may extend in a longitudinal direction of the absorbent core 130 as illustrated in FIGS. 36M, 36O and 36P. Alternatively an angle between the first front attachment zone 140 and a longitudinal direction of the absorbent core and an angle between the second front attachment zone 150 and the longitudinal direction of the absorbent core may be smaller than 5° such as illustrated in FIG. 36N, wherein the first and second front attachment zones 140, 150 diverge in the direction of the front transverse edge 133.

Preferably, a minimal width of the bridging zone 145 is at least 5 mm, preferably at least 10 mm and more preferably at least 15 mm. In this manner, a sufficient width is available to allow liquid to flow and/or travel through the bridging zone 145. The minimal width of the bridging zone 145 is the smallest distance between the front attachment zone 140, 150 and the rear attachment zone 160, 170 between which liquid is allowed to flow by means of the bridging zone.

It is clear to the skilled person that in the above described embodiments, alternatively or in addition to bridging zones comprising substantially no attachments, bridging zones comprising at least one semi-permanent attachment can be provided, and vice versa. It is further clear to the skilled person, that although not explicitly indicated in FIGS. 15-26, these figures may illustrate alternative bridging zone configurations wherein liquid flow is enabled from one longitudinal portion to another longitudinal portion of the absorbent core wherein the liquid passes between at least one front attachment zone and one rear attachment zone.

It is further clear to the skilled person that in the above described embodiments, alternatively or in addition to bridging zones comprising semi-permanent attachments which are substantially aligned with the front and/or rear attachments zones 140, 150, 160, 170, semi-permanent attachments may be provided which are positioned either substantially perpendicular to the front and/or rear attachments zones 140, 150, 160, 170, or positioned in substantially the transverse direction of the absorbent core 130. In this manner, mass flow across and/or between and/or throughout the front and/or rear attachments zones is improved in a first stage of wetting. In a second stage of wetting, when the semi-permanent attachments have resolved, capillary action can take place to allow liquid flow across and/or between and/or throughout the front and/or rear attachments zones or the corresponding channels formed thereby.

FIGS. 37-41 and 42A-42B

Figure 37:
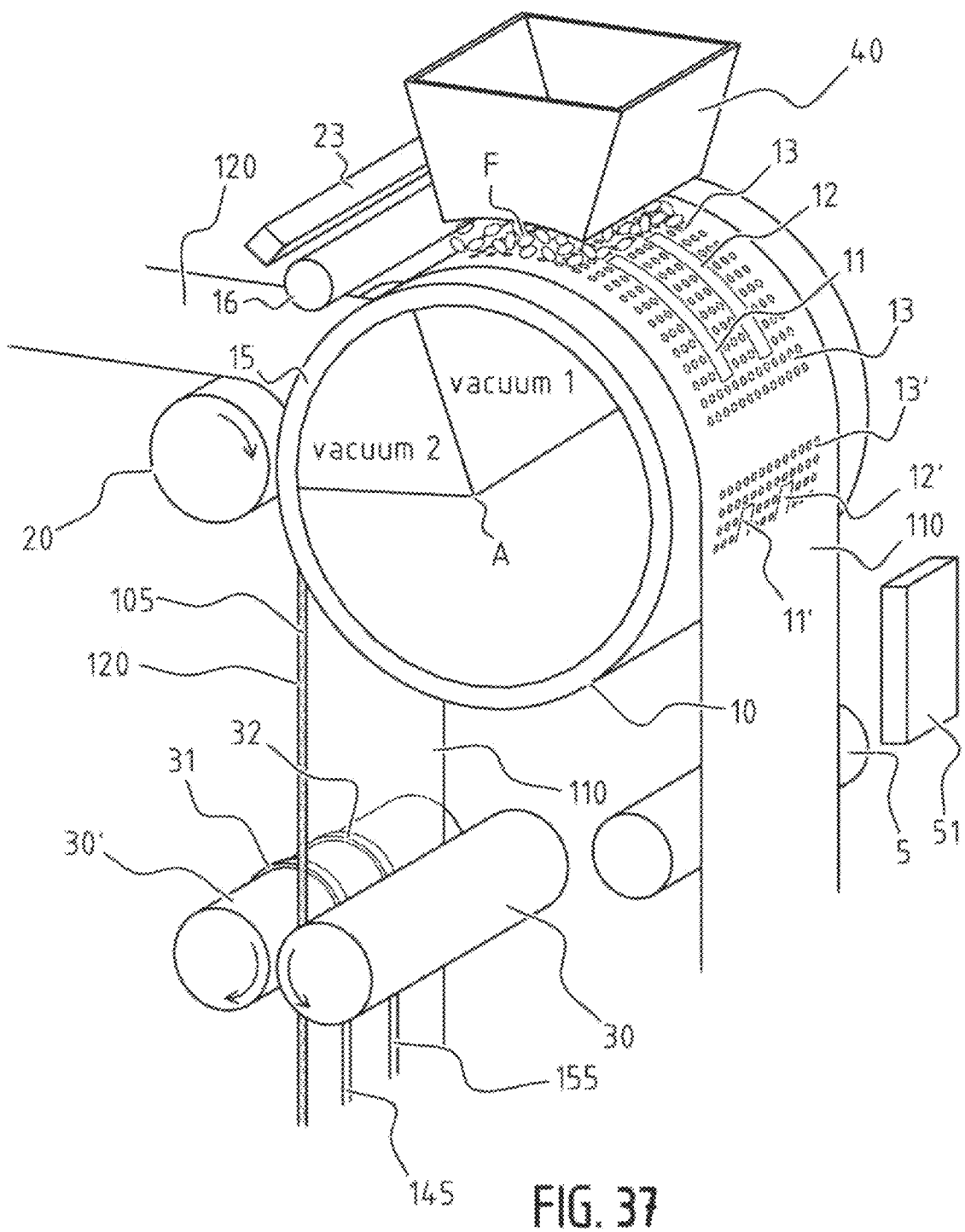
FIG. 37 illustrates schematically another exemplary embodiment of a method and apparatus for manufacturing an absorbent article.
Figure 42A:
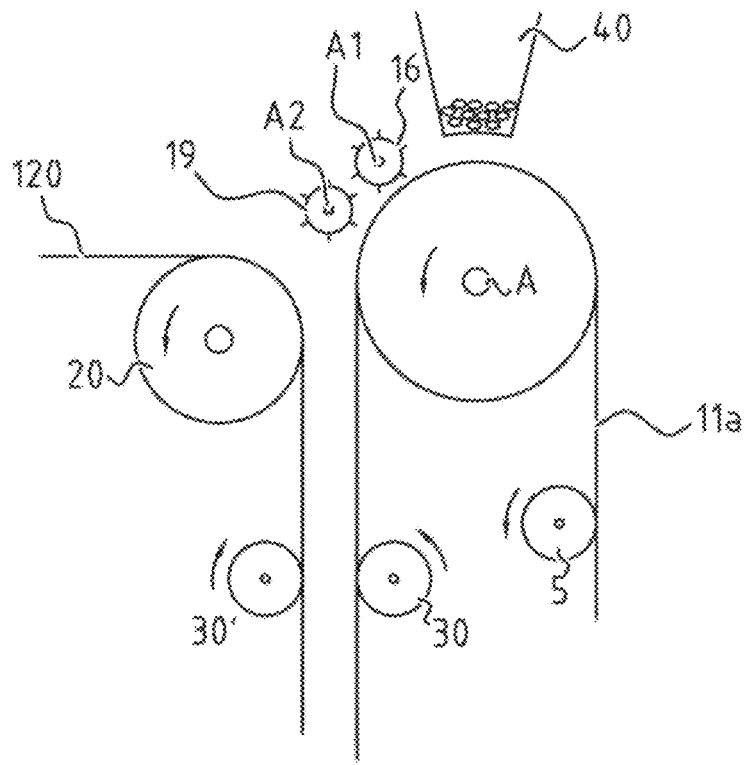
FIG. 42A-B show schematically other exemplary embodiments of a method and apparatus for manufacturing an absorbent article comprising a second roller brush.
Figure 42B:
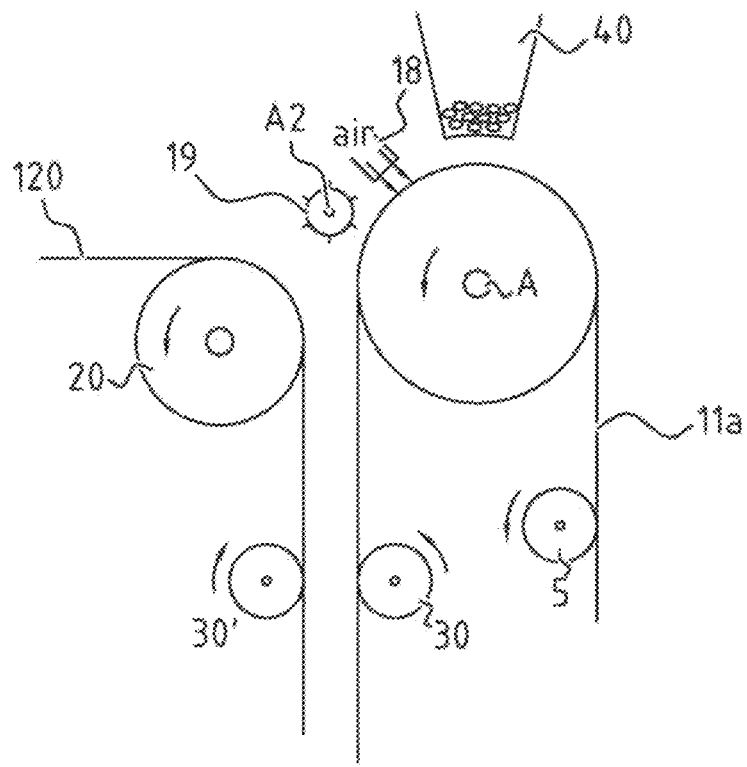

FIG. 37 illustrates an exemplary embodiment of a mechanical removal means. The locally removing of the absorbent material F may be done by a first roller brush 16. The first roller brush 16 is mounted above the first sheet material 110 on the rotating member 10, downstream of the hopper 40. Optionally, the first roller brush 16 may be mounted above the first sheet material 110 on the rotating member 10, directly downstream of a lower opening of the hopper 40. The axis of the first roller brush 16 is parallel to the axis of the rotating member 10. The rotation of the first roller brush 16 may be driven by a first variable-speed motor. Speed and/or direction of the rotating movement of the first roller brush 16 may be adjustable. The rotational movement of the first roller brush 16 scrapes or sweeps the absorbent material F applied on the attachment portions 14 such that substantially no absorbent material F is present on the attachment portions 14, and the remaining portions 21 are still covered with absorbent material F. A distance between the first roller brush 16 and the first sheet material 110 may be adjustable by a further first adjusting means. Further, as illustrated in FIGS. 42A and 42B, a second roller brush 19 may be provided downstream of first roller brush 18, in order to flatten the layer o absorbent material on the suction zones 13, 13'. The speed and/or direction of rotating movement of the second roller brush 19, and/or the distance between the second roller brush 19 and the first sheet material 110, may be adjusted depending on the material of the first sheet material 110 and/or the material of the absorbent material F and/or the channel(s) that are intended to be made.

Figure 41:
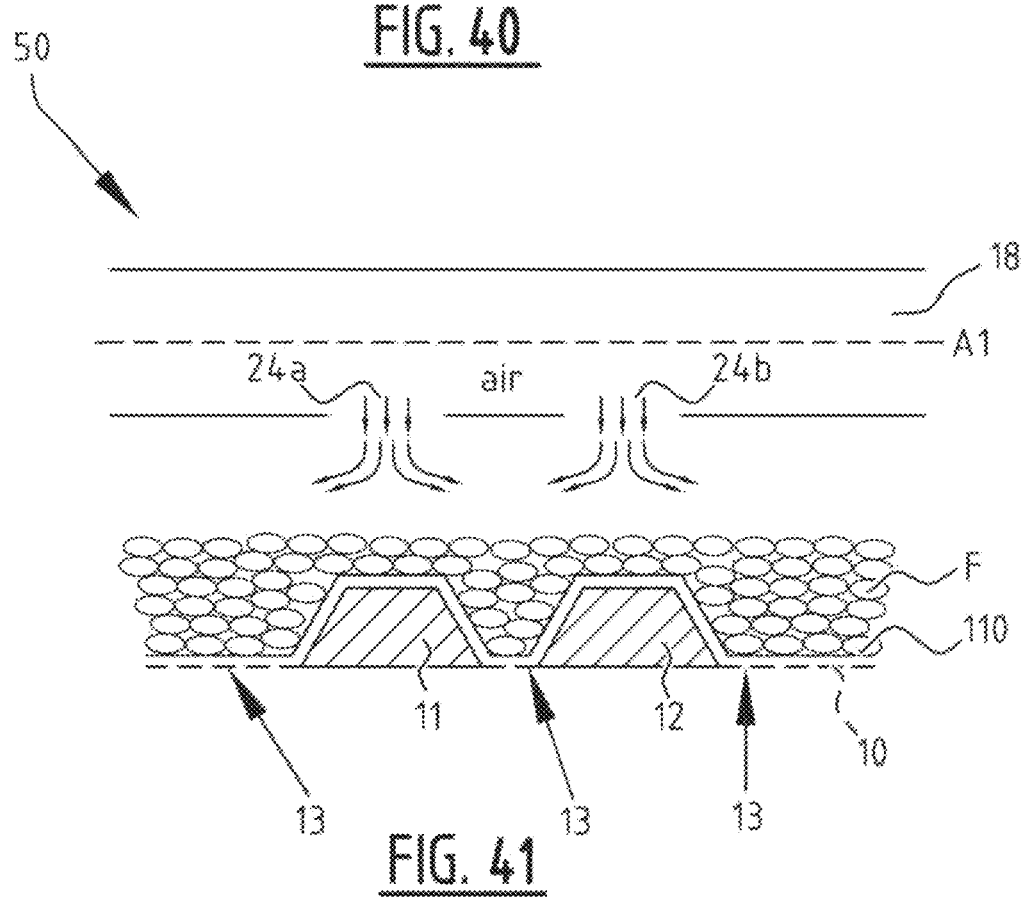
FIG. 41 shows a cross section of an exemplary embodiment of an air jet system being applied above the first sheet material.

In other embodiments, the locally removing of the absorbent material F may be done by an air jet system 18 as illustrated in FIG. 41, see further.

The removed absorbent material F may be discarded and/or collected and/or recycled by a further discharge means 23, such that the removed absorbent material can be further used. The discharge means preferably comprises a vacuum source to collect the removed absorbent material. In a fourth step a second sheet material 120 is applied on top of the absorbent material on the first sheet material 110, e.g. using a further rotating member 20. One of said first and second sheet material is a top core wrap sheet material, and the other one is a back core wrap sheet material. In the illustrated embodiment it is assumed that the first sheet material 110 is the top core wrap sheet material.

Figure 38:
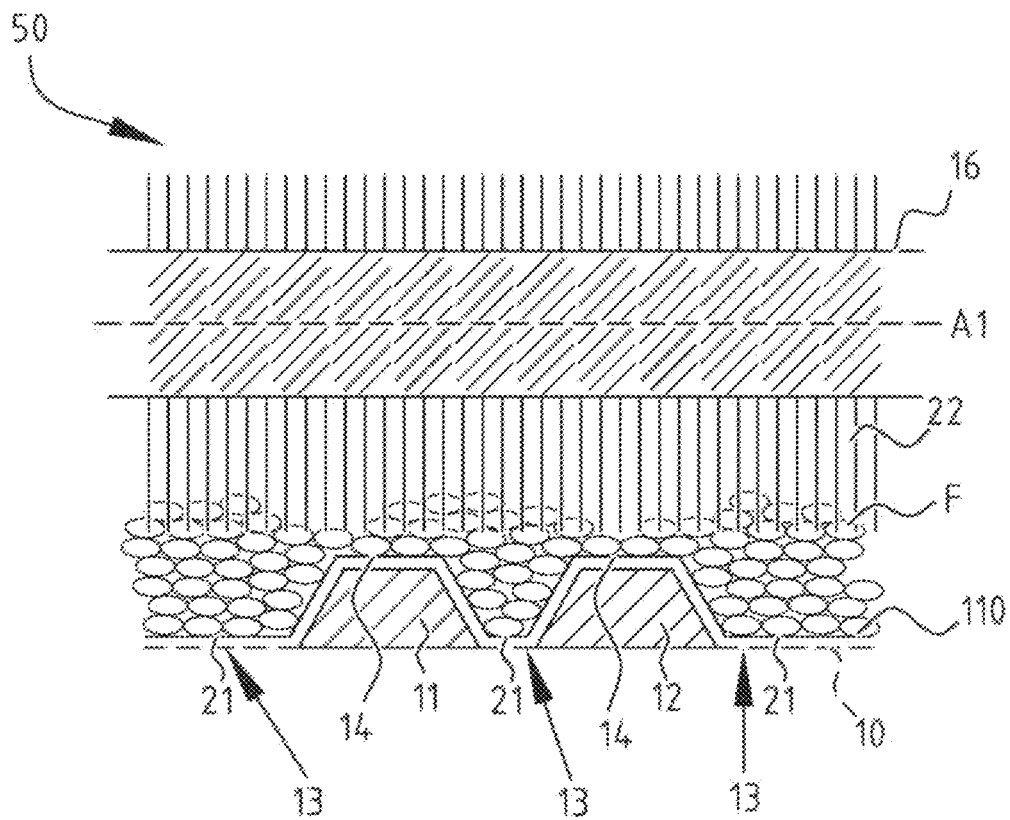
FIG. 38 shows a cross section of a first exemplary embodiment of a first roller brush being applied above the first sheet material.

In a fifth step the first sheet material 110 is attached to the second sheet material 120 at least in the attachment portions 14, and such that attachment zones 140 are formed. The attaching may be done by applying pressure and/or heat on the top core wrap sheet material 110 and/or on the back core wrap sheet material 120 in the attachment portions 14, e.g. by a rotating member 30 and/or opposite rotating member 30' which is provided with at least a first and a second seal rib 31, 32 dimensioned for applying pressure and/or heat on the top core wrap sheet material 110 in the attachment portions 14 in order to create the attachment zones 140. Additionally or alternatively adhesive may be applied to the back and/or top core wrap sheets, to release the bond between the top and back core wrap sheets, e.g. using the methods described in the embodiments above. FIG. 38 shows a cross section of a first exemplary embodiment of a first roller brush 16 being applied above a first sheet material 110. After the absorbent material F is applied via a hopper 40 on said first sheet material 110 on the rotating member 10 (as explained in connection with FIG. 37) with non-suction zones 11, 12 and suction zones 13, attachment portions 14 of the first sheet material located above the non-suction zones 11, 12; 11', 12' and remaining portions 21 of the first sheet material located above the suction zones 13, 13' are covered with the absorbent material F.

However, because of the suction effect more material will be sucked above the suction zones 13, 13'. The first roller brush 16 has bristles 22 which may have substantially the same length, the tips of which create a more or less even cylinder-shaped surface around the first roller brush 16. As the first roller brush 16 rotates, the bristles 19 scrape or sweep the absorbent material applied on the first sheet material 110 such that substantially no absorbent material F remains present on the attachment portions 14, whilst the remaining portions 21 remain covered with absorbent material. The bristles 22 of the first roller brush 16 may comprise a flexible material, preferably plastic, e.g. nylon, such that damage to the first sheet material 110 can be prevented or reduced during the removal of absorbent material.

Figure 39:
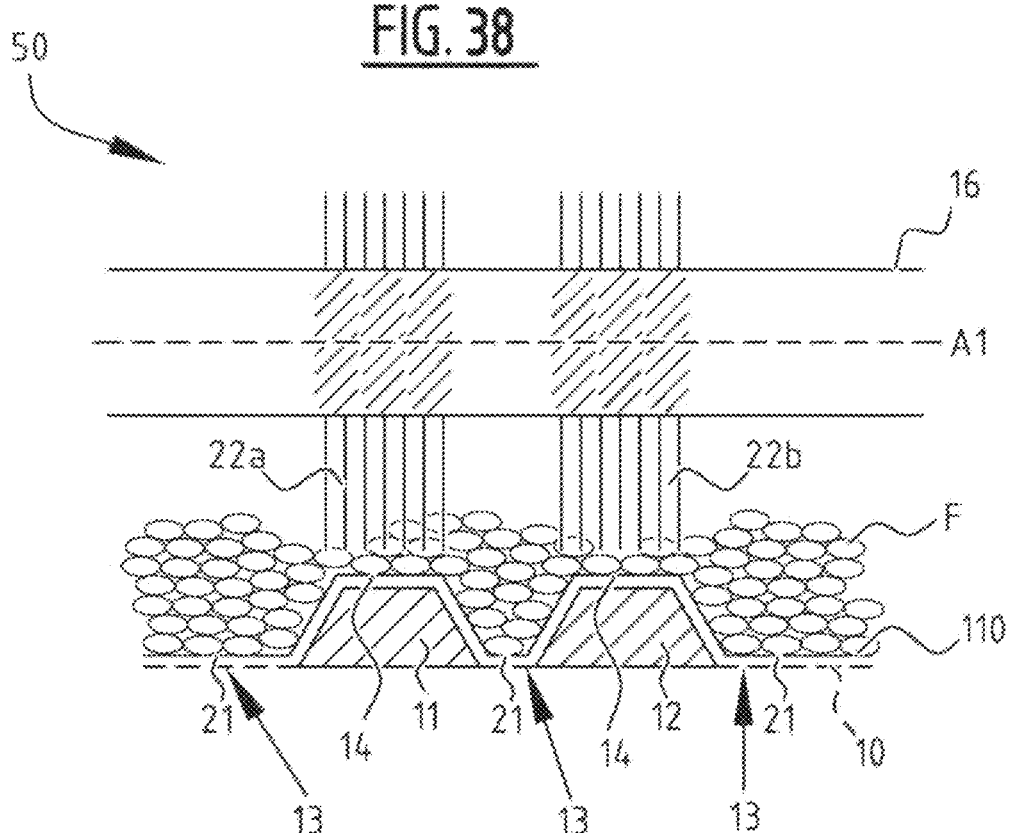
FIG. 39 shows a cross section of a second exemplary embodiment of a first roller brush being applied above the first sheet material.

FIG. 39 shows a cross section of a second exemplary embodiment of a first roller brush 16 having an axis A1 and being applied above a first sheet material 110 on a rotating member 10 and with non-suction zones 11, 12 and suction zones 13. In this embodiment, the bristles 22a, 22b are amounted on the first roller brush 16 to target the attachment portions 14 of the first sheet material 110 located above the non-suction zones 11, 12. The advantage of this embodiment is that it results in a more specific removal of absorbent material F on the attachment portions 14, without effecting or with minimal effects on the absorbent material F on the remaining portions 21 of the first sheet material 110. The bristles 22a, 22b of the first roller brush 16 may comprise a flexible material, preferably plastic, e.g. nylon, such that damage to the first sheet material 11 can be prevented or reduced during the removal of absorbent material. The position of the bristles 22a, 22b targeting the attachment portions 14 may be configured to be adjustable depending on the size of the articles to be made, and/or the intended position of the channels, and/or other configurations known to a skilled person.

Figure 40:
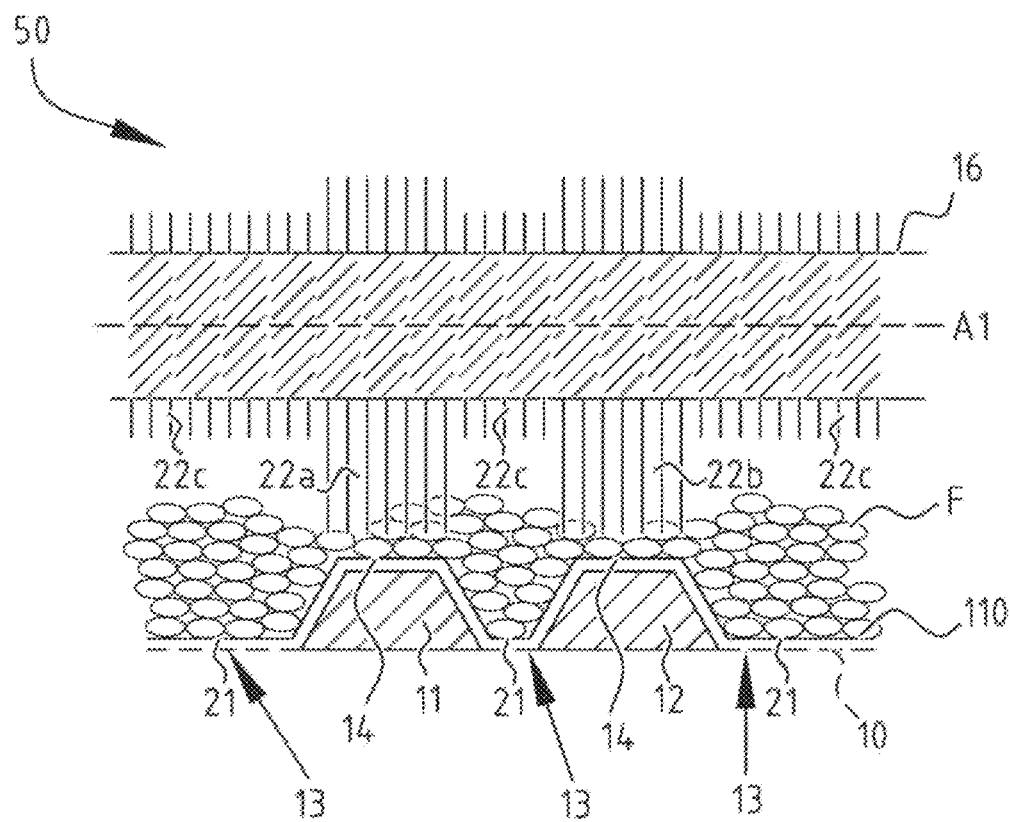
FIG. 40 shows a cross section of a third exemplary embodiment of a first roller brush being applied above the first sheet material.

FIG. 40 shows a cross section of a third exemplary embodiment of a first roller brush 16 being applied above the first sheet material 110 on a rotating member 10 with non-suction zones 11, 12 and suction zones 13. In this embodiment, the bristles 22a, 22b. 22c form a stepped profile with bristle zones 22a, 22b located above the attachment portions 14 and zones 22c above the remaining portion. The bristles 22c are preferably less flexible and/or less bendable that the bristles 22a, 22b. Preferably the length of the bristles 22a, 22b targeting the attachment portions 14 is longer than the length of the bristles 22c targeting the remaining portions 21. The bristles 22a. 22b, 22c of the first roller brush 16 may comprise a flexible material, preferably plastic. e.g. nylon, such that damage to the first sheet material 11 can be prevented or reduced during the removal of absorbent material. In a further embodiment, the bristles 22a. 22b targeting the attachment portions 14 comprise a flexible material, preferably plastic, e.g. nylon, while the bristles 22c targeting the remaining portions 21 comprise a rigid material, such as metal, such that while the bristles 22a, 22b targeting the attachment portions 14 remove the absorbent material on the attachment portions 14, the bristles 22c targeting the remaining portions 21 scrapes the absorbent material applied on the remaining portions 21 to make the surface of the absorbent material even.

FIG. 41 shows a cross section of an exemplary embodiment of an air jet system 18 being applied above the first sheet material 110 on a rotating member 10 with non-suction zones 11, 12 and suction zones 13. The air jet system is configured to blow air onto the attachment portions 14 to remove the absorbent material F thereon. Position of the air outlets 24a, 24b of the air jet system 18 may be configured to be adjustable depending on the size of the articles to be made, and/or intended position of the channels, and/or other configurations known to a skilled person. A second roller brush 19 may be implemented in the apparatus, in combination with the first roller brush 16 or in combination with the air jet system 18 as is shown in FIGS. 42A and 42B respectively. The two brushes 18, 19 may be arranged in series, wherein the task of brush 18 is to perform cleaning of the attachment portions 14, and the task of brush 19 is to make the surface of the absorbent layer on the remaining portion 21 more even. The material of the bristles of brush 18 is preferably more flexible that the material of the bristles of brush 19. The second roller brush 19 is configured to scraping the absorbent material applied on the remaining portions 21 such that surface of the absorbent material F is even. Preferably bristles of the second roller brush 19 comprise a rigid material, such as metal. Preferably the second roller brush 19 is mounted above the first sheet material 110 on the rotating member 10, downstream of the first roller brush 16, or downstream of the air jet system 18. Optionally, the first roller brush 16 may be mounted above the first sheet material 110 immediately downstream of the lower opening of the hopper 40. The axis A2 of the second roller brush 19 is parallel to the axis A of the rotating member 10. The rotation of the second roller brush 19 may be driven by a second variable-speed motor. Speed and/or direction of the rotating movement of the second roller brush 19 may be adjustable. The rotational movement of the second roller brush 19 scrapes the absorbent material remaining on the remaining portions 21 such that the absorbent material creates an even surface on the remaining portions 21. A distance between the second roller brush 19 and the first sheet material 110 may be adjustable by a further second adjusting means (not shown). The speed and/or direction of the rotating movement of the second roller brush 19, and/or the distance between the second roller brush 19 and the first sheet material 110, may be adjusted depending on the material of the first sheet material and/or the material of the absorbent material and/or the channel(s) that are intended to be made, and/or other configurations known to a skilled person.

The above-described method may yield an absorbent article with higher dry and especially wet integrity and which avoids unwanted migration of absorbent material, while avoiding the risk of damaging the attachment zones during manufacture which may impede the formation of channels. The skilled person will understand that this method is not limited to this particular configuration of attachment zones and will know how to best adapt the binder application zones on the first and second sheet materials 110, 120 for other configurations, such as the ones described in the present application. More in particular the skilled person understands that the method is also useful for absorbent cores with only one attachment zone or with more than two attachment zones.

In non-illustrated embodiments, the brushes 18 may be provided with flexible scraping or wiping element, at least in the zones of the attachment portions 14, instead of with a plurality of bristles. In yet other embodiments the brushes 18 may be replaced with other local mechanical removing means. e.g. a non-rotating mechanical removal means such as a scraper or wiper in combination with a suction means to suck the material scraped off in the attachment portions 14.

It is further noted that the use of a brush 18 in not required in all embodiments of the invention. In certain embodiments, the inserts 11, 12 may have a shape and height which is such that substantially no absorbent material is present on the attachment portions 14. Increasing the height od the inserts 11, 12 may be useful when the layer of absorbent material F is thicker. The inserts 11, 12 in FIG. 10A have a trapezoidal shape with a bottom side B1, a top side B2, and a height H. However other shapes are possible. Also, the dimensions may vary. The height H may be e.g. between 2 and 10 mm, preferably between 3 and 7 mm. The inserts may be removably fixed so that they can be easily changed in function of the materials used.

Whilst the principles of the invention have been set out above in connection with specific embodiments, it is to be understood that this description is merely made by way of example and not as a limitation of the scope of protection which is determined by the appended claims.

The invention claimed is:

1. An apparatus for manufacturing an absorbent article, said apparatus comprising:
   a. a rotating member for guiding a first sheet material along a surface thereof, wherein the surface of said rotating member is provided with at least one suction zone and at least one non-suction zone;
   b. an application unit configured for applying an absorbent material on said first sheet material on the rotating member;
   c. a first roller brush configured for locally removing the absorbent material applied on at least one attachment portion of the first sheet material located above the at least one non-suction zone, such that at least one remaining portion of the first sheet material located above the at least one suction zone is covered with absorbent material and substantially no absorbent material is present on the at least one attachment portion;
   d. a sheet feed unit configured for applying a second sheet material on top of the absorbent material on the first sheet material; wherein one of said first and second sheet material is a top core wrap sheet material, and the other one is a back core wrap sheet material;
   e. an attachment unit configured for attaching said first sheet material to said second sheet material at least in the at least one attachment portion.

2. The apparatus of claim 1, wherein the first roller brush has bristles of a flexible material.

3. The apparatus of claim 1, wherein the first roller brush has bristles of substantially the same length extending around a circumference creating a more or less even cylinder-shaped surface of the one or more first bristle zones around the first roller brush.

4. The apparatus of claim 1, wherein the first roller brush has one or more first bristle zones located above the attachment portions and one or more second bristle zones located above the remaining portions, wherein the first bristle zones are different from the second bristle zones.

5. The apparatus of claim 1, further comprising a second roller brush configured for scraping the absorbent material applied on the at least one suction zone such that a surface of the absorbent material above the at least one suction zone is substantially even.

6. The apparatus of claim 5, wherein the second roller brush has bristles which are less flexible than bristles of the first roller brush.

7. The apparatus of claim 1, wherein the first roller brush is mounted above the first sheet material immediately downstream of a lower opening of the application unit.

8. An apparatus for manufacturing an absorbent article, said apparatus comprising:
   a. a rotating member for guiding a first sheet material along a surface thereof, wherein the surface of said rotating member is provided with at least one suction zone and at least one non-suction zone;
   b. an application unit configured for applying an absorbent material on said first sheet material on the rotating member;
   c. an air jet system configured for locally removing the absorbent material applied on at least one attachment portion of the first sheet material located above the at least one non-suction zone, such that at least one remaining portion of the first sheet material located above the at least one suction zone is covered with absorbent material and substantially no absorbent material is present on the at least one attachment portion;
   d. a sheet feed unit configured for applying a second sheet material on top of the absorbent material on the first sheet material; wherein one of said first and second sheet material is a top core wrap sheet material, and the other one is a back core wrap sheet material;

e. an attachment unit configured for attaching said first sheet material to said second sheet material at least in the at least one attachment portion.

9. The apparatus of claim 8, further comprising a roller brush configured for scraping the absorbent material applied on the at least one suction zone such that a surface of the absorbent material above the at least one suction zone is substantially even.

10. The apparatus of claim 9, wherein said at least one non-suction zone comprises at least one elongate zone extending in a circumferential direction of the rotating member.

11. The apparatus of claim 9, wherein the at least one non-suction zone is formed by at least one element protruding outwardly from an outer surface of the rotating member.

12. The apparatus of claim 11, wherein said at least one element comprises at least one removable insert.

13. An apparatus for manufacturing an absorbent article, said apparatus comprising:
   a. a rotating member for guiding a first sheet material along a surface thereof, wherein the surface of said rotating member is provided with at least one suction zone and at least one non-suction zone;
   b. an application unit configured for applying an absorbent material on said first sheet material on the rotating member;
   c. a roller brush configured for scraping the absorbent material applied on said first sheet material such that a surface of the absorbent material is substantially even;
   d. an air jet system configured for locally removing the absorbent material applied on at least one attachment portion of the first sheet material located above the at least one non-suction zone, such that at least one remaining portion of the first sheet material located above the at least one suction zone is covered with absorbent material and substantially no absorbent material is present on the at least one attachment portion;
   e. a sheet feed unit configured for applying a second sheet material on top of the absorbent material on the first sheet material; wherein one of said first and second sheet material is a top core wrap sheet material, and the other one is a back core wrap sheet material; and
   f. an attachment unit configured for attaching said first sheet material to said second sheet material at least in the at least one attachment portion.

14. The apparatus of claim 13, wherein the roller brush is mounted above the first sheet material immediately downstream of a lower opening of the application unit.

15. The apparatus of claim 13, wherein said at least one non-suction zone comprises at least one elongate zone extending in a circumferential direction of the rotating member.

16. The apparatus of claim 13, wherein the at least one non-suction zone is formed by at least one element protruding outwardly from an outer surface of the rotating member.

17. The apparatus of claim 16, wherein said at least one element comprises at least one removable insert.

18. The apparatus of claim 17, wherein the at least one insert has a trapezoidal cross section.

19. The apparatus of claim 13, wherein the air jet system is configured to blow air onto the at least one attachment portion via air outlets of the air jet system.

20. The apparatus of claim 19, wherein a position of the air outlets of the air jet system is adjustable depending on the size of the absorbent article and/or intended position of the at least one attachment portion.

* * * * *